US011155581B2

(12) United States Patent
D'aoust et al.

(10) Patent No.: US 11,155,581 B2
(45) Date of Patent: Oct. 26, 2021

(54) INCREASING VIRUS-LIKE PARTICLE YIELD IN PLANTS

(71) Applicant: MEDICAGO INC., Quebec (CA)

(72) Inventors: Marc-Andre D'aoust, Quebec (CA); Manon Couture, St-Auqustin-de-Desmaures (CA); Louis-Philippe Vezina, Neuville (CA)

(73) Assignee: MEDICAGO INC., Quebec (CA)

( * ) Notice: Subject to any disclaimer, the term of this patent is extended or adjusted under 35 U.S.C. 154(b) by 621 days.

(21) Appl. No.: 14/347,804

(22) PCT Filed: Sep. 28, 2012

(86) PCT No.: PCT/CA2012/050681
§ 371 (c)(1),
(2) Date: Mar. 27, 2014

(87) PCT Pub. No.: WO2013/044390
PCT Pub. Date: Apr. 4, 2013

(65) Prior Publication Data

US 2015/0104480 A1 Apr. 16, 2015

Related U.S. Application Data

(60) Provisional application No. 61/541,780, filed on Sep. 30, 2011.

(51) Int. Cl.

| | |
|---|---|
| ***C07K 14/005*** | (2006.01) |
| ***C12N 15/82*** | (2006.01) |
| ***A61K 39/145*** | (2006.01) |
| ***C12N 7/00*** | (2006.01) |
| ***C07K 16/10*** | (2006.01) |

(52) U.S. Cl.
CPC .......... *C07K 14/005* (2013.01); *A61K 39/145* (2013.01); *C07K 16/1018* (2013.01); *C12N 7/00* (2013.01); *C12N 15/8257* (2013.01); *C12N 15/8258* (2013.01); *C12N 2760/16223* (2013.01); *C12N 2760/16234* (2013.01); *C12N 2760/16251* (2013.01)

(58) Field of Classification Search
None
See application file for complete search history.

(56) References Cited

U.S. PATENT DOCUMENTS

| | | | | |
|---|---|---|---|---|
| 4,962,028 A | 10/1990 | Bedbrook et al. | | |
| 5,232,833 A | 8/1993 | Sanders et al. | | |
| 7,132,291 B2 * | 11/2006 | Cardineau | C12N 15/8258 | 435/320.1 |
| 9,017,987 B2 * | 4/2015 | Williamson | C12N 15/8214 | 435/252.3 |
| 9,056,901 B2 | 6/2015 | Song et al. | | |
| 9,505,806 B2 | 11/2016 | Sirko et al. | | |
| 9,546,375 B2 * | 1/2017 | Couture | A61K 39/145 | |
| 9,555,094 B2 | 1/2017 | Kuroda et al. | | |
| 2004/0268442 A1 | 12/2004 | Miller et al. | | |
| 2010/0143393 A1 | 6/2010 | Smith et al. | | |
| 2015/0218579 A1 * | 8/2015 | D'aoust | C12N 15/8258 | 530/350 |

FOREIGN PATENT DOCUMENTS

| | | | |
|---|---|---|---|
| WO | 00/20557 A2 | 4/2000 | |
| WO | 2007/047831 A2 | 4/2007 | |
| WO | 2007/100584 A2 | 9/2007 | |
| WO | 20071135480 A1 | 11/2007 | |
| WO | 2008/148104 A1 | 12/2008 | |
| WO | 2009/009876 A1 | 1/2009 | |
| WO | 2009/076778 A1 | 6/2009 | |
| WO | WO 2009076778 A1 * | 6/2009 | C12N 15/82 |
| WO | 20091087391 A1 | 7/2009 | |
| WO | 2010/003225 A1 | 1/2010 | |
| WO | 2010/003235 A1 | 1/2010 | |
| WO | 2010/006452 A1 | 1/2010 | |
| WO | 2010/025285 A1 | 3/2010 | |
| WO | 2010/117786 A1 | 10/2010 | |
| WO | 2010/148511 A1 | 12/2010 | |
| WO | 2011/011390 A1 | 1/2011 | |
| WO | 2011/035422 A1 | 3/2011 | |
| WO | 2011/102900 A1 | 8/2011 | |
| WO | 2012/047941 A2 | 4/2012 | |
| WO | 2012/083445 A1 | 6/2012 | |

(Continued)

OTHER PUBLICATIONS

Kang et al (Virus Research, 2009, 143: 140-146).*
D'Aoust et al (Plant Biotechnology Journal, 2010, 8(5): 607-619).*
D'Aoust et al (Plant Biotechnology Journal 2010, 8: 607-619).*
Betakova (Arch. Virol., 2009, 154:1619-1624).*
Beyer et al (Archives of Virology, 1986, 90: 173-181).*
Leikina et al (EMBO, 2002, 21(21):5701-5710).*
GenBank FJ766840 (published 2009; appended to action).*
GenBank AXV41427 (published Jan. 2010; appeneded to action).*
Huang et al (Biotechnology and Bioengineering, 2009, 103(4): 706-714).*
Robinson et al (Protoplasma, 2004, 224: 255-260).*
Ito et al (J. Virol., 1991,65(10): 5491-5498).*
Redkiewicz et al (ABP, 2014, 61(3): 551-560).*
Wiley et al (Ann. Rev. Biochem, 1987, 56: 365-394).*
Kalthoff et al (J. Virol., 2010, 84(22): 12002-12010).*

(Continued)

*Primary Examiner* — Stephen Uyeno
(74) *Attorney, Agent, or Firm* — J.A. Lindeman & Co., PLLC

(57) ABSTRACT

A method of producing a virus like particle (VLP) in a plant is provided. The method comprises introducing a first nucleic acid and a second nucleic acid into the plant, or portion of the plant. The first nucleic acid comprises a first regulatory region active in the plant and operatively linked to a nucleotide sequence encoding a structural virus protein. The second nucleic acid comprises a second regulatory region active in the plant and operatively linked to a nucleotide sequence encoding a channel protein, for example but not limited to a proton channel protein. The plant or portion of the plant is incubated under conditions that permit the expression of the nucleic acids, thereby producing the VLP.

31 Claims, 63 Drawing Sheets

Specification includes a Sequence Listing.

(56) References Cited

FOREIGN PATENT DOCUMENTS

| | | | |
|---|---|---|---|
| WO | 2013/044390 | A1 | 4/2013 |
| WO | 2014/153674 | A1 | 10/2014 |

OTHER PUBLICATIONS

Sakaguchi et al (The Journal of Cell Biology, 1996, 133(4): 733-747).*
Harvey et al (J. Virol., 2004, 78(1): 502-507).*
Shoji et al (Human Vaccines & Immunotherapeutics, 2015, 11(1): 118-123).*
Translated Office Action in corresponding Thailand application No. 1401001699, dated Feb. 22, 2016.
Shoji, Y., et al. A plant-produced H1N1 trimeric hemagglutinin protects mice from a lethal influenza virus challenge. Human Vaccines and Immunotherapeutics, vol. 9, 2013, pp. 553-560.
Gomez-Puertas, P., et al., "Efficient formation of influenza virus-like particles: dependence on the expression level of viral proteins," J. Gen. Viral. (1999) 80 :1635-1645.
Hartl, F. Ulrich, "Molecular chaperones in cellular protein folding," Nature, (1996) vol. 381, Jun. 13, pp. 571-580.
Nemchinov, L.G. et al, "Transient expression of the ectodomain of matrix protein (M2e) of avian influenza A virus in plants," Protein Expression and Purification. (2007) 56:153-159.
Sakaguchi, T., et al, "The Ion Channel Activity of the Influenza Virus M2 Protein Affects Transport through the Golgi Apparatus," J of Cell Bio, vol. 133:4, 1996, pp. 733-747.
Wang, K., et al, "Viral proteins function as ion channels," Biochimica et Biophysica Acta. vol. 1808:2, Feb. 2011, pp. 510-515.
Office Action from related Canadian Application No. 2,850,407, dated Jun. 1, 2015.
English translation of Office Action from related Chinese Application No. 201280047819.2, dated Jun. 24, 2015.
Extended European Search Report from EP 12836545.9, dated May 12, 2015.
First Examination Report from related NZ Application No. 622731, dated Jan. 30, 2015.
Beyer, W.E.P., et al.: "Influenza Virus Strains with a Fusion Threshold of pH 5.5 or Lower are Inhibited by Amantadine," Archives of Virology, vol. 90, pp. 173-181, 1986.
Bianchi, E., et al.: "Universal Influenza B Vaccine Based on the Maturational Cleavage Site of the Hemagglutinin Precursor," Journal of Virology, vol. 79, No. 12, pp. 7380-7388, Jun. 2005.
Bullough, P., et al.: "Structure of Influenza Haemagglutinin at the pH of Membrane Fusion," Nature, vol. 371, No. 1, pp. 37-43, Sep. 1, 1994.
Chen, J. et al.: "Structure of the Hemagglutinin Precursor Cleavage Site, a Determinant of Influenza Pathogenicity and the Origin of the Labile Conformation," Cell, vol. 95, pp. 409-417, Oct. 30, 1998.
Chiba, M., et al.: "Diverse Suppressors of RNA Silencing Enhance Agroinfection by a Viral Replicon," Virology, vol. 346, pp. 7-14, 2006.
Frugis, G. et al.: "MsJ1, an Alfalfa DnaJ-Like Gene, is Tissue Specific and Transcriptionally Regulated During Cell Cycle," Plant Molecular Biology, vol. 40, pp. 397-408, 1999.
Holsinger, L. et al.: "Influenza Virus M2 Integral Membrane Protein is a Homotetramer Stabilized by Formation of Disulfide Bonds," Virology, vol. 183, pp. 32-43, 1991.
M. Hatta et al.: "Molecular Basis for High Virulence of Hong Jong H5N1 Influenze a Viruses," Science, vol. 293, pp. 1840-1842, Sep. 7, 2001.
Henkel, J.R. et al.: "Influenza Virus M2 Protein Slows Traffic Along the Secretory Pathway: pH Perturbation of Acidified Compartments Affects Early Golgi Transport Steps," Journal of Biological Chemistry, vol. 273, No. 11, pp. 6518-6524, 1998.
Hoffmann, E., et al.,: "Eight-plasmid System for Rapid Generation of Influenza Virus Vaccines," Vaccine, vol. 20, pp. 3165-3170, 2002.
T. Horimoto et al.: "The Development and Characterization of H5 Influenza Virus Vaccines Derived from a 2003 Human Isolate," Vaccine, vol. 24, pp. 3669-3676, 2006.
Huang, et al.: "A DNA Replicon System for Rapid High-Level Production of Virus-Like Particles in Plants," Biotechnology Bioengeering, vol. 103, No. 4, pp. 706-714, Jul. 1, 2009.
Huang, et al. "High-Level Rapid Production of Full-Size Monoclonal Antibodies in Plants by a Single-Vector DNA Replicon System," Biotechnology Bioengeering, vol. 106, No. 1, pp. 9-17, May 1, 2010.
Lamb, Robert A. et al.: "Influenza Virus M2 Protein is an Integral Membrane Protein Expressed on the Infected-Cell Surface," Cell, vol. 40, No. 3, pp. 627-633, 1985.
Latham, T., et al.: "Formation of Wild-type and Chimeric Influenza Virus-like Particles Following Simultaneous Expression of Only Four Structural Proteins," Journal of Virology, vol. 75, No. 13, pp. 6154-6165, Jul. 2001.
Lin et al.: "Genomic Analysis of the Hsp70 Superfamily in Arabidopsis Thaliana," Cell Stress & Chaperones, vol. 6, No. 3, pp. 201-208, 2001.
Liu, L., et al.: "Cowpea Mosaic Virus RNA-1 Acts as an Amplicon Whose Effects can be Counteracted by a RNA-2-Encoded Suppressor of Silencing," Virology vol. 323, pp. 37-48, 2004.
A.J.L. Macario, "Heat-shock Proteins and Molecular Chaperones: Implications for Pathogenesis, Diagnostics and Therapeutics," International Journal of Clinical Laboratory Research, vol. 25, pp. 59-70, 1995.
Neumann, G., et al.: "Plasmid-driven Formation of Influenza Virus-like Particles," Journal of Virology, vol. 74, No. 1, pp. 547-551, Jan. 2000.
Noad, R., et al.: "Virus-like Particles as Immunogens," Trends in Microbiology, vol. 11, No. 9, pp. 438-444, Sep. 2003.
Parsell et al.: "The Function of Heat-shock Proteins in Stress Tolerance: Degradation and Reactivation of Damaged Proteins," Annual Review Genetics, vol. 27, pp. 437-496, 1993.
M. Paul et al.: "Mutational Analysis of the Human Immunodeficiency Virus Type 1 Vpu Transmembrane Domain that Promotes the Enhanced Release of Virus-Like Particles from the Plasma Membrane of Mammalian Cells," Journal of Virology, vol. 72, pp. 1270-1279, 1998.
Reed, M.L., et al.: "The pH of Activation of the Hemagglutinin Protein Regulates H5N1 Influenza Virus Pathogenicity and Transmissability in Ducks," Journal of Virology, vol. 84, No. 3, pp. 1527-1535, Feb. 2010.
Sainsbury, F. et al.: "Expression of Multiple Proteins Using Full-length and Deleted Versions of Cowpea Mosaic Virus RNA-2," Plant Biotechnology Journal, vol. 6, pp. 82-92, 2008.
Sainsbury et al.: "Extremely High-level and Rapid Transient Protein Production in Plants Without the Use of Viral Replication," Plant Physiology, vol. 148, pp. 1212-1218, Nov. 2008.
Sainsbury, F., et al.: "pEAQ: Versatile Expression Vectors for Easy and Quick Transient Expression of Heterologous Proteins in Plants," Plant Biotechnology Journal, vol. 7, pp. 682-693, 2009.
Skehel, J. et al.: "The Three-dimensional Structure and Antigenic Variation of the Influenza Virus Haemagglutinin," PNAS, pp. 107-111, 1982.
Song, J., et al.: "Influenza Virus-Like Particles Containing M2 Induce Broadly Cross Protective Immunity," PlosS One, vol. 6, No. 1, pp. 1-11, Jan. 2011.
Sugrue, R.J. et al.: "Structural Characteristics of the M2 Protein of Influenza A Viruses: Evidence that it Forms a Tetrameric Channel," Virology, vol. 180, No. 2, pp. 617-624, 1991.
Sugrue, R.J. et al.: "Palmitoylation of the Influenza A Virus M2 Protein," Virology, vol. 179, No. 1, pp. 51-56, 1990.
Szecsi, Judit et al.: "Induction of Neutralising Antibodies by Virus-like Particles Harbouring Surface Proteins from Highly Pathogenic H5N1 and H7N1 Influenza Viruses," Virology Journal, vol. 3, No. 70, pp. 1-7, 2006.
Wakefield L., et al.: "RNA-binding Properties of Influenza a Virus Matrix Protein M1," Nucleic Acid Research, vol. 17, No. 21, 8569-8580, 1989.

(56) References Cited

OTHER PUBLICATIONS

Zhang, X. et al.: "Bean Yellow Dwarf Virus Replicons for High-Level Transgene Expression in Transgenic Plants and Cell Cultures," Biotechnology and Bioengineering, vol. 93, No. 2, pp. 271-279, Feb. 5, 2006.
Zebedee, S. et al.: "Influenza A Virus M2 Protein: Monoclonal Antibody Restriction of Virus Growth and Detection of M2 in Virions," Journal of Virology, vol. 62, No. 8, pp. 2762-2772, 1988.
International Search Report from PCT/CA2012/050681 dated Jan. 3, 2013.
International Preliminary Report on Patentability from PCT/CA2012/050681 dated Mar. 31, 2014.
International Search Report from PCT/CA2014/050326 dated Jul. 16, 2014.
M.-A. D'Aoust et al.: "The Production of Hemagglutinin-Based Virus-Like Particles in Plants: A Rapid, Efficient and Safe Response to Pandemic Influenza," Plant Biotechnology Journal, vol. 8, pp. 607-619, 2010.
D'Aoust, M. A. et al.: "Influenza Virus-Like Particles Produced by Transient Expression in Nicotiana Benthamiana Induce a Protective Immune Response Against a Lethal Viral Challenge in Mice," Plant Biotechnology Journal, vol. 6, No. 9, pp. 930-940, Dec. 2008.
Landry, N. et al.: "Preclinical and Clinical Development of Plant-Made Virus-Like Particle Vaccine Against Avian H5N1 Influenza," PLoS One, vol. 5, No. 12, pp. 1-12, Dec. 22, 2010.
Mortimer, E. et al.: "Setting up a Platform for Plant-Based Influenza Virus Vaccine Production in South Africa," BMC Biotechnology, vol. 12, No. 14, pp. 1-10, Apr. 26, 2012.
Shoji, Y. et al.: "A Plant-Produced H1N1 Trimeric Hemagglutinin Protects Mice from a Letha Influenza Virus Challenge," Human Vaccines and Immunotherapeutics, vol. 9, No. 3, pp. 553-560, Mar. 1, 2013.
Office Action in corresponding Canadian Application No. 2,850,407, dated Jul. 12, 2016.
Translated Second Office Action in corresponding Chinese Application No. 201280047819.2, dated Mar. 2, 2016.
Translated Office Action in corresponding Japanese Application No. 2014-532198, dated Jul. 22, 2016.
Office Action in corresponding Mexican Application No. MX/a/2014/003776, dated Jun. 30, 2016.
New Zealand Letters Patent Np. 622731, dated Aug. 2, 2016.
Translated Office Action in corresponding Russian Application No. 2014116371, dated Jul. 15, 2016.
Translated Office Action in corresponding Taiwanese Application No. 101135891, dated Jul. 15, 2016.
Extended European Search Report in corresponding EP Application No. 14773061.8, dated Nov. 7, 2016.
Patent Examination Report No. 1 in corresponding Australian Application No. 2012315421, dated Oct. 12, 2016.
Translated Third Office Action in corresponding Chinese Application No. 201280047819.2, dated Nov. 8, 2016.
Translated Office Action in corresponding Israeli Application No. 231587, dated Feb. 16, 2017.
Office Action in corresponding Mexican Application No. MX/a/2014/003776, dated Feb. 14, 2017.
Translated Office Action in corresponding Russian Application No. 2014116371, dated Jan. 11, 2017.
Nritten Opinion and Search Report in corresponding Singapore Application No. 11201507928Q, dated Dec. 15, 2016.
Translated Rejection Decision in corresponding Taiwanese Application No. 101135891, dated Feb. 23, 2017.
NCBI Blast:Protein Sequence, https://blast.ncbi.nlm.nih.gov/Blast.cgi, accessed Oct. 30, 2016.
Binary vector pEAQ-HT-DEST3, complete sequence—Nucleotide, https://www.ncbi.nlm.nih.gov/nucleotide/257196409?report=genbanklog$=nucltop&bl, accessed Oct. 31, 2016.
Office Action in U.S. Appl. No. 14/779,423 dated Nov. 4, 2016.
Hatta et al., "Molecular Basis for High Virulence of Hong Kong H5N1 Influenza A Viruses", Science, 2001, vol. 293, pp. 1840-1842.
Kanagarajan et al., "Transient Expression of Hemagglutinin Antigen from Low Pathogenic Avian Influenza A (H7N7) in Nicotiana benthamiana", PLoS ONE, 2012, vol. 7, Issue 3, e33010, pp. 1-10.
Song et al., "Protective immunity against H5N1 influenza virus by a single dose vaccination with virus-like particles", Virology, 2010, 405(1), pp. 165-175.
Office Action in corresponding CA Application No. 2,850,407, dated Jul. 4, 2017.
English translation Office Action in corresponding CN Application No. 201280047819.2, dated Jun. 14, 2017.
English translation Office Action in corresponding CN Application No. 201480029001.7, dated Jul. 24, 2017.
Office Action in corresponding EP Application No. 12836545.9, dated Jul. 21, 2017.
English translation of Office Action in corresponding JP Application No. 2014-532198, dated Jun. 28, 2017.
Substantive Examination Adverse Report in corresponding MY Application No. PI 2014700716, dated Nov. 30, 2017.
Office Action in corresponding U.S. Appl. No. 14/779,423, dated Jul. 19, 2017.
English translation in corresponding MX Application No. MX/a/2014/003776, dated Aug. 30, 2017.
GenBank Accession ABU99194.1, dated Jul. 26, 2016.
GenBank Accession ACN29380.1, dated Feb. 28, 2009.
GenBank Accession ACS71642.1, dated Jun. 29, 2009.
GenBank Accession ACU12738.1, dated Aug. 24, 2017.
Klenk, Hans-Dieter, et al. Host cell proteases controlling virus pathogenicity. Trends in Microbiology, vol. 2:2, 1994, pp. 39-43.
Harvey, R., et al. Restrictions to the Adaptation of Influenza A Virus H5 Hemagglutinin to the Human Host. Journal of Virology, 2004, pp. 502-507, vol. 78:1.
Stech, J. et al. A new approach to an influenza live vaccine: modification of the cleavage site of hemagglutinin. Nature Medicagon, vol. 11:6, 2005 pp. 683-689.
Stech, J., et al. Influenza B Virus with Modified Hemagglutinin Cleavage Site as a Novel Attenuated Live Vaccine. Journal of Infectious Diseases, vol. 204:10, 2011, pp. 1483-1490.
Sun, X., et al. Modification to the Hemagglutinin Cleavage Site Control the Virulence of a Neurotropic H1N1 Influenza Virus. Journal of Virology, 2010, pp. 8683-8690.
Banerjee, Indranil, et al. High-content analysis of sequential events during the early phase of Influenza A virus Infection. PLOS one, 2013, vol. 8:7, pp. 109.
Skeik, N., et al. Influenza viruses and the evolution of avian influenza virus H5N1. Int. Journal of Infectious diseases, 2008, vol. 12, pp. 233-238.
Accession AFN19371, dated Nov. 28, 2019.
GenBank AET22022.1, dated Aug. 24, 2017.

* cited by examiner

A-2X35S/CPMV-HT/H5 Indonesia/NOS (Construct number 489)

IF-H5A-I-05.s1+3c SEQ ID NO: 2

AAATTTGTCGGGCCCATGGAGAAAATAGTGCTTCTTCTTGC

IF-H5dTm.r SEQ ID NO: 3

ACTAAAGAAAATAGGCCTTTAAATGCAAATTCTGCATTGTAACGATCCAT

Schematic representation of construct 1191. SacII and StuI restriction enzyme sites used for plasmid linearization are annotated on the representation.

FIG. 1D

Construct 1191 from left to right t-DNA borders (underlined). 2X35S/CPMV-HT/NOS with Plastocyanine-P19-Plastocyanine silencing inhibitor expression cassette (SEQ ID NO: 4)

TGGCAGGATATATTGTGGTGTAAACAAATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA
CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGACAAGCTTGCATGCCGGTCAACATGGTGGAGCACGACACACTTGTCT
ACTCCAAAAATATCAAAGATACAGTCTCAGAAGACCAAAGGGCAATTGAGACTTTTCAACAAAGGGTAA
TATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGT
GGTCCCAAAGATGGACCCCCACCCACGAGGAGCATCGTGGAAAAAGAAGACGTTCCAACCACGTCTTCA
AAGCAAGTGGATTGATGTGATAACATGGTGGAGCACGACACACTTGTCTACTCCAAAAATATCAAAGAT
ACAGTCTCAGAAGACCAAAGGGCAATTGAGACTTTTCAACAAAGGGTAATATCCGGAAACCTCCTCGGA
TTCCATTGCCCAGCTATCTGTCACTTTATTGTGAAGATAGTGGAAAAGGAAGGTGGCTCCTACAAATGCC
ATCATTGCGATAAAGGAAAGGCCATCGTTGAAGATGCCTCTGCCGACAGTGGTCCCAAAGATGGACCCC
CACCCACGAGGAGCATCGTGGAAAAAGAAGACGTTCCAACCACGTCTTCAAAGCAAGTGGATTGATGTG
ATATCTCCACTGACGTAAGGGATGACGCACAATCCCACTATCCTTCGCAAGACCCTTCCTCTATATAAGG
AAGTTCATTTCATTTGGAGAGGTATTAAAATCTTAATAGGTTTTGATAAAAGCGAACGTGGGGAAACCCG
AACCAAACCTTCTTCTAAACTCTCTCTCATCTCTCTTAAAGCAAACTTCTCTCTTGTCTTTCTTGCGTGAGC
GATCTTCAACGTTGTCAGATCGTGCTTCGGCACCAGTACAACGTTTTCTTTCACTGAAGCGAAATCAAAG
ATCTCTTTGTGGACACGTAGTGCGGCGCCATTAAATAACGTGTACTTGTCCTATTCTTGTCGGTGTGGTCT
TGGGAAAAGAAAGCTTGCTGGAGGCTGCTGTTCAGCCCCATACATTACTTGTTACGATTCTGCTGACTTTC
GGCGGGTGCAATATCTCTACTTCTGCTTGACGAGGTATTGTTGCCTGTACTTCTTTCTTCTTCTTCTTGCTG

FIG. 1D cont'd

ATTGGTTCTATAAGAAATCTAGTATTTTCTTTGAAACAGAGTTTTCCCGTGGTTTTCGAACTTGGAGAAAG
ATTGTTAAGCTTCTGTATATTCTGCCCAAATTTGTCGGGCCCGCGGATGGCGAAAAACGTTGCGATTTTCG
GCTTATTGTTTTCTCTTCTTGTGTTGGTTCCTTCTCAGATCTTCGCCTGCAGGCTCCTCAGCCAAAACGACA
CCCCCATCTGTCTATCCACTGGCCCCTGGATCTGCTGCCCAAACTAACTCCATGGTGACCCTGGGATGCCT
GGTCAAGGGCTATTTCCCTGAGCCAGTGACAGTGACCTGGAACTCTGGATCCCTGTCCAGCGGTGTGCAC
ACCTTCCCAGCTGTCCTGCAGTCTGACCTCTACACTCTGAGCAGCTCAGTGACTGTCCCCTCCAGCACCTG
GCCCAGCGAGACCGTCACCTGCAACGTTGCCCACCCGGCCAGCAGCACCAAGGTGGACAAGAAAATTGT
GCCCAGGGATTGTGGTTGTAAGCCTTGCATATGTACAGTCCCAGAAGTATCATCTGTCTTCATCTTCCCCC
CAAAGCCCAAGGATGTGCTCACCATTACTCTGACTCCTAAGGTCACGTGTGTTGTGGTAGACATCAGCAA
GGATGATCCCGAGGTCCAGTTCAGCTGGTTTGTAGATGATGTGGAGGTGCACACAGCTCAGACGCAACCC
CGGGAGGAGCAGTTCAACAGCACTTTCCGCTCAGTCAGTGAACTTCCCATCATGCACCAGGACTGGCTCA
ATGGCAAGGAGCGATCGCTCACCATCACCATCACCATCACCATCACCATTAAAGGCCTATTTTCTTTAGTT
TGAATTTACTGTTATTCGGTGTGCATTTCTATGTTTGGTGAGCGGTTTTCTGTGCTCAGAGTGTGTTTATTT
TATGTAATTTAATTTCTTTGTGAGCTCCTGTTTAGCAGGTCGTCCCTTCAGCAAGGACACAAAAAGATTTT
AATTTTATTAAAAAAAAAAAAAAAAAAGACCGGGAATTCGATATCAAGCTTATCGACCTGCAGATCGTT
CAAACATTTGGCAATAAAGTTTCTTAAGATTGAATCCTGTTGCCGGTCTTGCGATGATTATCATATAATTT
CTGTTGAATTACGTTAAGCATGTAATAATTAACATGTAATGCATGACGTTATTTATGAGATGGGTTTTTAT
GATTAGAGTCCCGCAATTATACATTTAATACGCGATAGAAAACAAAATATAGCGCGCAAACTAGGATAA
ATTATCGCGCGCGGTGTCATCTATGTTACTAGATCTCTAGAGTCTCAAGCTTGGCGCGCCCACGTGACTAG
TGGCACTGGCCGTCGTTTTACAACGTCGTGACTGGGAAAACCCTGGCGTTACCCAACTTAATCGCCTTGC
AGCACATCCCCCTTTCGCCAGCTGGCGTAATAGCGAAGAGGCCCGCACCGATCGCCCTTCCCAACAGTTG
CGCAGCCTGAATGGCGAATGCTAGAGCAGCTTGAGCTTGGATCAGATTGTCGTTTCCCGCCTTCAGTTTA
AACTATCAGTGTTTGACAGGATATATTGGCGGGTAAACCTAAGAGAAAAGAGCGTTTA

FIG. 1E

Expression cassette number 489 from 2X35S promoter to NOS terminator. H5 from influenza A/Indonesia/5/2005 (H5N1) is underlined. SEQ ID NO: 5

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGAGAAAATAGTGCTTCTTCTTGCAATAGTCAGTCTTGTTAAAAGTGATCAGATTTGCATTGGTTAC
CATGCAAACAATTCAACAGAGCAGGTTGACACAATCATGGAAAAGAACGTTACTGTTACACATGCCCAA
GACATACTGGAAAAGACACACAACGGGAAGCTCTGCGATCTAGATGGAGTGAAGCCTCTAATTTTAAGA
GATTGTAGTGTAGCTGGATGGCTCCTCGGGAACCCAATGTGTGACGAATTCATCAATGTACCGGAATGGT
CTTACATAGTGGAGAAGGCCAATCCAACCAATGACCTCTGTTACCCAGGGAGTTTCAACGACTATGAAGA

FIG. 1E cont'd

ACTGAAACACCTATTGAGCAGAATAAACCATTTTGAGAAAATTCAAATCATCCCCAAAAGTTCTTGGTCC
GATCATGAAGCCTCATCAGGAGTTAGCTCAGCATGTCCATACCTGGGAAGTCCCTCCTTTTTTAGAAATGT
GGTATGGCTTATCAAAAAGAACAGTACATACCCAACAATAAAGAAAAGCTACAATAATACCAACCAAGA
GGATCTTTTGGTACTGTGGGGAATTCACCATCCTAATGATGCGGCAGAGCAGACAAGGCTATATCAAAAC
CCAACCACCTATATTTCCATTGGGACATCAACACTAAACCAGAGATTGGTACCAAAAATAGCTACTAGAT
CCAAAGTAAACGGGCAAAGTGGAAGGATGGAGTTCTTCTGGACAATTTTAAAACCTAATGATGCAATCA
ACTTCGAGAGTAATGGAAATTTCATTGCTCCAGAATATGCATACAAAATTGTCAAGAAAGGGGACTCAGC
AATTATGAAAAGTGAATTGGAATATGGTAACTGCAACACCAAGTGTCAAACTCCAATGGGGGCGATAAA
CTCTAGTATGCCATTCCACAACATACACCCTCTCACCATCGGGGAATGCCCCAAATATGTGAAATCAAAC
AGATTAGTCCTTGCAACAGGGCTCAGAAATAGCCCTCAAAGAGAGAGCAGAAGAAAAAAGAGAGGACT
ATTTGGAGCTATAGCAGGTTTTATAGAGGGAGGATGGCAGGGAATGGTAGATGGTTGGTATGGGTACCA
CCATAGCAATGAGCAGGGGAGTGGGTACGCTGCAGACAAAGAATCCACTCAAAAGGCAATAGATGGAGT
CACCAATAAGGTCAACTCAATCATTGACAAAATGAACACTCAGTTTGAGGCCGTTGGAAGGGAATTTAAT
AACTTAGAAAGGAGAATAGAGAATTTAAACAAGAAGATGGAAGACGGGTTTCTAGATGTCTGGACTTAT
AATGCCGAACTTCTGGTTCTCATGGAAAATGAGAGAACTCTAGACTTTCATGACTCAAATGTTAAGAACC
TCTACGACAAGGTCCGACTACAGCTTAGGGATAATGCAAAGGAGCTGGGTAACGGTTGTTTCGAGTTCTA
TCACAAATGTGATAATGAATGTATGGAAAGTATAAGAAACGGAACGTACAACTATCCGCAGTATTCAGA
AGAAGCAAGATTAAAAAGAGAGGAAATAAGTGGGGTAAAATTGGAATCAATAGGAACTTACCAAATAC
TGTCAATTTATTCAACAGTGGCGAGTTCCCTAGCACTGGCAATCATGATGGCTGGTCTATCTTTATGGATG
TGCTCCAATGGATCGTTACAATGCAGAATTTGCATTTAAAGGCCTATTTTCTTTAGTTTGAATTTACTGTT
ATTCGGTGTGCATTTCTATGTTTGGTGAGCGGTTTTCTGTGCTCAGAGTGTGTTTATTTTATGTAATTTAAT
TTCTTTGTGAGCTCCTGTTTAGCAGGTCGTCCCTTCAGCAAGGACACAAAAAGATTTTAATTTTATTAAAA
AAAAAAAAAAAAAAGACCGGGAATTCGATATCAAGCTTATCGACCTGCAGATCGTTCAAACATTTGGCA
ATAAAGTTTCTTAAGATTGAATCCTGTTGCCGGTCTTGCGATGATTATCATATAATTTCTGTTGAATTACG
TTAAGCATGTAATAATTAACATGTAATGCATGACGTTATTTATGAGATGGGTTTTTATGATTAGAGTCCCG
CAATTATACATTTAATACGCGATAGAAAACAAAATATAGCGCGCAAACTAGGATAAATTATCGCGCGCG
GTGTCATCTATGTTACTAGAT

FIG. 1F

Amino acid sequence of H5 from influenza A/Indonesia/5/2005 (H5N1) SEQ ID NO: 6

MEKIVLLLAIVSLVKSDQICIGYHANNSTEQVDTIMEKNVTVTHAQDILEKTHNGKLCDL
DGVKPLILRDCSVAGWLLGNPMCDEFINVPEWSYIVEKANPTNDLCYPGSFNDYEELKH
LLSRINHFEKIQIIPKSSWSDHEASSGVSSACPYLGSPSFFRNVVWLIKKNSTYPTIKKSYN
NTNQEDLLVLWGIHHPNDAAEQTRLYQNPTTYISIGTSTLNQRLVPKIATRSKVNGQSGR
MEFFWTILKPNDAINFESNGNFIAPEYAYKIVKKGDSAIMKSELEYGNCNTKCQTPMGAI
NSSMPFHNIHPLTIGECPKYVKSNRLVLATGLRNSPQRESRRKKRGLFGAIAGFIEGGWQ
GMVDGWYGYHHSNEQGSGYAADKESTQKAIDGVTNKVNSIIDKMNTQFEAVGREFNN
LERRIENLNKKMEDGFLDVWTYNAELLVLMENERTLDFHDSNVKNLYDKVRLQLRDN
AKELGNGCFEFYHKCDNECMESIRNGTYNYPQYSEEARLKREEISGVKLESIGTYQILSIY
STVASSLALAIMMAGLSLWMCSNGSLQCRICI

FIG. 1G nucleotide sequence encoding H5 from influenza A/Indonesia/5/2005 (H5N1) SEQ ID NO: 42)

ATGGAGAAAATAGTGCTTCTTCTTGCAATAGTCAGTCTTGTTAAAAGTGATCAGATTTGCATTGGTTACCA
TGCAAACAATTCAACAGAGCAGGTTGACACAATCATGGAAAAGAACGTTACTGTTACACATGCCCAAGA
CATACTGGAAAAGACACACAACGGGAAGCTCTGCGATCTAGATGGAGTGAAGCCTCTAATTTTAAGAGA
TTGTAGTGTAGCTGGATGGCTCCTCGGGAACCCAATGTGTGACGAATTCATCAATGTACCGGAATGGTCT
TACATAGTGGAGAAGGCCAATCCAACCAATGACCTCTGTTACCCAGGGAGTTTCAACGACTATGAAGAA
CTGAAACACCTATTGAGCAGAATAAACCATTTTGAGAAAATTCAAATCATCCCCAAAAGTTCTTGGTCCG
ATCATGAAGCCTCATCAGGAGTTAGCTCAGCATGTCCATACCTGGGAAGTCCCTCCTTTTTTAGAAATGTG
GTATGGCTTATCAAAAAGAACAGTACATACCCAACAATAAAGAAAAGCTACAATAATACCAACCAAGAG
GATCTTTTGGTACTGTGGGGAATTCACCATCCTAATGATGCGGCAGAGCAGACAAGGCTATATCAAAACC
CAACCACCTATATTTCCATTGGGACATCAACACTAAACCAGAGATTGGTACCAAAAATAGCTACTAGATC
CAAAGTAAACGGGCAAAGTGGAAGGATGGAGTTCTTCTGGACAATTTTAAAACCTAATGATGCAATCAA
CTTCGAGAGTAATGGAAATTTCATTGCTCCAGAATATGCATACAAAATTGTCAAGAAAGGGGACTCAGCA
ATTATGAAAAGTGAATTGGAATATGGTAACTGCAACACCAAGTGTCAAACTCCAATGGGGGCGATAAAC
TCTAGTATGCCATTCCACAACATACACCCTCTCACCATCGGGGAATGCCCCAAATATGTGAAATCAAACA
GATTAGTCCTTGCAACAGGGCTCAGAAATAGCCCTCAAAGAGAGAGCAGAAGAAAAAGAGAGGACTA
TTTGGAGCTATAGCAGGTTTTATAGAGGGAGGATGGCAGGGAATGGTAGATGGTTGGTATGGGTACCAC
CATAGCAATGAGCAGGGGAGTGGGTACGCTGCAGACAAAGAATCCACTCAAAAGGCAATAGATGGAGTC
ACCAATAAGGTCAACTCAATCATTGACAAAATGAACACTCAGTTTGAGGCCGTTGGAAGGGAATTTAATA
ACTTAGAAAGGAGAATAGAGAATTTAAACAAGAAGATGGAAGACGGGTTTCTAGATGTCTGGACTTATA
ATGCCGAACTTCTGGTTCTCATGGAAAATGAGAGAACTCTAGACTTTCATGACTCAAATGTTAAGAACCT
CTACGACAAGGTCCGACTACAGCTTAGGGATAATGCAAAGGAGCTGGGTAACGGTTGTTTCGAGTTCTAT
CACAAATGTGATAATGAATGTATGGAAAGTATAAGAAACGGAACGTACAACTATCCGCAGTATTCAGAA
GAAGCAAGATTAAAAAGAGAGGAAATAAGTGGGGTAAAATTGGAATCAATAGGAACTTACCAAATACT
GTCAATTTATTCAACAGTGGCGAGTTCCCTAGCACTGGCAATCATGATGGCTGGTCTATCTTTATGGATGT
GCTCCAATGGATCGTTACAATGCAGAATTTGCATTTAA

B-2X35S/CPMV HT/M2 New Caledonia/NOS (Construct number 1261)

FIG. 2A

IF-S1-M1+M2ANC.c (SEQ ID NO:7)

AAATTTGTCGGGCCCATGAGTCTTCTAACCGAGGTCGAAACG

FIG. 2B

IF-S1-4-M2ANC.r (SEQ ID NO: 8)

ACTAAAGAAAATAGGCCTTTACTCCAGCTCTATGCTGACAAAA

FIG. 2C

Synthesized M2 gene (corresponding to nt 1-26 joined to 715-982 from Genbank accession number DQ508860) (SEQ ID NO: 9)

ATGAGTCTTCTAACCGAGGTCGAAACGCCTATCAGAAACGAATGGGGGTGCAGATGCAACGATTCAAGT
GATCCTCTTGTTGTTGCCGCAAGTATAATTGGGATTGTGCACCTGATATTGTGGATTATTGATCGCCTTTTT
TCCAAAAGCATTTATCGTATCTTTAAACACGGTTTAAAAAGAGGGCCTTCTACGGAAGGAGTACCAGAGT
CTATGAGGGAAGAATATCGAGAGGAACAGCAGAATGCTGTGGATGCTGACGATGGTCATTTTGTCAGCA
TAGAGCTGGAGTAA

FIG. 2D

Expression cassette number 1261 from 2X35S promoter to NOS terminator. M2 from influenza A/New Caledonia/20/1999 (H1N1) is underlined. (SEQ ID NO: 10)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA

FIG. 2D cont'd

TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGAGTCTTCTAACCGAGGTCGAAACGCCTATCAGAAACGAATGGGGGTGCAGATGCAACGATTCAA
GTGATCCTCTTGTTGTTGCCGCAAGTATAATTGGGATTGTGCACCTGATATTGTGGATTATTGATCGCCTT
TTTTCCAAAAGCATTTATCGTATCTTTAAACACGGTTTAAAAAGAGGGCCTTCTACGGAAGGAGTACCAG
AGTCTATGAGGGAAGAATATCGAGAGGAACAGCAGAATGCTGTGGATGCTGACGATGGTCATTTTGTCA
GCATAGAGCTGGAGTAAAGGCCTATTTTCTTTAGTTTGAATTTACTGTTATTCGGTGTGCATTTCTATGTTT
GGTGAGCGGTTTTCTGTGCTCAGAGTGTGTTTATTTTATGTAATTTAATTTCTTTGTGAGCTCCTGTTTAGC
AGGTCGTCCCTTCAGCAAGGACACAAAAAGATTTTAATTTTATTAAAAAAAAAAAAAAAAAAAAGACCGGG
AATTCGATATCAAGCTTATCGACCTGCAGATCGTTCAAACATTTGGCAATAAAGTTTCTTAAGATTGAATC
CTGTTGCCGGTCTTGCGATGATTATCATATAATTTCTGTTGAATTACGTTAAGCATGTAATAATTAACATG
TAATGCATGACGTTATTTATGAGATGGGTTTTTATGATTAGAGTCCCGCAATTATACATTTAATACGCGAT
AGAAAACAAAATATAGCGCGCAAACTAGGATAAATTATCGCGCGCGGTGTCATCTATGTTACTAGAT

FIG. 2E

Amino acid sequence of M2 from influenza A/New Caledonia/20/1999 (H1N1) (SEQ ID NO: 11)

MSLLTEVETPIRNEWGCRCNDSSDPLVVAASIIGIVHLILWIIDRLFSKSIYRIFKHGLKRGP
STEGVPESMREEYREEQQNAVDADDGHFVSIELE

C-2X35S/CPMV-HT/M2 Puerto Rico/NOS (Construct number 859)

FIG. 3A

Synthesized M2 gene (corresponding to nt 26-51 joined to nt 740-1007 from Genebank accession number EF467824) (SEQ ID NO: 12)

ATGAGTCTTCTAACCGAGGTCGAAACGCCTATCAGAAACGAATGGGGGTGCAGATGCAACGGTTCAAGT
GATCCTCTCACTATTGCCGCAAATATCATTGGGATCTTGCACTTGACATTGTGGATTCTTGATCGTCTTTTT
TTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCA
TAGAGCTGGAGTAA

FIG. 3B

Expression cassette number 859 from 2X35S promoter to NOS terminator. M2 from Influenza A/Puerto Rico/8/1934 (H1N1) is underlined. (SEQ ID NO: 13)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGAGTCTTCTAACCGAGGTCGAAACGCCTATCAGAAACGAATGGGGGTGCAGATGCAACGGTTCAA
GTGATCCTCTCACTATTGCCGCAAATATCATTGGGATCTTGCACTTGACATTGTGGATTCTTGATCGTCTTT
TTTTCAAATGCATTTACCGTCGCTTTAAATACGGACTGAAAGGAGGGCCTTCTACGGAAGGAGTGCCAAA
GTCTATGAGGGAAGAATATCGAAAGGAACAGCAGAGTGCTGTGGATGCTGACGATGGTCATTTTGTCAG
CATAGAGCTGGAGTAAAGGCCTATTTTCTTTAGTTTGAATTTACTGTTATTCGGTGTGCATTTCTATGTTTG
GTGAGCGGTTTTCTGTGCTCAGAGTGTGTTTATTTTATGTAATTTAATTTCTTTGTGAGCTCCTGTTTAGCA
GGTCGTCCCTTCAGCAAGGACACAAAAAGATTTTAATTTTATTAAAAAAAAAAAAAAAAAAAGACCGGGA
ATTCGATATCAAGCTTATCGACCTGCAGATCGTTCAAACATTTGGCAATAAAGTTTCTTAAGATTGAATCC
TGTTGCCGGTCTTGCGATGATTATCATATAATTTCTGTTGAATTACGTTAAGCATGTAATAATTAACATGT
AATGCATGACGTTATTTATGAGATGGGTTTTTATGATTAGAGTCCCGCAATTATACATTTAATACGCGATA
GAAAACAAAATATAGCGCGCAAACTAGGATAAATTATCGCGCGCGGTGTCATCTATGTTACTAGAT

FIG. 3C

Amino acid sequence of M2 from influenza A/Puerto Rico/8/1934 (H1N1) (SEQ ID NO:14)

MSLLTEVETPIRNEWGCRCNGSSDPLTIAANIIGILHLTLWILDRLFFKCIYRRFKYGLKGG
PSTEGVPKSMREEYRKEQQSAVDADDGHFVSIELE

D-2X35S/CPMV-HT/PDISP/H1 California/NOS (Construct number 484)

FIG. 4A

IF-H1A-C-09.s2+4c (SEQ ID NO: 15)

TCTCAGATCTTCGCCGACACATTATGTATAGGTTATCATGCGAACA

FIG. 4B

IF-H1A-C-09.s1-4r (SEQ ID NO: 16)

ACTAAAGAAAATAGGCCTTTAAATACATATTCTACACTGTAGAGACCCA

FIG. 4C

Synthesized H1 gene (Genbank accession number FJ966974) (SEQ ID NO: 17)

ATGAAGGCAATACTAGTAGTTCTGCTATATACATTTGCAACCGCAAATGCAGACACATTATGTATAGGTT
ATCATGCGAACAATTCAACAGACACTGTAGACACAGTACTAGAAAAGAATGTAACAGTAACACACTCTG
TTAACCTTCTAGAAGACAAGCATAACGGGAAACTATGCAAACTAAGAGGGGTAGCCCCATTGCATTTGG
GTAAATGTAACATTGCTGGCTGGATCCTGGGAAATCCAGAGTGTGAATCACTCTCCACAGCAAGCTCATG
GTCCTACATTGTGGAAACACCTAGTTCAGACAATGGAACGTGTTACCCAGGAGATTTCATCGATTATGAG
GAGCTAAGAGAGCAATTGAGCTCAGTGTCATCATTTGAAAGGTTTGAGATATTCCCCAAGACAAGTTCAT
GGCCCAATCATGACTCGAACAAAGGTGTAACGGCAGCATGTCCTCATGCTGGAGCAAAAAGCTTCTACA
AAAATTTAATATGGCTAGTTAAAAAAGGAAATTCATACCCAAAGCTCAGCAAATCCTACATTAATGATAA
AGGGAAAGAAGTCCTCGTGCTATGGGGCATTCACCATCCATCTACTAGTGCTGACCAACAAAGTCTCTAT
CAGAATGCAGATGCATATGTTTTTGTGGGGTCATCAAGATACAGCAAGAAGTTCAAGCCGGAAATAGCA
ATAAGACCCAAAGTGAGGGATCAAGAAGGGAGAATGAACTATTACTGGACACTAGTAGAGCCGGGAGA
CAAAATAACATTCGAAGCAACTGGAAATCTAGTGGTACCGAGATATGCATTCGCAATGGAAAGAAATGC
TGGATCTGGTATTATCATTTCAGATACACCAGTCCACGATTGCAATACAACTTGTCAAACACCCAAGGGT
GCTATAAACACCAGCCTCCCATTTCAGAATATACATCCGATCACAATTGGAAAATGTCCAAAATATGTAA
AAAGCACAAAATTGAGACTGGCCACAGGATTGAGGAATATCCCGTCTATTCAATCTAGAGGCCTATTTGG
GGCCATTGCCGGTTTCATTGAAGGGGGGTGGACAGGGATGGTAGATGGATGGTACGGTTATCACCATCA
AAATGAGCAGGGGTCAGGATATGCAGCCGACCTGAAGAGCACACAGAATGCCATTGACGAGATTACTAA
CAAAGTAAATTCTGTTATTGAAAAGATGAATACACAGTTCACAGCAGTAGGTAAAGAGTTCAACCACCTG
GAAAAAAGAATAGAGAATTTAAATAAAAAAGTTGATGATGGTTTCCTGGACATTTGGACTTACAATGCC
GAACTGTTGGTTCTATTGGAAAATGAAAGAACTTTGGACTACCACGATTCAAATGTGAAGAACTTATATG
AAAAGGTAAGAAGCCAGCTAAAAAACAATGCCAAGGAAATTGGAAACGGCTGCTTTGAATTTTACCACA
AATGCGATAACACGTGCATGGAAAGTGTCAAAAATGGGACTTATGACTACCCAAAATACTCAGAGGAAG
CAAAATTAAACAGAGAAGAAATAGATGGGGTAAAGCTGGAATCAACAAGGATTTACCAGATTTTGGCGA
TCTATTCAACTGTCGCCAGTTCATTGGTACTGGTAGTCTCCCTGGGGGCAATCAGTTTCTGGATGTGCTCT
AATGGGTCTCTACAGTGTAGAATATGTATTTAA

FIG. 4D

Schematic representation of construct 1192. SacII and StuI restriction enzyme sites used for plasmid linearization are annotated on the representation.

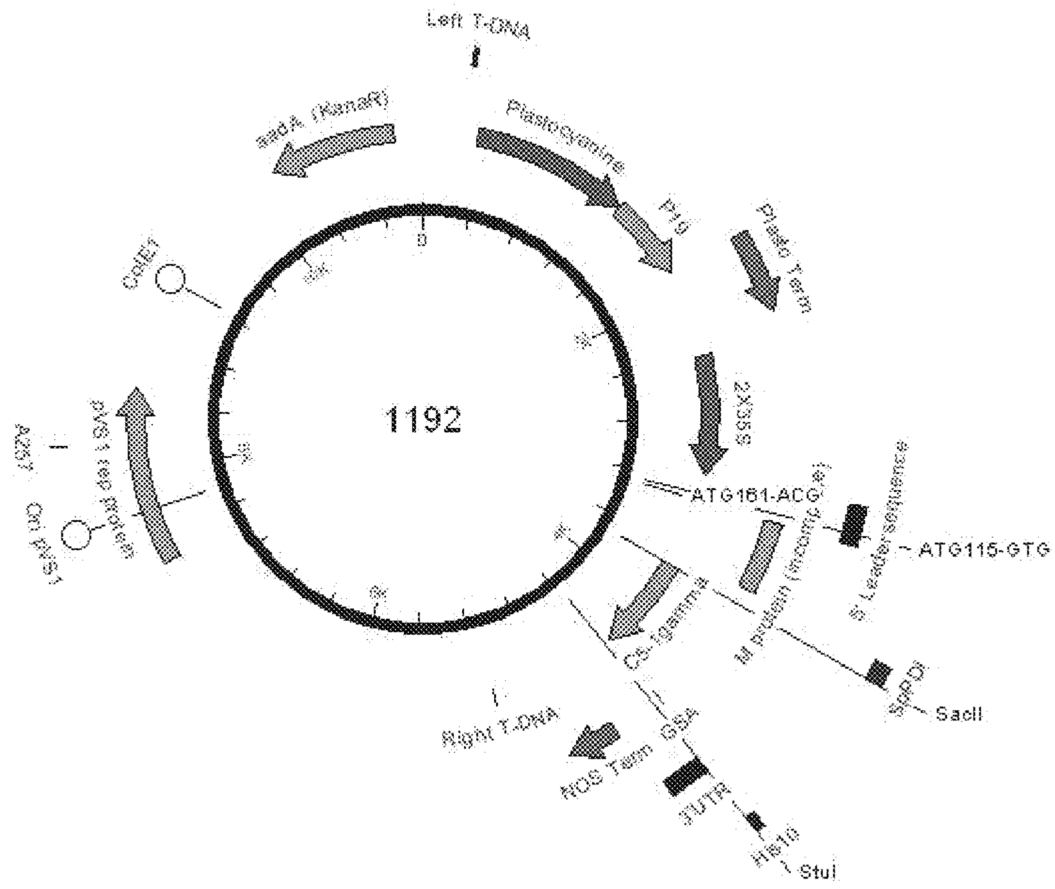

FIG. 4E

Construct 1192 from left to right t-DNA borders (underlined). 2X35S/CPMV-HT/PDISP/NOS with Plastocyanine-P19-Plastocyanine silencing inhibitor expression cassette (SEQ ID NO: 18)

TGGCAGGATATATTGTGGTGTAAACAAATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA
CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA

FIG. 4E cont'd

ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGACAAGCTTGCATGCCGGTCAACATGGTGGAGCACGACACACTTGTCT
ACTCCAAAAATATCAAAGATACAGTCTCAGAAGACCAAAGGGCAATTGAGACTTTTCAACAAAGGGTAA
TATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGT
GGTCCCAAAGATGGACCCCCACCCACGAGGAGCATCGTGGAAAAAGAAGACGTTCCAACCACGTCTTCA
AAGCAAGTGGATTGATGTGATAACATGGTGGAGCACGACACACTTGTCTACTCCAAAAATATCAAAGAT
ACAGTCTCAGAAGACCAAAGGGCAATTGAGACTTTTCAACAAAGGGTAATATCCGGAAACCTCCTCGGA
TTCCATTGCCCAGCTATCTGTCACTTTATTGTGAAGATAGTGGAAAAGGAAGGTGGCTCCTACAAATGCC
ATCATTGCGATAAAGGAAAGGCCATCGTTGAAGATGCCTCTGCCGACAGTGGTCCCAAAGATGGACCCC
CACCCACGAGGAGCATCGTGGAAAAAGAAGACGTTCCAACCACGTCTTCAAAGCAAGTGGATTGATGTG
ATATCTCCACTGACGTAAGGGATGACGCACAATCCCACTATCCTTCGCAAGACCCTTCCTCTATATAAGG
AAGTTCATTTCATTTGGAGAGGTATTAAAATCTTAATAGGTTTTGATAAAAGCGAACGTGGGGAAACCCG
AACCAAACCTTCTTCTAAACTCTCTCTCATCTCTCTTAAAGCAAACTTCTCTCTTGTCTTTCTTGCGTGAGC
GATCTTCAACGTTGTCAGATCGTGCTTCGGCACCAGTACAACGTTTTCTTTCACTGAAGCGAAATCAAAG
ATCTCTTTGTGGACACGTAGTGCGGCGCCATTAAATAACGTGTACTTGTCCTATTCTTGTCGGTGTGGTCT
TGGGAAAAGAAAGCTTGCTGGAGGCTGCTGTTCAGCCCCATACATTACTTGTTACGATTCTGCTGACTTTC
GGCGGGTGCAATATCTCTACTTCTGCTTGACGAGGTATTGTTGCCTGTACTTCTTTCTTCTTCTTCTTGCTG
ATTGGTTCTATAAGAAATCTAGTATTTTCTTTGAAACAGAGTTTTCCCGTGGTTTTCGAACTTGGAGAAAG
ATTGTTAAGCTTCTGTATATTCTGCCCAAATTTGTCGGGCCCATGGCGAAAAACGTTGCGATTTTCGGCTT
ATTGTTTTCTCTTCTTGTGTTGGTTCCTTCTCAGATCTTCGCCGCGGCTCCTCAGCCAAAACGACACCCCCA
TCTGTCTATCCACTGGCCCCTGGATCTGCTGCCCAAACTAACTCCATGGTGACCCTGGGATGCCTGGTCAA
GGGCTATTTCCCTGAGCCAGTGACAGTGACCTGGAACTCTGGATCCCTGTCCAGCGGTGTGCACACCTTC
CCAGCTGTCCTGCAGTCTGACCTCTACACTCTGAGCAGCTCAGTGACTGTCCCCTCCAGCACCTGGCCCA
GCGAGACCGTCACCTGCAACGTTGCCCACCCGGCCAGCAGCACCAAGGTGGACAAGAAAATTGTGCCCA
GGGATTGTGGTTGTAAGCCTTGCATATGTACAGTCCCAGAAGTATCATCTGTCTTCATCTTCCCCCCAAAG
CCCAAGGATGTGCTCACCATTACTCTGACTCCTAAGGTCACGTGTGTTGTGGTAGACATCAGCAAGGATG
ATCCCGAGGTCCAGTTCAGCTGGTTTGTAGATGATGTGGAGGTGCACACAGCTCAGACGCAACCCCGGGA
GGAGCAGTTCAACAGCACTTTCCGCTCAGTCAGTGAACTTCCCATCATGCACCAGGACTGGCTCAATGGC
AAGGAGCGATCGCTCACCATCACCATCACCATCACCATCACCATTAAAGGCCTATTTTCTTTAGTTTGAAT
TTACTGTTATTCGGTGTGCATTTCTATGTTTGGTGAGCGGTTTTCTGTGCTCAGAGTGTGTTTATTTTATGT
AATTTAATTTCTTTGTGAGCTCCTGTTTAGCAGGTCGTCCCTTCAGCAAGGACACAAAAAGATTTTAATTT
TATTAAAAAAAAAAAAAAAAAAAGACCGGGAATTCGATATCAAGCTTATCGACCTGCAGATCGTTCAAAC
ATTTGGCAATAAAGTTTCTTAAGATTGAATCCTGTTGCCGGTCTTGCGATGATTATCATATAATTTCTGTT
GAATTACGTTAAGCATGTAATAATTAACATGTAATGCATGACGTTATTTATGAGATGGGTTTTTATGATTA
GAGTCCCGCAATTATACATTTAATACGCGATAGAAAACAAAATATAGCGCGCAAACTAGGATAAATTAT
CGCGCGCGGTGTCATCTATGTTACTAGATCTCTAGAGTCTCAAGCTTGGCGCGCCCACGTGACTAGTGGC

FIG. 4E cont'd

ACTGGCCGTCGTTTTACAACGTCGTGACTGGGAAAACCCTGGCGTTACCCAACTTAATCGCCTTGCAGCA
CATCCCCCTTTCGCCAGCTGGCGTAATAGCGAAGAGGCCCGCACCGATCGCCCTTCCCAACAGTTGCGCA
GCCTGAATGGCGAATGCTAGAGCAGCTTGAGCTTGGATCAGATTGTCGTTTCCCGCCTTCAGTTTAAACT
ATCAGTGTTTGACAGGATATATTGGCGGGTAAACCTAAGAGAAAAGAGCGTTTA

FIG. 4F

Expression cassette number 484 from 2X35S promoter to NOS terminator. PDISP/H1 from influenza A/California/7/2009 (H1N1) is underlined. (SEQ ID NO: 19)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTGTTGGTTCCTTCTCAGATCTTCG
CCGACACATTATGTATAGGTTATCATGCGAACAATTCAACAGACACTGTAGACACAGTACTAGAAAAGA
ATGTAACAGTAACACACTCTGTTAACCTTCTAGAAGACAAGCATAACGGGAAACTATGCAAACTAAGAG
GGGTAGCCCCATTGCATTTGGGTAAATGTAACATTGCTGGCTGGATCCTGGGAAATCCAGAGTGTGAATC
ACTCTCCACAGCAAGCTCATGGTCCTACATTGTGGAAACACCTAGTTCAGACAATGGAACGTGTTACCCA
GGAGATTTCATCGATTATGAGGAGCTAAGAGAGCAATTGAGCTCAGTGTCATCATTTGAAAGGTTTGAGA
TATTCCCCAAGACAAGTTCATGGCCCAATCATGACTCGAACAAAGGTGTAACGGCAGCATGTCCTCATGC
TGGAGCAAAAAGCTTCTACAAAAATTTAATATGGCTAGTTAAAAAAGGAAATTCATACCCAAAGCTCAG
CAAATCCTACATTAATGATAAAGGGAAAGAAGTCCTCGTGCTATGGGGCATTCACCATCCATCTACTAGT
GCTGACCAACAAAGTCTCTATCAGAATGCAGATGCATATGTTTTTGTGGGGTCATCAAGATACAGCAAGA
AGTTCAAGCCGGAAATAGCAATAAGACCCAAAGTGAGGGATCAAGAAGGGAGAATGAACTATTACTGG
ACACTAGTAGAGCCGGGAGACAAAATAACATTCGAAGCAACTGGAAATCTAGTGGTACCGAGATATGCA
TTCGCAATGGAAAGAAATGCTGGATCTGGTATTATCATTTCAGATACACCAGTCCACGATTGCAATACAA
CTTGTCAAACACCCAAGGGTGCTATAAACACCAGCCTCCCATTTCAGAATATACATCCGATCACAATTGG
AAAATGTCCAAAATATGTAAAAAGCACAAAATTGAGACTGGCCACAGGATTGAGGAATATCCCGTCTAT
TCAATCTAGAGGCCTATTTGGGGCCATTGCCGGTTTCATTGAAGGGGGGTGGACAGGGATGGTAGATGGA
TGGTACGGTTATCACCATCAAAATGAGCAGGGGTCAGGATATGCAGCCGACCTGAAGAGCACACAGAAT
GCCATTGACGAGATTACTAACAAAGTAAATTCTGTTATTGAAAAGATGAATACACAGTTCACAGCAGTAG
GTAAAGAGTTCAACCACCTGGAAAAAAGAATAGAGAATTTAAATAAAAAAGTTGATGATGGTTTCCTGG
ACATTTGGACTTACAATGCCGAACTGTTGGTTCTATTGGAAAATGAAAGAACTTTGGACTACCACGATTC
AAATGTGAAGAACTTATATGAAAAGGTAAGAAGCCAGCTAAAAAACAATGCCAAGGAAATTGGAAACG
GCTGCTTTGAATTTTACCACAAATGCGATAACACGTGCATGGAAAGTGTCAAAAATGGGACTTATGACTA
CCCAAAATACTCAGAGGAAGCAAAATTAAACAGAGAAGAAATAGATGGGGTAAAGCTGGAATCAACAA
GGATTTACCAGATTTTGGCGATCTATTCAACTGTCGCCAGTTCATTGGTACTGGTAGTCTCCCTGGGGGCA

FIG. 4F cont'd

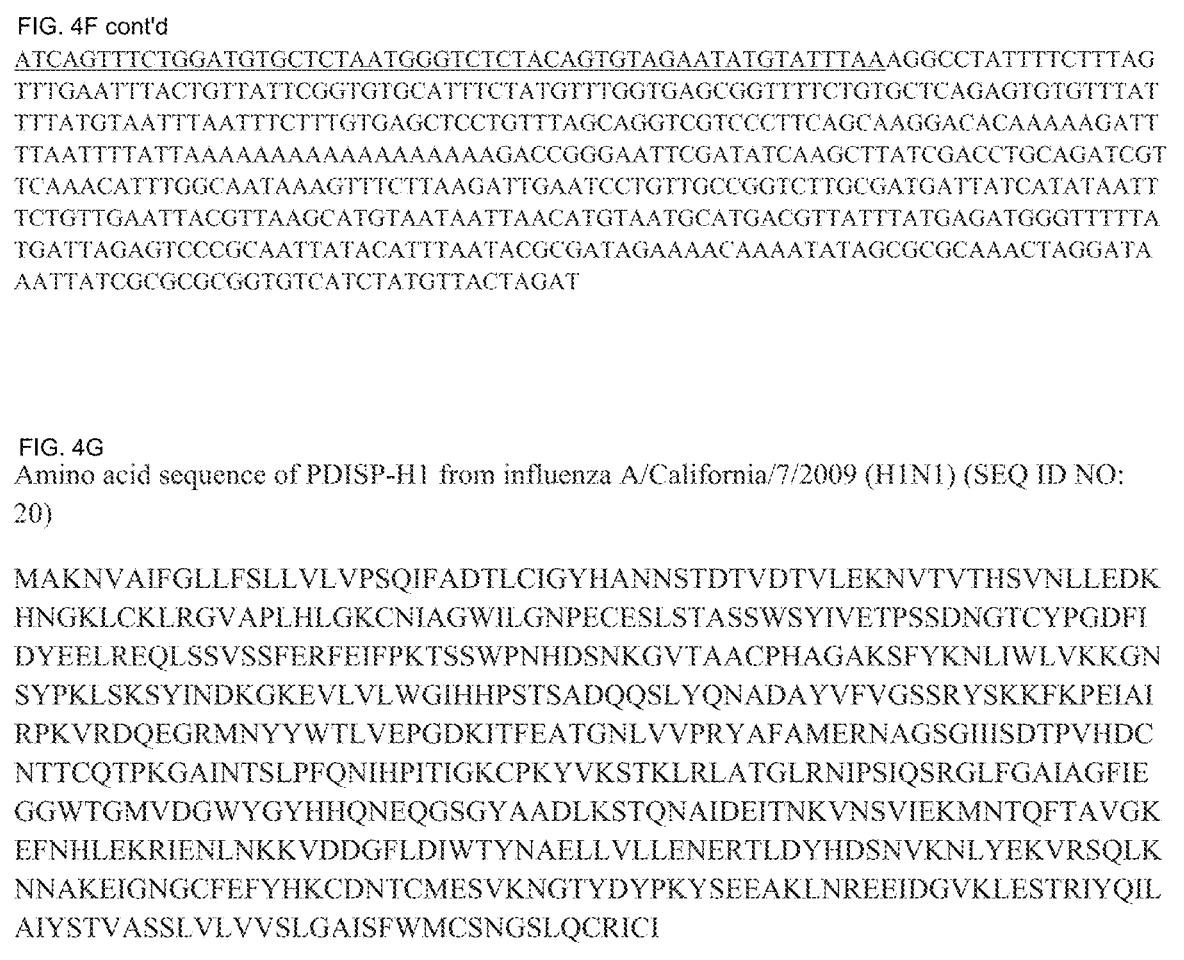

ATCAGTTTCTGGATGTGCTCTAATGGGTCTCTACAGTGTAGAATATGTATTTAAAGGCCTATTTTCTTTAG
TTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATT
TTAATTTTATTAAAAAAAAAAAAAAAAAAGACCGGGAATTCGATATCAAGCTTATCGACCTGCAGATCGT
TCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTA
TGATTAGAGTCCCGCAATTATACATTTAATACGCGATAGAAAACAAAATATAGCGCGCAAACTAGGATA
AATTATCGCGCGCGGTGTCATCTATGTTACTAGAT

FIG. 4G
Amino acid sequence of PDISP-H1 from influenza A/California/7/2009 (H1N1) (SEQ ID NO: 20)

MAKNVAIFGLLFSLLVLVPSQIFADTLCIGYHANNSTDTVDTVLEKNVTVTHSVNLLEDK
HNGKLCKLRGVAPLHLGKCNIAGWILGNPECESLSTASSWSYIVETPSSDNGTCYPGDFI
DYEELREQLSSVSSFERFEIFPKTSSWPNHDSNKGVTAACPHAGAKSFYKNLIWLVKKGN
SYPKLSKSYINDKGKEVLVLWGIHHPSTSADQQSLYQNADAYVFVGSSRYSKKFKPEIAI
RPKVRDQEGRMNYYWTLVEPGDKITFEATGNLVVPRYAFAMERNAGSGIIISDTPVHDC
NTTCQTPKGAINTSLPFQNIHPITIGKCPKYVKSTKLRLATGLRNIPSIQSRGLFGAIAGFIE
GGWTGMVDGWYGYHHQNEQGSGYAADLKSTQNAIDEITNKVNSVIEKMNTQFTAVGK
EFNHLEKRIENLNKKVDDGFLDIWTYNAELLVLLENERTLDYHDSNVKNLYEKVRSQLK
NNAKEIGNGCFEFYHKCDNTCMESVKNGTYDYPKYSEEAKLNREEIDGVKLESTRIYQIL
AIYSTVASSLVLVVSLGAISFWMCSNGSLQCRICI

E-2X35S/CPMV-HT/PDISP/H3 Perth/NOS (Construct number 1019)

FIG. 5A

IF-S2+S4-H3 Per.c (SEQ ID NO: 21)

TCTCAGATCTTCGCCCAAAAACTTCCTGGAAATGACAACA

FIG. 5B

IF-S1a4-H3 Per.r (SEQ ID NO: 22)

ACTAAAGAAAATAGGCCTTCAAATGCAAATGTTGCACCTAATGTT

FIG. 5C

Synthesized H3 gene (corresponding to nt 26-1726 from Genbank accession number GQ293081) (SEQ ID NO: 23)

ATGAAGACTATCATTGCTTTGAGCTACATTCTATGTCTGGTTTTCGCTCAAAAACTTCCTGGAAATGACAA
CAGCACGGCAACGCTGTGCCTTGGGCACCATGCAGTACCAAACGGAACGATAGTGAAAACAATCACGAA
TGACCAAATTGAAGTTACTAATGCTACTGAGCTGGTTCAGAGTTCCTCAACAGGTGAAATATGCGACAGT
CCTCATCAGATCCTTGATGGAAAAAACTGCACACTAATAGATGCTCTATTGGGAGACCCTCAGTGTGATG
GCTTCCAAAATAAGAAATGGGACCTTTTTGTTGAACGCAGCAAAGCCTACAGCAACTGTTACCCTTATGA
TGTGCCGGATTATGCCTCCCTTAGGTCACTAGTTGCCTCATCCGGCACACTGGAGTTTAACAATGAAAGCT
TCAATTGGACTGGAGTCACTCAAAACGGAACAAGCTCTGCTTGCATAAGGAGATCTAAAAACAGTTTCTT
TAGTAGATTGAATTGGTTGACCCACTTAAACTTCAAATACCCAGCATTGAACGTGACTATGCCAAACAAT
GAACAATTTGACAAATTGTACATTTGGGGGGTTCACCACCCGGGTACGGACAAAGACCAAATCTTCCTGT
ATGCTCAAGCATCAGGAAGAATCACAGTCTCTACCAAAAGAAGCCAACAAACCGTAAGCCCGAATATCG
GATCTAGACCCAGAGTAAGGAATATCCCTAGCAGAATAAGCATCTATTGGACAATAGTAAAACCGGGAG
ACATACTTTTGATTAACAGCACAGGGAATCTAATTGCTCCTAGGGGTTACTTCAAAATACGAAGTGGGAA
AAGCTCAATAATGAGATCAGATGCACCCATTGGCAAATGCAATTCTGAATGCATCACTCCAAATGGAAGC
ATTCCCAATGACAAACCATTCCAAAATGTAAACAGGATCACATACGGGGCCTGTCCCAGATATGTTAAGC
AAAACACTCTGAAATTGGCAACAGGGATGCGAAATGTACCAGAGAAACAAACTAGAGGCATATTTGGCG
CAATCGCGGGTTTCATAGAAAATGGTTGGGAGGGAATGGTGGATGGTTGGTACGGTTTCAGGCATCAAA
ATTCTGAGGGAAGAGGACAAGCAGCAGATCTCAAAAGCACTCAAGCAGCAATCGATCAAATCAATGGGA
AGCTGAATAGATTGATCGGGAAAACCAACGAGAAATTCCATCAGATTGAAAAAGAATTCTCAGAAGTCG
AAGGGAGAATTCAGGACCTTGAGAAATATGTTGAGGACACTAAAATAGATCTCTGGTCATACAACGCGG
AGCTTCTTGTTGCCCTGGAGAACCAACATACAATTGATCTAACTGACTCAGAAATGAACAAACTGTTTGA
AAAAACAAAGAAGCAACTGAGGGAAAATGCTGAGGATATGGGCAATGGTTGTTTCAAAATATACCACAA
ATGTGACAATGCCTGCATAGGATCAATCAGAAATGGAACTTATGACCACGATGTATACAGAGATGAAGC
ATTAAACAACCGGTTTCAGATCAAGGGAGTTGAGCTGAAGTCAGGGTACAAAGATTGGATCCTATGGATT
TCCTTTGCCATATCATGTTTTTTGCTTTGTGTTGCTTTGTTGGGGTTCATCATGTGGGCCTGCCAAAAAGGC
AACATTAGGTGCAACATTTGCATTTGA

FIG. 5D

Expression cassette number 1019 from 2X35S promoter to NOS terminator. PDISP/H3 from influenza A/Perth/16/2009 (H3N2) is underlined. (SEQ ID NO: 24)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTGTTGGTTCCTTCTCAGATCTTCG
CCCAAAAACTTCCTGGAAATGACAACAGCACGGCAACGCTGTGCCTTGGGCACCATGCAGTACCAAACG
GAACGATAGTGAAAACAATCACGAATGACCAAATTGAAGTTACTAATGCTACTGAGCTGGTTCAGAGTTC
CTCAACAGGTGAAATATGCGACAGTCCTCATCAGATCCTTGATGGAAAAAACTGCACACTAATAGATGCT
CTATTGGGAGACCCTCAGTGTGATGGCTTCCAAAATAAGAAATGGGACCTTTTTGTTGAACGCAGCAAAG
CCTACAGCAACTGTTACCCTTATGATGTGCCGGATTATGCCTCCCTTAGGTCACTAGTTGCCTCATCCGGC
ACACTGGAGTTTAACAATGAAAGCTTCAATTGGACTGGAGTCACTCAAAACGGAACAAGCTCTGCTTGCA
TAAGGAGATCTAAAAACAGTTTCTTTAGTAGATTGAATTGGTTGACCCACTTAAACTTCAAATACCCAGC
ATTGAACGTGACTATGCCAAACAATGAACAATTTGACAAATTGTACATTTGGGGGGTTCACCACCCGGGT
ACGGACAAAGACCAAATCTTCCTGTATGCTCAAGCATCAGGAAGAATCACAGTCTCTACCAAAAGAAGC
CAACAAACCGTAAGCCCGAATATCGGATCTAGACCCAGAGTAAGGAATATCCCTAGCAGAATAAGCATC
TATTGGACAATAGTAAAACCGGGAGACATACTTTTGATTAACAGCACAGGGAATCTAATTGCTCCTAGGG
GTTACTTCAAAATACGAAGTGGGAAAAGCTCAATAATGAGATCAGATGCACCCATTGGCAAATGCAATT
CTGAATGCATCACTCCAAATGGAAGCATTCCCAATGACAAACCATTCCAAAATGTAAACAGGATCACATA
CGGGGCCTGTCCCAGATATGTTAAGCAAAACACTCTGAAATTGGCAACAGGGATGCGAAATGTACCAGA
GAAACAAACTAGAGGCATATTTGGCGCAATCGCGGGTTTCATAGAAAATGGTTGGGAGGGAATGGTGGA
TGGTTGGTACGGTTTCAGGCATCAAAATTCTGAGGGAAGAGGACAAGCAGCAGATCTCAAAAGCACTCA
AGCAGCAATCGATCAAATCAATGGGAAGCTGAATAGATTGATCGGGAAAACCAACGAGAAATTCCATCA
GATTGAAAAAGAATTCTCAGAAGTCGAAGGGAGAATTCAGGACCTTGAGAAATATGTTGAGGACACTAA
AATAGATCTCTGGTCATACAACGCGGAGCTTCTTGTTGCCCTGGAGAACCAACATACAATTGATCTAACT
GACTCAGAAATGAACAAACTGTTTGAAAAAACAAAGAAGCAACTGAGGGAAAATGCTGAGGATATGGG
CAATGGTTGTTTCAAAATATACCACAAATGTGACAATGCCTGCATAGGATCAATCAGAAATGGAACTTAT
GACCACGATGTATACAGAGATGAAGCATTAAACAACCGGTTTCAGATCAAGGGAGTTGAGCTGAAGTCA
GGGTACAAAGATTGGATCCTATGGATTTCCTTTGCCATATCATGTTTTTTGCTTTGTGTTGCTTTGTTGGGG
TTCATCATGTGGGCCTGCCAAAAAGGCAACATTAGGTGCAACATTTGCATTTGAAGGCCTATTTTCTTTAG
TTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATT
TTAATTTTATTAAAAAAAAAAAAAAAAAAAGACCGGGAATTCGATATCAAGCTTATCGACCTGCAGATCGT
TCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTA

FIG. 5D cont'd

TGATTAGAGTCCCGCAATTATACATTTAATACGCGATAGAAAACAAAATATAGCGCGCAAACTAGGATA
AATTATCGCGCGCGGTGTCATCTATGTTACTAGAT

FIG. 5E

Amino acid sequence of PDISP/H3 from influenza A/Perth/16/2009 (H3N2) (SEQ ID NO: 25)

MAKNVAIFGLLFSLLVLVPSQIFAQKLPGNDNSTATLCLGHHAVPNGTIVKTITNDQIEVT
NATELVQSSSTGEICDSPHQILDGKNCTLIDALLGDPQCDGFQNKKWDLFVERSKAYSNC
YPYDVPDYASLRSLVASSGTLEFNNESFNWTGVTQNGTSSACIRRSKNSFFSRLNWLTHL
NFKYPALNVTMPNNEQFDKLYIWGVHHPGTDKDQIFLYAQASGRITVSTKRSQQTVSPNI
GSRPRVRNIPSRISIYWTIVKPGDILLINSTGNLIAPRGYFKIRSGKSSIMRSDAPIGKCNSEC
ITPNGSIPNDKPFQNVNRITYGACPRYVKQNTLKLATGMRNVPEKQTRGIFGAIAGFIENG
WEGMVDGWYGFRHQNSEGRGQAADLKSTQAAIDQINGKLNRLIGKTNEKFHQIEKEFS
EVEGRIQDLEKYVEDTKIDLWSYNAELLVALENQHTIDLTDSEMNKLFEKTKKQLRENA
EDMGNGCFKIYHKCDNACIGSIRNGTYDHDVYRDEALNNRFQIKGVELKSGYKDWILWI
SFAISCFLLCVALLGFIMWACQKGNIRCNICI

F-2X35S/CPMV-HT/PDISP/HA B Brisbane/NOS (Construct number 1029)

FIG. 6A

IF-S2+S4-B Bris.c (SEQ ID NO: 26)

TCTCAGATCTTCGCCGATCGAATCTGCACTGGAATAACAT

FIG. 6B

IF-S1a4-B Bris.r (SEQ ID NO: 27)

ACTAAAGAAAATAGGCCTTTATAGACAGATGGAGCAAGAAACA

FIG. 6C

Synthesized HA B Brisbane gene (corresponding to nt 34-1791 from Genbank accession number FJ766840) (SEQ ID NO: 28)

ATGAAGGCAATAATTGTACTACTCATGGTAGTAACATCCAATGCAGATCGAATCTGCACTGGAATAACAT
CGTCAAACTCACCACATGTCGTCAAAACTGCTACTCAAGGGGAGGTCAATGTGACTGGTGTAATACCACT
GACAACAACACCCACCAAATCTCATTTTGCAAATCTCAAAGGAACAGAAACCAGGGGGAAACTATGCCC
AAAATGCCTCAACTGCACAGATCTGGACGTAGCCTTGGGCAGACCAAAATGCACGGGGAAAATACCCTC
GGCAAGAGTTTCAATACTCCATGAAGTCAGACCTGTTACATCTGGGTGCTTTCCTATAATGCACGACAGA
ACAAAAATTAGACAGCTGCCTAACCTTCTCCGAGGATACGAACATATCAGGTTATCAACCCATAACGTTA
TCAATGCAGAAAATGCACCAGGAGGACCCTACAAAATTGGAACCTCAGGGTCTTGCCCTAACATTACCA
ATGGAAACGGATTTTTCGCAACAATGGCTTGGGCCGTCCCAAAAAACGACAAAAACAAAACAGCAACAA
ATCCATTAACAATAGAAGTACCATACATTTGTACAGAAGGAGAAGACCAAATTACCGTTTGGGGGTTCCA
CTCTGACAACGAGACCCAAATGGCAAAGCTCTATGGGGACTCAAAGCCCCAGAAGTTCACCTCATCTGCC
AACGGAGTGACCACACATTACGTTTCACAGATTGGTGGCTTCCCAAATCAAACAGAAGACGGAGGACTA
CCACAAAGTGGTAGAATTGTTGTTGATTACATGGTGCAAAAATCTGGGAAAACAGGAACAATTACCTATC
AAAGGGGTATTTTATTGCCTCAAAAGGTGTGGTGCGCAAGTGGCAGGAGCAAGGTAATAAAAGGATCCT
TGCCTTTAATTGGAGAAGCAGATTGCCTCCACGAAAAATACGGTGGATTAAACAAAAGCAAGCCTTACTA
CACAGGGGAACATGCAAAGGCCATAGGAAATTGCCCAATATGGGTGAAAACACCCTTGAAGCTGGCCAA
TGGAACCAAATATAGACCTCCTGCAAAACTATTAAAGGAAAGGGGTTTCTTCGGAGCTATTGCTGGTTTC
TTAGAAGGAGGATGGGAAGGAATGATTGCAGGTTGGCACGGATACACATCCCATGGGGCACATGGAGTA
GCGGTGGCAGCAGACCTTAAGAGCACTCAAGAGGCCATAAACAAGATAACAAAAAATCTCAACTCTTTG
AGTGAGCTGGAAGTAAAGAATCTTCAAAGACTAAGCGGTGCCATGGATGAACTCCACAACGAAATACTA
GAACTAGATGAGAAAGTGGATGATCTCAGAGCTGATACAATAAGCTCACAAATAGAACTCGCAGTCCTG
CTTTCCAATGAAGGAATAATAAACAGTGAAGATGAACATCTCTTGGCGCTTGAAAGAAAGCTGAAGAAA
ATGCTGGGCCCCTCTGCTGTAGAGATAGGGAATGGATGCTTTGAAACCAAACACAAGTGCAACCAGACC
TGTCTCGACAGAATAGCTGCTGGTACCTTTGATGCAGGAGAATTTTCTCTCCCCACCTTTGATTCACTGAA
TATTACTGCTGCATCTTTAAATGACGATGGATTGGATAATCATACTATACTGCTTTACTACTCAACTGCTG
CCTCCAGTTTGGCTGTAACACTGATGATAGCTATCTTTGTTGTTTATATGGTCTCCAGAGACAATGTTTCTT
GCTCCATCTGTCTATAA

FIG. 6D

Expression cassette number 1029 from 2X35S promoter to NOS terminator. PDISP/HA from influenza B/Brisbane/60/2008 is underlined. (SEQ ID NO: 29)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTGTTGGTTCCTTCTCAGATCTTCG
CCGATCGAATCTGCACTGGAATAACATCGTCAAACTCACCACATGTCGTCAAAACTGCTACTCAAGGGGA
GGTCAATGTGACTGGTGTAATACCACTGACAACAACACCCACCAAATCTCATTTTGCAAATCTCAAAGGA
ACAGAAACCAGGGGGAAACTATGCCCAAAATGCCTCAACTGCACAGATCTGGACGTAGCCTTGGGCAGA
CCAAAATGCACGGGGAAAATACCCTCGGCAAGAGTTTCAATACTCCATGAAGTCAGACCTGTTACATCTG
GGTGCTTTCCTATAATGCACGACAGAACAAAAATTAGACAGCTGCCTAACCTTCTCCGAGGATACGAACA
TATCAGGTTATCAACCCATAACGTTATCAATGCAGAAAATGCACCAGGAGGACCCTACAAAATTGGAAC
CTCAGGGTCTTGCCCTAACATTACCAATGGAAACGGATTTTTCGCAACAATGGCTTGGGCCGTCCCAAAA
AACGACAAAAACAAAACAGCAACAAATCCATTAACAATAGAAGTACCATACATTTGTACAGAAGGAGAA
GACCAAATTACCGTTTGGGGGTTCCACTCTGACAACGAGACCCAAATGGCAAAGCTCTATGGGGACTCAA
AGCCCCAGAAGTTCACCTCATCTGCCAACGGAGTGACCACACATTACGTTTCACAGATTGGTGGCTTCCC
AAATCAAACAGAAGACGGAGGACTACCACAAAGTGGTAGAATTGTTGTTGATTACATGGTGCAAAAATC
TGGGAAAACAGGAACAATTACCTATCAAAGGGGTATTTTATTGCCTCAAAAGGTGTGGTGCGCAAGTGG
CAGGAGCAAGGTAATAAAAGGATCCTTGCCTTTAATTGGAGAAGCAGATTGCCTCCACGAAAAATACGG
TGGATTAAACAAAAGCAAGCCTTACTACACAGGGGAACATGCAAAGGCCATAGGAAATTGCCCAATATG
GGTGAAAACACCCTTGAAGCTGGCCAATGGAACCAAATATAGACCTCCTGCAAAACTATTAAAGGAAAG
GGGTTTCTTCGGAGCTATTGCTGGTTTCTTAGAAGGAGGATGGGAAGGAATGATTGCAGGTTGGCACGGA
TACACATCCCATGGGGCACATGGAGTAGCGGTGGCAGCAGACCTTAAGAGCACTCAAGAGGCCATAAAC
AAGATAACAAAAAATCTCAACTCTTTGAGTGAGCTGGAAGTAAAGAATCTTCAAAGACTAAGCGGTGCC
ATGGATGAACTCCACAACGAAATACTAGAACTAGATGAGAAAGTGGATGATCTCAGAGCTGATACAATA
AGCTCACAAATAGAACTCGCAGTCCTGCTTTCCAATGAAGGAATAATAAACAGTGAAGATGAACATCTCT
TGGCGCTTGAAAGAAAGCTGAAGAAAATGCTGGGCCCCTCTGCTGTAGAGATAGGGAATGGATGCTTTG
AAACCAAACACAAGTGCAACCAGACCTGTCTCGACAGAATAGCTGCTGGTACCTTTGATGCAGGAGAAT
TTTCTCTCCCCACCTTTGATTCACTGAATATTACTGCTGCATCTTTAAATGACGATGGATTGGATAATCAT
ACTATACTGCTTTACTACTCAACTGCTGCCTCCAGTTTGGCTGTAACACTGATGATAGCTATCTTTGTTGTT
TATATGGTCTCCAGAGACAATGTTTCTTGCTCCATCTGTCTATAAAGGCCTATTTTCTTTAGTTTGAATTTA
CTGTTATTCGGTGTGCATTTCTATGTTTGGTGAGCGGTTTTCTGTGCTCAGAGTGTGTTTATTTTATGTAAT
TTAATTTCTTTGTGAGCTCCTGTTTAGCAGGTCGTCCCTTCAGCAAGGACACAAAAAGATTTTAATTTTAT
TAAAAAAAAAAAAAAAAAAGACCGGGAATTCGATATCAAGCTTATCGACCTGCAGATCGTTCAAACATT
TGGCAATAAAGTTTCTTAAGATTGAATCCTGTTGCCGGTCTTGCGATGATTATCATATAATTTCTGTTGAA
TTACGTTAAGCATGTAATAATTAACATGTAATGCATGACGTTATTTATGAGATGGGTTTTTATGATTAGAG

FIG. 6D cont'd

TCCCGCAATTATACATTTAATACGCGATAGAAAACAAAATATAGCGCGCAAACTAGGATAAATTATCGCG
CGCGGTGTCATCTATGTTACTAGAT

FIG. 6E

Amino acid sequence of PDISP/HA from influenza B/Brisbane/60/2008 SEQ ID NO: 30

MAKNVAIFGLLFSLLVLVPSQIFADRICTGITSSNSPHVVKTATQGEVNVTGVIPLTTTPTK
SHFANLKGTETRGKLCPKCLNCTDLDVALGRPKCTGKIPSARVSILHEVRPVTSGCFPIM
HDRTKIRQLPNLLRGYEHIRLSTHNVINAENAPGGPYKIGTSGSCPNITNGNGFFATMAW
AVPKNDKNKTATNPLTIEVPYICTEGEDQITVWGFHSDNETQMAKLYGDSKPQKFTSSA
NGVTTHYVSQIGGFPNQTEDGGLPQSGRIVVDYMVQKSGKTGTITYQRGILLPQKVWCA
SGRSKVIKGSLPLIGEADCLHEKYGGLNKSKPYYTGEHAKAIGNCPIWVKTPLKLANGTK
YRPPAKLLKERGFFGAIAGFLEGGWEGMIAGWHGYTSHGAHGVAVAADLKSTQEAINK
ITKNLNSLSELEVKNLQRLSGAMDELHNEILELDEKVDDLRADTISSQIELAVLLSNEGIIN
SEDEHLLALERKLKKMLGPSAVEIGNGCFETKHKCNQTCLDRIAAGTFDAGEFSLPTFDS
LNITAASLNDDGLDNHTILLYYSTAASSLAVTLMIAIFVVYMVSRDNVSCSICL

G-2X35S/CPMV-HT/PDISP/HA B Brisbane/NOS into BeYDV+Replicase amplification system (Construct number 1008)

FIG. 6F

Schematic representation of construct 1194. SacII and StuI restriction enzyme sites used for plasmid linearization are annotated on the representation.

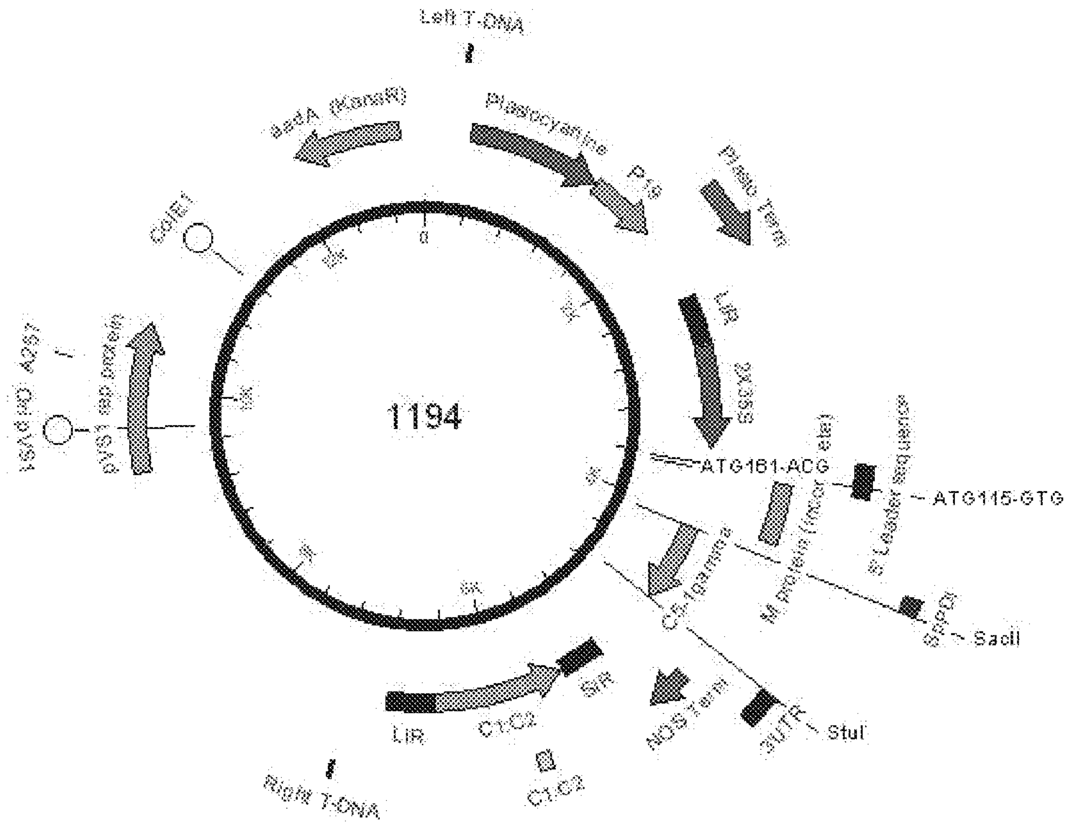

FIG. 6G

Construct 1194 from left to right t-DNA borders (underlined). 2X35S/CPMV-HT/PDISP/NOS into BeYDV+Replicase amplification system with Plastocyanine-P19-Plastocyanine silencing inhibitor expression cassette (SEQ ID NO: 31)

<u>TGGCAGGATATATTGTGGTGTAAACA</u>AATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA

FIG. 6G cont'd

CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGACACGCGTGGCGCGCCCTAGCAGAAGGCATGTTGTTGTGACTCCGAG
GGGTTGCCTCAAACTCTATCTTATAACCGGCGTGGAGGCATGGAGGCAAGGGCATTTTGGTAATTTAAGT
AGTTAGTGGAAAATGACGTCATTTACTTAAAGACGAAGTCTTGCGACAAGGGGGGCCCACGCCGAATTTT
AATATTACCGGCGTGGCCCCACCTTATCGCGAGTGCTTTAGCACGAGCGGTCCAGATTTAAAGTAGAAAA
GTTCCCGCCCACTAGGGTTAAAGGTGTTCACACTATAAAAGCATATACGATGTGATGGTATTTGATAAAG
CGTATATTGTATCAGGTATTTCCGTCGGATACGAATTATTCGTACAAGCTTCTTAAGCCGGTCAACATGGT
GGAGCACGACACACTTGTCTACTCCAAAAATATCAAAGATACAGTCTCAGAAGACCAAAGGGCAATTGA
GACTTTTCAACAAAGGGTAATATCCGGAAACCTCCTCGGATTCCATTGCCCAGCTATCTGTCACTTTATTG
TGAAGATAGTGGAAAAGGAAGGTGGCTCCTACAAATGCCATCATTGCGATAAAGGAAAGGCCATCGTTG
AAGATGCCTCTGCCGACAGTGGTCCCAAAGATGGACCCCCACCCACGAGGAGCATCGTGGAAAAAGAAG
ACGTTCCAACCACGTCTTCAAAGCAAGTGGATTGATGTGATAACATGGTGGAGCACGACACACTTGTCTA
CTCCAAAAATATCAAAGATACAGTCTCAGAAGACCAAAGGGCAATTGAGACTTTTCAACAAAGGGTAAT
ATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAA
AGCAAGTGGATTGATGTGATATCTCCACTGACGTAAGGGATGACGCACAATCCCACTATCCTTCGCAAGA
CCCTTCCTCTATATAAGGAAGTTCATTTCATTTGGAGAGGTATTAAAATCTTAATAGGTTTTGATAAAAGC
GAACGTGGGGAAACCCGAACCAAACCTTCTTCTAAACTCTCTCTCATCTCTCTTAAAGCAAACTTCTCTCT
TGTCTTTCTTGCGTGAGCGATCTTCAACGTTGTCAGATCGTGCTTCGGCACCAGTACAACGTTTTCTTTCA
CTGAAGCGAAATCAAAGATCTCTTTGTGGACACGTAGTGCGGCGCCATTAAATAACGTGTACTTGTCCTA
TTCTTGTCGGTGTGGTCTTGGGAAAAGAAAGCTTGCTGGAGGCTGCTGTTCAGCCCCATACATTACTTGTT
ACGATTCTGCTGACTTTCGGCGGGTGCAATATCTCTACTTCTGCTTGACGAGGTATTGTTGCCTGTACTTC
TTTCTTCTTCTTCTTGCTGATTGGTTCTATAAGAAATCTAGTATTTTCTTTGAAACAGAGTTTTCCCGTGGT
TTTCGAACTTGGAGAAAGATTGTTAAGCTTCTGTATATTCTGCCCAAATTTGTCGGGCCCATGGCGAAAA
ACGTTGCGATTTTCGGCTTATTGTTTCTCTTCTTGTGTTGGTTCCTTCTCAGATCTTCGCCGCGGCTCCTC
AGCCAAAACGACACCCCCATCTGTCTATCCACTGGCCCCTGGATCTGCTGCCCAAACTAACTCCATGGTG
ACCCTGGGATGCCTGGTCAAGGGCTATTTCCCTGAGCCAGTGACAGTGACCTGGAACTCTGGATCCCTGT
CCAGCGGTGTGCACACCTTCCCAGCTGTCCTGCAGTCTGACCTCTACACTCTGAGCAGCTCAGTGACTGTC
CCCTCCAGCACCTGGCCCAGCGAGACCGTCACCTGCAACGTTGCCCACCCGGCCAGCAGCACCAAGGTG
GACAAGAAAATTGTGCCCAGGGATTGTGGTTGTAAGCCTTGCATATGTACAGTCCCAGAAGTATCATCTG
TCTTCATCTTCCCCCCAAAGCCCAAGGATGTGCTCACCATTACTCTGACTCCTAAGGTCACGTGTGTTGTG

FIG. 6G cont'd

GTAGACATCAGCAAGGATGATCCCGAGGTCCAGTTCAGCTGGTTTGTAGATGATGTGGAGGTGCACACA
GCTCAGACGCAACCCCGGGAGGAGCAGTTCAACAGCACTTTCCGCTCAGTCAGTGAACTTCCCATCATGC
ACCAGGACTGGCTCAATGGCAAGGAAGGCCTATTTTCTTTAGTTTGAATTTACTGTTATTCGGTGTGCATT
TCTATGTTTGGTGAGCGGTTTTCTGTGCTCAGAGTGTGTTTATTTTATGTAATTTAATTTCTTTGTGAGCTC
CTGTTTAGCAGGTCGTCCCTTCAGCAAGGACACAAAAAGATTTTAATTTTATTAAAAAAAAAAAAAAAAA
AGACCGGGAATTCGATATCAAGCTTATCGACCTGCAGATCGTTCAAACATTTGGCAATAAAGTTTCTTAA
GATTGAATCCTGTTGCCGGTCTTGCGATGATTATCATATAATTTCTGTTGAATTACGTTAAGCATGTAATA
ATTAACATGTAATGCATGACGTTATTTATGAGATGGGTTTTTATGATTAGAGTCCCGCAATTATACATTTA
ATACGCGATAGAAAACAAAATATAGCGCGCAAACTAGGATAAATTATCGCGCGCGGTGTCATCTATGTT
ACTAGATCTCTAGAGTCTCAAGCTTGGCGCGGGGTACCGAGCTCGAATTCCGAGTGTACTTCAAGTCAGT
TGGAAATCAATAAAATGATTATTTTATGAATATATTTCATTGTGCAAGTAGATAGAAATTACATATGTTAC
ATAACACACGAAATAAACAAAAAAACACAATCCAAAACAAACACCCCAAACAAAATAACACTATATAT
ATCCTCGTATGAGGAGAGGCACGTTCAGTGACTCGACGATTCCCGAGCAAAAAAAGTCTCCCCGTCACAC
ATATAGTGGGTGACGCAATTATCTTCAAAGTAATCCTTCTGTTGACTTGTCATTGATAACATCCAGTCTTC
GTCAGGATTGCAAAGAATTATAGAAGGGATCCCACCTTTTATTTTCTTCTTTTTTCCATATTTAGGGTTGA
CAGTGAAATCAGACTGGCAACCTATTAATTGCTTCCACAATGGGACGAACTTGAAGGGGATGTCGTCGAT
GATATTATAGGTGGCGTGTTCATCGTAGTTGGTGAAGTCGATGGTCCCGTTCCAGTAGTTGTGTCGCCCGA
GACTTCTAGCCCAGGTGGTCTTTCCGGTACGAGTTGGTCCGCAGATGTAGAGGCTGGGGTGTCTGACCCC
AGTCCTTCCCTCATCCTGGTTAGATCGGCCATCCACTCAAGGTCAGATTGTGCTTGATCGTAGGAGACAG
GATGTATGAAAGTGTAGGCATCGATGCTTACATGATATAGGTGCGTCTCTCTCCAGTTGTGCAGATCTTCG
TGGCAGCGGAGATCTGATTCTGTGAAGGGCGACACGTACTGCTCAGGTTGTGGAGGAAATAATTTGTTGG
CTGAATATTCCAGCCATTGAAGCTTTGTTGCCCATTCATGAGGGAATTCTTCTTTGATCATGTCAAGATAC
TCCTCCTTAGACGTTGCAGTCTGGATAATAGTTCGCCATCGTGCGTCAGATTTGCGAGGAGAGACCTTAT
GATCTCGGAAATCTCCTCTGGTTTTAATATCTCCGTCCTTTGATATGTAATCAAGGACTTGTTTAGAGTTTC
TAGCTGGCTGGATATTAGGGTGATTTCCTTCAAAATCGAAAAAAGAAGGATCCCTAATACAAGGTTTTTT
ATCAAGCTGGATAAGAGCATGATAGTGGGTAGTGCCATCTTGATGAAGCTCAGAAGCAACACCAAGGAA
GAAAATAAGAAAAGGTGTGAGTTTCTCCCAGAGAAACTGGAATAAATCATCTCTTTGAGATGAGCACTTG
GGGTAGGTAAGGAAAACATATTTAGATTGGAGTCTGAAGTTCTTGCTAGCAGAAGGCATGTTGTTGTGAC
TCCGAGGGGTTGCCTCAAACTCTATCTTATAACCGGCGTGGAGGCATGGAGGCAAGGGCATTTTGGTAAT
TTAAGTAGTTAGTGGAAAATGACGTCATTTACTTAAAGACGAAGTCTTGCGACAAGGGGGGCCCACGCC
GAATTTTAATATTACCGGCGTGGCCCCACCTTATCGCGAGTGCTTTAGCACGAGCGGTCCAGATTTAAAG
TAGAAAAGTTCCCGCCCACTAGGGTTAAAGGTGTTCACACTATAAAAGCATATACGATGTGATGGTATTT
GATGGAGCGTATATTGTATCAGGTATTTCCGTCGGATACGAATTATTCGTACGGCCGGCCACTAGTGGCA
CTGGCCGTCGTTTTACAACGTCGTGACTGGGAAAACCCTGGCGTTACCCAACTTAATCGCCTTGCAGCAC
ATCCCCCTTTCGCCAGCTGGCGTAATAGCGAAGAGGCCCGCACCGATCGCCCTTCCCAACAGTTGCGCAG
CCTGAATGGCGAATGCTAGAGCAGCTTGAGCTTGGATCAGATTGTCGTTTCCCGCCTTCAGTTTAAACTAT
CAGTGTTTGACAGGATATATTGGCGGGTAAACCTAAGAGAAAAGAGCGTTTA

FIG. 6H

Expression cassette number 1008 from BeYDV left LIR to BeYDV right LIR. PDISP/HA from influenza B/Brisbane/60/2008 is underlined. (SEQ ID NO: 32)

CTAGCAGAAGGCATGTTGTTGTGACTCCGAGGGGTTGCCTCAAACTCTATCTTATAACCGGCGTGGAGGC
ATGGAGGCAAGGGCATTTTGGTAATTTAAGTAGTTAGTGGAAAATGACGTCATTTACTTAAAGACGAAGT
CTTGCGACAAGGGGGGCCCACGCCGAATTTTAATATTACCGGCGTGGCCCCACCTTATCGCGAGTGCTTT
AGCACGAGCGGTCCAGATTTAAAGTAGAAAAGTTCCCGCCCACTAGGGTTAAAGGTGTTCACACTATAA
AAGCATATACGATGTGATGGTATTTGATAAAGCGTATATTGTATCAGGTATTTCCGTCGGATACGAATTA
TTCGTACAAGCTTCTTAAGCCGGTCAACATGGTGGAGCACGACACACTTGTCTACTCCAAAAATATCAAA
GATACAGTCTCAGAAGACCAAAGGGCAATTGAGACTTTTCAACAAAGGGTAATATCCGGAAACCTCCTC
GGATTCCATTGCCCAGCTATCTGTCACTTTATTGTGAAGATAGTGGAAAAGGAAGGTGGCTCCTACAAAT
GCCATCATTGCGATAAAGGAAAGGCCATCGTTGAAGATGCCTCTGCCGACAGTGGTCCCAAAGATGGAC

FIG. 6H cont'd

CCCCACCCACGAGGAGCATCGTGGAAAAAGAAGACGTTCCAACCACGTCTTCAAAGCAAGTGGATTGAT
GTGATAACATGGTGGAGCACGACACACTTGTCTACTCCAAAAATATCAAAGATACAGTCTCAGAAGACC
AAAGGGCAATTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAAGAAGACGTTCCAACCACGTCTTCAAAGCAAGTGGATTGATGTGATATCTCCACTGACGTAA
GGGATGACGCACAATCCCACTATCCTTCGCAAGACCCTTCCTCTATATAAGGAAGTTCATTTCATTTGGAG
AGGTATTAAAATCTTAATAGGTTTTGATAAAAGCGAACGTGGGGAAACCCGAACCAAACCTTCTTCTAAA
CTCTCTCTCATCTCTCTTAAAGCAAACTTCTCTCTTGTCTTTCTTGCGTGAGCGATCTTCAACGTTGTCAGA
TCGTGCTTCGGCACCAGTACAACGTTTTCTTTCACTGAAGCGAAATCAAAGATCTCTTTGTGGACACGTAG
TGCGGCGCCATTAAATAACGTGTACTTGTCCTATTCTTGTCGGTGTGGTCTTGGGAAAAGAAAGCTTGCTG
GAGGCTGCTGTTCAGCCCCATACATTACTTGTTACGATTCTGCTGACTTTCGGCGGGTGCAATATCTCTAC
TTCTGCTTGACGAGGTATTGTTGCCTGTACTTCTTTCTTCTTCTTCTTGCTGATTGGTTCTATAAGAAATCT
AGTATTTTCTTTGAAACAGAGTTTTCCCGTGGTTTTCGAACTTGGAGAAAGATTGTTAAGCTTCTGTATAT
TCTGCCCAAATTTGTCGGGCCCATGGCGAAAAACGTTGCGATTTTCGGCTTATTGTTTTCTCTTCTTGTGTT
GGTTCCTTCTCAGATCTTCGCCGATCGAATCTGCACTGGAATAACATCGTCAAACTCACCACATGTCGTCA
AAACTGCTACTCAAGGGGAGGTCAATGTGACTGGTGTAATACCACTGACAACAACACCCACCAAATCTC
ATTTTGCAAATCTCAAAGGAACAGAAACCAGGGGGAAACTATGCCCAAAATGCCTCAACTGCACAGATC
TGGACGTAGCCTTGGGCAGACCAAAATGCACGGGGAAAATACCCTCGGCAAGAGTTTCAATACTCCATG
AAGTCAGACCTGTTACATCTGGGTGCTTTCCTATAATGCACGACAGAACAAAAATTAGACAGCTGCCTAA
CCTTCTCCGAGGATACGAACATATCAGGTTATCAACCCATAACGTTATCAATGCAGAAAATGCACCAGGA
GGACCCTACAAAATTGGAACCTCAGGGTCTTGCCCTAACATTACCAATGGAAACGGATTTTTCGCAACAA
TGGCTTGGGCCGTCCCAAAAAACGACAAAAACAAAACAGCAACAAATCCATTAACAATAGAAGTACCAT
ACATTTGTACAGAAGGAGAAGACCAAATTACCGTTTGGGGGTTCCACTCTGACAACGAGACCCAAATGG
CAAAGCTCTATGGGGACTCAAAGCCCCAGAAGTTCACCTCATCTGCCAACGGAGTGACCACACATTACGT
TTCACAGATTGGTGGCTTCCCAAATCAAACAGAAGACGGAGGACTACCACAAAGTGGTAGAATTGTTGTT
GATTACATGGTGCAAAAATCTGGGAAAACAGGAACAATTACCTATCAAAGGGGTATTTTATTGCCTCAAA
AGGTGTGGTGCGCAAGTGGCAGGAGCAAGGTAATAAAAGGATCCTTGCCTTTAATTGGAGAAGCAGATT
GCCTCCACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACCTCCTG
CAAAACTATTAAAGGAAAGGGGTTTCTTCGGAGCTATTGCTGGTTTCTTAGAAGGAGGATGGGAAGGAA
TGATTGCAGGTTGGCACGGATACACATCCCATGGGGCACATGGAGTAGCGGTGGCAGCAGACCTTAAGA
GCACTCAAGAGGCCATAAACAAGATAACAAAAAATCTCAACTCTTTGAGTGAGCTGGAAGTAAAGAATC
TTCAAAGACTAAGCGGTGCCATGGATGAACTCCACAACGAAATACTAGAACTAGATGAGAAAGTGGATG
ATCTCAGAGCTGATACAATAAGCTCACAAATAGAACTCGCAGTCCTGCTTTCCAATGAAGGAATAATAAA
CAGTGAAGATGAACATCTCTTGGCGCTTGAAAGAAAGCTGAAGAAAATGCTGGGCCCCTCTGCTGTAGA
GATAGGGAATGGATGCTTTGAAACCAAACACAAGTGCAACCAGACCTGTCTCGACAGAATAGCTGCTGG
TACCTTTGATGCAGGAGAATTTTCTCTCCCCACCTTTGATTCACTGAATATTACTGCTGCATCTTTAAATG
ACGATGGATTGGATAATCATACTATACTGCTTTACTACTCAACTGCTGCCTCCAGTTTGGCTGTAACACTG
ATGATAGCTATCTTTGTTGTTTATATGGTCTCCAGAGACAATGTTTCTTGCTCCATCTGTCTATAAAGGCCT
ATTTTCTTTAGTTTGAATTTACTGTTATTCGGTGTGCATTTCTATGTTTGGTGAGCGGTTTTCTGTGCTCAG
AGTGTGTTTATTTTATGTAATTTAATTTCTTTGTGAGCTCCTGTTTAGCAGGTCGTCCCTTCAGCAAGGACA
CAAAAAGATTTTAATTTTATTAAAAAAAAAAAAAAAAAAGACCGGGAATTCGATATCAAGCTTATCGAC
CTGCAGATCGTTCAAACATTTGGCAATAAAGTTTCTTAAGATTGAATCCTGTTGCCGGTCTTGCGATGATT
ATCATATAATTTCTGTTGAATTACGTTAAGCATGTAATAATTAACATGTAATGCATGACGTTATTTATGAG
ATGGGTTTTTATGATTAGAGTCCCGCAATTATACATTTAATACGCGATAGAAAACAAAATATAGCGCGCA
AACTAGGATAAATTATCGCGCGCGGTGTCATCTATGTTACTAGATCTCTAGAGTCTCAAGCTTGGCGCGG
GGTACCGAGCTCGAATTCCGAGTGTACTTCAAGTCAGTTGGAAATCAATAAAATGATTATTTTATGAATA
TATTTCATTGTGCAAGTAGATAGAAATTACATATGTTACATAACACACGAAATAAACAAAAAAACACAAT
CCAAAACAAACACCCCAAACAAAATAACACTATATATATCCTCGTATGAGGAGAGGCACGTTCAGTGAC
TCGACGATTCCCGAGCAAAAAAAGTCTCCCCGTCACACATATAGTGGGTGACGCAATTATCTTCAAAGTA
ATCCTTCTGTTGACTTGTCATTGATAACATCCAGTCTTCGTCAGGATTGCAAAGAATTATAGAAGGGATCC
CACCTTTTATTTTCTTCTTTTTTCCATATTTAGGGTTGACAGTGAAATCAGACTGGCAACCTATTAATTGCT
TCCACAATGGGACGAACTTGAAGGGGATGTCGTCGATGATATTATAGGTGGCGTGTTCATCGTAGTTGGT

FIG. 6H cont'd

GAAGTCGATGGTCCCGTTCCAGTAGTTGTGTCGCCCGAGACTTCTAGCCCAGGTGGTCTTTCCGGTACGA
GTTGGTCCGCAGATGTAGAGGCTGGGGTGTCTGACCCCAGTCCTTCCCTCATCCTGGTTAGATCGGCCATC
CACTCAAGGTCAGATTGTGCTTGATCGTAGGAGACAGGATGTATGAAAGTGTAGGCATCGATGCTTACAT
GATATAGGTGCGTCTCTCTCCAGTTGTGCAGATCTTCGTGGCAGCGGAGATCTGATTCTGTGAAGGGCGA
CACGTACTGCTCAGGTTGTGGAGGAAATAATTTGTTGGCTGAATATTCCAGCCATTGAAGCTTTGTTGCCC
ATTCATGAGGGAATTCTTCTTTGATCATGTCAAGATACTCCTCCTTAGACGTTGCAGTCTGGATAATAGTT
CGCCATCGTGCGTCAGATTTGCGAGGAGAGACCTTATGATCTCGGAAATCTCCTCTGGTTTTAATATCTCC
GTCCTTTGATATGTAATCAAGGACTTGTTTAGAGTTTCTAGCTGGCTGGATATTAGGGTGATTTCCTTCAA
AATCGAAAAAAGAAGGATCCCTAATACAAGGTTTTTTATCAAGCTGGATAAGAGCATGATAGTGGGTAG
TGCCATCTTGATGAAGCTCAGAAGCAACACCAAGGAAGAAAATAAGAAAAGGTGTGAGTTTCTCCCAGA
GAAACTGGAATAAATCATCTCTTTGAGATGAGCACTTGGGGTAGGTAAGGAAAACATATTTAGATTGGA
GTCTGAAGTTCTTGCTAGCAGAAGGCATGTTGTTGTGACTCCGAGGGGTTGCCTCAAACTCTATCTTATAA
CCGGCGTGGAGGCATGGAGGCAAGGGCATTTTGGTAATTTAAGTAGTTAGTGGAAAATGACGTCATTTAC
TTAAAGACGAAGTCTTGCGACAAGGGGGGCCCACGCCGAATTTTAATATTACCGGCGTGGCCCCACCTTA
TCGCGAGTGCTTTAGCACGAGCGGTCCAGATTTAAAGTAGAAAAGTTCCCGCCCACTAGGGTTAAAGGTG
TTCACACTATAAAAGCATATACGATGTGATGGTATTTGATGGAGCGTATATTGTATCAGGTATTTCCGTCG
GATACGAATTATTCGTAC

H-2X35S/CPMV-HT/PDISP/HA B Brisbane/H5 Indonesia transmembrane domain and cytoplasmic tail (H5Indo TMCT)/NOS into BeYDV+Replicase amplification system (Construct number 1009)

FIG. 7A
dTmH5I-B Bris.r (SEQ ID NO: 33)

TTGACAGTATTTGGTAATTATCCAATCCATCGTCATTTAAAGATGCAGCA

FIG. 7B
B Bris-dTmH5I.c (SEQ ID NO: 34)

CATCTTTAAATGACGATGGATTGGATAATTACCAAATACTGTCAATTTAT

FIG 7C

IF-S1aS4-dTmH5I.r (SEQ ID NO: 35)

ACTAAAGAAAATAGGCCTTTAAATGCAAATTCTGCATTGTAACGATCCAT

FIG. 7D
Expression cassette number 1009 from BeYDV left LIR to BeYDV right LIR. PDISP/HA B Brisbane/H5Indo TMCT is underlined. SEQ ID NO:36

CTAGCAGAAGGCATGTTGTTGTGACTCCGAGGGGTTGCCTCAAACTCTATCTTATAACCGGCGTGGAGGC
ATGGAGGCAAGGGCATTTTGGTAATTTAAGTAGTTAGTGGAAAATGACGTCATTTACTTAAAGACGAAGT
CTTGCGACAAGGGGGGCCCACGCCGAATTTTAATATTACCGGCGTGGCCCCACCTTATCGCGAGTGCTTT
AGCACGAGCGGTCCAGATTTAAAGTAGAAAAGTTCCCGCCCACTAGGGTTAAAGGTGTTCACACTATAA
AAGCATATACGATGTGATGGTATTTGATAAAGCGTATATTGTATCAGGTATTTCCGTCGGATACGAATTA
TTCGTACAAGCTTCTTAAGCCGGTCAACATGGTGGAGCACGACACACTTGTCTACTCCAAAAATATCAAA
GATACAGTCTCAGAAGACCAAAGGGCAATTGAGACTTTTCAACAAAGGGTAATATCCGGAAACCTCCTC
GGATTCCATTGCCCAGCTATCTGTCACTTTATTGTGAAGATAGTGGAAAAGGAAGGTGGCTCCTACAAAT
GCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGAT
GTGATAACATGGTGGAGCACGACACACTTGTCTACTCCAAAAATATCAAAGATACAGTCTCAGAAGACC
AAAGGGCAATTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAAGAAGACGTTCCAACCACGTCTTCAAAGCAAGTGGATTGATGTGATATCTCCACTGACGTAA
GGGATGACGCACAATCCCACTATCCTTCGCAAGACCCTTCCTCTATATAAGGAAGTTCATTTCATTTGGAG
AGGTATTAAAATCTTAATAGGTTTTGATAAAAGCGAACGTGGGGAAACCCGAACCAAACCTTCTTCTAAA

FIG. 7D cont'd

CTCTCTCTCATCTCTCTTAAAGCAAACTTCTCTCTTGTCTTTCTTGCGTGAGCGATCTTCAACGTTGTCAGA
TCGTGCTTCGGCACCAGTACAACGTTTTCTTTCACTGAAGCGAAATCAAAGATCTCTTTGTGGACACGTAG
TGCGGCGCCATTAAATAACGTGTACTTGTCCTATTCTTGTCGGTGTGGTCTTGGGAAAAGAAAGCTTGCTG
GAGGCTGCTGTTCAGCCCCATACATTACTTGTTACGATTCTGCTGACTTTCGGCGGGTGCAATATCTCTAC
TTCTGCTTGACGAGGTATTGTTGCCTGTACTTCTTTCTTCTTCTTCTTGCTGATTGGTTCTATAAGAAATCT
AGTATTTTCTTTGAAACAGAGTTTTCCCGTGGTTTTCGAACTTGGAGAAAGATTGTTAAGCTTCTGTATAT
TCTGCCCAAATTTGTCGGGCCCATGGCGAAAAACGTTGCGATTTTCGGCTTATTGTTTTCTCTTCTTGTGTT
GGTTCCTTCTCAGATCTTCGCCGATCGAATCTGCACTGGAATAACATCGTCAAACTCACCACATGTCGTCA
AAACTGCTACTCAAGGGGAGGTCAATGTGACTGGTGTAATACCACTGACAACAACACCCACCAAATCTC
ATTTTGCAAATCTCAAAGGAACAGAAACCAGGGGGAAACTATGCCCAAAATGCCTCAACTGCACAGATC
TGGACGTAGCCTTGGGCAGACCAAAATGCACGGGGAAAATACCCTCGGCAAGAGTTTCAATACTCCATG
AAGTCAGACCTGTTACATCTGGGTGCTTTCCTATAATGCACGACAGAACAAAAATTAGACAGCTGCCTAA
CCTTCTCCGAGGATACGAACATATCAGGTTATCAACCCATAACGTTATCAATGCAGAAAATGCACCAGGA
GGACCCTACAAAATTGGAACCTCAGGGTCTTGCCCTAACATTACCAATGGAAACGGATTTTTCGCAACAA
TGGCTTGGGCCGTCCCAAAAAACGACAAAAACAAAACAGCAACAAATCCATTAACAATAGAAGTACCAT
ACATTTGTACAGAAGGAGAAGACCAAATTACCGTTTGGGGGTTCCACTCTGACAACGAGACCCAAATGG
CAAAGCTCTATGGGGACTCAAAGCCCCAGAAGTTCACCTCATCTGCCAACGGAGTGACCACACATTACGT
TTCACAGATTGGTGGCTTCCCAAATCAAACAGAAGACGGAGGACTACCACAAAGTGGTAGAATTGTTGTT
GATTACATGGTGCAAAAATCTGGGAAAACAGGAACAATTACCTATCAAAGGGGTATTTTATTGCCTCAAA
AGGTGTGGTGCGCAAGTGGCAGGAGCAAGGTAATAAAAGGATCCTTGCCTTTAATTGGAGAAGCAGATT
GCCTCCACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACCTCCTG
CAAAACTATTAAAGGAAAGGGGTTTCTTCGGAGCTATTGCTGGTTTCTTAGAAGGAGGATGGGAAGGAA
TGATTGCAGGTTGGCACGGATACACATCCCATGGGGCACATGGAGTAGCGGTGGCAGCAGACCTTAAGA
GCACTCAAGAGGCCATAAACAAGATAACAAAAAATCTCAACTCTTTGAGTGAGCTGGAAGTAAAGAATC
TTCAAAGACTAAGCGGTGCCATGGATGAACTCCACAACGAAATACTAGAACTAGATGAGAAAGTGGATG
ATCTCAGAGCTGATACAATAAGCTCACAAATAGAACTCGCAGTCCTGCTTTCCAATGAAGGAATAATAAA
CAGTGAAGATGAACATCTCTTGGCGCTTGAAAGAAAGCTGAAGAAAATGCTGGGCCCCTCTGCTGTAGA
GATAGGGAATGGATGCTTTGAAACCAAACACAAGTGCAACCAGACCTGTCTCGACAGAATAGCTGCTGG
TACCTTTGATGCAGGAGAATTTTCTCTCCCCACCTTTGATTCACTGAATATTACTGCTGCATCTTTAAATG
ACGATGGATTGGATAATTACCAAATACTGTCAATTTATTCAACAGTGGCGAGTTCCCTAGCACTGGCAAT
CATGATGGCTGGTCTATCTTTATGGATGTGCTCCAATGGATCGTTACAATGCAGAATTTGCATTTAAAGGC
CTATTTTCTTTAGTTTGAATTTACTGTTATTCGGTGTGCATTTCTATGTTTGGTGAGCGGTTTTCTGTGCTC
AGAGTGTGTTTATTTTATGTAATTTAATTTCTTTGTGAGCTCCTGTTTAGCAGGTCGTCCCTTCAGCAAGG
ACACAAAAAGATTTTAATTTTATTAAAAAAAAAAAAAAAAAAAGACCGGGAATTCGATATCAAGCTTATC
GACCTGCAGATCGTTCAAACATTTGGCAATAAAGTTTCTTAAGATTGAATCCTGTTGCCGGTCTTGCGATG
ATTATCATATAATTTCTGTTGAATTACGTTAAGCATGTAATAATTAACATGTAATGCATGACGTTATTTAT
GAGATGGGTTTTTATGATTAGAGTCCCGCAATTATACATTTAATACGCGATAGAAAACAAAATATAGCGC
GCAAACTAGGATAAATTATCGCGCGCGGTGTCATCTATGTTACTAGATCTCTAGAGTCTCAAGCTTGGCG
CGGGGTACCGAGCTCGAATTCCGAGTGTACTTCAAGTCAGTTGGAAATCAATAAAATGATTATTTTATGA
ATATATTTCATTGTGCAAGTAGATAGAAATTACATATGTTACATAACACACGAAATAAACAAAAAAACAC
AATCCAAAACAAACACCCCAAACAAAATAACACTATATATATCCTCGTATGAGGAGAGGCACGTTCAGT
GACTCGACGATTCCCGAGCAAAAAAAGTCTCCCCGTCACACATATAGTGGGTGACGCAATTATCTTCAAA
GTAATCCTTCTGTTGACTTGTCATTGATAACATCCAGTCTTCGTCAGGATTGCAAAGAATTATAGAAGGG
ATCCCACCTTTTATTTTCTTCTTTTTTCCATATTTAGGGTTGACAGTGAAATCAGACTGGCAACCTATTAAT
TGCTTCCACAATGGGACGAACTTGAAGGGGATGTCGTCGATGATATTATAGGTGGCGTGTTCATCGTAGT
TGGTGAAGTCGATGGTCCCGTTCCAGTAGTTGTGTCGCCCGAGACTTCTAGCCCAGGTGGTCTTTCCGGTA
CGAGTTGGTCCGCAGATGTAGAGGCTGGGGTGTCTGACCCCAGTCCTTCCCTCATCCTGGTTAGATCGGC
CATCCACTCAAGGTCAGATTGTGCTTGATCGTAGGAGACAGGATGTATGAAAGTGTAGGCATCGATGCTT
ACATGATATAGGTGCGTCTCTCTCCAGTTGTGCAGATCTTCGTGGCAGCGGAGATCTGATTCTGTGAAGG
GCGACACGTACTGCTCAGGTTGTGGAGGAAATAATTTGTTGGCTGAATATTCCAGCCATTGAAGCTTTGT
TGCCCATTCATGAGGGAATTCTTCTTTGATCATGTCAAGATACTCCTCCTTAGACGTTGCAGTCTGGATAA
TAGTTCGCCATCGTGCGTCAGATTTGCGAGGAGAGACCTTATGATCTCGGAAATCTCCTCTGGTTTTAATA
TCTCCGTCCTTTGATATGTAATCAAGGACTTGTTTAGAGTTTCTAGCTGGCTGGATATTAGGGTGATTTCC

FIG. 7D cont'd

TTCAAAATCGAAAAAAGAAGGATCCCTAATACAAGGTTTTTTATCAAGCTGGATAAGAGCATGATAGTG
GGTAGTGCCATCTTGATGAAGCTCAGAAGCAACACCAAGGAAGAAAATAAGAAAAGGTGTGAGTTTCTC
CCAGAGAAACTGGAATAAATCATCTCTTTGAGATGAGCACTTGGGGTAGGTAAGGAAAACATATTTAGA
TTGGAGTCTGAAGTTCTTGCTAGCAGAAGGCATGTTGTTGTGACTCCGAGGGGTTGCCTCAAACTCTATCT
TATAACCGGCGTGGAGGCATGGAGGCAAGGGCATTTTGGTAATTTAAGTAGTTAGTGGAAAATGACGTC
ATTTACTTAAAGACGAAGTCTTGCGACAAGGGGGGCCCACGCCGAATTTTAATATTACCGGCGTGGCCCC
ACCTTATCGCGAGTGCTTTAGCACGAGCGGTCCAGATTTAAAGTAGAAAAGTTCCCGCCCACTAGGGTTA
AAGGTGTTCACACTATAAAAGCATATACGATGTGATGGTATTTGATGGAGCGTATATTGTATCAGGTATT
TCCGTCGGATACGAATTATTCGTAC

FIG. 7E

Amino acid sequence of PDISP/HA B Brisbane/H5Indo TMCT (SEQ ID NO: 37)

MAKNVAIFGLLFSLLVLVPSQIFADRICTGITSSNSPHVVKTATQGEVNVTGVIPLTTTPTK
SHFANLKGTETRGKLCPKCLNCTDLDVALGRPKCTGKIPSARVSILHEVRPVTSGCFPIM
HDRTKIRQLPNLLRGYEHIRLSTHNVINAENAPGGPYKIGTSGSCPNITNGNGFFATMAW
AVPKNDKNKTATNPLTIEVPYICTEGEDQITVWGFHSDNETQMAKLYGDSKPQKFTSSA
NGVTTHYVSQIGGFPNQTEDGGLPQSGRIVVDYMVQKSGKTGTITYQRGILLPQKVWCA
SGRSKVIKGSLPLIGEADCLHEKYGGLNKSKPYYTGEHAKAIGNCPIWVKTPLKLANGTK
YRPPAKLLKERGFFGAIAGFLEGGWEGMIAGWHGYTSHGAHGVAVAADLKSTQEAINK
ITKNLNSLSELEVKNLQRLSGAMDELHNEILELDEKVDDLRADTISSQIELAVLLSNEGIIN
SEDEHLLALERKLKKMLGPSAVEIGNGCFETKHKCNQTCLDRIAAGTFDAGEFSLPTFDS
LNITAASLNDDGLDNYQILSIYSTVASSLALAIMMAGLSLWMCSNGSLQCRICI

<u>I-2X35S/CPMV-HT/PDISP/HA B Brisbane with deleted proteolytic loop/NOS into BeYDV+Replicase amplification system (Construct number 1059)</u>

FIG. 8A

1039+1059.r (SEQ ID NO: 38)

CTTCCCATCCTCCACCAGGAGGTCTATATTTGGTTCCATTGGCCAGCTTCAA

FIG. 8B

1039+1059.c (SEQ ID NO: 39)

CAAATATAGACCTCCTGGTGGAGGATGGGAAGGAATGATTGCAGGTTGGCAC

FIG 8C

Expression cassette number 1059 from BeYDV left LIR to BeYDV right LIR. PDISP/HA from influenza B/Brisbane/60/2008 with deleted proteolytic loop is underlined. (SEQ ID NO: 40)

CTAGCAGAAGGCATGTTGTTGTGACTCCGAGGGGTTGCCTCAAACTCTATCTTATAACCGGCGTGGAGGC
ATGGAGGCAAGGGCATTTTGGTAATTTAAGTAGTTAGTGGAAAATGACGTCATTTACTTAAAGACGAAGT
CTTGCGACAAGGGGGGCCCACGCCGAATTTTAATATTACCGGCGTGGCCCCACCTTATCGCGAGTGCTTT
AGCACGAGCGGTCCAGATTTAAAGTAGAAAAGTTCCCGCCCACTAGGGTTAAAGGTGTTCACACTATAA
AAGCATATACGATGTGATGGTATTTGATAAAGCGTATATTGTATCAGGTATTTCCGTCGGATACGAATTA
TTCGTACAAGCTTCTTAAGCCGGTCAACATGGTGGAGCACGACACACTTGTCTACTCCAAAAATATCAAA
GATACAGTCTCAGAAGACCAAAGGGCAATTGAGACTTTTCAACAAAGGGTAATATCCGGAAACCTCCTC
GGATTCCATTGCCCAGCTATCTGTCACTTTATTGTGAAGATAGTGGAAAAGGAAGGTGGCTCCTACAAAT
GCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGAT
GTGATAACATGGTGGAGCACGACACACTTGTCTACTCCAAAAATATCAAAGATACAGTCTCAGAAGACC
AAAGGGCAATTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAAGAAGACGTTCCAACCACGTCTTCAAAGCAAGTGGATTGATGTGATATCTCCACTGACGTAA
GGGATGACGCACAATCCCACTATCCTTCGCAAGACCCTTCCTCTATATAAGGAAGTTCATTTCATTTGGAG
AGGTATTAAAATCTTAATAGGTTTTGATAAAAGCGAACGTGGGGAAACCCGAACCAAACCTTCTTCTAAA
CTCTCTCTCATCTCTCTTAAAGCAAACTTCTCTCTTGTCTTTCTTGCGTGAGCGATCTTCAACGTTGTCAGA
TCGTGCTTCGGCACCAGTACAACGTTTTCTTTCACTGAAGCGAAATCAAAGATCTCTTTGTGGACACGTAG
TGCGGCGCCATTAAATAACGTGTACTTGTCCTATTCTTGTCGGTGTGGTCTTGGGAAAAGAAAGCTTGCTG
GAGGCTGCTGTTCAGCCCCATACATTACTTGTTACGATTCTGCTGACTTTCGGCGGGTGCAATATCTCTAC
TTCTGCTTGACGAGGTATTGTTGCCTGTACTTCTTTCTTCTTCTTCTTGCTGATTGGTTCTATAAGAAATCT
AGTATTTTCTTTGAAACAGAGTTTTCCCGTGGTTTTCGAACTTGGAGAAAGATTGTTAAGCTTCTGTATAT
TCTGCCCAAATTTGTCGGGCCC<u>ATGGCGAAAAACGTTGCGATTTTCGGCTTATTGTTTTCTCTTCTTGTGTT</u>
<u>GGTTCCTTCTCAGATCTTCGCCGATCGAATCTGCACTGGAATAACATCGTCAAACTCACCACATGTCGTCA</u>
<u>AAACTGCTACTCAAGGGGAGGTCAATGTGACTGGTGTAATACCACTGACAACAACACCCACCAAATCTC</u>
<u>ATTTTGCAAATCTCAAAGGAACAGAAACCAGGGGGAAACTATGCCCAAAATGCCTCAACTGCACAGATC</u>

FIG. 8C cont'd

TGGACGTAGCCTTGGGCAGACCAAAATGCACGGGGAAAATACCCTCGGCAAGAGTTTCAATACTCCATG
AAGTCAGACCTGTTACATCTGGGTGCTTTCCTATAATGCACGACAGAACAAAAATTAGACAGCTGCCTAA
CCTTCTCCGAGGATACGAACATATCAGGTTATCAACCCATAACGTTATCAATGCAGAAAATGCACCAGGA
GGACCCTACAAAATTGGAACCTCAGGGTCTTGCCCTAACATTACCAATGGAAACGGATTTTTCGCAACAA
TGGCTTGGGCCGTCCCAAAAAACGACAAAAACAAAACAGCAACAAATCCATTAACAATAGAAGTACCAT
ACATTTGTACAGAAGGAGAAGACCAAATTACCGTTTGGGGGTTCCACTCTGACAACGAGACCCAAATGG
CAAAGCTCTATGGGGACTCAAAGCCCCAGAAGTTCACCTCATCTGCCAACGGAGTGACCACACATTACGT
TTCACAGATTGGTGGCTTCCCAAATCAAACAGAAGACGGAGGACTACCACAAAGTGGTAGAATTGTTGTT
GATTACATGGTGCAAAAATCTGGGAAAACAGGAACAATTACCTATCAAAGGGGTATTTTATTGCCTCAAA
AGGTGTGGTGCGCAAGTGGCAGGAGCAAGGTAATAAAAGGATCCTTGCCTTTAATTGGAGAAGCAGATT
GCCTCCACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACCTCCTG
GTGGAGGATGGGAAGGAATGATTGCAGGTTGGCACGGATACACATCCCATGGGGCACATGGAGTAGCGG
TGGCAGCAGACCTTAAGAGCACTCAAGAGGCCATAAACAAGATAACAAAAAATCTCAACTCTTTGAGTG
AGCTGGAAGTAAAGAATCTTCAAAGACTAAGCGGTGCCATGGATGAACTCCACAACGAAATACTAGAAC
TAGATGAGAAAGTGGATGATCTCAGAGCTGATACAATAAGCTCACAAATAGAACTCGCAGTCCTGCTTTC
CAATGAAGGAATAATAAACAGTGAAGATGAACATCTCTTGGCGCTTGAAAGAAAGCTGAAGAAAATGCT
GGGCCCCTCTGCTGTAGAGATAGGGAATGGATGCTTTGAAACCAAACACAAGTGCAACCAGACCTGTCTC
GACAGAATAGCTGCTGGTACCTTTGATGCAGGAGAATTTTCTCTCCCCACCTTTGATTCACTGAATATTAC
TGCTGCATCTTTAAATGACGATGGATTGGATAATCATACTATACTGCTTTACTACTCAACTGCTGCCTCCA
GTTTGGCTGTAACACTGATGATAGCTATCTTTGTTGTTTATATGGTCTCCAGAGACAATGTTTCTTGCTCC
ATCTGTCTATAAAGGCCTATTTTCTTTAGTTTGAATTTACTGTTATTCGGTGTGCATTTCTATGTTTGGTGA
GCGGTTTTCTGTGCTCAGAGTGTGTTTATTTTATGTAATTTAATTTCTTTGTGAGCTCCTGTTTAGCAGGTC
GTCCCTTCAGCAAGGACACAAAAAGATTTTAATTTTATTAAAAAAAAAAAAAAAAAAAGACCGGGAATTC
GATATCAAGCTTATCGACCTGCAGATCGTTCAAACATTTGGCAATAAAGTTTCTTAAGATTGAATCCTGTT
GCCGGTCTTGCGATGATTATCATATAATTTCTGTTGAATTACGTTAAGCATGTAATAATTAACATGTAATG
CATGACGTTATTTATGAGATGGGTTTTTATGATTAGAGTCCCGCAATTATACATTTAATACGCGATAGAAA
ACAAAATATAGCGCGCAAACTAGGATAAATTATCGCGCGCGGTGTCATCTATGTTACTAGATCTCTAGAG
TCTCAAGCTTGGCGCGGGGTACCGAGCTCGAATTCCGAGTGTACTTCAAGTCAGTTGGAAATCAATAAAA
TGATTATTTTATGAATATATTTCATTGTGCAAGTAGATAGAAATTACATATGTTACATAACACACGAAATA
AACAAAAAAACACAATCCAAAACAAACACCCCAAACAAAATAACACTATATATATCCTCGTATGAGGAG
AGGCACGTTCAGTGACTCGACGATTCCCGAGCAAAAAAAGTCTCCCCGTCACACATATAGTGGGTGACG
CAATTATCTTCAAAGTAATCCTTCTGTTGACTTGTCATTGATAACATCCAGTCTTCGTCAGGATTGCAAAG
AATTATAGAAGGGATCCCACCTTTTATTTTCTTCTTTTTTCCATATTTAGGGTTGACAGTGAAATCAGACT
GGCAACCTATTAATTGCTTCCACAATGGGACGAACTTGAAGGGGATGTCGTCGATGATATTATAGGTGGC
GTGTTCATCGTAGTTGGTGAAGTCGATGGTCCCGTTCCAGTAGTTGTGTCGCCCGAGACTTCTAGCCCAGG
TGGTCTTTCCGGTACGAGTTGGTCCGCAGATGTAGAGGCTGGGGTGTCTGACCCCAGTCCTTCCCTCATCC
TGGTTAGATCGGCCATCCACTCAAGGTCAGATTGTGCTTGATCGTAGGAGACAGGATGTATGAAAGTGTA
GGCATCGATGCTTACATGATATAGGTGCGTCTCTCTCCAGTTGTGCAGATCTTCGTGGCAGCGGAGATCT
GATTCTGTGAAGGGCGACACGTACTGCTCAGGTTGTGGAGGAAATAATTTGTTGGCTGAATATTCCAGCC
ATTGAAGCTTTGTTGCCCATTCATGAGGGAATTCTTCTTTGATCATGTCAAGATACTCCTCCTTAGACGTT
GCAGTCTGGATAATAGTTCGCCATCGTGCGTCAGATTTGCGAGGAGAGACCTTATGATCTCGGAAATCTC
CTCTGGTTTTAATATCTCCGTCCTTTGATATGTAATCAAGGACTTGTTTAGAGTTTCTAGCTGGCTGGATAT
TAGGGTGATTTCCTTCAAAATCGAAAAAAGAAGGATCCCTAATACAAGGTTTTTTATCAAGCTGGATAAG
AGCATGATAGTGGGTAGTGCCATCTTGATGAAGCTCAGAAGCAACACCAAGGAAGAAAATAAGAAAAG
GTGTGAGTTTCTCCCAGAGAAACTGGAATAAATCATCTCTTTGAGATGAGCACTTGGGGTAGGTAAGGAA
AACATATTTAGATTGGAGTCTGAAGTTCTTGCTAGCAGAAGGCATGTTGTTGTGACTCCGAGGGGTTGCC
TCAAACTCTATCTTATAACCGGCGTGGAGGCATGGAGGCAAGGGCATTTTGGTAATTTAAGTAGTTAGTG
GAAAATGACGTCATTTACTTAAAGACGAAGTCTTGCGACAAGGGGGGCCCACGCCGAATTTTAATATTAC
CGGCGTGGCCCCACCTTATCGCGAGTGCTTTAGCACGAGCGGTCCAGATTTAAAGTAGAAAAGTTCCCGC
CCACTAGGGTTAAAGGTGTTCACACTATAAAAGCATATACGATGTGATGGTATTTGATGGAGCGTATATT
GTATCAGGTATTTCCGTCGGATACGAATTATTCGTAC

FIG. 8D

Amino acid sequence of PDISP/HA from influenza B/Brisbane/60/2008 with deleted proteolytic loop (SEQ ID NO: 41)

MAKNVAIFGLLFSLLVLVPSQIFADRICTGITSSNSPHVVKTATQGEVNVTGVIPLTTTPTK
SHFANLKGTETRGKLCPKCLNCTDLDVALGRPKCTGKIPSARVSILHEVRPVTSGCFPIM
HDRTKIRQLPNLLRGYEHIRLSTHNVINAENAPGGPYKIGTSGSCPNITNGNGFFATMAW
AVPKNDKNKTATNPLTIEVPYICTEGEDQITVWGFHSDNETQMAKLYGDSKPQKFTSSA
NGVTTHYVSQIGGFPNQTEDGGLPQSGRIVVDYMVQKSGKTGTITYQRGILLPQKVWCA
SGRSKVIKGSLPLIGEADCLHEKYGGLNKSKPYYTGEHAKAIGNCPIWVKTPLKLANGTK
YRPPGGGWEGMIAGWHGYTSHGAHGVAVAADLKSTQEAINKITKNLNSLSELEVKNLQ
RLSGAMDELHNEILELDEKVDDLRADTISSQIELAVLLSNEGIINSEDEHLLALERKLKKM
LGPSAVEIGNGCFETKHKCNQTCLDRIAAGTFDAGEFSLPTFDSLNITAASLNDDGLDNH
TILLYYSTAASSLAVTLMIAIFVVYMVSRDNVSCSICL

FIG. 8E nucleotide sequence of PDISP/HA from influenza B/Brisbane/60/2008 with deleted proteolytic loop (SEQ ID NO: 43)

ATGGCGAAAAACGTTGCGATTTTCGGCTTATTGTTTTCTCTTCTTGTGTTGGTTCCTTCTCAGATCTTCGCC
GATCGAATCTGCACTGGAATAACATCGTCAAACTCACCACATGTCGTCAAAACTGCTACTCAAGGGGAGG
TCAATGTGACTGGTGTAATACCACTGACAACAACACCCACCAAATCTCATTTTGCAAATCTCAAAGGAAC
AGAAACCAGGGGGAAACTATGCCCAAAATGCCTCAACTGCACAGATCTGGACGTAGCCTTGGGCAGACC
AAAATGCACGGGGAAAATACCCTCGGCAAGAGTTTCAATACTCCATGAAGTCAGACCTGTTACATCTGGG
TGCTTTCCTATAATGCACGACAGAACAAAAATTAGACAGCTGCCTAACCTTCTCCGAGGATACGAACATA
TCAGGTTATCAACCCATAACGTTATCAATGCAGAAAATGCACCAGGAGGACCCTACAAAATTGGAACCTC
AGGGTCTTGCCCTAACATTACCAATGGAAACGGATTTTTCGCAACAATGGCTTGGGCCGTCCCAAAAAAC
GACAAAAACAAAACAGCAACAAATCCATTAACAATAGAAGTACCATACATTTGTACAGAAGGAGAAGAC
CAAATTACCGTTTGGGGGTTCCACTCTGACAACGAGACCCAAATGGCAAAGCTCTATGGGGACTCAAAGC
CCCAGAAGTTCACCTCATCTGCCAACGGAGTGACCACACATTACGTTTCACAGATTGGTGGCTTCCCAAA
TCAAACAGAAGACGGAGGACTACCACAAAGTGGTAGAATTGTTGTTGATTACATGGTGCAAAAATCTGG
GAAAACAGGAACAATTACCTATCAAAGGGGTATTTTATTGCCTCAAAAGGTGTGGTGCGCAAGTGGCAG
GAGCAAGGTAATAAAAGGATCCTTGCCTTTAATTGGAGAAGCAGATTGCCTCCACGAAAAATACGGTGG
ATTAAACAAAAGCAAGCCTTACTACACAGGGGAACATGCAAAGGCCATAGGAAATTGCCCAATATGGGT
GAAAACACCCTTGAAGCTGGCCAATGGAACCAAATATAGACCTCCTGGTGGAGGATGGGAAGGAATGAT
TGCAGGTTGGCACGGATACACATCCCATGGGGCACATGGAGTAGCGGTGGCAGCAGACCTTAAGAGCAC
TCAAGAGGCCATAAACAAGATAACAAAAAATCTCAACTCTTTGAGTGAGCTGGAAGTAAAGAATCTTCA
AAGACTAAGCGGTGCCATGGATGAACTCCACAACGAAATACTAGAACTAGATGAGAAAGTGGATGATCT
CAGAGCTGATACAATAAGCTCACAAATAGAACTCGCAGTCCTGCTTTCCAATGAAGGAATAATAAACAG
TGAAGATGAACATCTCTTGGCGCTTGAAAGAAAGCTGAAGAAAATGCTGGGCCCCTCTGCTGTAGAGAT
AGGGAATGGATGCTTTGAAACCAAACACAAGTGCAACCAGACCTGTCTCGACAGAATAGCTGCTGGTAC
CTTTGATGCAGGAGAATTTTCTCTCCCCACCTTTGATTCACTGAATATTACTGCTGCATCTTTAAATGACG
ATGGATTGGATAATCATACTATACTGCTTTACTACTCAACTGCTGCCTCCAGTTTGGCTGTAACACTGATG
ATAGCTATCTTTGTTGTTTATATGGTCTCCAGAGACAATGTTTCTTGCTCCATCTGTCTATAA

| Construct number | Hemagglutination capacity (HA units / mg protein)[a] |
|---|---|
| 1008 | 533 |
| 1008 + 1261 (4:1) | 3200 |
| 1059 | 4267 |
| 1059 + 1261 (4:1) | 34133 |

[a] Inverse of the smallest amount of total protein required for positive hemagglutination reaction in a final volume of 200 µl.

A-2X35S/CPMV-HT/PDISP/H3 Victoria/NOS (Construct number 1391)

FIG. 25A, SEQ ID NO: 44

IF-H3V36111.S2+4c

TCTCAGATCTTCGCCCAAAAACTTCCTGGAAATGACAACAGCACGGCA

FIG. 25B, SEQ ID NO: 45

IF-H3V36111.s1-4r

ACTAAAGAAAATAGGCCTTCAAATGCAAATGTTGCACCTAATGTTGCCCTT

FIG. 25C SEQ ID NO: 46

Synthesized H3 gene (corresponding to nt 25 to 1725 from GISAID isolate number EPI_ISL_101506 HA sequence)

ATGAAGACTATCATTGCTTTGAGCCACATTCTATGTCTGGTTTTCGCTCAAAAACTTCCTGGAAATGACAA
CAGCACGGCAACGCTGTGCCTTGGGCACCATGCAGTACCAAACGGAACGATAGTGAAAACAATCACGAA
TGACCAAATTGAAGTTACTAATGCTACTGAGCTGGTTCAGAATTCCTCAATAGGTGAAATATGCGACAGT
CCTCATCAGATCCTTGATGGAGAAAACTGCACACTAATAGATGCTCTATTGGGAGACCCTCAGTGTGATG
GCTTCCAAAATAAGAAATGGGACCTTTTTGTTGAACGAAGCAAAGCCTACAGCAACTGTTACCCTTATGA
TGTGCCGGATTATGCCTCCCTTAGGTCACTAGTTGCCTCATCCGGCACACTGGAGTTTAACAATGAAAGCT
TCAATTGGACTGGAGTCACTCAAAACGGAACAAGTTCTGCTTGCATAAGGAGATCTAATAATAGTTTCTT
TAGTAGATTAAATTGGTTGACCCACTTAAACTTCAAATACCCAGCATTGAACGTGACTATGCCAAACAAT
GAACAATTTGACAAATTGTACATTTGGGGGGTTCACCACCCGGGTACGGACAAGGACCAAATCTTCCTGT
ATGCTCAATCATCAGGAAGAATCACAGTATCTACCAAAAGAAGCCAACAAGCTGTAATCCCGAATATCG
GATCTAGACCCAGAATAAGGAATATCCCTAGCAGAATAAGCATCTATTGGACAATAGTAAAACCGGGAG
ACATACTTTTGATTAACAGCACAGGGAATCTAATTGCTCCTAGGGGTTACTTCAAAATACGAAGTGGGAA
AAGCTCAATAATGAGATCAGATGCACCCATTGGCAAATGCAATTCTGAATGCATCACTCCAAATGGAAGC
ATTCCCAATGACAAACCATTCCAAAATGTAAACAGGATCACATACGGGGCCTGTCCCAGATATGTTAAGC
AAAGCACTCTGAAATTGGCAACAGGAATGCGAAATGTACCAGAGAAACAAACTAGAGGCATATTTGGCG
CAATAGCGGGTTTCATAGAAAATGGTTGGGAGGGAATGGTGGATGGTTGGTACGGTTTCAGGCATCAAA
ATTCTGAGGGAAGAGGACAAGCAGCAGATCTCAAAAGCACTCAAGCAGCAATCGATCAAATCAATGGGA
AGCTGAATCGATTGATCGGGAAAACCAACGAGAAATTCCATCAGATTGAAAAAGAATTCTCAGAAGTCG
AAGGGAGAATTCAGGACCTTGAGAAATATGTTGAGGACACTAAAATAGATCTCTGGTCATACAACGCGG
AGCTTCTTGTTGCCCTGGAGAACCAACATACAATTGATCTAACTGACTCAGAAATGAACAAACTGTTTGA
AAAAACAAAGAAGCAACTAAGGGAAAATGCTGAGGATATGGGCAATGGTTGTTTCAAAATATACCACAA
ATGTGACAATGCCTGCATAGGATCAATCAGAAATGGAACTTATGACCACGATGTATACAGAGATGAAGC
ATTAAACAACCGGTTCCAGATCAAGGGAGTTGAGCTGAAGTCAGGGTACAAAGATTGGATCCTATGGAT
TTCCTTTGCCATATCATGTTTTTTGCTTTGTGTTGCTTTGTTGGGGTTCATCATGTGGGCCTGCCAAAAGGG
CAACATTAGGTGCAACATTTGCATTTGA

FIG. 25D, SEQ ID NO: 47

Expression cassette number 1391 from 2X35S promoter to NOS terminator. PDISP/H3 from influenza A/Victoria/361/2011 (H3N2) is underlined.

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTGTTGGTTCCTTCTCAGATCTTCG
CCCAAAAACTTCCTGGAAATGACAACAGCACGGCAACGCTGTGCCTTGGGCACCATGCAGTACCAAACG
GAACGATAGTGAAAACAATCACGAATGACCAAATTGAAGTTACTAATGCTACTGAGCTGGTTCAGAATTC
CTCAATAGGTGAAATATGCGACAGTCCTCATCAGATCCTTGATGGAGAAAACTGCACACTAATAGATGCT
CTATTGGGAGACCCTCAGTGTGATGGCTTCCAAAATAAGAAATGGGACCTTTTTGTTGAACGAAGCAAAG
CCTACAGCAACTGTTACCCTTATGATGTGCCGGATTATGCCTCCCTTAGGTCACTAGTTGCCTCATCCGGC
ACACTGGAGTTTAACAATGAAAGCTTCAATTGGACTGGAGTCACTCAAAACGGAACAAGTTCTGCTTGCA
TAAGGAGATCTAATAATAGTTTCTTTAGTAGATTAAATTGGTTGACCCACTTAAACTTCAAATACCCAGC
ATTGAACGTGACTATGCCAAACAATGAACAATTTGACAAATTGTACATTTGGGGGGTTCACCACCCGGGT
ACGGACAAGGACCAAATCTTCCTGTATGCTCAATCATCAGGAAGAATCACAGTATCTACCAAAAGAAGC
CAACAAGCTGTAATCCCGAATATCGGATCTAGACCCAGAATAAGGAATATCCCTAGCAGAATAAGCATC
TATTGGACAATAGTAAAACCGGGAGACATACTTTTGATTAACAGCACAGGGAATCTAATTGCTCCTAGGG
GTTACTTCAAAATACGAAGTGGGAAAAGCTCAATAATGAGATCAGATGCACCCATTGGCAAATGCAATT
CTGAATGCATCACTCCAAATGGAAGCATTCCCAATGACAAACCATTCCAAAATGTAAACAGGATCACATA
CGGGGCCTGTCCCAGATATGTTAAGCAAAGCACTCTGAAATTGGCAACAGGAATGCGAAATGTACCAGA
GAAACAAACTAGAGGCATATTTGGCGCAATAGCGGGTTTCATAGAAAATGGTTGGGAGGGAATGGTGGA
TGGTTGGTACGGTTTCAGGCATCAAAATTCTGAGGGAAGAGGACAAGCAGCAGATCTCAAAAGCACTCA
AGCAGCAATCGATCAAATCAATGGGAAGCTGAATCGATTGATCGGGAAAACCAACGAGAAATTCCATCA
GATTGAAAAAGAATTCTCAGAAGTCGAAGGGAGAATTCAGGACCTTGAGAAATATGTTGAGGACACTAA
AATAGATCTCTGGTCATACAACGCGGAGCTTCTTGTTGCCCTGGAGAACCAACATACAATTGATCTAACT
GACTCAGAAATGAACAAACTGTTTGAAAAAACAAAGAAGCAACTAAGGGAAAATGCTGAGGATATGGG
CAATGGTTGTTTCAAAATATACCACAAATGTGACAATGCCTGCATAGGATCAATCAGAAATGGAACTTAT
GACCACGATGTATACAGAGATGAAGCATTAAACAACCGGTTCCAGATCAAGGGAGTTGAGCTGAAGTCA
GGGTACAAAGATTGGATCCTATGGATTTCCTTTGCCATATCATGTTTTTTGCTTTGTGTTGCTTTGTTGGGG
TTCATCATGTGGGCCTGCCAAAAGGGCAACATTAGGTGCAACATTTGCATTTGAAGGCCTATTTTCTTTAG
TTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATT
TTAATTTTATTAAAAAAAAAAAAAAAAAAAGACCGGGAATTCGATATCAAGCTTATCGACCTGCAGATCGT
TCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTA

FIG. 25D cont'd

TGATTAGAGTCCCGCAATTATACATTTAATACGCGATAGAAAACAAAATATAGCGCGCAAACTAGGATA
AATTATCGCGCGCGGTGTCATCTATGTTACTAGAT

FIG. 25E, SEQ ID NO: 48

Amino acid sequence of PDISP-H3 from influenza A/ Victoria/361/2011 (H3N2)

MAKNVAIFGLLFSLLVLVPSQIFAQKLPGNDNSTATLCLGHHAVPNGTIVKTITNDQIEVT
NATELVQNSSIGEICDSPHQILDGENCTLIDALLGDPQCDGFQNKKWDLFVERSKAYSNC
YPYDVPDYASLRSLVASSGTLEFNNESFNWTGVTQNGTSSACIRRSNNSFFSRLNWLTHL
NFKYPALNVTMPNNEQFDKLYIWGVHHPGTDKDQIFLYAQSSGRITVSTKRSQQAVIPNI
GSRPRIRNIPSRISIYWTIVKPGDILLINSTGNLIAPRGYFKIRSGKSSIMRSDAPIGKCNSECI
TPNGSIPNDKPFQNVNRITYGACPRYVKQSTLKLATGMRNVPEKQTRGIFGAIAGFIENG
WEGMVDGWYGFRHQNSEGRGQAADLKSTQAAIDQINGKLNRLIGKTNEKFHQIEKEFS
EVEGRIQDLEKYVEDTKIDLWSYNAELLVALENQHTIDLTDSEMNKLFEKTKKQLRENA
EDMGNGCFKIYHKCDNACIGSIRNGTYDHDVYRDEALNNRFQIKGVELKSGYKDWILWI
SFAISCFLLCVALLGFIMWACQKGNIRCNICI*

FIG. 25F

Schematic representation of construct number 1391

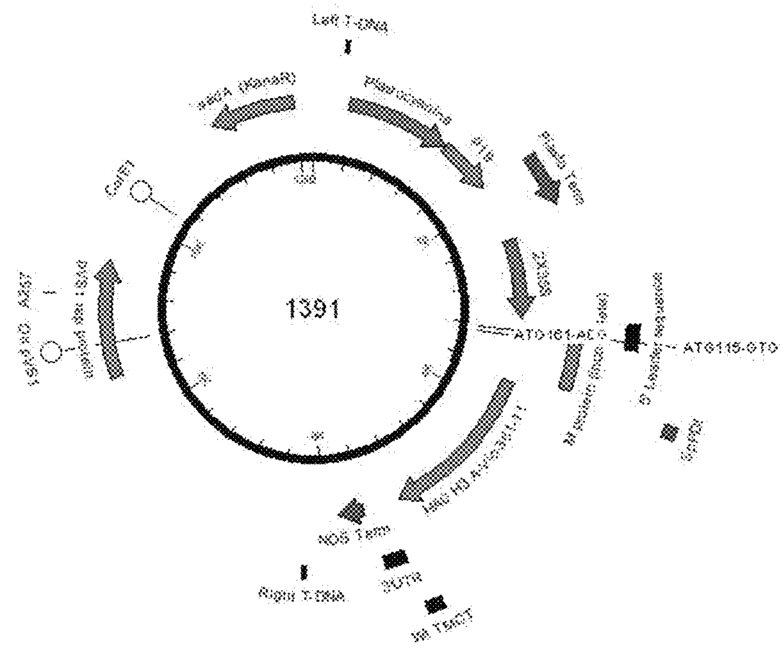

B-2X35S/CPMV-HT/HA B Wisconsin/NOS into BeYDV(m)+Replicase amplification system (Construct number 1462)

FIG. 26A SEQ ID NO: 49

IF-HAB110.S1+3c

AAATTTGTCGGGCCCATGAAGGCAATAATTGTACTACTCATGGTAG

FIG. 26B SEQ ID NO: 50

IF-HAB110.s1-4r

ACTAAAGAAAATAGGCCTTTATAGACAGATGGAGCATGAAACGTTGTCTCTG

FIG. 26C SEQ ID NO: 51

Synthesized HA B Wisconsin (Genbank accession number JN993010)

ATGAAGGCAATAATTGTACTACTCATGGTAGTAACATCCAATGCAGATCGAATCTGCACTGGGATAACAT
CTTCAAACTCACCTCATGTGGTCAAAACAGCTACTCAAGGGGAGGTCAATGTGACTGGCGTGATACCACT
GACAACAACACCAACAAAATCTTATTTTGCAAATCTCAAAGGAACAAGGACCAGAGGGAAACTATGCCC
GGACTGTCTCAACTGTACAGATCTGGATGTGGCCTTGGGCAGGCCAATGTGTGTGGGGACCACACCTTCT
GCTAAAGCTTCAATACTCCACGAGGTCAGACCTGTTACATCCGGGTGCTTTCCTATAATGCACGACAGAA
CAAAAATCAGGCAACTACCCAATCTTCTCAGAGGATATGAAAATATCAGGTTATCAACCCAAAACGTTAT
CGATGCAGAAAAAGCACCAGGAGGACCCTACAGACTTGGAACCTCAGGATCTTGCCCTAACGCTACCAG
TAAAATCGGATTTTTTGCAACAATGGCTTGGGCTGTCCCAAAGGACAACTACAAAAATGCAACGAACCCA
CTAACAGTAGAAGTACCATACATTTGTACAGAAGGGGAAGACCAAATTACTGTTTGGGGGTTCCATTCAG
ATAACAAAACCCAAATGAAGAGCCTCTATGGAGACTCAAATCCTCAAAAGTTCACCTCATCTGCTAATGG
AGTAACCACACATTATGTTTCTCAGATTGGCGACTTCCCAGATCAAACAGAAGACGGAGGACTACCACAA
AGCGGCAGAATTGTTGTTGATTACATGATGCAAAAACCTGGGAAAACAGGAACAATTGTCTATCAAAGA
GGTGTTTTGTTGCCTCAAAAGGTGTGGTGCGCGAGTGGCAGGAGCAAAGTAATAAAAGGGTCATTGCCTT
TAATTGGTGAAGCAGATTGCCTTCATGAAAAATACGGTGGATTAAACAAAAGCAAGCCTTACTACACAG
GAGAACATGCAAAAGCCATAGGAAATTGCCCAATATGGGTAAAAACACCTTTGAAGCTTGCCAATGGAA
CCAAATATAGACCTCCTGCAAAACTATTGAAGGAAAGGGGTTTCTTCGGAGCTATTGCTGGTTTCCTAGA
AGGAGGATGGGAAGGAATGATTGCAGGTTGGCACGGATACACATCTCACGGAGCACATGGAGTGGCAGT
GGCGGCAGACCTTAAGAGTACACAAGAAGCTATAAATAAGATAACAAAAAATCTCAATTCTTTGAGTGA
GCTAGAAGTAAAGAACCTTCAAAGACTAAGTGGTGCCATGGATGAACTCCACAACGAAATACTCGAGCT
GGATGAGAAAGTGGATGATCTCAGAGCTGACACTATAAGCTCACAAATAGAACTTGCAGTCTTGCTTTCC
AACGAAGGAATAATAAACAGTGAAGACGAGCATCTATTGGCACTTGAGAGAAAACTAAAGAAAATGCTG
GGTCCCTCTGCTGTAGACATAGGAAACGGATGCTTCGAAACCAAACACAAATGCAACCAGACCTGCTTA
GACAGGATAGCTGCTGGCACCTTTAATGCAGGAGAATTTTCTCTCCCCACTTTTGATTCATTGAACATTAC
TGCTGCATCTTTAAATGATGATGGATTGGATAACCATACTATACTGCTCTATTACTCAACTGCTGCTTCTA
GTTTGGCTGTAACATTAATGCTAGCTATTTTTATTGTTTATATGGTCTCCAGAGACAACGTTTCATGCTCC
ATCTGTCTATAA

FIG. 26D

Schematic representation of construct 193. SacII and StuI restriction enzyme sites used for plasmid linearization are annotated on the representation.

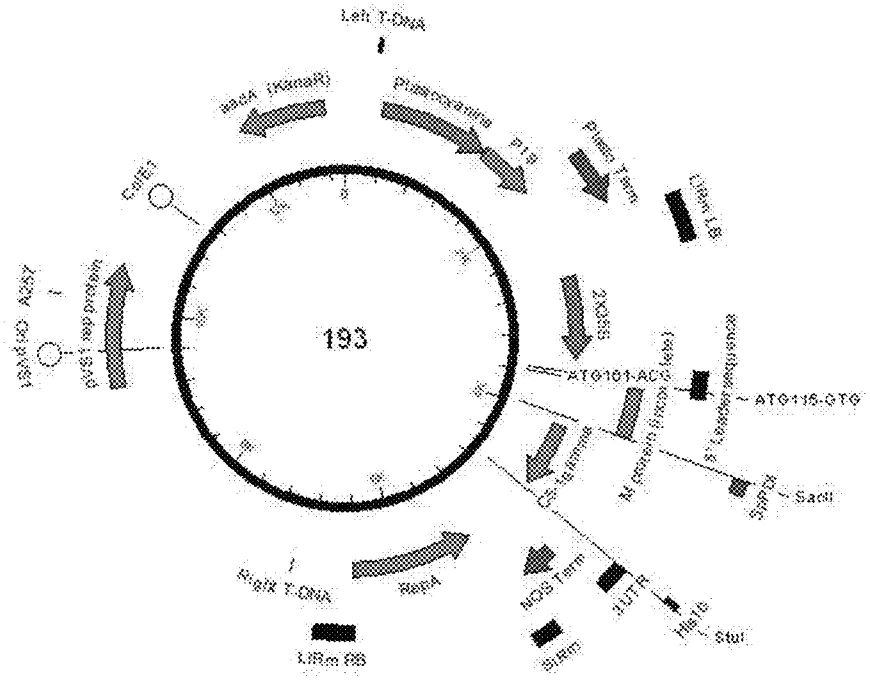

FIG. 26E, SEQ ID NO: 52

Construct 193 from left to right t-DNA borders (underlined). 2X35S/CPMV-HT/NOS into BeYDV(m)+Replicase amplification system with Plastocyanine-P19-Plastocyanine silencing inhibitor expression cassette TGGCAGGATATATTGTGGTGTAAACAAATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA
CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC

FIG. 26E, cont'd

AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGAGACGCGTTGTTGTTGTGACTCCGAGGGGTTGCCTCAAACTCTATCTT
ATAACCGGCGTGGAGGCATGGAGGCAGGGGTATTTTGGTCATTTTAATAGATAGTGGAAAATGACGTGG
AATTTACTTAAAGACGAAGTCTTTGCGACAAGGGGGGGCCCACGCCGAATTTAATATTACCGGCGTGGCC
CCCCCTTATCGCGAGTGCTTTAGCACGAGCGGTCCAGATTTAAAGTAGAAAATTTCCCGCCCACTAGGGT
TAAAGGTGTTCACACTATAAAAGCATATACGATGTGATGGTATTTGGTCGACAAGCTTGCATGCCGGTCA
ACATGGTGGAGCACGACACACTTGTCTACTCCAAAAATATCAAAGATACAGTCTCAGAAGACCAAAGGG
CAATTGAGACTTTTCAACAAAGGGTAATATCCGGAAACCTCCTCGGATTCCATTGCCCAGCTATCTGTCA
CTTTATTGTGAAGATAGTGGAAAAGGAAGGTGGCTCCTACAAATGCCATCATTGCGATAAAGGAAAGGC
CATCGTTGAAGATGCCTCTGCCGACAGTGGTCCCAAAGATGGACCCCCACCCACGAGGAGCATCGTGGA
AAAAGAAGACGTTCCAACCACGTCTTCAAAGCAAGTGGATTGATGTGATAACATGGTGGAGCACGACAC
ACTTGTCTACTCCAAAAATATCAAAGATACAGTCTCAGAAGACCAAAGGGCAATTGAGACTTTTCAACAA
AGGGTAATATCCGGAAACCTCCTCGGATTCCATTGCCCAGCTATCTGTCACTTTATTGTGAAGATAGTGG
AAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAAGAAGACGTTCCAACCA
CGTCTTCAAAGCAAGTGGATTGATGTGATATCTCCACTGACGTAAGGGATGACGCACAATCCCACTATCC
TTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAA
ACTTCTCTCTTGTCTTTCTTGCGTGAGCGATCTTCAACGTTGTCAGATCGTGCTTCGGCACCAGTACAACG
TTTTCTTTCACTGAAGCGAAATCAAAGATCTCTTTGTGGACACGTAGTGCGGCGCCATTAAATAACGTGT
ACTTGTCCTATTCTTGTCGGTGTGGTCTTGGGAAAAGAAAGCTTGCTGGAGGCTGCTGTTCAGCCCCATAC
ATTACTTGTTACGATTCTGCTGACTTTCGGCGGGTGCAATATCTCTACTTCTGCTTGACGAGGTATTGTTG
CCTGTACTTCTTTCTTCTTCTTCTTGCTGATTGGTTCTATAAGAAATCTAGTATTTTCTTTGAAACAGAGTT
TTCCCGTGGTTTTCGAACTTGGAGAAAGATTGTTAAGCTTCTGTATATTCTGCCCAAATTTGTCGGGCCCG
CGGATGGCGAAAAACGTTGCGATTTTCGGCTTATTGTTTTCTCTTCTTGTGTTGGTTCCTTCTCAGATCTTC
GCCTGCAGGCTCCTCAGCCAAAACGACACCCCCATCTGTCTATCCACTGGCCCCTGGATCTGCTGCCCAA
ACTAACTCCATGGTGACCCTGGGATGCCTGGTCAAGGGCTATTTCCCTGAGCCAGTGACAGTGACCTGGA
ACTCTGGATCCCTGTCCAGCGGTGTGCACACCTTCCCAGCTGTCCTGCAGTCTGACCTCTACACTCTGAGC
AGCTCAGTGACTGTCCCCTCCAGCACCTGGCCCAGCGAGACCGTCACCTGCAACGTTGCCCACCCGGCCA
GCAGCACCAAGGTGGACAAGAAAATTGTGCCCAGGGATTGTGGTTGTAAGCCTTGCATATGTACAGTCCC
AGAAGTATCATCTGTCTTCATCTTCCCCCCAAAGCCCAAGGATGTGCTCACCATTACTCTGACTCCTAAGG
TCACGTGTGTTGTGGTAGACATCAGCAAGGATGATCCCGAGGTCCAGTTCAGCTGGTTTGTAGATGATGT
GGAGGTGCACACAGCTCAGACGCAACCCCGGGAGGAGCAGTTCAACAGCACTTTCCGCTCAGTCAGTGA
ACTTCCCATCATGCACCAGGACTGGCTCAATGGCAAGGAGCGATCGCTCACCATCACCATCACCATCACC
ATCACCATTAAAGGCCTATTTTCTTTAGTTTGAATTTACTGTTATTCGGTGTGCATTTCTATGTTTGGTGAG
CGGTTTTCTGTGCTCAGAGTGTGTTTATTTTATGTAATTTAATTTCTTTGTGAGCTCCTGTTTAGCAGGTCG
TCCCTTCAGCAAGGACACAAAAAGATTTTAATTTTATTAAAAAAAAAAAAAAAAAAAGACCGGGAATTCG
ATATCAAGCTTATCGACCTGCAGATCGTTCAAACATTTGGCAATAAAGTTTCTTAAGATTGAATCCTGTTG
CCGGTCTTGCGATGATTATCATATAATTTCTGTTGAATTACGTTAAGCATGTAATAATTAACATGTAATGC
ATGACGTTATTTATGAGATGGGTTTTTATGATTAGAGTCCCGCAATTATACATTTAATACGCGATAGAAA
ACAAAATATAGCGCGCAAACTAGGATAAATTATCGCGCGCGGTGTCATCTATGTTACTAGATCTCTAGAG

FIG. 26E, cont'd

TCTCAAGCTTGGCGCGCCATAAAATGATTATTTTATGAATATATTTCATTGTGCAAGTAGATAGAAATTAC
ATATGTTACATAACACACGAAATAAACAAAAAAAGACAATCCAAAAACAAACACCCCAAAAAAAATAA
TCACTTTAGATAAACTCGTATGAGGAGAGGCACGTTCAGTGACTCGACGATTCCCGAGCAAAAAAAGTCT
CCCCGTCACACATATAGTGGGTGACGCAATTATCTTTAAAGTAATCCTTCTGTTGACTTGTCATTGATAAC
ATCCAGTCTTCGTCAGGATTGCAAAGAATTATAGAAGGGATCCCACCTTTTATTTTCTTCTTTTTTCCATAT
TTAGGGTTGACAGTGAAATCAGACTGGCAACCTATTAATTGCTTCCACAATGGGACGAACTTGAAGGGGA
TGTCGTCGATGATATTATAGGTGGCGTGTTCATCGTAGTTGGTGAAATCGATGGTACCGTTCCAATAGTTG
TGTCGTCCGAGACTTCTAGCCCAGGTGGTCTTTCCGGTACGAGTTGGTCCGCAGATGTAGAGGCTGGGGT
GTCGGATTCCATTCCTTCCATTGTCCTGGTTAAATCGGCCATCCATTCAAGGTCAGATTGAGCTTGTTGGT
ATGAGACAGGATGTATGTAAGTATAAGCGTCTATGCTTACATGGTATAGATGGGTTTCCCTCCAGGAGTG
TAGATCTTCGTGGCAGCGAAGATCTGATTCTGTGAAGGGCGACACATACGGTTCAGGTTGTGGAGGGAAT
AATTTGTTGGCTGAATATTCCAGCCATTGAAGTTTTGTTGCCCATTCATGAGGGAATTCTTCCTTGATCAT
GTCAAGATATTCCTCCTTAGACGTTGCAGTCTGGATAATAGTTCTCCATCGTGCGTCAGATTTGCGAGGAG
AGACCTTATGATCTCGGAAATCTCCTCTGGTTTTAATATCTCCGTCCTTTGATATGTAATCAAGGACTTGT
TTAGAGTTTCTAGCTGGCTGGATATTAGGGTGATTTCCTTCAAAATCGAAAAAAGAAGGATCCCTAATAC
AAGGTTTTTTATCAAGCTGGAGAAGAGCATGATAGTGGGTAGTGCCATCTTGATGAAGCTCAGAAGCAAC
ACCAAGGAAGAAAATAAGAAAAGGTGTGAGTTTCTCCCAGAGAAACTGGAATAAATCATCTCTTTGAGA
TGAGCACTTGGGATAGGTAAGGAAAACATATTTAGATTGGAGTCTGAAGTTCTTACTAGCAGAAGGCATG
TTGTTGTGACTCCGAGGGGTTGCCTCAAACTCTATCTTATAACCGGCGTGGAGGCATGGAGGCAGGGGTA
TTTTGGTCATTTTAATAGATAGTGGAAAATGACGTGGAATTTACTTAAAGACGAAGTCTTTGCGACAAGG
GGGGGCCCACGCCGAATTTAATATTACCGGCGTGGCCCCCCCTTATCGCGAGTGCTTTAGCACGAGCGGT
CCAGATTTAAAGTAGAAAATTTCCCGCCCACTAGGGTTAAAGGTGTTCACACTATAAAAGCATATACGAT
GTGATGGTATTTGACTAGTGGCACTGGCCGTCGTTTTACAACGTCGTGACTGGGAAAACCCTGGCGTTAC
CCAACTTAATCGCCTTGCAGCACATCCCCCTTTCGCCAGCTGGCGTAATAGCGAAGAGGCCCGCACCGAT
CGCCCTTCCCAACAGTTGCGCAGCCTGAATGGCGAATGCTAGAGCAGCTTGAGCTTGGATCAGATTGTCG
TTTCCCGCCTTCAGTTTAAACTATCAGTGTTTGACAGGATATATTGGCGGGTAAACCTAAGAGAAAAGAG
CGTTTA

FIG. 26F, SEQ ID NO: 53

Expression cassette number 1462 from 2X35S promoter to NOS terminator. HA from influenza B/Wisconsin/1/2010 is underlined.

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGAAGGCAATAATTGTACTACTCATGGTAGTAACATCCAATGCAGATCGAATCTGCACTGGGATAAC

FIG 26F, cont'd

ATCTTCAAACTCACCTCATGTGGTCAAAACAGCTACTCAAGGGGAGGTCAATGTGACTGGCGTGATACCA
CTGACAACAACACCAACAAAATCTTATTTTGCAAATCTCAAAGGAACAAGGACCAGAGGGAAACTATGC
CCGGACTGTCTCAACTGTACAGATCTGGATGTGGCCTTGGGCAGGCCAATGTGTGTGGGGACCACACCTT
CTGCTAAAGCTTCAATACTCCACGAGGTCAGACCTGTTACATCCGGGTGCTTTCCTATAATGCACGACAG
AACAAAAATCAGGCAACTACCCAATCTTCTCAGAGGATATGAAAATATCAGGTTATCAACCCAAAACGTT
ATCGATGCAGAAAAAGCACCAGGAGGACCCTACAGACTTGGAACCTCAGGATCTTGCCCTAACGCTACC
AGTAAAATCGGATTTTTTGCAACAATGGCTTGGGCTGTCCCAAAGGACAACTACAAAAATGCAACGAAC
CCACTAACAGTAGAAGTACCATACATTTGTACAGAAGGGGAAGACCAAATTACTGTTTGGGGGTTCCATT
CAGATAACAAAACCCAAATGAAGAGCCTCTATGGAGACTCAAATCCTCAAAAGTTCACCTCATCTGCTAA
TGGAGTAACCACACATTATGTTTCTCAGATTGGCGACTTCCCAGATCAAACAGAAGACGGAGGACTACCA
CAAAGCGGCAGAATTGTTGTTGATTACATGATGCAAAAACCTGGGAAAACAGGAACAATTGTCTATCAA
AGAGGTGTTTTGTTGCCTCAAAAGGTGTGGTGCGCGAGTGGCAGGAGCAAAGTAATAAAAGGGTCATTG
CCTTTAATTGGTGAAGCAGATTGCCTTCATGAAAAATACGGTGGATTAAACAAAAGCAAGCCTTACTACA
CAGGAGAACATGCAAAAGCCATAGGAAATTGCCCAATATGGGTAAAAACACCTTTGAAGCTTGCCAATG
GAACCAAATATAGACCTCCTGCAAAACTATTGAAGGAAAGGGGTTTCTTCGGAGCTATTGCTGGTTTCCT
AGAAGGAGGATGGGAAGGAATGATTGCAGGTTGGCACGGATACACATCTCACGGAGCACATGGAGTGGC
AGTGGCGGCAGACCTTAAGAGTACACAAGAAGCTATAAATAAGATAACAAAAAATCTCAATTCTTTGAG
TGAGCTAGAAGTAAAGAACCTTCAAAGACTAAGTGGTGCCATGGATGAACTCCACAACGAAATACTCGA
GCTGGATGAGAAAGTGGATGATCTCAGAGCTGACACTATAAGCTCACAAATAGAACTTGCAGTCTTGCTT
TCCAACGAAGGAATAATAAACAGTGAAGACGAGCATCTATTGGCACTTGAGAGAAAACTAAAGAAAATG
CTGGGTCCCTCTGCTGTAGACATAGGAAACGGATGCTTCGAAACCAAACACAAATGCAACCAGACCTGC
TTAGACAGGATAGCTGCTGGCACCTTTAATGCAGGAGAATTTTCTCTCCCCACTTTTGATTCATTGAACAT
TACTGCTGCATCTTTAAATGATGATGGATTGGATAACCATACTATACTGCTCTATTACTCAACTGCTGCTT
CTAGTTTGGCTGTAACATTAATGCTAGCTATTTTTATTGTTTATATGGTCTCCAGAGACAACGTTTCATGCT
CCATCTGTCTATAAAGGCCTATTTTCTTTAGTTTGAATTTACTGTTATTCGGTGTGCATTTCTATGTTTGGT
GAGCGGTTTTCTGTGCTCAGAGTGTGTTTATTTTATGTAATTTAATTTCTTTGTGAGCTCCTGTTTAGCAGG
TCGTCCCTTCAGCAAGGACACAAAAAGATTTTAATTTTATTAAAAAAAAAAAAAAAAAAAGACCGGGAAT
TCGATATCAAGCTTATCGACCTGCAGATCGTTCAAACATTTGGCAATAAAGTTTCTTAAGATTGAATCCTG
TTGCCGGTCTTGCGATGATTATCATATAATTTCTGTTGAATTACGTTAAGCATGTAATAATTAACATGTAA
TGCATGACGTTATTTATGAGATGGGTTTTTATGATTAGAGTCCCGCAATTATACATTTAATACGCGATAGA
AAACAAAATATAGCGCGCAAACTAGGATAAATTATCGCGCGCGGTGTCATCTATGTTACTAGAT

FIG. 26G, SEQ ID NO: 54

Amino acid sequence of HA from influenza B/Wisconsin/1/2010

MKAIIVLLMVVTSNADRICTGITSSNSPHVVKTATQGEVNVTGVIPLTTTPTKSYFANLKGTRTRGKLCPDCLN
CTDLDVALGRPMCVGTTPSAKASILHEVRPVTSGCFPIMHDRTKIRQLPNLLRGYENIRLSTQNVIDAEKAPGG
PYRLGTSGSCPNATSKIGFFATMAWAVPKDNYKNATNPLTVEVPYICTEGEDQITVWGFHSDNKTQMKSLYG
DSNPQKFTSSANGVTTHYVSQIGDFPDQTEDGGLPQSGRIVVDYMMQKPGKTGTIVYQRGVLLPQKVWCASG
RSKVIKGSLPLIGEADCLHEKYGGLNKSKPYYTGEHAKAIGNCPIWVKTPLKLANGTKYRPPAKLLKERGFFG
AIAGFLEGGWEGMIAGWHGYTSHGAHGVAVAADLKSTQEAINKITKNLNSLSELEVKNLQRLSGAMDELHN
EILELDEKVDDLRADTISSQIELAVLLSNEGIINSEDEHLLALERKLKKMLGPSAVDIGNGCFETKHKCNQTCLD
RIAAGTFNAGEFSLPTFDSLNITAASLNDDGLDNHTILLYYSTAASSLAVTLMLAIFIVYMVSRDNVSCSICL*

FIG. 26H
Schematic representation of construct 1462

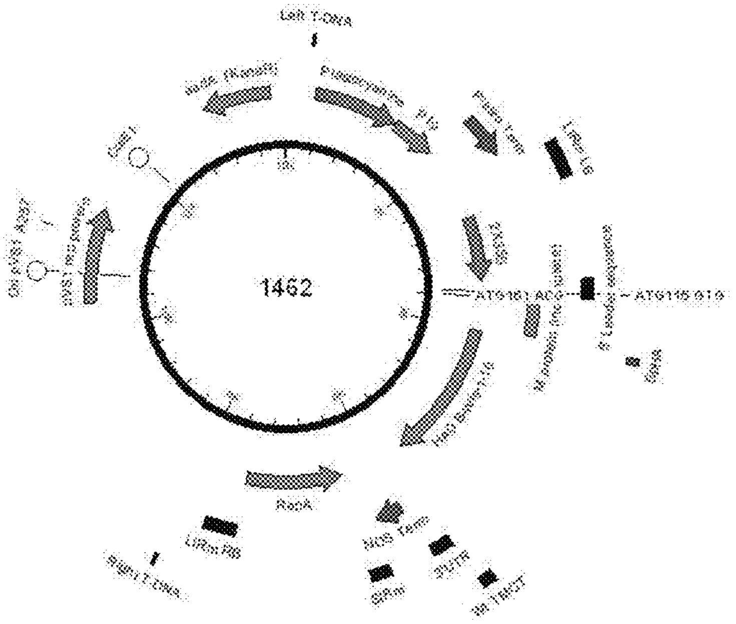

C-2X35S/CPMV-HT/HA B Wisconsin with deleted proteolytic loop/NOS into BeYDV(m)+Replicase amplification system (Construct number 1467)

FIG. 27A, SEQ ID NO: 55

HAB110(PrL-).r

TCCTTCCCATCCTCCACCAGGAGGTCTATATTTGGTTCCATTGGCAAGCTTCAAAG

FIG. 27B, SEQ ID NO: 56

HAB110(PrL-).c

ATATAGACCTCCTGGTGGAGGATGGGAAGGAATGATTGCAGGTTGGCACGGA

FIG. 27C, SEQ ID NO: 57

Expression cassette number 1467 from 2X35S promoter to NOS terminator. HA from influenza B/Wisconsin/1/2010 with deleted proteolytic loop is underlined.

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA

FIG. 27C cont'd

AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGAAGGCAATAATTGTACTACTCATGGTAGTAACATCCAATGCAGATCGAATCTGCACTGGGATAAC
ATCTTCAAACTCACCTCATGTGGTCAAAACAGCTACTCAAGGGGAGGTCAATGTGACTGGCGTGATACCA
CTGACAACAACACCAACAAAATCTTATTTTGCAAATCTCAAAGGAACAAGGACCAGAGGGAAACTATGC
CCGGACTGTCTCAACTGTACAGATCTGGATGTGGCCTTGGGCAGGCCAATGTGTGTGGGGACCACACCTT
CTGCTAAAGCTTCAATACTCCACGAGGTCAGACCTGTTACATCCGGGTGCTTTCCTATAATGCACGACAG
AACAAAAATCAGGCAACTACCCAATCTTCTCAGAGGATATGAAAATATCAGGTTATCAACCCAAAACGTT
ATCGATGCAGAAAAAGCACCAGGAGGACCCTACAGACTTGGAACCTCAGGATCTTGCCCTAACGCTACC
AGTAAAATCGGATTTTTTGCAACAATGGCTTGGGCTGTCCCAAAGGACAACTACAAAAATGCAACGAAC
CCACTAACAGTAGAAGTACCATACATTTGTACAGAAGGGGAAGACCAAATTACTGTTTGGGGGTTCCATT
CAGATAACAAAACCCAAATGAAGAGCCTCTATGGAGACTCAAATCCTCAAAAGTTCACCTCATCTGCTAA
TGGAGTAACCACACATTATGTTTCTCAGATTGGCGACTTCCCAGATCAAACAGAAGACGGAGGACTACCA
CAAAGCGGCAGAATTGTTGTTGATTACATGATGCAAAAACCTGGGAAAACAGGAACAATTGTCTATCAA
AGAGGTGTTTTGTTGCCTCAAAAGGTGTGGTGCGCGAGTGGCAGGAGCAAAGTAATAAAAGGGTCATTG
CCTTTAATTGGTGAAGCAGATTGCCTTCATGAAAAATACGGTGGATTAAACAAAAGCAAGCCTTACTACA
CAGGAGAACATGCAAAAGCCATAGGAAATTGCCCAATATGGGTAAAAACACCTTTGAAGCTTGCCAATG
GAACCAAATATAGACCTCCTGGTGGAGGATGGGAAGGAATGATTGCAGGTTGGCACGGATACACATCTC
ACGGAGCACATGGAGTGGCAGTGGCGGCAGACCTTAAGAGTACACAAGAAGCTATAAATAAGATAACA
AAAAATCTCAATTCTTTGAGTGAGCTAGAAGTAAAGAACCTTCAAAGACTAAGTGGTGCCATGGATGAA
CTCCACAACGAAATACTCGAGCTGGATGAGAAAGTGGATGATCTCAGAGCTGACACTATAAGCTCACAA
ATAGAACTTGCAGTCTTGCTTTCCAACGAAGGAATAATAAACAGTGAAGACGAGCATCTATTGGCACTTG
AGAGAAAACTAAAGAAAATGCTGGGTCCCTCTGCTGTAGACATAGGAAACGGATGCTTCGAAACCAAAC
ACAAATGCAACCAGACCTGCTTAGACAGGATAGCTGCTGGCACCTTTAATGCAGGAGAATTTTCTCTCCC
CACTTTTGATTCATTGAACATTACTGCTGCATCTTTAAATGATGATGGATTGGATAACCATACTATACTGC
TCTATTACTCAACTGCTGCTTCTAGTTTGGCTGTAACATTAATGCTAGCTATTTTTATTGTTTATATGGTCT
CCAGAGACAACGTTTCATGCTCCATCTGTCTATAAAGGCCTATTTTCTTTAGTTTGAATTTACTGTTATTCG
GTGTGCATTTCTATGTTTGGTGAGCGGTTTTCTGTGCTCAGAGTGTGTTTATTTTATGTAATTTAATTTCTT
TGTGAGCTCCTGTTTAGCAGGTCGTCCCTTCAGCAAGGACACAAAAAGATTTTAATTTTATTAAAAAAA
AAAAAAAAAAGACCGGGAATTCGATATCAAGCTTATCGACCTGCAGATCGTTCAAACATTTGGCAATAA
AGTTTCTTAAGATTGAATCCTGTTGCCGGTCTTGCGATGATTATCATATAATTTCTGTTGAATTACGTTAA
GCATGTAATAATTAACATGTAATGCATGACGTTATTTATGAGATGGGTTTTTATGATTAGAGTCCCGCAAT
TATACATTTAATACGCGATAGAAAACAAAATATAGCGCGCAAACTAGGATAAATTATCGCGCGCGGTGT
CATCTATGTTACTAGAT

FIG. 27D, SEQ ID NO: 58

Amino acid sequence of HA from influenza B/Wisconsin/1/2010 with deleted proteolytic loop

FIG. 27D, cont'd

MKAIIVLLMVVTSNADRICTGITSSNSPHVVKTATQGEVNVTGVIPLTTTPTKSYFANLKG
TRTRGKLCPDCLNCTDLDVALGRPMCVGTTPSAKASILHEVRPVTSGCFPIMHDRTKIRQ
LPNLLRGYENIRLSTQNVIDAEKAPGGPYRLGTSGSCPNATSKIGFFATMAWAVPKDNY
KNATNPLTVEVPYICTEGEDQITVWGFHSDNKTQMKSLYGDSNPQKFTSSANGVTTHYV
SQIGDFPDQTEDGGLPQSGRIVVDYMMQKPGKTGTIVYQRGVLLPQKVWCASGRSKVIK
GSLPLIGEADCLHEKYGGLNKSKPYYTGEHAKAIGNCPIWVKTPLKLANGTKYRPPGGG
WEGMIAGWHGYTSHGAHGVAVAADLKSTQEAINKITKNLNSLSELEVKNLQRLSGAMD
ELHNEILELDEKVDDLRADTISSQIELAVLLSNEGIINSEDEHLLALERKLKKMLGPSAVDI
GNGCFETKHKCNQTCLDRIAAGTFNAGEFSLPTFDSLNITAASLNDDGLDNHTILLYYST
AASSLAVTLMLAIFIVYMVSRDNVSCSICL*

FIG. 27E

Schematic representation of construct number 1467

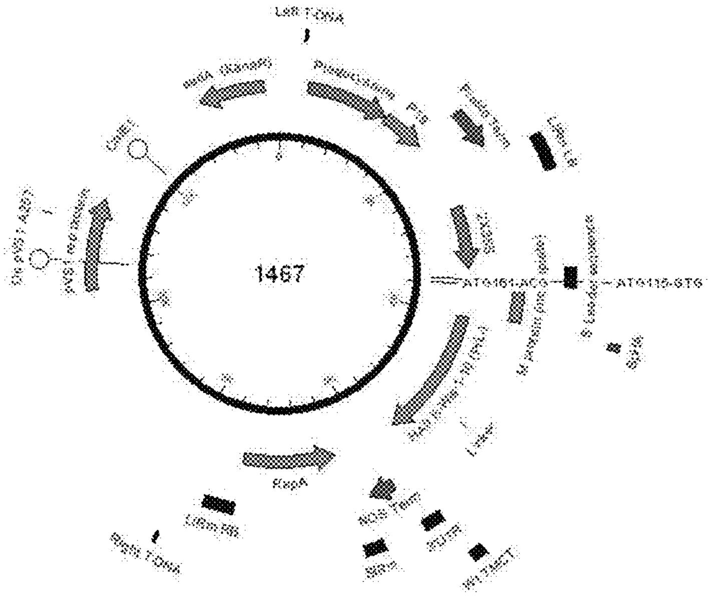

D-2X35S/CPMV-HT/PDISP/HA B Malaysia/NOS into BeYDV(m)+Replicase amplification system (Construct number 1631)

FIG. 28A SEQ ID NO: 59

IF-HB-M-04.s2+4c

TCTCAGATCTTCGCCGATCGAATCTGCACTGGGATAACATCGTC

FIG. 28B SEQ ID NO: 60

IF-HB-M-04.s1-4r

ACTAAAGAAAATAGGCCTTTATAGACAGATGGAGCAAGAAACATTG

FIG. 28C SEQ ID NO: 61

Synthesized HA B Malaysia (corresponding to nt 31-1743 from Genbank accession number EU124275). T759C and C888G mutations are underlined.

GATCGAATCTGCACTGGGATAACATCGTCAAACTCACCACATGTTGTCAAAACTGCTACTCAAGGGGAGG
TCAATGTGACTGGTGTAATACCACTGACAACAACACCCACCAAATCTCATTTTGCAAATCTCAAAGGAAC
AGAAACCAGAGGGAAACTATGCCCAAAATGCCTCAACTGCACAGATCTGGACGTGGCCTTGGGCAGACC
AAAATGCACGGGGAACATACCCTCGGCAAGAGTTTCAATACTCCATGAAGTCAGACCTGTTACATCTGGG
TGCTTTCCTATAATGCACGACAGAACAAAAATTAGACAGCTGCCTAAACTTCTCAGAGGATACGAACATA
TCAGGTTATCAACTCATAACGTTATCAATGCAGAAAATGCACCAGGAGGACCCTACAAAATTGGAACCTC
AGGGTCTTGCCCTAACGTTACCAATGGAAACGGATTTTTCGCAACAATGGCTTGGGCCGTCCCAAAAAAC
GACAACAACAAAACAGCAACAAATTCATTAACAATAGAAGTACCATACATTTGTACAGAAGGAGAAGAC
CAAATTACCGTTTGGGGGTTCCACTCTGATAACGAAACCCAAATGGCAAAGCTCTATGGGGACTCAAAGC
CCCAGAAGTTCACCTCATCTGCCAACGGAGTGACCACACATTACGTTTCACAGATTGGTGGCTTCCCAAA
TCAAACAGAAGACGGAGGACTACCACAAAGCGGTAGAATTGTTGTTGATTACATGGTGCAAAAATCTGG
GAAAACAGGAACAATTACCTATCAAAGAGGTATTTTATTGCCTCAAAAAGTGTGGTGCGCAAGTGGCAG
GAGCAAGGTAATAAAAGGATCGTTGCCTTTAATTGGAGAAGCAGATTGCCTCCACGAAAAATACGGTGG
ATTAAACAAAAGCAAGCCTTACTACACAGGGGAACATGCAAAGGCCATAGGAAATTGCCCAATATGGGT
GAAAACACCCTTGAAGCTGGCCAATGGAACCAAATATAGACCTCCTGCAAAACTATTAAAGGAAAGGGG
TTTCTTCGGAGCTATTGCTGGTTTCTTAGAAGGAGGATGGGAAGGAATGATTGCAGGTTGGCACGGATAC
ACATCCCATGGGGCACATGGAGTAGCGGTGGCAGCAGACCTTAAGAGCACTCAAGAGGCCATAAACAAG
ATAACAAAAAATCTCAACTCTTTGAGTGAGCTGGAAGTAAAGAATCTTCAAAGACTAAGCGGTGCCATG
GATGAACTCCACAACGAAATACTAGAACTAGACGAGAAAGTGGATGATCTCAGAGCTGATACAATAAGC
TCACAAATAGAACTCGCAGTCCTGCTTTCCAATGAAGGAATAATAAACAGTGAAGATGAGCATCTCTTGG
CGCTTGAAAGAAAGCTGAAGAAAATGCTGGGCCCCTCTGCTGTAGAGATAGGGAATGGATGCTTTGAAA
CCAAACACAAGTGCAACCAGACCTGTCTCGACAGAATAGCTGCTGGTACCTTTGATGCAGGAGAATTTTC
TCTCCCCACTTTTGATTCACTGAATATTACTGCTGCATCTTTAAATGACGATGGATTGGATAATCATACTA
TACTGCTTTACTACTCAACTGCTGCCTCCAGTTTGGCTGTAACATTGATGATAGCTATCTTTGTTGTTTATA
TGGTCTCCAGAGACAATGTTTCTTGCTCCATCTGTCTATAA

FIG. 28D

Schematic representation of construct 194. SacII and StuI restriction enzyme sites used for plasmid linearization are annotated on the representation.

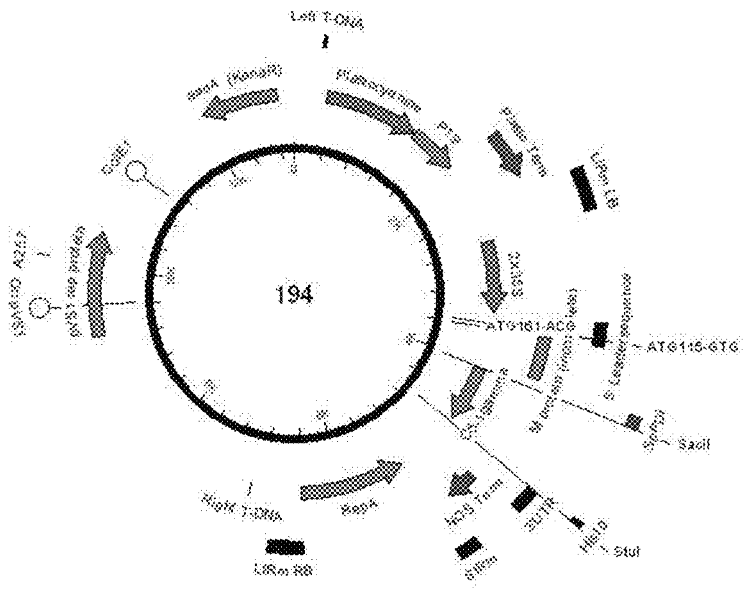

FIG. 28E. SEQ ID NO: 62

Construct 194 from left to right t-DNA borders (underlined). 2X35S/CPMV-HT/NOS into BeYDV(m)+Replicase amplification system with Plastocyanine-P19-Plastocyanine silencing inhibitor expression cassette <u>TGGCAGGATATATTGTGGTGTAAACA</u>AATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA
CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC

FIG. 28E, cont'd

AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGAGACGCGTTGTTGTTGTGACTCCGAGGGGTTGCCTCAAACTCTATCTT
ATAACCGGCGTGGAGGCATGGAGGCAGGGGTATTTTGGTCATTTTAATAGATAGTGGAAAATGACGTGG
AATTTACTTAAAGACGAAGTCTTTGCGACAAGGGGGGGCCCACGCCGAATTTAATATTACCGGCGTGGCC
CCCCCTTATCGCGAGTGCTTTAGCACGAGCGGTCCAGATTTAAAGTAGAAAATTTCCCGCCCACTAGGGT
TAAAGGTGTTCACACTATAAAAGCATATACGATGTGATGGTATTTGGTCGACAAGCTTGCATGCCGGTCA
ACATGGTGGAGCACGACACACTTGTCTACTCCAAAAATATCAAAGATACAGTCTCAGAAGACCAAAGGG
CAATTGAGACTTTTCAACAAAGGGTAATATCCGGAAACCTCCTCGGATTCCATTGCCCAGCTATCTGTCA
CTTTATTGTGAAGATAGTGGAAAAGGAAGGTGGCTCCTACAAATGCCATCATTGCGATAAAGGAAAGGC
CATCGTTGAAGATGCCTCTGCCGACAGTGGTCCCAAAGATGGACCCCCACCCACGAGGAGCATCGTGGA
AAAAGAAGACGTTCCAACCACGTCTTCAAAGCAAGTGGATTGATGTGATAACATGGTGGAGCACGACAC
ACTTGTCTACTCCAAAAATATCAAAGATACAGTCTCAGAAGACCAAAGGGCAATTGAGACTTTTCAACAA
AGGGTAATATCCGGAAACCTCCTCGGATTCCATTGCCCAGCTATCTGTCACTTTATTGTGAAGATAGTGG
AAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAAGAAGACGTTCCAACCA
CGTCTTCAAAGCAAGTGGATTGATGTGATATCTCCACTGACGTAAGGGATGACGCACAATCCCACTATCC
TTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAA
ACTTCTCTCTTGTCTTTCTTGCGTGAGCGATCTTCAACGTTGTCAGATCGTGCTTCGGCACCAGTACAACG
TTTTCTTTCACTGAAGCGAAATCAAAGATCTCTTTGTGGACACGTAGTGCGGCGCCATTAAATAACGTGT
ACTTGTCCTATTCTTGTCGGTGTGGTCTTGGGAAAAGAAAGCTTGCTGGAGGCTGCTGTTCAGCCCCATAC
ATTACTTGTTACGATTCTGCTGACTTTCGGCGGGTGCAATATCTCTACTTCTGCTTGACGAGGTATTGTTG
CCTGTACTTCTTTCTTCTTCTTCTTGCTGATTGGTTCTATAAGAAATCTAGTATTTTCTTTGAAACAGAGTT
TTCCCGTGGTTTTCGAACTTGGAGAAAGATTGTTAAGCTTCTGTATATTCTGCCCAAATTTGTCGGGCCCA
TGGCGAAAAACGTTGCGATTTTCGGCTTATTGTTTTCTCTTCTTGTGTTGGTTCCTTCTCAGATCTTCGCCG
CGGCTCCTCAGCCAAAACGACACCCCCATCTGTCTATCCACTGGCCCCTGGATCTGCTGCCCAAACTAAC
TCCATGGTGACCCTGGGATGCCTGGTCAAGGGCTATTTCCCTGAGCCAGTGACAGTGACCTGGAACTCTG
GATCCCTGTCCAGCGGTGTGCACACCTTCCCAGCTGTCCTGCAGTCTGACCTCTACACTCTGAGCAGCTCA
GTGACTGTCCCCTCCAGCACCTGGCCCAGCGAGACCGTCACCTGCAACGTTGCCCACCCGGCCAGCAGCA
CCAAGGTGGACAAGAAAATTGTGCCCAGGGATTGTGGTTGTAAGCCTTGCATATGTACAGTCCCAGAAGT
ATCATCTGTCTTCATCTTCCCCCCAAAGCCCAAGGATGTGCTCACCATTACTCTGACTCCTAAGGTCACGT
GTGTTGTGGTAGACATCAGCAAGGATGATCCCGAGGTCCAGTTCAGCTGGTTTGTAGATGATGTGGAGGT
GCACACAGCTCAGACGCAACCCCGGGAGGAGCAGTTCAACAGCACTTTCCGCTCAGTCAGTGAACTTCCC
ATCATGCACCAGGACTGGCTCAATGGCAAGGAGCGATCGCTCACCATCACCATCACCATCACCATCACCA
TTAAAGGCCTATTTTCTTTAGTTTGAATTTACTGTTATTCGGTGTGCATTTCTATGTTTGGTGAGCGGTTTT
CTGTGCTCAGAGTGTGTTTATTTTATGTAATTTAATTTCTTTGTGAGCTCCTGTTTAGCAGGTCGTCCCTTC
AGCAAGGACACAAAAAGATTTTAATTTTATTAAAAAAAAAAAAAAAAAAGACCGGGAATTCGATATCAA
GCTTATCGACCTGCAGATCGTTCAAACATTTGGCAATAAAGTTTCTTAAGATTGAATCCTGTTGCCGGTCT
TGCGATGATTATCATATAATTTCTGTTGAATTACGTTAAGCATGTAATAATTAACATGTAATGCATGACGT
TATTTATGAGATGGGTTTTTATGATTAGAGTCCCGCAATTATACATTTAATACGCGATAGAAAACAAAAT
ATAGCGCGCAAACTAGGATAAATTATCGCGCGCGGTGTCATCTATGTTACTAGATCTCTAGAGTCTCAAG
CTTGGCGCGCCATAAAATGATTATTTTATGAATATATTTCATTGTGCAAGTAGATAGAAATTACATATGTT
ACATAACACACGAAATAAACAAAAAAAGACAATCCAAAAACAAACACCCCAAAAAAAATAATCACTTT
AGATAAACTCGTATGAGGAGAGGCACGTTCAGTGACTCGACGATTCCCGAGCAAAAAAAGTCTCCCCGT
CACACATATAGTGGGTGACGCAATTATCTTTAAAGTAATCCTTCTGTTGACTTGTCATTGATAACATCCAG
TCTTCGTCAGGATTGCAAAGAATTATAGAAGGGATCCCACCTTTTATTTTCTTCTTTTTTCCATATTTAGGG
TTGACAGTGAAATCAGACTGGCAACCTATTAATTGCTTCCACAATGGGACGAACTTGAAGGGGATGTCGT
CGATGATATTATAGGTGGCGTGTTCATCGTAGTTGGTGAAATCGATGGTACCGTTCCAATAGTTGTGTCGT
CCGAGACTTCTAGCCCAGGTGGTCTTTCCGGTACGAGTTGGTCCGCAGATGTAGAGGCTGGGGTGTCGGA
TTCCATTCCTTCCATTGTCCTGGTTAAATCGGCCATCCATTCAAGGTCAGATTGAGCTTGTTGGTATGAGA

FIG. 28E, cont'd

CAGGATGTATGTAAGTATAAGCGTCTATGCTTACATGGTATAGATGGGTTTCCCTCCAGGAGTGTAGATC
TTCGTGGCAGCGAAGATCTGATTCTGTGAAGGGCGACACATACGGTTCAGGTTGTGGAGGGAATAATTTG
TTGGCTGAATATTCCAGCCATTGAAGTTTTGTTGCCCATTCATGAGGGAATTCTTCCTTGATCATGTCAAG
ATATTCCTCCTTAGACGTTGCAGTCTGGATAATAGTTCTCCATCGTGCGTCAGATTTGCGAGGAGAGACCT
TATGATCTCGGAAATCTCCTCTGGTTTTAATATCTCCGTCCTTTGATATGTAATCAAGGACTTGTTTAGAG
TTTCTAGCTGGCTGGATATTAGGGTGATTTCCTTCAAAATCGAAAAAAGAAGGATCCCTAATACAAGGTT
TTTTATCAAGCTGGAGAAGAGCATGATAGTGGGTAGTGCCATCTTGATGAAGCTCAGAAGCAACACCAA
GGAAGAAAATAAGAAAAGGTGTGAGTTTCTCCCAGAGAAACTGGAATAAATCATCTCTTTGAGATGAGC
ACTTGGGATAGGTAAGGAAAACATATTTAGATTGGAGTCTGAAGTTCTTACTAGCAGAAGGCATGTTGTT
GTGACTCCGAGGGGTTGCCTCAAACTCTATCTTATAACCGGCGTGGAGGCATGGAGGCAGGGGTATTTTG
GTCATTTTAATAGATAGTGGAAAATGACGTGGAATTTACTTAAAGACGAAGTCTTTGCGACAAGGGGGG
GCCCACGCCGAATTTAATATTACCGGCGTGGCCCCCCCTTATCGCGAGTGCTTTAGCACGAGCGGTCCAG
ATTTAAAGTAGAAAATTTCCCGCCCACTAGGGTTAAAGGTGTTCACACTATAAAAGCATATACGATGTGA
TGGTATTTGACTAGTGGCACTGGCCGTCGTTTTACAACGTCGTGACTGGGAAAACCCTGGCGTTACCCAA
CTTAATCGCCTTGCAGCACATCCCCCTTTCGCCAGCTGGCGTAATAGCGAAGAGGCCCGCACCGATCGCC
CTTCCCAACAGTTGCGCAGCCTGAATGGCGAATGCTAGAGCAGCTTGAGCTTGGATCAGATTGTCGTTTC
CCGCCTTCAGTTTAAACTATCAGTGTTTGACAGGATATATTGGCGGGTAAACCTAAGAGAAAAGAGCGTT
TA

FIG. 28F, SEQ ID NO: 63

Expression cassette number 1631 from 2X35S promoter to NOS terminator. PDISP-HA from influenza B/ Malaysia/2506/2004 is underlined.

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTGTTGGTTCCTTCTCAGATCTTCG
CCGATCGAATCTGCACTGGGATAACATCGTCAAACTCACCACATGTTGTCAAAACTGCTACTCAAGGGGA
GGTCAATGTGACTGGTGTAATACCACTGACAACAACACCCACCAAATCTCATTTTGCAAATCTCAAAGGA
ACAGAAACCAGAGGGAAACTATGCCCAAAATGCCTCAACTGCACAGATCTGGACGTGGCCTTGGGCAGA
CCAAAATGCACGGGGAACATACCCTCGGCAAGAGTTTCAATACTCCATGAAGTCAGACCTGTTACATCTG
GGTGCTTTCCTATAATGCACGACAGAACAAAAATTAGACAGCTGCCTAAACTTCTCAGAGGATACGAACA
TATCAGGTTATCAACTCATAACGTTATCAATGCAGAAAATGCACCAGGAGGACCCTACAAAATTGGAACC
TCAGGGTCTTGCCCTAACGTTACCAATGGAAACGGATTTTTCGCAACAATGGCTTGGGCCGTCCCAAAAA
ACGACAACAACAAAACAGCAACAAATTCATTAACAATAGAAGTACCATACATTTGTACAGAAGGAGAAG
ACCAAATTACCGTTTGGGGGTTCCACTCTGATAACGAAACCCAAATGGCAAAGCTCTATGGGGACTCAAA

FIG. 28F, cont'd

GCCCCAGAAGTTCACCTCATCTGCCAACGGAGTGACCACACATTACGTTTCACAGATTGGTGGCTTCCCA
AATCAAACAGAAGACGGAGGACTACCACAAAGCGGTAGAATTGTTGTTGATTACATGGTGCAAAAATCT
GGGAAAACAGGAACAATTACCTATCAAAGAGGTATTTTATTGCCTCAAAAAGTGTGGTGCGCAAGTGGC
AGGAGCAAGGTAATAAAAGGATCGTTGCCTTTAATTGGAGAAGCAGATTGCCTCCACGAAAAATACGGT
GGATTAAACAAAAGCAAGCCTTACTACACAGGGGAACATGCAAAGGCCATAGGAAATTGCCCAATATGG
GTGAAAACACCCTTGAAGCTGGCCAATGGAACCAAATATAGACCTCCTGCAAAACTATTAAAGGAAAGG
GGTTTCTTCGGAGCTATTGCTGGTTTCTTAGAAGGAGGATGGGAAGGAATGATTGCAGGTTGGCACGGAT
ACACATCCCATGGGGCACATGGAGTAGCGGTGGCAGCAGACCTTAAGAGCACTCAAGAGGCCATAAACA
AGATAACAAAAAATCTCAACTCTTTGAGTGAGCTGGAAGTAAAGAATCTTCAAAGACTAAGCGGTGCCA
TGGATGAACTCCACAACGAAATACTAGAACTAGACGAGAAAGTGGATGATCTCAGAGCTGATACAATAA
GCTCACAAATAGAACTCGCAGTCCTGCTTTCCAATGAAGGAATAATAAACAGTGAAGATGAGCATCTCTT
GGCGCTTGAAAGAAAGCTGAAGAAAATGCTGGGCCCCTCTGCTGTAGAGATAGGGAATGGATGCTTTGA
AACCAAACACAAGTGCAACCAGACCTGTCTCGACAGAATAGCTGCTGGTACCTTTGATGCAGGAGAATTT
TCTCTCCCCACTTTTGATTCACTGAATATTACTGCTGCATCTTTAAATGACGATGGATTGGATAATCATAC
TATACTGCTTTACTACTCAACTGCTGCCTCCAGTTTGGCTGTAACATTGATGATAGCTATCTTTGTTGTTTA
TATGGTCTCCAGAGACAATGTTTCTTGCTCCATCTGTCTATAAAGGCCTATTTTCTTTAGTTTGAATTTACT
GTTATTCGGTGTGCATTTCTATGTTTGGTGAGCGGTTTTCTGTGCTCAGAGTGTGTTTATTTTATGTAATTT
AATTTCTTTGTGAGCTCCTGTTTAGCAGGTCGTCCCTTCAGCAAGGACACAAAAAGATTTTAATTTTATTA
AAAAAAAAAAAAAAAAAGACCGGGAATTCGATATCAAGCTTATCGACCTGCAGATCGTTCAAACATTTG
GCAATAAAGTTTCTTAAGATTGAATCCTGTTGCCGGTCTTGCGATGATTATCATATAATTTCTGTTGAATT
ACGTTAAGCATGTAATAATTAACATGTAATGCATGACGTTATTTATGAGATGGGTTTTTATGATTAGAGTC
CCGCAATTATACATTTAATACGCGATAGAAAACAAAATATAGCGCGCAAACTAGGATAAATTATCGCGC
GCGGTGTCATCTATGTTACTAGAT

FIG. 28G, SEQ ID NO: 64

Amino acid sequence of PDISP-HA from influenza B/Malaysia/2506/2004

MAKNVAIFGLLFSLLVLVPSQIFADRICTGITSSNSPHVVKTATQGEVNVTGVIPLTTTPTKSHFANLKGTETRG
KLCPKCLNCTDLDVALGRPKCTGNIPSARVSILHEVRPVTSGCFPIMHDRTKIRQLPKLLRGYEHIRLSTHNVIN
AENAPGGPYKIGTSGSCPNVTNGNGFFATMAWAVPKNDNNKTATNSLTIEVPYICTEGEDQITVWGFHSDNET
QMAKLYGDSKPQKFTSSANGVTTHYVSQIGGFPNQTEDGGLPQSGRIVVDYMVQKSGKTGTITYQRGILLPQ
KVWCASGRSKVIKGSLPLIGEADCLHEKYGGLNKSKPYYTGEHAKAIGNCPIWVKTPLKLANGTKYRPPAKL
LKERGFFGAIAGFLEGGWEGMIAGWHGYTSHGAHGVAVAADLKSTQEAINKITKNLNSLSELEVKNLQRLSG
AMDELHNEILELDEKVDDLRADTISSQIELAVLLSNEGIINSEDEHLLALERKLKKMLGPSAVEIGNGCFETKH
KCNQTCLDRIAAGTFDAGEFSLPTFDSLNITAASLNDDGLDNHTILLYYSTAASSLAVTLMIAIFVVYMVSRDN
VSCSICL*

Schematic representation of construct number 1631

| Construct number | Hemagglutination capacity (HA titer)[a] |
|---|---|
| 1462 (0.8) | 136 ± 48 |
| 1467 (0.8) | 2660 ± 384 |
| 1462 + 1261 (0.8:0.2) | 941 ± 192 |
| 1467 + 1261 (0.8:0.2) | 4344 ± 1536 |

[a] Inverse of the highest dilution capable of agglutinating red blood cells.

INCREASING VIRUS-LIKE PARTICLE YIELD IN PLANTS

FIELD OF INVENTION

The present invention relates to producing viral proteins in plants. More specifically, the present invention relates to producing and increasing virus-like particles production in plants.

BACKGROUND OF THE INVENTION

Influenza is caused by an RNA virus of the orthomyxoviridae family. There are three types of these viruses and they cause three different types of influenza: type A, B and C. Influenza virus type A viruses infect mammals (humans, pigs, ferrets, horses) and birds. This is very important to mankind, as this is the type of virus that has caused worldwide pandemics. Influenza virus type B (also known simply as influenza B) infects only humans. It occasionally causes local outbreaks of flu. Influenza C viruses also infect only humans. They infect most people when they are young and rarely causes serious illness.

Vaccination provides protection against disease caused by a like agent by inducing a subject to mount a defense prior to infection. Conventionally, this has been accomplished through the use of live attenuated or whole inactivated forms of the infectious agents as immunogens. To avoid the danger of using the whole virus (such as killed or attenuated viruses) as a vaccine, recombinant viral proteins, for example subunits, have been pursued as vaccines. Both peptide and subunit vaccines are subject to a number of potential limitations. Subunit vaccines may exhibit poor immunogenicity, owing to incorrect folding or poor antigen presentation. A major problem is the difficulty of ensuring that the conformation of the engineered proteins mimics that of the antigens in their natural environment. Suitable adjuvants and, in the case of peptides, carrier proteins, must be used to boost the immune response. In addition these vaccines elicit primarily humoral responses, and thus may fail to evoke effective immunity. Subunit vaccines are often ineffective for diseases in which whole inactivated virus can be demonstrated to provide protection.

Virus-like particles (VLPs) are potential candidates for inclusion in immunogenic compositions. VLPs closely resemble mature virions, but they do not contain viral genomic material. Therefore, VLPs are nonreplicative in nature, which make them safe for administration as a vaccine. In addition, VLPs can be engineered to express viral glycoproteins on the surface of the VLP, which is their most native physiological configuration. Moreover, since VLPs resemble intact virions and are multivalent particulate structures, VLPs may be more effective in inducing neutralizing antibodies to the glycoprotein than soluble envelope protein antigens.

VLPs have been produced in plants (WO2009/009876; WO 2009/076778; WO 2010/003225; WO 2010/003235; WO 2011/03522; WO 2010/148511; which are incorporated herein by reference), and in insect and mammalian systems (Noad, R. and Roy, P., 2003, *Trends Microbiol* 11: 438-44; Neumann et al., 2000, J. Virol., 74, 547-551). Latham and Galarza (2001, J. Virol., 75, 6154-6165) reported the formation of influenza VLPs in insect cells infected with recombinant baculovirus co-expressing hemagglutinin (HA), neuraminidase (NA), M1, and M2 genes. This study demonstrated that influenza virion proteins self-assemble upon co-expression in eukaryotic cells and that the M1 matrix protein was required for VLP production. However, Gomez-Puertas et al., (1999, J. Gen. Virol, 80, 1635-1645) also showed that overexpression of M2 completely blocked CAT RNA transmission to MDCK cultures.

M2 functions as an ion channel protein and it has been shown that, when this protein is overexpressed, the intracellular transport of co-expressed HA is inhibited and the accumulation of hemaglutinin (HA) at the plasma membrane is reduced by 75-80% (Sakaguchi et al., 1996; Henkel & Weisz, 1998). Furthermore, by overexpressing M2, the accumulation of virus membrane proteins at the plasma membrane is reduced and hence there is a drastic reduction in the number of functional VLPs produced.

The M2 protein is abundantly expressed at the cell surface of influenza A infected cells (Lamb et al. (1985) Cell, 40, 627 to 633). The protein is also found in the membrane of the virus particle itself, but in much smaller quantities, 14 to 68 molecules of M2 per virion (Zebedee and Lamb (1988) J. Virol. 62, 2762 to 72). The M2 protein is posttranslationally modified by the addition of a palmitic acid on cysteine at position 50 (Sugrue et al. (1990) Virology 179, 51 to 56).

The M2 protein is a homotetramer composed of two disulfide-linked dimers, which are held together by noncovalent interactions (Sugrue and Hay (1991) Virology 180, 617 to 624). By site-directed mutagenesis, Holsinger and Lamb, (1991) Virology 183, 32 to 43, demonstrated that the cysteine residues at positions 17 and 19 are involved in disulfide bridge formation. Only the cysteine at position 17 is present in all viruses analyzed. In the virus strains where cysteine 19 is also present, it is not known whether a second disulfide bridge is formed in the same dimer (already linked by Cys 17-Cys 17) or with the other dimer.

Smith et al. (US Patent Application 2010/0143393) and Song et al. (Plos ONE 2011 6(1):e14538) describe vaccines and VLPs that comprise influenza M2 protein. The VLPs comprise at least a viral core protein such as M1. This core protein drives budding and release of the particles from the insect host cells.

Szecsi et al. (Virology Journal, 2006, 3:70) assembled VLPs on replication-defective core particles derived from murine leukaemia virus (MLV). The engineered influenza VLP are derived by transiently co-expressing cells surface (HA, NA, M2) and internal viral components (Gag, GFP marker genome) and harbour at their surface HA, HA and either NA or M2, or all three proteins derived from the H7N1 or H5N1 virus. According to Szecsi et al. the expression of M2 during Flu-VLP production did not influence the incorporation of HA or NA onto viral particles (page 2, right column, second paragraph in Szecsi et al.).

SUMMARY OF THE INVENTION

The present invention relates to producing viral proteins in plants. More specifically, the present invention relates to producing and increasing virus-like particles production in plants.

It is an object of the invention to provide an improved method to increase virus like particle production in plants.

According to the present invention there is provided a method (A) of producing a virus like particle (VLP) in a plant comprising, a) introducing a first nucleic acid comprising a first regulatory region active in the plant and operatively linked to a nucleotide sequence encoding a structural virus protein into the plant, or portion of the plant, b) introducing a second nucleic acid comprising a second regulatory region active in the plant and operatively linked to a nucleotide sequence encoding a channel protein c) incubating the plant or portion of the plant under conditions that permit the expression of the nucleic acids, thereby producing the VLP.

The first regulatory region active in the plant, and the second regulatory region active in the plant may be the same or different.

The channel protein of the method (A) described above may be a proton channel protein. The proton channel protein may be selected from M2 or BM2. Furthermore, the proton channel protein may comprise the proton channel signature sequence HXXXW. The M2 protein may be an M2 protein obtained from influenza A/Puerto Rico/8/1934 (SEQ ID NO:14) or from influenza A/New Caledonia/20/1999 (SEQ ID NO:11).

The present invention also provides the method (A) as described above, wherein the structural virus protein comprises a trimerization domain. Furthermore, the nucleotide sequence encoding the structural virus protein comprises a chimeric nucleotide sequence encoding, in series, an antigenic viral protein or fragment thereof, an influenza transmembrane domain, and a cytoplasmic tail. The structural virus protein may comprise an influenza HA protein. Furthermore one or more proteolytic loop of the influenza HA protein may be deleted.

The present invention provides the method (A) as described above wherein, the nucleotide sequence encoding the structural virus protein may be selected from the group consisting of B HA, C, HA, H2, H3, H4, H6, H7, H8, H9, H10, H11, H12, H13, H14, H15, and H16. For example, the nucleotide sequence encoding the structural virus protein may be Type B HA or H3. The nucleotide sequence encoding the structural virus protein may be for example HA from influenza B/Brisbane/60/2008, B/Malaysia/2506/2004 or B/Wisconsin/1/2010, or H3 from influenza A/Perth/16/2009 or A/Victoria/361/2011. Furthermore, the nucleotide sequence encoding a structural virus protein has at least 70% sequence identity to SEQ ID NO: 23, 28, 43, 46, 51, 57 or 61. The sequence of the structural virus protein may also be comprise the sequence of SEQ ID NO:25, 30, 41, 48, 54, 58 or 64.

The present invention also includes the method (A) as described above, wherein the first nucleic acid sequence comprises the first regulatory region operatively linked with a one or more than one comovirus enhancer, the nucleotide sequence encoding the structural virus protein, and one or more than one geminivirus amplification element, and a third nucleic acid encoding a geminivirus replicase is introduced into the plant or portion of the plant. The one or more than one comovirus enhancer may be a comovirus UTR, for example, a Cowpea Mosaic Virus hyperanslatable (CPMV-HT) UTR such as the CPMV-HT 5' and/or 3'UTR. The one or more than one geminivirus amplification element may be selected from a Bean Yellow Dwarf Virus long intergenic region (BeYDV LIR), and a BeYDV short intergenic region (BeYDV SIR). Furthermore, the nucleotide sequence encoding the structural virus protein may be Type B HA or H3, for example, the nucleotide sequence encoding a structural virus protein may have at least 70% sequence identity to SEQ ID NO: 23, 28, 43, 46, 51, 57 or 61. The sequence of the structural virus protein may also be comprise the sequence of SEQ ID NO:25, 30, 41, 48, 54, 58 or 64.

The method as described above (Method A) may also involving introducing another nucleic acid sequence encoding a suppressor of silencing, for example HcPro or p19.

The present invention also includes the method (A) as described above, wherein in the step of introducing (step a), the nucleic acid is transiently expressed in the plant. Alternatively, in the step of introducing (step a), the nucleic acid is stably expressed in the plant.

The method (A) as described above may further comprising a step of:

d) harvesting the plant and purifying the VLPs.

The present invention also includes the method (A) as described above, wherein the VLP does not contain a viral matrix or a core protein.

The present invention provides a VLP produced by the method (A) as described above. The VLP may further comprising one or more than one lipid derived from a plant. The VLP may also be characterized by not containing the channel protein. Furthermore, the structural virus protein of the VLP may be an HA0 protein. The one or more virus protein comprises of the VLP may comprise plant-specific N-glycans, or modified N-glycans. The present invention also provides a polyclonal antibody prepared using the VLP.

The present invention includes a composition comprising an effective dose of the VLP as just described for inducing an immune response, and a pharmaceutically acceptable carrier.

The present invention also includes a method of inducing immunity to an influenza virus infection in a subject, comprising administering the VLP as just described to the subject. The VLP may be administered to a subject orally, intradermally, intranasally, intramuscularly, intraperitoneally, intravenously, or subcutaneously.

The present invention also provides plant matter comprising a VLP produced by the method (A) described above. The plant matter may be used in inducing immunity to an influenza virus infection in a subject. The plant matter may also be admixed as a food supplement.

The present invention also provides a method (B) of producing a virus like particle (VLP) comprising, a) providing a plant or portion of the plant comprising a first nucleic acid comprising a first regulatory region active in the plant and operatively linked to a nucleotide sequence encoding a structural virus protein into the plant, or portion of the plant, and a second nucleic acid comprising a second regulatory region active in the plant and operatively linked to a nucleotide sequence encoding a channel protein b) incubating the plant or portion of the plant under conditions that permit the expression of the nucleic acids, thereby producing the VLP.

The first regulatory region active in the plant, and the second regulatory region active in the plant may be the same or different.

The channel protein of the method (B) described above may be a proton channel protein. The proton channel protein may be selected from M2 or BM2. Furthermore, the proton channel protein may comprise the proton channel signature sequence HXXXW.

The present invention also provides the method (B) as described above, wherein the structural virus protein comprises a trimerization domain. Furthermore, the nucleotide sequence encoding the structural virus protein comprises a chimeric nucleotide sequence encoding, in series, an antigenic viral protein or fragment thereof, an influenza transmembrane domain, and a cytoplasmic tail. The structural virus protein may comprise an influenza HA protein. Furthermore one or more proteolytic loop of the influenza HA protein may be deleted.

The present invention provides the method (B) as described above wherein, the nucleotide sequence encoding the structural virus protein may be selected from the group consisting of B HA, C, HA, H2, H3, H4, H6, H7, H8, H9, H10, H11, H12, H13, H14, H15, and H16. For example, the nucleotide sequence encoding the structural virus protein may be Type B HA or H3. The nucleotide sequence encoding the structural virus protein may be for example HA from influenza B/Brisbane/60/2008, B/Malaysia/2506/2004 or B/Wisconsin/1/2010, or H3 from influenza A/Perth/16/2009 or A/Victoria/361/2011.

The Present invention also includes the method (B) as described above, wherein the first nucleic acid sequence comprises the first regulatory region operatively linked with a one or more than one comovirus enhancer, the nucleotide sequence encoding the structural virus protein, and one or more than one geminivirus amplification element, and a third nucleic acid encoding a geminivirus replicase is introduced into the plant or portion of the plant. The one or more than one comovirus enhancer may be a comovirus UTR, for example, a Cowpea Mosaic Virus hyperanslatable (CPMV-HT) UTR such as the CPMV-HT 5' and/or 3'UTR. Additionally, the one or more than one geminivirus amplification element may be selected from a Bean Yellow Dwarf Virus long intergenic region (BeYDV LIR), and a BeYDV short intergenic region (BeYDV SIR).

The method as described above (Method B) may also involving introducing another nucleic acid sequence encoding a suppressor of silencing, for example HcPro or p19.

The present invention also includes the method (B) as described above, wherein in the step of introducing (step a), the nucleic acid is transiently expressed in the plant. Alternatively, in the step of introducing (step a), the nucleic acid is stably expressed in the plant.

The method (B) as described above may further comprising a step of:

d) harvesting the plant and purifying the VLPs.

The present invention also includes the method (B) as described above, wherein the VLP does not contain a viral matrix or a core protein.

The present invention provides a VLP produced by the method (B) as described above. The VLP may further comprising one or more than one lipid derived from a plant. The VLP may also be characterized by not containing the channel protein. Furthermore, the structural virus protein of the VLP may be an HA0 protein. The one or more virus protein comprises of the VLP may comprise plant-specific N-glycans, or modified N-glycans. The present invention also provides a polyclonal antibody prepared using the VLP.

The present invention includes a composition comprising an effective dose of the VLP made by the method (B) as just described, for inducing an immune response, and a pharmaceutically acceptable carrier.

The present invention also includes a method of inducing immunity to an influenza virus infection in a subject, comprising administering the VLP as just described, to the subject. The VLP may be administered to a subject orally, intradermally, intranasally, intramuscularly, intraperitoneally, intravenously, or subcutaneously.

The present invention also provides plant matter comprising a VLP produced by the method (B) described above. The plant matter may be used in inducing immunity to an influenza virus infection in a subject. The plant matter may also be admixed as a food supplement.

The present invention provides a polypeptide comprising the amino acid sequence of SEQ ID NO:41 (PDISP/HA from influenza B/Brisbane/60/2008 with deleted proteolytic loop), and a nucleic acid sequence encoding the polypeptide of SEQ ID NO:41. The nucleic acid sequence may comprises the nucleotide sequence of SEQ ID NO:43. The present invention provides a VLP comprising the polypeptide comprising the amino acid sequence of SEQ ID NO:41. The VLP may further comprising one or more than one lipid derived from a plant. The VLP may also be characterized by not containing the channel protein. The VLP may comprise plant-specific N-glycans, or modified N-glycans. The present invention provides a composition comprising an effective dose of the VLP comprising the amino acid sequence of SEQ ID NO:41, for inducing an immune response, and a pharmaceutically acceptable carrier. The present invention also includes a method of inducing immunity to an influenza virus infection in a subject, comprising administering the VLP comprising the amino acid sequence of SEQ ID NO:41, to the subject. The VLP may be administered to a subject orally, intradermally, intranasally, intramuscularly, intraperitoneally, intravenously, or subcutaneously. The present invention also provides plant matter comprising a VLP comprising the amino acid sequence of SEQ ID NO:41. The plant matter may be used in inducing immunity to an influenza virus infection in a subject. The plant matter may also be admixed as a food supplement.

By co-expressing a structural virus protein along with a channel protein, for example but not limited to a proton channel protein, increased yield of the structural virus protein and VLPs are observed. HA's are known to under go pH-dependant conformation change. Without wishing to bound by theory, the pH within the Golgi apparatus of the HA producing cells during maturation and migration may influence HA folding, effects stability and increase degradation, or a combination thereof, of the HA. By co-expressing a channel protein, for example but not limited to a proton channel protein, along with an HA, the pH within the Golgi apparatus may increase, and result in an increase in stability, reduction of degradation, or a combination thereof, and increase HA yield.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1D shows Construct 1191 (SEQ ID NO 4). FIG. 1E shows expression cassette number 489 (SEQ ID NO 5). FIG. 1F shows amino acid sequence of H5 from influenza A/Indonesia/5/2005 (H5N1) (SEQ ID NO: 6). FIG. 1G shows a nucleotide sequence encoding H5 from influenza A/Indonesia/5/2005 (H5N1) (SEQ ID NO: 42).

FIG. 2A shows primer IF-S1-M1+M2ANC.c (SEQ ID NO:7). FIG. 2B shows primer IF-S1-4-M2ANC.r (SEQ ID NO: 8). FIG. 2C shows the nucleotide sequence for the synthesized M2 gene (corresponding to nt 1-26 joined to 715-982 from Genbank accession number DQ508860) (SEQ ID NO: 9). FIG. 2D shows the expression cassette number 1261 from 2X358 promoter to NOS terminator. M2 from influenza A/New Caledonia/20/1999 (H1N1) is underlined.

(SEQ ID NO: 10). FIG. 2E shows the amino acid sequence of M2 from influenza A/New Caledonia/20/1999 (H1N1) (SEQ ID NO: 11).

FIG. 3A shows the nucleotide sequence of the synthesized M2 gene (corresponding to nt 26-51 joined to nt 740-1007 from Genebank accession number EF467824) (SEQ ID NO: 12). FIG. 3B shows the expression cassette number 859 from 2X358 promoter to NOS terminator. M2 from Influenza A/Puerto Rico/8/1934 (H1N1) is underlined. (SEQ ID NO: 13). FIG. 3C shows the amino acid sequence of M2 from influenza A/Puerto Rico/8/1934 (H1N1) (SEQ ID NO:14).

FIG. 4A shows primer IF-H1A-C-09.s2+4c (SEQ ID NO: 15). FIG. 4B shows primer IF-H1A-C-09.s1-4r (SEQ ID NO: 16). FIG. 4C shows the nucleotide sequence of the synthesized H1 gene (Genbank accession number FJ966974) (SEQ ID NO: 17). FIG. 4D shows a schematic representation of construct 1192. SacII and StuI restriction enzyme sites used for plasmid linearization are annotated on the representation. FIG. 4E shows construct 1192 from left to right t-DNA borders (underlined). 2X35S/CPMV-HT/PDISP/NOS with Plastocyanine-P19-Plastocyanine silencing inhibitor expression cassette (SEQ ID NO: 18). FIG. 4F shows expression cassette number 484 from 2X355 promoter to NOS terminator. PDISP/H1 from influenza A/California/7/2009 (H1N1) is underlined. (SEQ ID NO: 19). FIG. 4G shows amino acid sequence of PDISP-H1 from influenza A/California/7/2009 (H1N1) (SEQ ID NO: 20).

FIG. 5A shows primer IF-S2+S4-H3 Per.c (SEQ ID NO: 21). FIG. 5B shows primer IF-S1a4-H3 Per.r (SEQ ID NO: 22). FIG. 5C shows the nucleotide sequence of the synthesized H3 gene (corresponding to nt 26-1726 from Genbank accession number GQ293081) (SEQ ID NO: 23). FIG. 5D shows the expression cassette number 1019 from 2X355 promoter to NOS terminator. PDISP/H3 from influenza A/Perth/16/2009 (H3N2) is underlined. (SEQ ID NO: 24). FIG. 5E shows the amino acid sequence of PDISP/H3 from influenza A/Perth/16/2009 (H3N2) (SEQ ID NO: 25).

FIG. 6A shows primer IF-S2+S4-B Bris.c (SEQ ID NO: 26). FIG. 6B shows primer IF-S1a4-B Bris.r (SEQ ID NO: 27). FIG. 6C shows the nucleotide sequence of synthesized HA B Brisbane gene (corresponding to nt 34-1791 from Genbank accession number FJ766840) (SEQ ID NO: 28). FIG. 6D shows the nucleotide sequence of expression cassette number 1029 from 2X355 promoter to NOS terminator. PDISP/HA from influenza B/Brisbane/60/2008 is underlined. (SEQ ID NO: 29). FIG. 6E shows the amino acid sequence of PDISP/HA from influenza B/Brisbane/60/2008 (SEQ ID NO: 30). FIG. 6F shows a schematic representation of construct 1194. SacII and StuI restriction enzyme sites used for plasmid linearization are annotated on the representation. FIG. 6G shows construct 1194 from left to right t-DNA borders (underlined). 2X35S/CPMV-HT/PDISP/NOS into BeYDV+Replicase amplification system with Plastocyanine-P19-Plastocyanine silencing inhibitor expression cassette (SEQ ID NO: 31). FIG. 6H shows expression cassette number 1008 from BeYDV left LIR to BeYDV right LIR. PDISP/HA from influenza B/Brisbane/60/2008 is underlined. (SEQ ID NO: 32).

FIG. 7A shows primer dTmH5I-B Bris.r (SEQ ID NO: 33). FIG. 7B shows primer B Bris-dTmH5I.c (SEQ ID NO: 34). FIG. 7C shows primer IF-51a54-dTmH5I.r (SEQ ID NO: 35). FIG. 7D shows expression cassette number 1009 from BeYDV left LIR to BeYDV right LIR. PDISP/HA B Brisbane/H5Indo TMCT is underlined. (SEQ ID NO:36). FIG. 7E shows amino acid sequence of PDISP/HA B Brisbane/H5Indo TMCT (SEQ ID NO: 37).

FIG. 8A shows primer 1039+1059.r (SEQ ID NO: 38). FIG. 8B shows primer 1039+1059.c (SEQ ID NO: 39). FIG. 8C shows expression cassette number 1059 from BeYDV left LIR to BeYDV right LIR. PDISP/HA from influenza B/Brisbane/60/2008 with deleted proteolytic loop is underlined. (SEQ ID NO: 40). FIG. 8D shows amino acid sequence of PDISP/HA from influenza B/Brisbane/60/2008 with deleted proteolytic loop (SEQ ID NO: 41). FIG. 8E shows nucleotide sequence of PDISP/HA from influenza B/Brisbane/60/2008 with deleted proteolytic loop (SEQ ID NO: 43).

Figure 19:
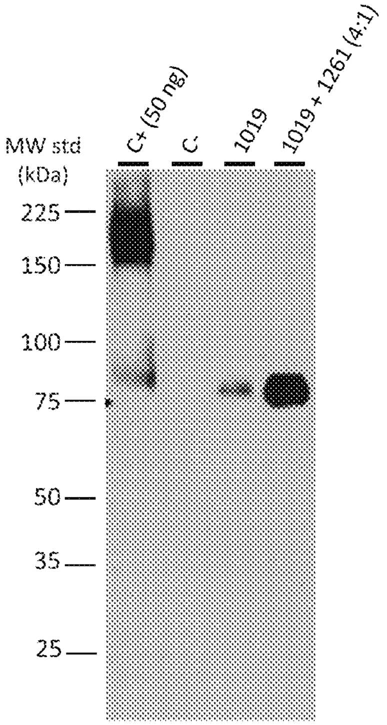

FIG. 19 shows a Western blot analysis of HA protein expression in agroinfiltrated *Nicotiana benthamiana* leaves. Lane "C+": Positive control, semi-purified A/Wisconsin/15/2009 (H3N2) virus from the Therapeutic Goods Administration, Australia; "C-": negative control, mock-infiltrated plants; "'1019": expression of wild-type HA from A/Perth/16/2009 (H3N2); "1019+1261": co-expression of wild-type HA from A/Perth/16/2009 (H3N2) with M2 from A/New Caledonia/20/99. The ratio indicates the proportion of *Agrobacterium* cultures used in co-expression experiments.

Figure 20:
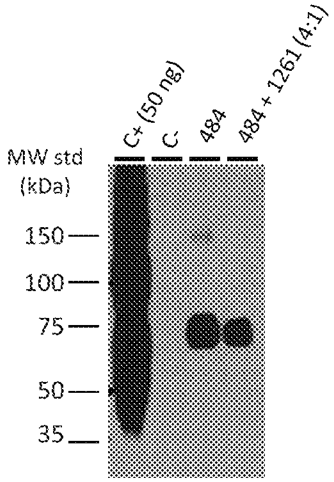

FIG. 20 shows a Western blot analysis of HA protein expression in agroinfiltrated *Nicotiana benthamiana* leaves. Lane "C+": Positive control, semi-purified A/California/7/2009 (H1N1) NYMC X-179A from NIBSC virus (NIBSC code 09/146); "C-": negative control, mock-infiltrated plants; "484": expression of wild-type HA from A/California/7/2009 (H1N1); "484+1261": co-expression of wild-type HA from A/California/7/2009 (H1N1) with M2 from A/New Caledonia/20/99. The ratio indicates the proportion of *Agrobacterium* cultures used in co-expression experiments.

Figure 21:
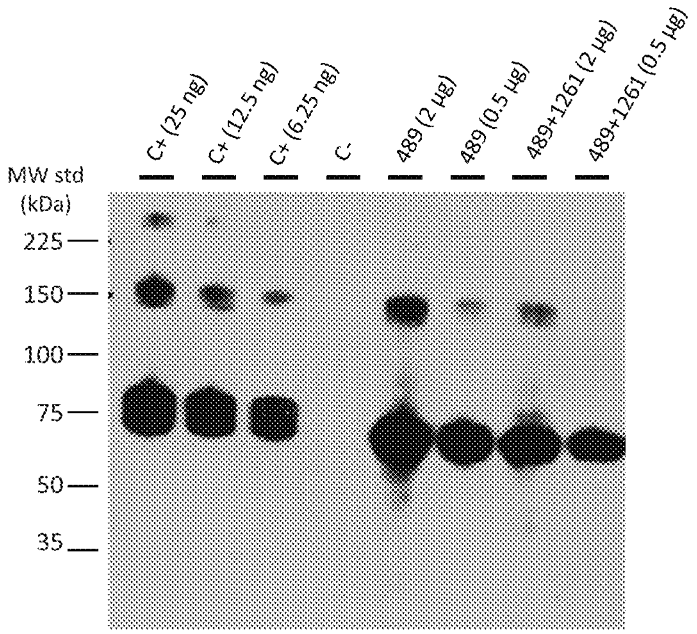

FIG. 21 shows a Western blot analysis of HA protein expression in agroinfiltrated *Nicotiana benthamiana* leaves. Lane "C+": Positive control, purified recombinant H5 from A/Indonesia/05/2005, Immune Technology Corporation (product no. IT-003-052p); "C-": negative control, mock-infiltrated plants; "489": expression of wild-type HA from A/Indonesia/5/05 (H5N1); "489+1261": co-expression of wild-type HA from A/Indonesia/5/05 (H5N1) with M2 from A/New Caledonia/20/99.

Figures 22A, 22B:
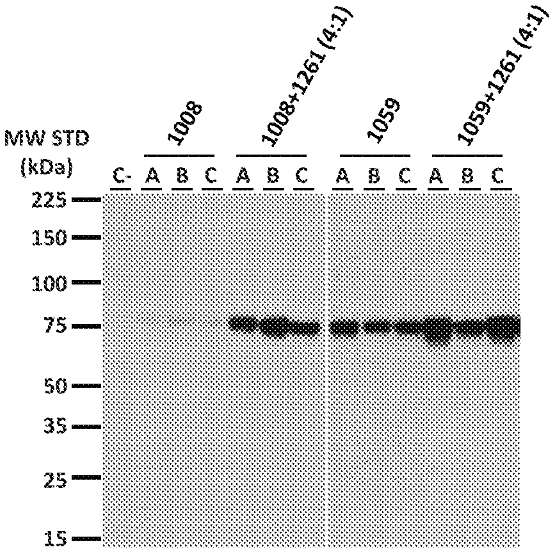

FIG. 22A shows a Western blot analysis of HA protein expression in agroinfiltrated *Nicotiana benthamiana* leaves. "1008": expression of wild-type HA from B/Brisbane/60/2008 in the presence of amplification elements (BeYDV); "1008+1261": co-expression of wild-type HA from B/Brisbane/60/2008 in the presence of amplification elements (BeYDV) with M2 from A/New Caledonia/20/99; "1059": expression of mutant HA from B/Brisbane/60/2008 in the presence of amplification elements (BeYDV); "1059+1261": co-expression of mutant HA from B/Brisbane/60/2008 in the presence of amplification elements (BeYDV) with M2 from A/New Caledonia/20/99. Plants from three separate infiltrations were analyzed (A, B and C). Ratios indicate the proportion of *Agrobacterium* cultures used in co-expression experiments. FIG. 22B shows a comparison of hemagglutination capacity of crude protein extracts from HA-producing plants.

Figure 23A:
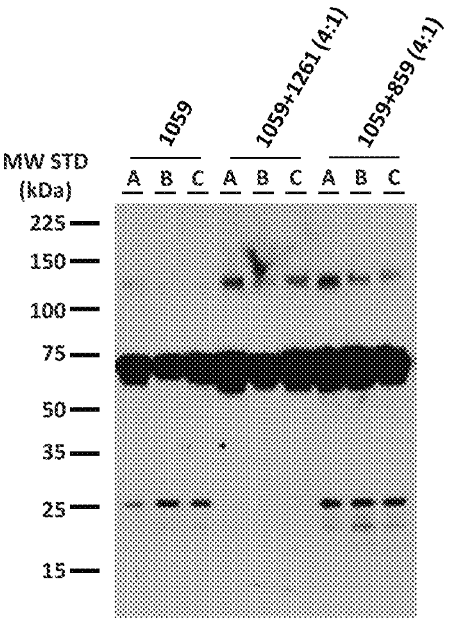
Figure 23B:
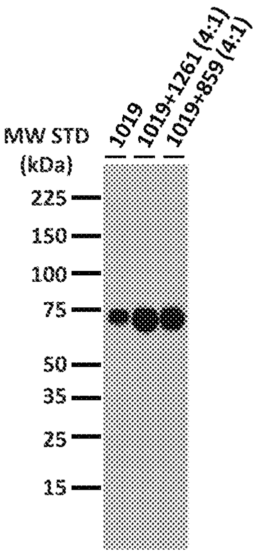

FIGS. 23A and 23B shows a Western blot analysis of HA protein expression in agroinfiltrated *Nicotiana benthamiana* leaves. FIG. 23A: "1059": expression of mutant HA from B/Brisbane/60/2008 in the presence of amplification elements (BeYDV); "1059+1261": co-expression of mutant HA from B/Brisbane/60/2008 in the presence of amplification elements (BeYDV) with M2 from A/New Caledonia/20/99. "1059+859": co-expression of mutant HA from B/Brisbane/60/2008 in the presence of amplification elements (BeYDV) with M2 from A/Puerto Rico/8/34. Plants from three separate infiltrations were analyzed (A, B and C). Ratios indicate the proportion of *Agrobacterium* cultures used in co-expression experiments. FIG. 23B: "1019": expression of wild-type HA from A/Perth/16/2009 (H3N2); "1019+1261": co-expression of wild-type HA from A/Perth/16/2009 (H3N2) with M2 from A/New Caledonia/20/99; "1019+859": co-expression of wild-type HA from A/Perth/16/2009 (H3N2) with M2 from A/Puerto Rico/8/34. Ratios indicate the proportion of *Agrobacterium* cultures used in co-expression experiments.

Figure 24:
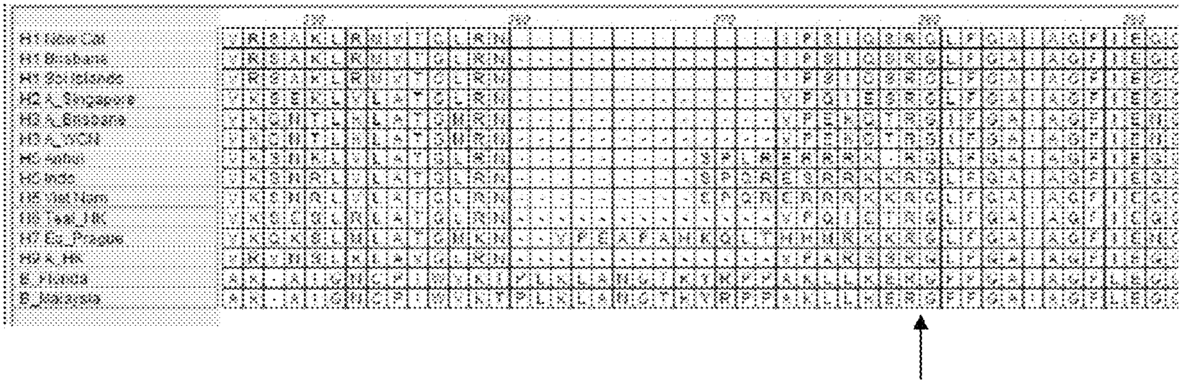

FIG. 24 shows the sequence alignment of HAs from several strains of influenza. The cleavage site of the precursor HA0 is indicated by an arrow.

FIG. 25A shows primer IF-H3V36111.S2+4c (SEQ ID NO: 44). FIG. 25B shows primer IF-H3V36111.s1-4r (SEQ ID NO: 45). FIG. 25C shows the nucleotide sequence of synthesized H3 gene (corresponding to nt 25 to 1725 from GISAID isolate number EPI ISL 101506 HA sequence) (SEQ ID NO: 46). FIG. 25D shows the nucleotide sequence of expression cassette number 1391 from 2X355 promoter to NOS terminator. PDISP/H3 from influenza A/Victoria/361/2011 (H3N2) is underlined. (SEQ ID NO: 47). FIG. 25E shows the amino acid sequence of PDISP-H3 from influenza A/Victoria/361/2011 (H3N2) (SEQ ID NO: 48). FIG. 25F shows a schematic representation of construct 1391.

FIG. 26A shows primer IF-HAB110.S1+3c (SEQ ID NO: 49). FIG. 26B shows primer IF-HAB110.s1-4r (SEQ ID NO: 50). FIG. 26C shows the nucleotide sequence of synthesized HA B Wisconsin (Genbank accession number JN993010) (SEQ ID NO: 51). FIG. 26D shows a schematic representation of construct 193. FIG. 26E shows construct 193 from left to right t-DNA borders (underlined). 2X355/CPMV-HT/NOS into BeYDV(m)+Replicase amplification system with Plastocyanine-P19-Plastocyanine silencing inhibitor expression cassette (SEQ ID NO: 52). FIG. 26F shows the nucleotide sequence of expression cassette number 1462 from 2X355 promoter to NOS terminator. HA from influenza B/Wisconsin/1/2010 is underlined (SEQ ID NO: 53). FIG. 26G shows the amino acid sequence of HA from influenza B/Wisconsin/1/2010 (SEQ ID NO: 54). FIG. 26H shows a schematic representation of construct 1462.

FIG. 27A shows primer HAB110(PrL-).r (SEQ ID NO: 55). FIG. 27B shows primer HAB110(PrL-).c (SEQ ID NO: 56). FIG. 27C shows the nucleotide sequence of expression cassette number 1467 from 2X355 promoter to NOS terminator. HA from influenza B/Wisconsin/1/2010 with deleted proteolytic loop is underlined (SEQ ID NO: 57). FIG. 27D shows the amino acid sequence of influenza B/Wisconsin/1/2010 with deleted proteolytic loop (SEQ ID NO: 58). FIG. 27E shows a schematic representation of construct 1467.

Figure 28H:
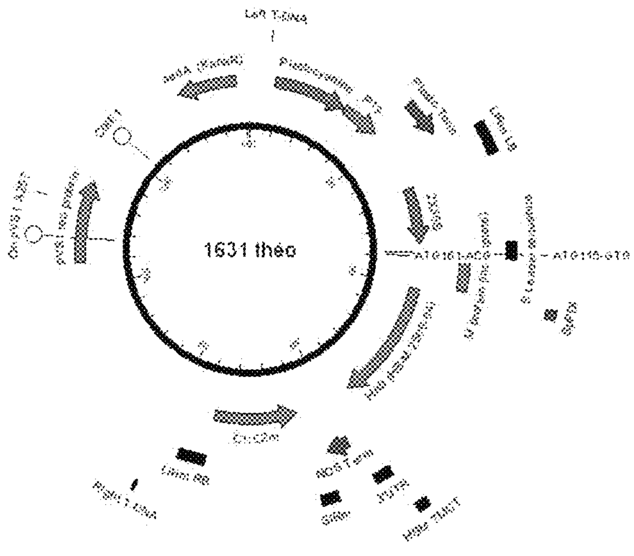

FIG. 28A shows primer IF-HB-M-04.s2+4c (SEQ ID NO: 59). FIG. 28B shows primer IF-HB-M-04.s1-4r (SEQ ID NO: 60). FIG. 28C shows the nucleotide sequence of synthesized HA B Malaysia (corresponding to nt 31-1743 from Genbank accession number EU124275) with T759C and C888G mutations being underlined. (SEQ ID NO: 61). FIG. 28D shows a schematic representation of construct 194, with SacII and StuI restriction enzyme sites used for plasmid linearization being annotated on the representation. FIG. 28E shows construct 194 from left to right t-DNA borders (underlined). 2X35S/CPMV-HT/NOS into BeYDV (m)+Replicase amplification system with Plastocyanine-P19-Plastocyanine silencing inhibitor expression cassette (SEQ ID NO: 62). FIG. 28F shows the nucleotide sequence of expression cassette number 1631 from 2X355 promoter to NOS terminator. PDISP-HA from influenza B/Malaysia/2506/2004 is underlined. (SEQ ID NO: 63). FIG. 28G shows the amino acid sequence of PDISP-HA from influenza B/Malaysia/2506/2004 (SEQ ID NO: 64). FIG. 28H shows a schematic representation of construct 1631.

Figure 29:
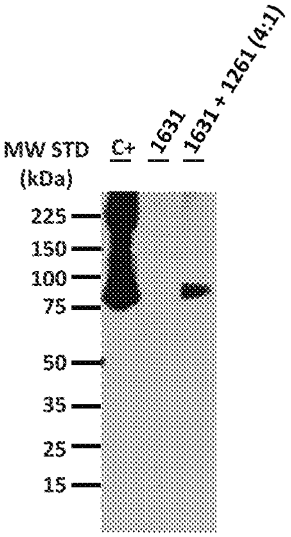

FIG. 29 shows a Western blot analysis of HA protein expression in agroinfiltrated *Nicotiana benthamiana* leaves. HA from B/Malaysia/2506/2004 is co-expressed with M2 from A/New Caledonia/20/99. Twenty micrograms of protein extract were loaded per lane. "C+": positive control, semi-purified B/Malaysia/2506/2004 virus from the National Institute for Biological Standards and Control, United Kingdom; "1631": expression of wild-type HA from B/Malaysia/2506/2004 in the presence of amplification elements (BeYDV); "1631+1261": co-expression of wild-type HA from B/Malaysia/2506/2004 in the presence of amplification elements (BeYDV) with M2. Ratios indicate the proportion of *Agrobacterium* cultures used in co-expression experiments.

Figures 30A, 30B:
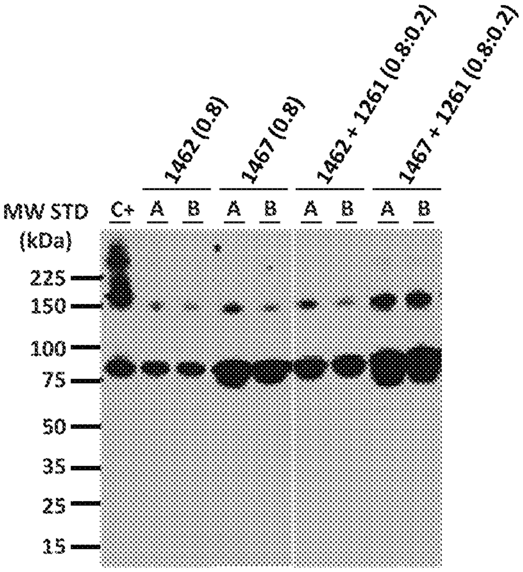

FIG. 30A shows a Western blot analysis of HA protein expression in agroinfiltrated *Nicotiana benthamiana* leaves. HA from B/Wisconsin/1/2010 is co-expressed with M2 from A/New Caledonia/20/99. Ten micrograms of protein extract were loaded per lane. "C+": positive control, semi-purified B/Wisconsin/1/2010 virus from the National Institute for Biological Standards and Control, United Kingdom; "1462": expression of wild-type HA from B/Wisconsin/1/2010 in the presence of amplification elements (BeYDV); "1467": expression of the mutant HA from B/Wisconsin/1/2010 in the presence of amplification elements (BeYDV); "1462+1261": co-expression of wild-type HA from B/Wisconsin/1/2010 in the presence of amplification elements (BeYDV) with M2; "1467+1261": co-expression of the mutant HA from B/Wisconsin/1/2010 in the presence of amplification elements (BeYDV) with M2. Ratios indicate the optical density for each *Agrobacterium* culture used in expression and co-expression experiments. FIG. 30B shows a comparison of hemagglutination capacity of crude protein extracts from plants transformed with AGL1/1462, AGL1/1467, AGL1/1462+AGL1/1261 and AGL1/1467+AGL1/1261.

Figure 31:
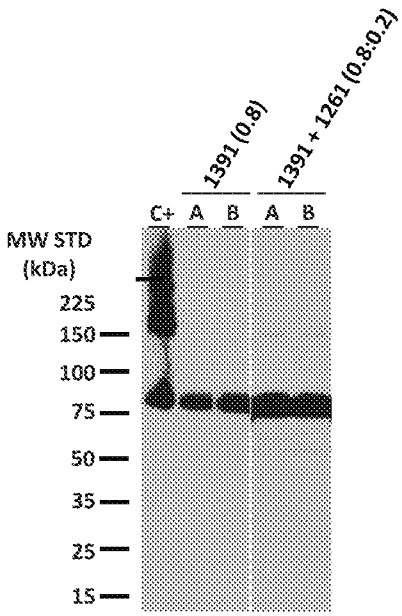

FIG. 31 shows a Western blot analysis of HA protein expression in agroinfiltrated *Nicotiana benthamiana* leaves. HA from H3/Victoria/361/2011 is co-expressed with M2 from A/New Caledonia/20/99. Twenty micrograms of protein extract were loaded per lane. "C+": positive control, semi-purified H3/Wisconsin/15/2009 virus from the Therapeutic Goods Administration, Australia; "1391": expression of wild-type HA from H3/Victoria/361/2011; "1391+1261": co-expression of wild-type HA from H3/Victoria/361/2011 with M2. Ratios indicate the optical density for each *Agrobacterium* culture used in expression and co-expression experiments.

DETAILED DESCRIPTION

The following description is of a preferred embodiment.

The present invention relates to virus-like particles (VLPs) and methods of producing and increasing VLP yield and production in plants.

The present invention provides, in part, a method of producing a virus like particle (VLP) in a plant, or portion of the plant. The method involves introducing a first nucleic acid and a second nucleic acid into the plant. The first nucleic acid comprises a first regulatory region active in the plant or portion of the plant, and operatively linked to a nucleotide sequence encoding a structural virus protein. The second nucleic acid comprising a second regulatory region active in the plant and operatively linked to a nucleotide sequence encoding a channel protein, for example but not limited to a proton channel protein. The first regulatory region and the second regulatory region may be the same or different. The plant or portion of the plant is incubated under conditions that permit the expression of the nucleic acids, thereby producing the VLP. If desired, the plant or portion of the plant may be harvested and the VLP purified. Preferably, the VLP does not contain M1, a viral matrix or a core protein. The present invention also provides a VLP produced by this method. The VLP may comprise one or more than one lipid derived from a plant. The VLP may be used to prepare a composition comprising an effective dose of the VLP for inducing an immune response, and a pharmaceutically acceptable carrier.

The present invention also provides plant matter comprising the VLP produced by expressing the first and second nucleic acids described above. The plant matter may be used in inducing immunity to an influenza virus infection in a subject. The plant matter may also be admixed as a food supplement.

The VLP of the present invention may also be produced by providing a plant or portion of the plant comprising a first nucleic acid and second nucleic acid as defined above, and incubating the plant or portion of the plant under conditions that permit the expression of the first and second nucleic acids, thereby producing the VLP. The VLP may comprise one or more than one lipid derived from a plant. The VLP may be used to prepare a composition comprising an effective dose of the VLP for inducing an immune response, and a pharmaceutically acceptable carrier. The present invention also provides plant matter comprising the VLP produced by expressing the first and second nucleic acids. The plant matter may be used in inducing immunity to an influenza virus infection in a subject. The plant matter may also be admixed as a food supplement.

The VLPs of the present invention comprise one or more virus proteins. For example, which is not to be considered limiting, the one or more virus protein may be a structural viral protein such as influenza hemagglutinin (HA) or a channel protein, for example but not limited to a proton channel protein, such as for example M2. The HA may be any HA, for example an H2, H3, H4, H6, H7, H8, H9, H10, H11, H12, H13, H14, H15, H16 or type B HA as described in WO 2009/009876; WO 2009/076778; WO 2010/003225; WO 2010/003235; WO 2011/03522; which are incorporated herein by reference).

As described in more detail below, VLPs may be produced in a plant by co-expressing a first nucleic acid encoding a virus protein with a second nucleic acid encoding a channel protein, for example but not limited to a proton channel protein. The first and second nucleic acids may be introduced to the plant in the same step, or they may be introduced to the plant sequentially. The first and second nucleic acids may be introduced in the plant in a transient manner, or in a stably manner. Furthermore, a plant that expresses a first nucleic acid encoding a viral protein may transformed with a channel protein, for example but not limited to a proton channel protein, (second nucleic acid) so that both the first and the second nucleic acids are co-expressed in the plant. Alternatively, a plant that expresses a channel protein, for example but not limited to a proton channel protein, (second nucleic acid) may transformed with a first nucleic acid encoding a viral protein so that both the first and the second nucleic acids are co-expressed in the plant. Additionally, a first plant expressing the first nucleic acid encoding a viral protein, may be crossed with a second plant expressing the second nucleic acid encoding the channel protein for example but not limited to a proton channel protein, to produce a progeny plant that co-expresses the first and second nucleic acids encoding the viral protein and the channel protein, for example but not limited to a proton channel protein, respectively.

The present invention also provides a method of increasing expression and yield of a virus protein in plant by co-expressing a first nucleic acid encoding a virus protein with a second nucleic acid encoding a channel protein, for example but not limited to a proton channel protein. The first and second nucleic acids may be introduced to the plant in the same step, or they may be introduced to the plant sequentially. The first and second nucleic acids may be introduced in the plant in a transient manner, or in a stably manner. Furthermore, a plant that expresses a first nucleic acid encoding a viral protein may transformed with a channel protein, for example but not limited to a proton channel protein (second nucleic acid) so that both the first and the second nucleic acids are co-expressed in the plant. Alternatively, a plant that expresses a channel protein, for example but not limited to a proton channel protein (second nucleic acid) may transformed with a first nucleic acid encoding a viral protein so that both the first and the second nucleic acids are co-expressed in the plant. Additionally, a first plant expressing the first nucleic acid encoding a viral protein, may be crossed with a second plant expressing the second nucleic acid encoding the channel protein, for example but not limited to a proton channel protein, to produce a progeny plant that co-expresses the first and second nucleic acids encoding the viral protein and the channel protein for example but not limited to a proton channel protein, respectively.

Channel Protein

By "channel protein" it is meant a protein that is capable of forming a channel across a phospholipid membrane that allows for the crossing of ions and/or small molecules through the membrane. Channel proteins may be selective for size and/or charge of the ions and/or small molecules. Non limiting examples of channel proteins are non-specific channel protein that alter permeability of membranes to low molecular weight compounds and ion channel protein, such as for example chloride channel, potassium channel, sodium channel, calcium channel and proton channel.

By "proton channel protein" it is meant a protein that is capable of forming a proton selective channel across a phospholipid bilayer. The proton channel protein may be a single pass membrane protein with a transmembrane (TM) domain flanked by hydrophobic domains. The TM domain of the proton channel may comprise the sequence HXXXW (SEQ ID NO. 1).

Following cleavage of HA0, HA becomes sensitive to pH, undergoing irreversible conformational change at the pH of endosome (<pH 6.0). The conformation of the precursor HA0 is stable at low pH, but the cleaved HA1-HA2 form, is metastable (Bullough P A et. al., 1994, Nature. Vol 371:37-43). Studies on the pH threshold that induce conformational changes in different HAs, show that this threshold is approx pH 5.8-5.9 for the B strains, whereas it is more acidic (pH 5.1 to 5.3) for type A HAs (Beyer W E P et al, 1986, Archives Virol, vol 90: 173). During extraction of the plant biomass (between pH 5-6), a conformational change of HA1-HA2 may also take place with type B HA.

Without wishing to be bound by theory, the pH of a cellular compartment comprising HA, including the Golgi apparatus, may therefore be important for the folding, stability and/or proteolysis of HA. Proton channel proteins, such as for example influenza M2 and BM2 protein may regulate the pH in cellular compartments. For example, M2 regulates the potentiation of membrane fusion by buffering intracellular compartments both in late and early stages of influenza viral replication. Early in infection of new cells after endocytic uptake of viral particles, activation of M2 proton channel activity leads to acidification of the interior of the virion during the uncoating process. Late in infection during virus production, M2 acts to raise the pH during transit through the trans-Golgi network and prevents the low pH-induced inactivation of co-transported proteins, such as HA in the case of influenza. By co-expressing a structural virus protein along with a channel protein, for example but not limited to a proton channel protein, increased yield of the structural virus protein and VLPs are observed. HA's are known to under go pH-dependent confirmation change. Without wishing to bound by theory, the pH within the Golgi apparatus of the HA producing cells during maturation and migration may influence HA folding, effects stability and increase degradation, or a combination thereof, of the HA. By co-expressing a channel protein, for example but not limited to a proton channel protein, along with an HA, the pH within the Golgi apparatus may increase, and result in an increase in stability, reduction of degradation, or a combination thereof, and increase expression levels and yield of HA and/or VLPs.

By co-expressing a structural virus protein along with a channel protein, for example but not limited to a proton channel protein, in a plant, increased yield of the structural virus protein and/or VLPs are observed, when compared to a plant that expressed the structural virus protein without co-expression of the channel protein, for example but not limited to a proton channel protein.

Furthermore, by co-expressing a structural virus protein such as HA with a channel protein, for example but not limited to a proton channel protein, in a plant, the HA protein may exhibits an increased activity as shown by a greater hemagglutination capacity, when compared to a HA protein that is not co-expressed with a channel protein, for example but not limited to a proton channel protein. By an increase in activity, it is meant an increase in hemagglutination capacity by about 2% to about 100%, or any amount therebetween as determined using standard techniques in the art, for example, from about 10% to about 50% or any value therebetween for example about 2, 5, 8, 10, 12, 15, 18, 20, 22, 24, 25, 26, 28, 30, 32, 34, 35, 36, 38, 40, 42, 44, 45, 46, 48, 50, 52, 54, 55, 56, 58, 60, 65, 70, 75, 80, 85, 90, 95, or 100%, when compared to the activity of the same HA protein produced in the absence of a channel protein, for example but not limited to a proton channel protein.

As used herein, the terms "M2," "M2 protein," "M2 sequence" and "M2 domain" refer to all or a portion of an M2 protein sequence isolated from, based upon or present in any naturally occurring or artificially produced influenza virus strain or isolate. Thus, the term M2 and the like include naturally occurring M2 sequence variants produced by mutation during the virus life-cycle or produced in response to a selective pressure (e.g., drug therapy, expansion of host cell tropism or infectivity, etc.), as well as recombinantly or synthetically produced M2 sequences. Examples of channel proteins that may be used include, but are not limited to proton channel proteins for example those listed in Table 1. Non-limiting example of sequences that may be used with the present invention include M2 from A/Puerto Rico/8/1934 and M2 from A/New Caledonia/20/1999. An exemplary M2 protein consists of the amino acid sequence as shown in SEQ ID NO: 11 or 14.

As used herein, the terms "BM2," "BM2 protein," "BM2 sequence" and "BM2 domain" refer to all or a portion of a BM2 protein sequence isolated from, based upon or present in any naturally occurring or artificially produced influenza virus strain or isolate. Thus, the term BM2 and the like include naturally occurring BM2 sequence variants produced by mutation during the virus life-cycle or produced in response to a selective pressure (e.g., drug therapy, expansion of host cell tropism or infectivity, etc.), as well as recombinantly or synthetically produced BM2 sequences.

Examples of channel proteins that may be used include, but are not limited to proton channel proteins those listed in Table 2.

Additional exemplary proton channel protein sequences consist of the sequences deposited under the GenBank accession numbers shown in Table 1 and Table 2.

TABLE 1

Accession numbers for amino acids sequences M2 proton channel proteins

| GenBank accession number | GenBank accession number | GenBank accession number | GenBank accession number | GenBank accession number |
|---|---|---|---|---|
| ABA42438.1 | ABB54697.1 | ABI36079.1 | ADM95491.1 | ADM29632.1 |
| ABA42436.1 | AAA43253.1 | ABI36077.1 | ADM95489.1 | ADM29566.1 |
| ABA42434.1 | BAB19809.1 | ABI36075.1 | ADM95487.1 | ADM29555.1 |
| AAD51268.1 | ABD59884.1 | ABI36073.1 | ADM95485.1 | ADM29544.1 |
| AAD51264.1 | ABD59882.1 | ABI36071.1 | ADM95483.1 | ADM29533.1 |
| AAC60735.1 | ABD59880.1 | ABI36069.1 | ADM95481.1 | ADM29445.1 |
| BAI77393.1 | BAD89348.1 | ABI36067.1 | ADM95479.1 | ADM29434.1 |
| BAI77450.1 | BAD89338.1 | ABI36065.1 | ADM95477.1 | ADM29423.1 |
| CAP58009.1 | BAD89328.1 | ABI36063.1 | ADM95475.1 | ADM29412.1 |
| CAP58007.1 | BAE47133.1 | ABI36061.1 | ADM95473.1 | ADM29401.1 |
| CAP58005.1 | ABD59890.1 | ABI36059.1 | ADM95471.1 | ADM29379.1 |
| BAH84754.1 | ABD59888.1 | ABI36037.1 | BAF37390.1 | ADM29368.1 |
| BAH86619.1 | ABD59886.1 | ABI36027.1 | ADG59188.1 | ADM29357.1 |
| BAH86616.1 | ABD59900.1 | ABI36016.1 | ADG59186.1 | ADM29313.1 |
| BAH84985.1 | ABD59898.1 | ABI36005.1 | ADG59184.1 | ADM29302.1 |
| YP_308853.1 | ABD59896.1 | AAY87447.1 | ADG59182.1 | ADM29291.1 |
| AAD49092.1 | ABD59894.1 | AAY87431.1 | ADG59180.1 | ADM29280.1 |
| AAD49090.1 | ABD59892.1 | AAV32647.1 | ADG59178.1 | ADM29269.1 |
| AAD49088.1 | AAC79578.1 | AAV32639.1 | ADG59176.1 | ADM29258.1 |
| ABQ12378.1 | ABB51968.1 | AAU00829.1 | ADG59174.1 | ADM29698.1 |
| AAO33518.1 | ABY75105.1 | AAU00827.1 | ADG59172.1 | ADM29687.1 |
| AAO33516.1 | ABY75039.1 | AAA91324.1 | ADG59170.1 | ADM29676.1 |
| AAO33514.1 | ABY75037.1 | ABG75620.1 | ADG59168.1 | ADM29665.1 |
| AAO33512.1 | AAL60446.1 | ACR09361.1 | ADG59166.1 | ADM29654.1 |
| AAO33510.1 | ABB00351.1 | ACR09359.1 | ADG59164.1 | ADM29621.1 |
| AAO33508.1 | AAA43312.1 | ACR09355.1 | ADG59162.1 | ADM29610.1 |
| AAO33506.1 | ABB00339.1 | ACR09353.1 | ADG59160.1 | ADM29599.1 |
| AAO33504.1 | ABW38094.1 | ACQ99604.1 | ADG59158.1 | ADM29522.1 |
| AAO33502.1 | AAM09299.1 | ACQ99602.1 | ADG59156.1 | ADM29511.1 |
| ABS52607.1 | AAM09297.1 | ACQ99600.1 | ADG59154.1 | ADM29500.1 |
| ABS52597.1 | ABS00915.1 | ACQ99592.1 | ADG59152.1 | ADM29489.1 |
| ABS52587.1 | ABS00914.1 | ACQ99590.1 | ADG59150.1 | ADM29478.1 |
| ABM21873.1 | ABS00913.1 | ACQ99588.1 | ADG59148.1 | ADM29467.1 |
| ABM21871.1 | ABS00912.1 | ACQ99586.1 | ADG59146.1 | ADM29456.1 |
| ABM21869.1 | ABS00911.1 | ACP41965.1 | ADG59144.1 | ADM29390.1 |
| ABM21867.1 | ABS00910.1 | ACP41955.1 | ADG59142.1 | ADM29346.1 |
| ABM21865.1 | ABS00909.1 | ACP41951.1 | ADG59140.1 | ADM29335.1 |
| ABM21863.1 | ABS00908.1 | ACP41946.1 | ADG59138.1 | ADM29324.1 |
| ABM21861.1 | ABS00907.1 | ACR49258.1 | ADG59136.1 | ADM29247.1 |
| AAO33500.1 | ABS00906.1 | ACR49256.1 | ADG59134.1 | AEE73588.1 |
| AAD49094.1 | ABS00905.1 | ACR49254.1 | ADG59132.1 | AEB89880.1 |
| AAD49086.1 | ABS00904.1 | ACR49252.1 | ADG59130.1 | AEB89869.1 |
| AAD49084.1 | ABS00903.1 | ACR49250.1 | ADG59128.1 | AEB89858.1 |
| AAD49082.1 | ABS00902.1 | ACR49248.1 | ADG59126.1 | AEA74023.1 |
| AAD49080.1 | ABB51974.1 | ACR49246.1 | ADG59124.1 | AEA74013.1 |
| AAD49078.1 | ABB51972.1 | ACR49244.1 | ADG59122.1 | ADF42731.1 |
| AAD49076.1 | ABB51970.1 | ACR38840.1 | ADG59120.1 | ADF42721.1 |
| AAD49074.1 | AAD00150.1 | ACR38838.1 | ADG59118.1 | ADF28007.1 |
| AAD49072.1 | AAD00148.1 | ACR38836.1 | ADG59116.1 | ADF27997.1 |
| AAD49070.1 | AAD00146.1 | ACR38834.1 | ADG59114.1 | ADF27987.1 |
| AAD49068.1 | AAD00144.1 | ACR38832.1 | ADG59112.1 | ADF27977.1 |
| ACA25333.1 | AAD00142.1 | ACR18965.1 | ADG59110.1 | ADF27967.1 |
| ACA25323.1 | AAD00140.1 | ACR18963.1 | ADG59108.1 | ADF27957.1 |
| ACA25313.1 | AAD00138.1 | ACR18958.1 | ADG59106.1 | ADF27947.1 |
| CAJ12148.1 | AAD00136.1 | ACR18957.1 | ADG59104.1 | ADF27937.1 |
| CAJ12154.1 | AAD00134.1 | ACR18953.1 | ADG59102.1 | ADF27927.1 |
| CAJ12152.1 | AAD00132.1 | ACR18949.1 | ADG59100.1 | ADF27917.1 |
| CAJ12150.1 | AAD00130.1 | ACR18946.1 | ADG59098.1 | ADF27907.1 |
| ACP41109.1 | AAC80168.1 | ACR18945.1 | ADG59096.1 | ADF27897.1 |
| ADG59536.1 | AAC80166.1 | ACR18943.1 | ADG59094.1 | ADF27887.1 |
| AAK14988.1 | AAC80164.1 | ACR08560.1 | ABO21713.1 | ACS87931.1 |
| AAK14984.1 | AAC80162.1 | ACR08556.1 | ADG59717.1 | ACU44926.1 |
| ACR67209.1 | AAC80160.1 | NP_040979.2 | ADG59706.1 | ACU44922.1 |
| ACP41929.2 | AAC80158.1 | ABZ91697.1 | AAF74335.1 | ACU44920.1 |
| ACR18961.1 | AAC80156.1 | ABZ91685.1 | AAF74333.1 | ACU44918.1 |
| ACR18955.1 | ABY75159.1 | ACB54711.1 | ADF56637.1 | ACU44916.1 |
| ACR18941.1 | ABY75157.1 | ABM90504.1 | ADF56636.1 | ACU44914.1 |
| ACR08564.1 | ABY75155.1 | ABM90493.1 | ADF56635.1 | ACU44912.1 |
| ACR08562.1 | ABY75153.1 | ABM90482.1 | ADF29921.1 | ACU44910.1 |

TABLE 1-continued

Accession numbers for amino acids sequences M2 proton channel proteins

| GenBank accession number | GenBank accession number | GenBank accession number | GenBank accession number | GenBank accession number |
|---|---|---|---|---|
| ACR08558.1 | ABY75151.1 | ABM90471.1 | ADE75385.1 | ACU44908.1 |
| ACQ99594.1 | ABY75149.1 | ABM90460.1 | ADE75374.1 | ACU44906.1 |
| ACQ83308.1 | ABY75147.1 | ABM90449.1 | ADE75365.1 | ACU44904.1 |
| ACQ76400.1 | ABY75145.1 | ABM90438.1 | ADE75354.1 | ACU44902.1 |
| ACQ76382.1 | ABY75143.1 | ABI49411.1 | ADE75344.1 | ACU44900.1 |
| ACQ76375.1 | ABY75141.1 | ABI49400.1 | ADE75327.1 | ACU44898.1 |
| ACQ76369.1 | ABY75139.1 | ABO31433.1 | ADE75298.1 | ACU44896.1 |
| ACQ76361.1 | ABY75137.1 | ABM90548.1 | ADE75287.1 | ACU44894.1 |
| ACQ76355.1 | ABY75135.1 | ABM90537.1 | ADE75276.1 | ACU44892.1 |
| ACQ76346.1 | ABY75133.1 | ABM90526.1 | ADE75265.1 | ACU44890.1 |
| ACQ76332.1 | ABY75131.1 | ABM90515.1 | ADE75254.1 | ACU44888.1 |
| ACQ76325.1 | ABY75129.1 | ABL31784.1 | ADE75244.1 | ACU44886.1 |
| ACQ76313.1 | ABY75127.1 | ABL31770.1 | ADE75235.1 | ACU44883.1 |
| ACQ76303.1 | ABY75125.1 | ABL31759.1 | ADE75228.1 | ACU44881.1 |
| ACQ76293.1 | ABY75123.1 | ABL31748.1 | ADE75218.1 | ACU44879.1 |
| ACQ63288.1 | ABY75121.1 | ABI49419.1 | ADE75207.1 | ACU44877.1 |
| ACQ63259.1 | ABY75119.1 | ABL07034.1 | ADE75196.1 | ACU44875.1 |
| ACQ63250.1 | ABY75117.1 | ABL07023.1 | ADE75187.1 | ACU44873.1 |
| ACQ63217.1 | ABY75115.1 | ABL07012.1 | ADE75178.1 | ACU44871.1 |
| ACQ63211.1 | ABY75113.1 | ACC55276.2 | ADE75170.1 | ACU44869.1 |
| ACQ55364.1 | ABY75111.1 | ABV53559.1 | ADE75152.1 | ACU44867.1 |
| ACQ55353.1 | ABY75109.1 | AEB71385.1 | ADE75143.1 | ACU44865.1 |
| ACP44171.1 | ABY75107.1 | AEB66897.1 | ADE75134.1 | ACU44863.1 |
| ACP44160.1 | ABY75103.1 | AEB40208.1 | ADE75124.1 | ACU44861.1 |
| ACP44153.1 | ABY75101.1 | ADX36111.1 | ADE75115.1 | ACU44859.1 |
| ACP44149.1 | ABY75099.1 | ADX21100.1 | ADE75095.1 | ACU44857.1 |
| ACR18951.2 | ABY75097.1 | ADX21090.1 | ADE75085.1 | ACU44855.1 |
| AAY87421.1 | ABY75095.1 | ADX21080.1 | ADE75075.1 | ACU44853.1 |
| AAY87413.1 | ABY75093.1 | ADW93762.1 | ADE75057.1 | ACU44851.1 |
| ACQ63284.1 | ABY75091.1 | ADW82270.1 | ADE75046.1 | ACU44849.1 |
| ACQ63275.1 | ABY75089.1 | ADW82260.1 | ADE75030.1 | ACU44847.1 |
| ACQ63266.1 | ABY75087.1 | ADW82250.1 | ACL11961.1 | ACU44845.1 |
| ACQ63225.1 | ABY75085.1 | ADW82240.1 | ABY40439.1 | ACU44843.1 |
| ACP44185.1 | ABY75083.1 | ADW82230.1 | ABY40432.1 | ACU44841.1 |
| ACP44178.1 | ABY75081.1 | ADW82220.1 | AAD25212.1 | ACU44839.1 |
| ACA28776.1 | ABY75079.1 | ADW82210.1 | AAD25206.1 | ACU44837.1 |
| ACA28772.1 | ABY75077.1 | ADW82200.1 | AAD25172.1 | ACU44835.1 |
| ACA28768.1 | ABY75075.1 | ADW82190.1 | BAF36962.1 | ACU44833.1 |
| ACR49240.1 | ABY75073.1 | ADW82179.1 | ABI94583.1 | ACU44831.1 |
| ACQ84453.1 | ABY75071.1 | ADW82168.1 | ACT21522.1 | ACU44829.1 |
| ACU00946.2 | ABY75069.1 | ADW82157.1 | ABY81638.1 | ACU44827.1 |
| ACR46665.1 | ABY75067.1 | ADW82148.1 | ACF40971.1 | ACU44825.1 |
| ACZ81655.1 | ABY75065.1 | ADW82137.1 | ACD88518.1 | ACU44823.1 |
| ACZ81651.1 | ABY75063.1 | ADW82126.1 | ACD88507.1 | ACU44821.1 |
| ACR46675.1 | ABY75061.1 | ADV19021.1 | ABW97453.1 | ACU44819.1 |
| ACU00956.1 | ABY75059.1 | ADL41167.1 | ACZ81646.1 | ACU44817.1 |
| ACU00936.1 | ABY75057.1 | AAF74337.1 | YP 308670.1 | ACU44815.1 |
| ACT21587.1 | ABY75055.1 | ACS92616.1 | AAA56808.1 | ACU44813.1 |
| ACT21581.1 | ABY75053.1 | ACC94117.1 | AAA56806.1 | ACU44811.1 |
| ACT21576.1 | ABY75051.1 | ACC94089.1 | ABS00311.1 | ACU44809.1 |
| ACR19302.2 | ABY75049.1 | ACC94087.1 | ABS00320.1 | ACU44807.1 |
| ACR19300.2 | ABY75047.1 | ACC94085.1 | ACR08491.1 | ACU44805.1 |
| ACR19298.2 | ABY75045.1 | ACC94071.1 | ACR01010.1 | ACU44803.1 |
| ACR19296.2 | ABY75043.1 | ACC94067.1 | ACR01006.1 | ACU44801.1 |
| ABX10529.1 | ABY75041.1 | ACC94065.1 | ACG80612.1 | ACU44799.1 |
| ABJ90284.2 | ABY75035.1 | ACC94059.1 | ABG78553.1 | ACU44797.1 |
| ABJ90273.2 | ABY75033.1 | ACC94057.1 | ABG78550.1 | ACU44795.1 |
| ABJ90230.1 | ABY75031.1 | ACC94051.1 | ACD37773.1 | ACU44793.1 |
| ADD21567.1 | ABY75029.1 | ACC94041.1 | ACD37763.1 | ACU44791.1 |
| ACU44924.1 | ABY75027.1 | ACC94033.1 | ACA64013.1 | ACU44789.1 |
| ACU44779.1 | ABY75025.1 | ABW97496.1 | ABX10519.1 | ACU44787.1 |
| ACU44773.1 | ABY75023.1 | ACA28780.1 | ABW95953.1 | ACU44785.1 |
| ADE48138.1 | ABY75021.1 | ACA28778.1 | ABW95942.1 | ACU44783.1 |
| ACG80349.1 | ABY75019.1 | ACA28774.1 | ABJ90263.1 | ACU44781.1 |
| ADN34731.1 | ABY75017.1 | ACA28770.1 | ABJ90251.1 | ACU44777.1 |
| ADN34711.1 | ABY75015.1 | ACA28766.1 | ABJ90241.1 | ACU44775.1 |
| ADG59534.1 | ABY75013.1 | ACZ81636.1 | BAF38386.1 | ACU44771.1 |
| ADG59532.1 | ABY75011.1 | ACU27045.1 | BAF37824.1 | ACU44769.1 |
| ADG59530.1 | ABY75009.1 | ACR54040.1 | BAF33431.1 | ACU44767.1 |
| ACX43975.1 | ABY75007.1 | ACH68522.1 | BAF33417.1 | ACU44765.1 |
| ACX43973.1 | ABY75005.1 | ACF04730.1 | BAF33412.1 | ACU44763.1 |
| ABG91471.1 | ABY75003.1 | ACF04728.1 | BAF33401.1 | ACU44761.1 |
| ABG91467.1 | ABY75001.1 | ACF04726.1 | ACN22341.1 | ACU44759.1 |
| ABF21313.1 | ABY74999.1 | ACF04724.1 | ACV49525.1 | ACU44757.1 |

TABLE 1-continued

| Accession numbers for amino acids sequences M2 proton channel proteins | | | | |
|---|---|---|---|---|
| GenBank accession number | GenBank accession number | GenBank accession number | GenBank accession number | GenBank accession number |
| ABF21301.1 | ABY74997.1 | ACF04722.1 | ACV49503.1 | ACU44755.1 |
| ABF21299.1 | ABY74995.1 | ACC69091.1 | ACU79906.1 | AEA92622.1 |
| ABF21297.1 | ABY74993.1 | ABV53579.1 | ACU79895.1 | AEA35548.1 |
| ABQ57382.1 | ABY74991.1 | ABV53569.1 | ACU79884.1 | ADM29588.1 |
| ACR09357.1 | ABY74989.1 | ABV53549.1 | ACU79873.1 | ADM29577.1 |
| ACQ99606.1 | ABY74987.1 | ABV53539.1 | ACI25792.1 | BAK08628.1 |
| ACQ99598.1 | ABY74985.1 | ABV53529.1 | ACI25781.1 | BAK08626.1 |
| ACQ99596.1 | ABY74983.1 | ABV53519.1 | ACI25770.1 | ADZ75331.1 |
| ACU43624.2 | ABV45404.1 | ABV53509.1 | ACI25759.1 | ADZ75320.1 |
| ACR67240.1 | AAC63486.1 | ABV53499.1 | ACI25748.1 | ADP07242.1 |
| ACR67238.1 | AAC63484.1 | ABV53489.1 | ACF54468.1 | ACZ54004.1 |
| ACR67235.1 | AAC63482.1 | ABV53479.1 | ACF54457.1 | ACX93288.1 |
| ACR67234.1 | AAC63480.1 | ABV53470.1 | ACF54446.1 | ACX93222.1 |
| ACR67232.1 | ABB00355.1 | ADP37370.1 | ACF54435.1 | ACD65198.1 |
| ACR67230.1 | ABB00353.1 | ADG21464.1 | ACF54424.1 | ACD65196.1 |
| ACR67228.1 | ABB00349.1 | ADG21457.1 | ACF54413.1 | ACD65194.1 |
| ACR67226.1 | ABB00347.1 | ACF17953.1 | ACF54402.1 | ACD65191.1 |
| ACR67224.1 | ABB00345.1 | ACF17943.1 | ACF41825.1 | ACD65189.1 |
| ACR67222.1 | ABB00343.1 | ADM95569.1 | ACF41814.1 | ACX93277.1 |
| ACR67220.1 | ABB00341.1 | ADM95567.1 | ACF41803.1 | ACX93269.1 |
| ACR67218.1 | ABB00337.1 | ADM95565.1 | ACF41792.1 | ABD79034.1 |
| ACR67216.1 | ABB00335.1 | ADM95563.1 | ACF41781.1 | ABJ16853.1 |
| ACR67214.1 | ABB00333.1 | ADM95561.1 | ACF41770.1 | ABJ16842.1 |
| ACR67212.1 | CAA30889.1 | ADM95559.1 | ACF41759.1 | ADI99547.1 |
| ACR67208.1 | CAA30887.1 | ADM95557.1 | ACF41748.1 | ADI99536.1 |
| ACR67206.1 | CAA30885.1 | ADM95555.1 | ACF41737.1 | ADB4045.1 |
| ACR54054.1 | CAA30893.1 | ADM95553.1 | ACF22399.1 | ADD21471.1 |
| ACR09363.1 | CAA30891.1 | ADM95551.1 | ACF22388.1 | ADD21461.1 |
| ACP41961.1 | AAA43091.1 | ADM95549.1 | ACF22377.1 | ADD21451.1 |
| ACP41938.1 | AAA43577.1 | ADM95547.1 | ACF22366.1 | ACZ48112.1 |
| ABI36484.1 | BAB19808.1 | ADM95545.1 | ACF22355.1 | ACF25678.1 |
| ABI36475.1 | CAA30883.1 | ADM95543.1 | ACF22344.1 | ACF25666.1 |
| ABI36464.1 | AAD51929.1 | ADM95541.1 | ACF22333.1 | ACF25466.1 |
| ABI36456.1 | BAA99398.1 | ADM95539.1 | ACF22322.1 | ACF25065.1 |
| ABI36445.1 | AAF99673.1 | ADM95537.1 | ACF22311.1 | ACF25057.1 |
| ABI36434.1 | AAF99671.1 | ADM95535.1 | ACF22300.1 | ACF24971.1 |
| ABI36425.1 | ABH04389.1 | ADM95533.1 | ACF22278.1 | ACV74288.1 |
| ABI36412.1 | ABB90274.1 | ADM95531.1 | ACF22256.1 | ACV74286.1 |
| ABI36401.1 | AAD51270.1 | ADM95529.1 | ACF22245.1 | ABV56243.1 |
| ABI36390.1 | AAM70004.1 | ADM95527.1 | ACF22234.1 | ACI25712.1 |
| ABI36379.1 | AAB19772.1 | ADM95525.1 | ACF22223.1 | ACI25710.1 |
| ABI36368.1 | AAD51266.1 | ADM95523.1 | ACF22212.1 | ADA81213.1 |
| ABI36357.1 | ABD59885.1 | ADM95521.1 | ACF22201.1 | ACZ56084.1 |
| ABI36346.1 | AAM70001.1 | ADM95519.1 | ACF22190.1 | ACZ45024.1 |
| ABI36335.1 | AAM69992.1 | ADM95517.1 | ACF22172.1 | ACV91683.1 |
| ABI36324.1 | AAM69982.1 | ADM95515.1 | ADL41185.1 | ACV91679.1 |
| ABI36313.1 | AAM69972.1 | ADM95513.1 | ADM07115.1 | ACV91675.1 |
| ABI36297.1 | AAM69961.1 | ADM95511.1 | ADM07104.1 | ACV72405.1 |
| ABI36277.1 | AAZ38741.1 | ADM95509.1 | ADM07093.1 | ACV72403.1 |
| ABI36202.1 | AAZ38739.1 | ADM95507.1 | ADM07082.1 | ACV72401.1 |
| ABI36191.1 | AAZ38737.1 | ADM95505.1 | ADM07071.1 | ACV72399.1 |
| ABI36181.1 | AAZ38735.1 | ADM95503.1 | ADM07060.1 | ACV72397.1 |
| ABI36170.1 | AAZ38733.1 | ADM95501.1 | ADE62289.1 | ACV72395.1 |
| ABI36159.1 | AAZ38731.1 | ADM95499.1 | AEG65177.1 | ACV72393.1 |
| ABI36148.1 | AAZ38729.1 | ADM95497.1 | AEC46386.1 | ACV72391.1 |
| ABI36083.1 | ABA42442.1 | ADM95495.1 | ADR78653.1 | ACV72389.1 |
| ABI36081.1 | ABA42440.1 | ADM95493.1 | ADM29643.1 | ACV72349.1 |

TABLE 2

| Accession numbers for amino acids sequences BM2 proton channel proteins | | | |
|---|---|---|---|
| GenBank accession number | GenBank accession number | GenBank accession number | GenBank accession number |
| AAU01002.1 | ACR15701.1 | ACA96576.1 | ABN50549.1 |
| BAC54010.1 | ACR15690.1 | ACA96565.1 | ABN50538.1 |
| BAC53999.1 | ACR15679.1 | ACA96554.1 | ABN50527.1 |
| P0C0X4.1 | ACR15668.1 | ACA65099.1 | ABN50516.1 |

TABLE 2-continued

| Accession numbers for amino acids sequences BM2 proton channel proteins | | | |
|---|---|---|---|
| GenBank accession number | GenBank accession number | GenBank accession number | GenBank accession number |
| P03493.2 | ACR15657.1 | ACA65088.1 | ABN50505.1 |
| P08383.2 | ACR15646.1 | ACA65077.1 | ABN50494.1 |
| P13882.2 | ACR15635.1 | ACA65066.1 | ABN50483.1 |
| P13881.2 | ACR15624.1 | ACA65055.1 | ABN50472.1 |

TABLE 2-continued

| Accession numbers for amino acids sequences BM2 proton channel proteins | | | |
|---|---|---|---|
| GenBank accession number | GenBank accession number | GenBank accession number | GenBank accession number |
| Q80DN6.1 | ACO94663.1 | ACA65044.1 | ABN50450.1 |
| ABF21319.1 | ACO06025.1 | ACA65033.1 | ABN50439.1 |
| ABN50461.1 | ACO06014.1 | ACA65022.1 | ABN50428.1 |
| YP_419283.1 | ACO06003.1 | ACA65011.1 | ABN50417.1 |
| ACN32784.1 | ACO05992.1 | ACA65000.1 | ABN50406.1 |
| ACN32773.1 | ACO05981.1 | ACA64989.1 | ABN50395.1 |
| ACN32719.1 | ACO05970.1 | ACA64978.1 | ABN50384.1 |
| ACN32613.1 | ACO05959.1 | ACA64967.1 | ABL77389.1 |
| ACN32602.1 | ACO05937.1 | ACA64956.1 | ABL77378.1 |
| ACN32591.1 | ACO05926.1 | ACA64945.1 | ABL77367.1 |
| ACN32580.1 | ACF54369.1 | ACA64934.1 | ABL77356.1 |
| ACN32569.1 | ACF54358.1 | ACA64923.1 | ABL77345.1 |
| ACN32558.1 | ACF54347.1 | ACA64912.1 | ABL77334.1 |
| ABL77103.1 | ACF54336.1 | ACA64901.1 | ABL77323.1 |
| ABN50725.1 | ACF54325.1 | ABR16019.1 | ABL77312.1 |
| ABX71689.1 | ACF54314.1 | ABR16008.1 | ABL77301.1 |
| ABF21321.1 | ACF54303.1 | ABR15997.1 | ABL77290.1 |
| AAD29209.1 | ACF54292.1 | ABR15986.1 | ABL77279.1 |
| AAD29207.1 | ACF54281.1 | ABR15975.1 | ABL77268.1 |
| AAD29205.1 | ACF54270.1 | ABO72379.1 | ABL77257.1 |
| AAD29203.1 | ACF54259.1 | ABN50637.1 | ABL77246.1 |
| AAD29201.1 | ACF54248.1 | ABN59447.1 | ABL77235.1 |
| AAD29199.1 | ACF54226.1 | ABN58663.1 | ABL77224.1 |
| AAD29197.1 | ACF54215.1 | ABN51197.1 | ABL77213.1 |
| AAD29195.1 | ACF54204.1 | ABN51186.1 | ABL77202.1 |
| AAD29193.1 | ACF54182.1 | ABN50747.1 | ABL77191.1 |
| AAD29191.1 | ACF54160.1 | ABN50736.1 | ABL77180.1 |
| AAD29189.1 | ACF54149.1 | ABN50714.1 | ABL77169.1 |
| AAD29185.1 | ACF54138.1 | ABN50703.1 | ABL77158.1 |
| AAD29183.1 | ACF41660.1 | ABN50692.1 | ABL77147.1 |
| AAD29181.1 | ACD56579.1 | ABN50681.1 | ABL77136.1 |
| AAD29179.1 | ACD56568.1 | ABN50670.1 | ABL77125.1 |
| AAD29177.1 | ACB06477.1 | ABN50659.1 | ABL77114.1 |
| AAD29175.1 | ACA96664.1 | ABN50648.1 | ABL77092.1 |
| AAD29173.1 | ACA96653.1 | ABN50626.1 | ABL77081.1 |
| AAT69452.1 | ACA96642.1 | ABN50615.1 | ABL77070.1 |
| AAT69441.1 | ACA96631.1 | ABN50604.1 | ABL77059.1 |
| AAT69430.1 | ACA96620.1 | ABN50593.1 | ABL77048.1 |
| ACR39338.1 | ACA96609.1 | ABN50582.1 | ABL77037.1 |
| ACR15734.1 | ACA96598.1 | ABN50571.1 | ABL77026.1 |
| ACR15723.1 | ACA96587.1 | ABN50560.1 | ABL77015.1 |
| ACR15712.1 | ACA96576.1 | ABN50549.1 | ABL77004.1 |

Structural Virus Protein

The structural virus protein (also referred to as structural viral protein) may be a viral antigenic protein or fragment thereof, for example but not limited to a virus glycoprotein or virus envelop protein. The structural virus protein may be a chimeric virus protein. The viral protein may exist as a monomer, a dimer, a trimer, or a combination thereof. A trimer is a macromolecular complex formed by three, usually non-covalently bound proteins. Without wishing to be bound by theory, the trimerization domain of a protein may be important for the formation such trimers. Therefore the structural viral protein or fragment thereof may comprise a trimerization domain. A non-limiting example of a structural virus protein is influenza hemagglutinin (HA), or a fragment of HA. Non-limiting examples of HA, or fragments of HA that may be used according to the present invention include those described in WO2009/009876, WO 2009/076778; WO 2010/003225, WO 2010/003235, WO 2011/03522, WO 2010/006452, WO 2010/148511, WO 2011/035422 (which are incorporated herein by reference).

Furthermore the structural virus protein may be the unprocessed precursor protein of HA. HA protein is synthesized as a precursor protein (HA0) of about 75 kDa, which assembles at the surface into an elongated trimeric protein. The precursor protein is cleaved at a conserved activation cleavage site into 2 polypeptide chains, HA1 and HA2 (comprising the transmembrane region), linked by a disulfide bond.

Proteolytic Loop (Cleavage Site) Modification

The structural virus protein may be an influenza B hemagglutinin or Influenza A hemagglutinin protein with a deletion or modification of the proteolytic loop (cleavage site) within the hemagglutinin protein. Deletion or modification of the proteolytic loop ensures that the HA molecule is mostly maintained as HA0 precursor.

HA is synthesised as a precursor protein HA0, which undergoes proteolytic processing into two subunits (HA1 and HA2) linked together by a disulfide bridge. Mammalian and apathogenic avian influenza virus strains cause anatomically localized infections as a result of the restricted range of cells secreting a protease that can cleave the HA0 precursor extracellularly (Chen J, et. al. 1998, Cell. Vol 95:409-417). The proteases responsible for cleavage of HA0 in influenza infections of humans, are secreted by cells of the respiratory tract, or by coinfecting bacteria or *mycoplasma*, or they may be produced in inflammatory responses to infections. A major protease candidate is the tryptase Clara, which is produced by Clara cells of the bronchiolar epithelium, and has limited tissue distribution (upper respiratory tract). The protease is specific for the monobasic sequence Q/E-X-R found at the cleavage site of the H1, H2, H3, and H6. HA from H9 and B strains show a slightly different monobasic cleavage site with SSR and KER sequence respectively (see FIG. 24). No protease has been identified for the majority of influenza viruses that cause enteric and respiratory infection seen in aquatic birds. In the laboratory, most cell lines do not support multi-cycle replication unless exogenous protease (usually trypsin) is added.

Highly pathogenic avian strains, however, are cleaved by a family of more widespread intracellular proteases, resulting in systemic infections. This difference in pathogenicity correlates with structural differences at the HA0 cleavage site. Pathogenic strains have inserts of polybasic amino acids within, or next to, the monobasic site. Cleavage in this case occurs intracellularly and the proteases involved have been identified as furin, and other subtilisin-like enzymes, found in the Golgi and involved in the post-translational processing of hormone and growth factor precursors. The furin recognition sequence R-X-R/K-R is a frequent insertion amino acid at the HA0 cleavage sites of H5 and H7 (see FIG. 24). The wide tissue distribution of the enzyme, and the efficiency of intracellular cleavage, contribute to the widespread and virulent systemic infection caused by these viruses.

Horimoto T, et.al. (2006, Vaccine, Vol 24:3669-3676) describes the abolition of the polybasic cleavage site of H5 (RERRRKKR↓G) (SEQ ID NO:65) in H5. Selected mutants were submitted to immunogenicity study in mice, including a mutant with a deletion of the 4 first charged amino acids (RERR) (SEQ ID NO:66) and a modification to inactivate the polybasic cleavage site (RKKR (SEQ ID NO:67) with TETR (SEQ ID NO:68)). Abolition of the cleavage site did not affect the immunogenic properties of the mutant H5. Abolition the polybasic site (GERRRKKR↓G (SEQ ID NO:69) replaced by RETR (SEQ ID NO:70)) to produce mutant NIBSC 05/240 NIBSC influenza reference virus NIBG-23, has also been reported. Hoffman et. al. (2002, 2002, Vaccine, Vol 20:3165-3170) replaced the polybasic cleavage site of a H5 HA with the monobasic site of H6 in order to boost the expression in eggs. The first 4 residues were deleted and replaced the four last amino acids of the polybasic site by IETR (SEQ ID NO:71) (replacement of RERRRKKR↓G (SEQ ID NO:65) with IETR↓G) (SEQ ID NO. 72). This mutant H5 showed a high expression level, potential proteolysis and conformational change at low pH, immunogenicity data were not reported. These studies show that modification of the cleavage site can be employed to diminishes the virulence of the viral particle in cases where the true viruses is replicated, allowing the virus to replicate without killing the host egg. Without such mutations, viruses kill the egg before reaching high titers.

During the folding of HA and secretion thorough the Golgi, the hemagglutinin precursor cleavage site, which is located on a loop at the surface of HA, is well accessible for proteolysis by proteases. Without wishing to be bound by theory, if proteolysis of precursor HA0 occurs at the mono or the polybasic site during folding of the HA in the ER, a conformational change of the protein may take place in the Golgi apparatus during secretion, because the pH environment inside the Golgi of the plant and in the apoplast is slightly acidic. A low-pH conformation HA may be produced, decreasing both the level of expression and intrinsic stability of the particle. Thus, mostly uncleaved HA0 precursor protein would be budding from plasma membrane.

By "proteolytic loop" or "cleavage site" is meant the consensus sequence of the proteolytic site that is involved in precursor HA0 cleavage. "Consensus" or "consensus sequence" as used herein means a sequence (either amino acid or nucleotide sequence) that comprises the sequence variability of related sequences based on analysis of alignment of multiple sequences, for example, subtypes of a particular influenza HA0 sequence. Consensus sequence of the influenza HA0 cleavage site may include influenza A consensus hemagglutinin amino acid sequences, including for example consensus H1, consensus H3, or influenza B consensus hemagglutinin amino acid sequences. Non limiting examples of consensus sequences are shown in FIG. 24.

In the amino acid sequence of the HA the proteolytic loop is located, before the fusion peptide that consist of the 20 first amino acids of the HA2 part. The crystal structure of HA0 from A/Hong Kong/68 has been determined (Chen, J., 1998. Cell 95:409-417; incorporated herein by reference). Residues that are exposed to solvent are generally thought of being part of the cleavage site which forms an extended, highly exposed surface loop. From this specific peptide sequence, the consensus sequence may be determined in this chosen region (Bianchi et al., 2005, Journal of Virology, 79:7380-7388; incorporated herein by reference).

In order to abolish the proteolytic loop, the structure of a B HA was examined. Deletion of only the proteolytic cleavage site of the HA would have left the C-terminal of HA1 and N-terminal of HA2 left apart and a long linker would have needed to be designed. However deleting part of the fusion peptide along with the proteolytic cleave site allowed to remove the complete proteolytic loop and join the remaining HA1 and HA2 sequence by a minimal peptide linker of 2 amino acids. In summary, the B variant contains a deletion of sequence ALKLLKER (SEQ ID NO: 73) at the C-terminus of HA1 in addition of deletion of the N-terminus amino acids GFFGAIAGFLEG (SEQ ID NO:74) of HA2. The shortened HA1-HA2 were linked together by a GG linker.

As show in FIG. 22B, by deleting the proteolytic loop of HA0, the resultant HA0 protein exhibits an increased activity as shown by a greater hemagglutination capacity, when compared to a HA protein that does not have its proteolytic loop removed. By an increase in activity, it is meant an increase in hemagglutination capacity by about 2% to about 100%, or any amount therebetween as determined using standard techniques in the art, for example, from about 10% to about 50% or any value therebetween for example about 2, 5, 8, 10, 12, 15, 18, 20, 22, 24, 25, 26, 28, 30, 32, 34, 35, 36, 38, 40, 42, 44, 45, 46, 48, 50, 52, 54, 55, 56, 58, 60, 65, 70, 75, 80, 85, 90, 95, or 100%, when compared to the activity of the same HA protein that does not have its proteolytic loop removed.

By "chimeric virus protein" or "chimeric virus polypeptide", also referred to as "chimeric protein" or "chimeric polypeptide", it is meant a protein or polypeptide that comprises amino acid sequences from two or more than two sources, for example but not limited to, two or more influenza types or subtypes, or influenza's of a different origin, that are fused as a single polypeptide. The chimeric protein or polypeptide may include a signal peptide that is the same as, or heterologous with, the remainder of the polypeptide or protein. The chimeric protein or chimeric polypeptide may be produced as a transcript from a chimeric nucleotide sequence, and the chimeric protein or chimeric polypeptide cleaved following synthesis, and as required, associated to form a multimeric protein. Therefore, a chimeric protein or a chimeric polypeptide also includes a protein or polypeptide comprising subunits that are associated via disulphide bridges (i.e. a multimeric protein). For example, a chimeric polypeptide comprising amino acid sequences from two or more than two sources may be processed into subunits, and the subunits associated via disulphide bridges to produce a chimeric protein or chimeric polypeptide. A chimeric virus protein may also comprises an antigenic protein or a fragment thereof of a first influenza virus, and a transmembrane domain complex (TDC) from an second virus influenza HA, including a transmembrane domain and cytosolic tail domains (TM/CT). The polypeptide may be hemagglutinin (HA), and each of the two or more than two amino acid sequences that make up the polypeptide may be obtained from different HA's to produce a chimeric HA, or chimeric influenza HA. A chimeric HA may also include an amino acid sequence comprising heterologous signal peptide (a chimeric HA preprotein) that is cleaved after or during protein synthesis. Preferably, the chimeric polypeptide, or chimeric influenza HA is not naturally occurring. A nucleic acid encoding a chimeric polypeptide may be described as a "chimeric nucleic acid", or a "chimeric nucleotide sequence". A virus-like particle comprised of chimeric HA may be described as a "chimeric VLP".

The chimeric protein or polypeptide may include a signal peptide that is the same as, or heterologous with, the remainder of the polypeptide or protein. The term "signal peptide" is well known in the art and refers generally to a short (about 5-30 amino acids) sequence of amino acids, found generally at the N-terminus of a polypeptide that may direct translocation of the newly-translated polypeptide to a particular organelle, or aid in positioning of specific domains of the polypeptide chain relative to others. As a non-limiting example, the signal peptide may target the translocation of the protein into the endoplasmic reticulum and/or aid in positioning of the N-terminus proximal domain relative to a membrane-anchor domain of the nascent polypeptide to aid in cleavage and folding of the mature protein, for example which is not to be considered limiting, a mature HA protein.

Non limiting examples of chimeric virus proteins or chimeric virus nucleic acids that may be used according to the present invention are described in, WO 2009/076778, WO 2010/003235, or WO 2010/148511 (which are incorporated herein by reference).

Signal Peptide

A signal peptide (SP) may be native to the antigenic protein or virus protein, or a signal peptide may be heterologous with respect to the primary sequence of the antigenic protein or virus protein being expressed. A antigenic protein or virus protein may comprise a signal peptide from a first influenza type, subtype or strain with the balance of the HA from one or more than one different influenza type, subtype or strain. For example the native signal peptide of HA subtypes H1, H2, H3, H5, H6, H7, H9 or influenza type B may be used to express the chimeric virus protein in a plant system. In some embodiments of the invention, the SP may be of an influenza type B, H1, H3 or H5; or of the subtype H1/Bri, H1/NC, H5/Indo, H3/Bri or B/Flo.

A signal peptide may also be non-native, for example, from a antigenic protein, viral protein or hemagglutinin of a virus other than virus protein, or from a plant, animal or bacterial polypeptide. A non limiting example of a signal peptide that may be used is that of alfalfa protein disulfide isomerase ("PDISP"; nucleotides 32-103 of Accession No. Z11499; also see WO 2009/076778; WO 2010/148511, or WO 2010/003235, which are incorporated herein by reference). The present invention therefore provides for a chimeric virus protein comprising a native, or a non-native signal peptide, and nucleic acids encoding such chimeric virus proteins.

The present invention therefore also provides for a method of producing chimeric VLP in a plant, wherein a first nucleic acid encoding a chimeric virus protein is co-expressed with a second nucleic acid encoding a channel protein, for example but not limited to a proton channel protein. The first and second nucleic acids may be introduced to the plant in the same step, or may be introduced to the plant sequentially.

HA

With reference to influenza virus, the term "hemagglutinin" or "HA" as used herein refers to a glycoprotein found on the outside of influenza viral particles. HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available—see, for example, the BioDefence Public Health base (Influenza Virus; see URL: biohealthbase.org) or National Center for Biotechnology Information (see URL: ncbi.nlm.nih.gov), both of which are incorporated herein by reference.

The term "homotrimer" or "homotrimeric" indicates that an oligomer is formed by three HA protein molecules. Without wishing to be bound by theory, HA protein is synthesized as monomeric precursor protein (HA0) of about 75 kDa in animal cells, which assembles at the surface into an elongated trimeric protein. Before trimerization occurs, the precursor protein is cleaved at a conserved activation cleavage site (also referred to as fusion peptide) into 2 polypeptide chains, HA1 and HA2 (comprising the transmembrane region), linked by a disulfide bond. The HA1 segment may be 328 amino acids in length, and the HA2 segment may be 221 amino acids in length. Although this cleavage may be important for virus infectivity, it may not be essential for the trimerization of the protein. Insertion of HA within the endoplasmic reticulum (ER) membrane of the host cell, signal peptide cleavage and protein glycosylation are co-translational events. Correct refolding of HA requires glycosylation of the protein and formation of 6 intra-chain disulfide bonds. The HA trimer assembles within the cis- and trans-Golgi complex, the transmembrane domain playing a role in the trimerization process. The crystal structures of bromelain-treated HA proteins, which lack the transmembrane domain, have shown a highly conserved structure amongst influenza strains. It has also been established that HA undergoes major conformational changes during the infection process, which requires the precursor HA0 to be cleaved into the 2 polypeptide chains HA1 and HA2. The HA protein may be processed (i.e., comprise HA1 and HA2 domains), or may be unprocessed (i.e. comprise the HA0 domain). The HA protein may be used in the production or formation of VLPs using a plant, or plant cell, expression system.

The HA of the present invention may be obtained from any subtype. For example, the HA may be of subtype H2, H3, H4, H6, H7, H8, H9, H10, H11, H12, H13, H14, H15, H16, or influenza type B HA. The recombinant HA of the present invention may also comprise an amino acid sequence based on the sequence any hemagglutinin known in the art—see, for example, the BioDefence Public Health base (Influenza Virus; see URL: biohealthbase.org) or National Center for Biotechnology Information (see URL: ncbi.nlm.nih.gov). Furthermore, the HA may be based on the sequence of a hemagglutinin that is isolated from one or more emerging or newly-identified influenza viruses.

Non-limiting examples of HA, or fragments of HA that may be used according to the present invention include those described in WO2009/009876, WO 2009/076778; WO 2010/003225, WO 2010/003235, WO 2010/006452, WO 2011/035422 or WO 2010/148511 (which are incorporated herein by reference).

Figure 18:
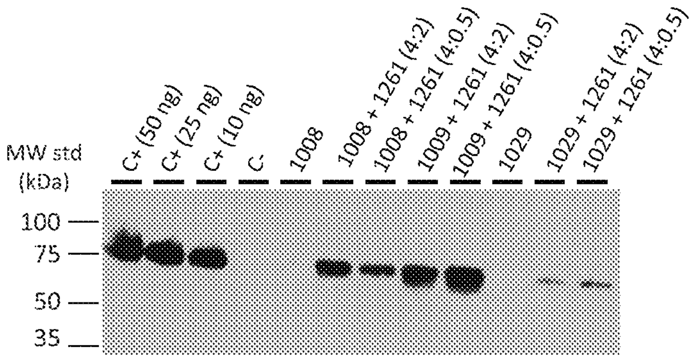
FIG. 18 shows Western blot analysis of HA protein expression in agroinfiltrated *Nicotiana benthamiana* leaves. HA from B/Brisbane/60/2008 is co-expressed with M2 from A/New Caledonia/20/99. "C+": positive control, semi-purified B/Brisbane/60/2008 virus from the Therapeutic Goods Administration, Australia; "C-": negative control, mock-infiltrated plants; "1008": expression of wild-type HA from B/Brisbane/60/2008 in the presence of amplification elements (BeYDV); "1008+1261": co-expression of wild-type HA from B/Brisbane/60/2008 in the presence of amplification elements (BeYDV) with M2; "1009+1261": co-expression of chimeric HA from B/Brisbane/60/2008 in the presence of amplification elements (BeYDV) with M2; "1029": expression of wild-type HA from B/Brisbane/60/2008 in the absence of amplification elements (BeYDV); "1029+1261": co-expression of wild-type HA from B/Brisbane/60/2008 in the absence of amplification elements (BeYDV) with M2 from A/New Caledonia/20/99. Ratios indicate the proportion of *Agrobacterium* cultures used in co-expression experiments.

As shown in FIG. 18, HA from B/Brisbane/60/2008 is poorly expressed in agroinfiltrated *Nicotiana benthamiana* leaves (see lanes "1008" or "1029"). However, co-expression of HA-type B with M2 from A/New Caledonia/20/99, results in a significant increase in HA expression (see lanes "1008+1261"; "1009+1261" and 1029+1261"). The increase in HA expression was observed in with both native type B HA or a chimeric HA type B. HA expression was observed in the presence or absence of amplification elements (BeYDV), and across various dilutions of *Agrobacterium*. A similar increase in H3 expression was observed when H3 from A/Perth/16/2009 was co-expressed with M2 from A/New Caledonia/20/99 (FIG. 19; compare lane "1019" H3 alone, with "1019+1261" H3 co-expressed with M2).

VLP

The term "virus like particle" (VLP), or "virus-like particles" or "VLPs" refers to structures that self-assemble and comprise virus proteins for example a structural viral protein such as influenza HA protein or a channel protein, for example but not limited to a proton channel protein, such as M2 or a combination of those proteins. VLPs are generally morphologically and antigenically similar to virions produced in an infection, but lack genetic information sufficient to replicate and thus are non-infectious. In some examples, VLPs may comprise a single protein species, or more than one protein species. For VLPs comprising more than one protein species, the protein species may be from the same species of virus, or may comprise a protein from a different species, genus, subfamily or family of virus (as designated by the ICTV nomenclature). In other examples, one or more of the protein species comprising a VLP may be modified from the naturally occurring sequence. VLPs may be produced in suitable host cells including plant and insect host cells. Following extraction from the host cell and upon isolation and further purification under suitable conditions, VLPs may be purified as intact structures.

Furthermore, VLPs may be produced that comprise a combination of HA subtypes. For example, VLPs may comprise one or more than one HA from the subtype H2, H3, H4, H6, H7, H8, H9, H10, H11, H12, H13, H14, H15, H16, subtype B HA or a combination thereof. Selection of the combination of HAs may be determined by the intended use of the vaccine prepared from the VLP. For example a vaccine for use in inoculating birds may comprise any combination of HA subtypes, while VLPs useful for inoculating humans may comprise subtypes one or more than one of subtypes H2, H3, H4, H6, H7, H8, H9, H10, H11, H12, H13, H14, H15, H16, subtype B HA. However, other HA subtype combinations may be prepared depending upon the use of the VLP. In order to produce VLPs comprising combinations of HA subtypes, the desired HA subtype may be co-expressed within the same cell, for example a plant cell.

As described in more detail below, the expression of a type B HA or H3 from B/Brisbane/60/2008 in agroinfiltrated *Nicotiana benthamiana* leaves is increased when co-expressed M2 from A/New Caledonia/20/99 (see FIGS. 18 and 19). A similar increase is not observed when H1 or H5 is co-expressed with M2, as high levels of H1 or H5 expression are observed in the presence or absence of M2 (FIGS. 20 and 21 respectively). HA are known to be processed in a pH-dependent manner (see Reed M. L. et. al. Journal of Virology, February 2010, p. 1527-1535, Vol. 84, No. 3), and to under go pH-dependent confirmation change (Skehel J. J. et. al. 1982, PNAS 79: 968-972). H1 and H5 exhibit a conformational change at a pH lower than that observed with either H3 and type B HA. Without wishing to bound by theory, the pH within the Golgi Apparatus during maturation and migration may not have an effect on H1 or H5 folding, however, a low pH within the Golgi Apparatus may effect H3 and type B HA folding. By co-expressing a channel protein, for example but not limited to a proton channel protein, long with H3 or Type B HA, the pH within the Golgi Apparatus may increase and result in HA folding leading to increased HA yield. Furthermore, H1 and H5 may be more stable at lower pH, than H3 and Type B HA. Therefore, by co-expressing a channel protein, for example but not limited to a proton channel protein, along with H3 or Type B HA, less HA is degraded within the Golgi apparatus.

The VLPs produced from influenza derived proteins, in accordance with the present invention do not comprise M1 protein. The M1 protein is known to bind RNA (Wakefield and Brownlee, 1989) which is a contaminant of the VLP preparation. The presence of RNA is undesired when obtaining regulatory approval for the VLP product, therefore a VLP preparation lacking RNA may be advantageous.

The VLPs produced as described herein do not typically comprise neuramindase (NA). However, NA may be co-expressed with HA should VLPs comprising HA and NA be desired.

The invention also includes, but is not limited to, virus derived VLPs that obtain a lipid envelope from the plasma membrane of the cell in which the VLP proteins are expressed. For example, if the VLP is expressed in a plant-based system, the VLP may obtain a lipid envelope from the plasma membrane of the cell.

Generally, the term "lipid" refers to a fat-soluble (lipophilic), naturally-occurring molecules. The term is also used more specifically to refer to fatty-acids and their derivatives (including tri-, di-, and monoglycerides and phospholipids), as well as other fat-soluble sterol-containing metabolites or sterols. Phospholipids are a major component of all biological membranes, along with glycolipids, sterols and proteins. Examples of phospholipids include phosphatidylethanolamine, phosphatidylcholine, phosphatidylinositol, phosphatidylserine, and the like. Examples of sterols include zoosterols (e.g., cholesterol) and phytosterols. Over 200 phytosterols have been identified in various plant species, the most common being campesterol, stigmasterol, ergosterol, brassicasterol, delta-7-stigmasterol, delta-7-avenasterol, daucosterol, sitosterol, 24-methylcholesterol, cholesterol or beta-sitosterol. As one of skill in the art would understand, the lipid composition of the plasma membrane of a cell may vary with the culture or growth conditions of the cell or organism from which the cell is obtained.

Cell membranes generally comprise lipid bilayers, as well as proteins for various functions. Localized concentrations of particular lipids may be found in the lipid bilayer, referred to as 'lipid rafts'. Without wishing to be bound by theory, lipid rafts may have significant roles in endo and exocytosis, entry or egress of viruses or other infectious agents, inter-cell signal transduction, interaction with other structural components of the cell or organism, such as intracellular and extracellular matrices.

In plants, influenza VLPs bud from the plasma membrane therefore the lipid composition of the VLPs reflects their origin. The VLPs produced according to the present invention comprise HA of one or more than one type or subtype of influenza, complexed with plant derived lipids. Plant lipids can stimulate specific immune cells and enhance the immune response induced. Plant membranes are made of lipids, phosphatidylcholine (PC) and phosphatidylethanolamine (PE), and also contain glycosphingolipids, saponins, and phytosterols. Additionally, lipid rafts are also found in plant plasma membranes—these microdomains are enriched in sphingolipids and sterols. In plants, a variety of phytosterols are known to occur, including stigmasterol, sitosterol, 24-methylcholesterol and cholesterol (Mongrand et al., 2004).

PC and PE, as well as glycosphingolipids can bind to CD1 molecules expressed by mammalian immune cells such as antigen-presenting cells (APCs) like dendritic cells and macrophages and other cells including B and T lymphocytes in the *thymus* and liver (Tsuji M, 2006). CD1 molecules are structurally similar to major histocompatibility complex (MHC) molecules of class I and their role is to present glycolipid antigens to NKT cells (Natural Killer T cells). Upon activation, NKT cells activate innate immune cells such as NK cells and dendritic cells and also activate adaptive immune cells like the antibody-producing B cells and T-cells.

A variety of phytosterols may be found in a plasma membrane—the specific complement may vary depending on the species, growth conditions, nutrient resources or pathogen state, to name a few factors. Generally, beta-sitosterol is the most abundant phytosterol.

The phytosterols present in an influenza VLP complexed with a lipid bilayer, such as an plasma-membrane derived envelope may provide for an advantageous vaccine composition. Without wishing to be bound by theory, plant-made VLPs complexed with a lipid bilayer, such as a plasma-membrane derived envelope, may induce a stronger immune reaction than VLPs made in other expression systems, and may be similar to the immune reaction induced by live or attenuated whole virus vaccines.

Therefore, in some embodiments, the invention provides for a VLP complexed with a plant-derived lipid bilayer. In some embodiments the plant-derived lipid bilayer may comprise the envelope of the VLP. The plant derived lipids may comprise lipid components of the plasma membrane of the plant where the VLP is produced, including, but not limited to, phosphatidylcholine (PC), phosphatidylethanolamine (PE), glycosphingolipids, phytosterols or a combination thereof. A plant-derived lipid may alternately be referred to as a 'plant lipid'. Examples of phytosterols are known in the art, and include, for example, stigmasterol, sitosterol, 24-methylcholesterol and cholesterol—see, for example, Mongrand et al., 2004.

VLPs may be assessed for structure and size by, for example, hemagglutination assay, electron microscopy, or by size exclusion chromatography.

For size exclusion chromatography, total soluble proteins may be extracted from plant tissue by homogenizing (Polytron) sample of frozen-crushed plant material in extraction buffer, and insoluble material removed by centrifugation. Precipitation with PEG may be used. The soluble protein is quantified, and the extract passed through a size exclusion matrix, for example but not limited to Sephacryl™. Following chromatography, fractions may be further analyzed by immunoblot to determine the protein complement of the fraction.

Without wishing to be bound by theory, the capacity of HA to bind to RBC from different animals is driven by the affinity of HA for sialic acids α2,3 or α2,3 and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guinea pigs, humans and sheep (see also Ito T. et al, 1997, Virology, vol 227, p 493-499; and Medeiros R et al, 2001, Virology, vol 289 p. 74-85).

Folding (Chaperon)

Correct folding of the expressed virus protein may be important for stability of the protein, formation of multimers, formation of VLPs, function of the virus protein and recognition of the virus protein by an antibody, among other characteristics. Folding and accumulation of a protein may be influenced by one or more factors, including, but not limited to, the sequence of the protein, the relative abundance of the protein, the degree of intracellular crowding, the pH in a cell compartment, the availability of cofactors that may bind or be transiently associated with the folded, partially folded or unfolded protein, the presence of one or more chaperone proteins, or the like.

Heat shock proteins (Hsp) or stress proteins are examples of chaperone proteins, which may participate in various cellular processes including protein synthesis, intracellular trafficking, prevention of misfolding, prevention of protein aggregation, assembly and disassembly of protein complexes, protein folding, and protein disaggregation. Examples of such chaperone proteins include, but are not limited to, Hsp60, Hsp65, Hsp 70, Hsp90, Hsp100, Hsp20-30, Hsp10, Hsp100-200, Hsp100, Hsp90, Lon, TF55, FKBPs, cyclophilins, C1pP, GrpE, ubiquitin, calnexin, and protein disulfide isomerases (see, for example, Macario, A. J. L., *Cold Spring Harbor Laboratory Res.* 25:59-70. 1995; Parsell, D. A. & Lindquist, *S. Ann. Rev. Genet.* 27:437-496 (1993); U.S. Pat. No. 5,232,833). As described herein, chaperone proteins, for example but not limited to Hsp40 and Hsp70 may be used to ensure folding of a virus protein.

Examples of Hsp70 include Hsp72 and Hsc73 from mammalian cells, DnaK from bacteria, particularly mycobacteria such as *Mycobacterium leprae, Mycobacterium tuberculosis*, and *Mycobacterium Bovis* (such as Bacille-Calmette Guerin: referred to herein as Hsp71). DnaK from *Escherichia coli*, yeast and other prokaryotes, and BiP and Grp78 from eukaryotes, such as *A. thaliana* (Lin et al. 2001 (Cell Stress and Chaperones 6:201-208). A particular example of an Hsp70 is *A. thaliana* Hsp70 (encoded by Genbank ref: AY120747.1). Hsp70 is capable of specifically binding ATP as well as unfolded polypeptides and peptides, thereby participating in protein folding and unfolding as well as in the assembly and disassembly of protein complexes.

Examples of Hsp40 include DnaJ from prokaryotes such as *E. coli* and mycobacteria and HSJ1, HDJ1 and Hsp40 from eukaryotes, such as alfalfa (Frugis et al., 1999. Plant Molecular Biology 40:397-408). A particular example of an Hsp40 is *M. sativa* MsJ1 (Genbank ref: AJ000995.1). Hsp40 plays a role as a molecular chaperone in protein folding, thermotolerance and DNA replication, among other cellular activities.

Among Hsps, Hsp70 and its co-chaperone, Hsp40, are involved in the stabilization of translating and newly synthesized polypeptides before the synthesis is complete. Without wishing to be bound by theory, Hsp40 binds to the hydrophobic patches of unfolded (nascent or newly transferred) polypeptides, thus facilitating the interaction of Hsp70-ATP complex with the polypeptide. ATP hydrolysis leads to the formation of a stable complex between the polypeptide, Hsp70 and ADP, and release of Hsp40. The association of Hsp70-ADP complex with the hydrophobic patches of the polypeptide prevents their interaction with other hydrophobic patches, preventing the incorrect folding and the formation of aggregates with other proteins (reviewed in Hartl, F U. 1996. Nature 381:571-579).

Native chaperone proteins may be able to facilitate correct folding of low levels of recombinant protein, but as the expression levels increase, the abundance of native chaperones may become a limiting factor. High levels of expression of virus protein in the agroinfiltrated leaves may lead to the accumulation of virus protein in the cytosol, and co-expression of one or more than one chaperone proteins such as Hsp70, Hsp40 or both Hsp70 and Hsp40 may reduce the level of misfolded or aggregated proteins, and increase the number of proteins exhibiting tertiary and quaternary structural characteristics that allow for formation of virus-like particles.

Therefore, the present invention also provides for a method of producing virus protein VLPs in a plant, wherein a first nucleic acid encoding a virus protein is co-expressed with a second nucleic acid encoding a channel protein, for example but not limited to a proton channel protein, and a third nucleic acid encoding a chaperone. The first, second and third nucleic acids may be introduced to the plant in the same step, or may be introduced to the plant sequentially.

N-Glycans

The VLP produced within a plant may induce an virus protein comprising plant-specific N-glycans. Therefore, this invention also provides for a VLP comprising virus protein having plant specific N-glycans.

Furthermore, modification of N-glycan in plants is known (see for example WO 2008/151440; WO 2010/006452; or U.S. 60/944,344; which are incorporated herein by reference) and virus protein having modified N-glycans may be produced. Virus protein comprising a modified glycosylation pattern, for example with reduced fucosylated, xylosylated, or both, fucosylated and xylosylated, N-glycans may be obtained, or virus protein having a modified glycosylation pattern may be obtained, wherein the protein lacks fucosylation, xylosylation, or both, and comprises increased galatosylation. Furthermore, modulation of post-translational modifications, for example, the addition of terminal galactose may result in a reduction of fucosylation and xylosylation of the expressed virus protein when compared to a wild-type plant expressing virus protein.

For example, which is not to be considered limiting, the synthesis of virus protein having a modified glycosylation pattern may be achieved by co-expressing the protein of interest along with a nucleotide sequence encoding beta-1.4galactosyltransferase (GalT), for example, but not limited to mammalian GalT, or human GalT however GalT from another sources may also be used. The catalytic domain of GalT may also be fused to a CTS domain (i.e. the cytoplasmic tail, transmembrane domain, stem region) of N-acetylglucosaminyl transferase (GNT1), to produce a GNT1-GalT hybrid enzyme, and the hybrid enzyme may be co-expressed with virus protein. The virus protein may also be co-expressed along with a nucleotide sequence encoding N-acetylglucosaminyltrasnferase III (GnT-III), for example but not limited to mammalian GnT-III or human GnT-III, GnT-III from other sources may also be used. Additionally, a GNT1-GnT-III hybrid enzyme, comprising the CTS of GNT1 fused to GnT-III may also be used.

Therefore the present invention also includes VLP's comprising one or more virus protein having modified N-glycans.

Sequences

Non-limiting example of sequences that may be used with the present invention include:

- H2 protein encoded by the nucleic acid molecule may be from the A/Singapore/1/57 (H2N2) strain;
- H3 protein encoded by the nucleic acid molecule may be from the A/Brisbane 10/2007 (H3N2), A/Wisconsin/67/2005 (H3N2) strain, A/Victoria/361/2011 (H3N2) or A/Perth/16/2009 (H3N2);
- H6 protein encoded by the nucleic acid molecule may be from the A/Teal/HongKong/W312/97 (H6N1) strain;
- H7 protein encoded by the nucleic acid molecule may also be from the A/Equine/Prague/56 (H7N7) strain;
- H9 protein encoded by the nucleic acid molecule may be from the A/HongKong/1073/99 (H9N2) strain;
- HA protein from B subtype encoded by the nucleic acid may be from the B/Florida/4/2006, B/Malaysia/2506/2004, B/Wisconsin/1/2010, or B/Brisbane/60/2008 strain.

Non-limiting example of sequences that may be used with the present invention also include those described in WO 2009/009876; WO 2009/076778; WO 2010/003225; WO 2010/148511; WO 2010/003235; WO 2010/006452 which are herein incorporated by reference). Examples of sequences of amino acid molecules encoding such HA proteins from H2, H3, H4, H6, H7, H8, H9, H10, H11, H12, H13, H14, H15, H16 and type B HA, which are known in the art. For example H3 or B subtypes include SEQ ID Nos: 25 or 30. The sequence encoding the structural virus protein may be for example HA from influenza B/Brisbane/60/2008, B/Malaysia/2506/2004 or B/Wisconsin/1/2010, or H3 from influenza A/Perth/16/2009 or A/Victoria/361/2011. Other examples include sequences of nucleic acid molecules that encode HA proteins wherein the proteolytic loop of the HA protein has been deleted such as for example, but not limited to the sequence defined by SEQ ID NO: 41.

The present invention also includes, but is not limited to, nucleotide sequences encoding HA from for example H2, H3, H4, H6, H7, H8, H9, H10, H11, H12, H13, H14, H15, H16 or type B HA. For example SEQ ID NO: 28, 43, 23, encoding an HA from B, B with deleted proteolytic loop or H3. respectively, a nucleotide sequence that hybridizes under stringent hybridisation conditions to SEQ ID NO: 28, 43, 23, or a nucleotide sequence that hybridizes under stringent hybridisation conditions to a compliment of SEQ ID NO: 28, 43, 23, wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA from B or H3. The VLP, when administered to a subject, induces an immune response. The nucleotide sequence may also be co-expressed with a second nucleotide sequence encoding a channel protein, for example but not limited to, nucleotide sequences SEQ ID NO: 9, 12, a nucleotide sequence that hybridizes under stringent hybridisation conditions to SEQ ID NO: 9, 12, or a nucleotide sequence that hybridizes under stringent hybridisation conditions to a compliment of SEQ ID NO: 9, 12, wherein the second nucleotide sequence encodes a proton channel protein forms a VLP. Preferably, the VLP induces the production of an antibody and the VLP, when administered to a subject, induces an immune response.

For example, expression of the nucleotide sequence within a plant cell forms a VLP, and the VLP may be used to produce an antibody that is capable of binding a virus protein such for example HA, including but not limited to HA0, HA0 protein with its proteolytic loop deleted or modified, HA1 or HA2 of one or more influenza types or subtypes, such for example but not limited to subtypes H2, H3, H4, H6, H7, H8, H9, H10, H11, H12, H13, H14, H15, H16, subtype B HA. The VLP, when administered to a subject, induces an immune response.

Hybridization under stringent hybridization conditions is known in the art (see for example Current Protocols in Molecular Biology, Ausubel et al., eds. 1995 and supplements; Maniatis et al., in Molecular Cloning (A Laboratory Manual), Cold Spring Harbor Laboratory, 1982; Sambrook and Russell, in Molecular Cloning: A Laboratory Manual, $3^{rd}$ edition 2001; each of which is incorporated herein by reference). An example of one such stringent hybridization conditions may be about 16-20 hours hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M $NaPO_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence encoding HA from B (SEQ ID NO: 28), B with deleted or modified proteolytic loop (SEQ ID NO: 43), H3 (SEQ ID NO:23), or an HA encoded by any one or more of SEQ ID NO:23, 28, 43, 46, 51, 57, or 61, wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including unprocessed and/or mature HA from B or H3, or unprocessed and/or mature HA wherein the proteolytic loop has been deleted. The VLP, when administered to a subject, induces an immune response.

The present invention also includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence encoding M2 (SEQ ID NO: 9, 12), wherein the nucleotide sequence encodes a channel protein, for example but not limited to a proton channel protein, that when co-expressed with a structural virus protein forms a VLP. Preferably, the VLP induces the production of an antibody and the VLP, when administered to a subject, induces an immune response.

Sequence identity or sequence similarity may be determined using a nucleotide sequence comparison program, such as that provided within DNASIS (for example, using, but not limited to, the following parameters: GAP penalty 5, # of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST)., or by manual alignment and visual inspection. An example of sequence alignment of HAs from different strains of influenza can be found in FIG. 24.

An "immune response" generally refers to a response of the adaptive immune system. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity is of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-influenza antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

Cross-reactivity HA1 titres may also be used to demonstrate the efficacy of an immune response to other strains of virus related to the vaccine subtype. For example, serum from a subject immunized with a vaccine composition of a first strain (e.g. VLPs of A/Indonesia 5/05) may be used in an HA1 assay with a second strain of whole virus or virus particles (e.g. A/Vietnam/1194/2004), and the HAI titer determined.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be obtained several ways, including: 1) enumeration of lysis plaques (plaque assay) following crystal violet fixation/coloration of cells; 2) microscopic observation of cell lysis in culture; 3) ELISA and spectrophotometric detection of NP virus protein (correlate with virus infection of host cells).

Constructs

The present invention is further directed to a gene construct comprising a nucleic acid encoding a channel protein, for example but not limited to a proton channel protein or a structural virus protein, as described above, operatively linked to a regulatory element that is operative in a plant. Examples of regulatory elements operative in a plant cell and that may be used in accordance with the present invention include but are not limited to a plastocyanin regulatory region (U.S. Pat. No. 7,125,978; which is incorporated herein by reference), or a regulatory region of Ribulose 1,5-bisphosphate carboxylase/oxygenase (RuBisCO; U.S. Pat. No. 4,962,028; which is incorporated herein by reference), chlorophyll a/b binding protein (CAB; Leutwiler et al; 1986; which is incorporated herein by reference), ST-LS1 (associated with the oxygen-evolving complex of photosystem II and described by Stockhaus et al. 1987, 1989; which is incorporated herein by reference).

Regulatory Elements

The use of the terms "regulatory region", "regulatory element" or "promoter" in the present application is meant to reflect a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" may includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, may also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, L R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama. T. and Chua, N. H., 1997, Plant 1. 2, 397-404; which is incorporated by reference) and ethanol-inducible promoter (Salter, M. G., et al, 1998, Plant 10urnal 16, 127-132; Caddick, M. X., et al, 1998, Nature Biotech. 16, 177-180, which are incorporated by reference) cytokinin inducible IB6 and CKI 1 genes (Brandstatter, I. and K.ieber, 1.1., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript (Odell et al., 1985, Nature, 313: 810-812), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995, Plant Mol. Biol. 29: 995-1004).

The term "constitutive" as used herein does not necessarily indicate that a gene under control of the constitutive regulatory region is expressed at the same level in all cell types, but that the gene is expressed in a wide range of cell types even though variation in abundance is often observed. Constitutive regulatory elements may be coupled with other sequences to further enhance the transcription and/or translation of the nucleotide sequence to which they are operatively linked. For example, the CPMV-HT system is derived from the untranslated regions of the Cowpea mosaic virus (CPMV) and demonstrates enhanced translation of the associated coding sequence. By "native" it is meant that the nucleic acid or amino acid sequence is naturally occurring, or "wild type". By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

The one or more virus protein such as a structural virus protein or channel protein, for example but not limited to a proton channel protein may be expressed in an expression system comprising a viral based, DNA or RNA, expression system, for example but not limited to, a comovirus-based expression cassette and geminivirus-based amplification element.

The expression system as described herein may comprise an expression cassette based on a bipartite virus, or a virus with a bipartite genome. For example, the bipartite viruses may be of the Comoviridae family. Genera of the Comoviridae family include Comovirus, Nepovirus, Fabavirus, Cheravirus and Sadwavirus. Comoviruses include Cowpea mosaic virus (CPMV), Cowpea severe mosaic virus (CPSMV), Squash mosaic virus (SqMV), Red clover mottle virus (RCMV), Bean pod mottle virus (BPMV), Turnip ringspot virus (TuRSV), Broad bean true mosaic virus (BBtMV), Broad bean stain virus (BBSV), Radish mosaic virus (RaMV). Examples of comoviruse RNA-2 sequences comprising enhancer elements that may be useful for various aspects of the invention include, but are not limited to:

CPMV RNA-2 (GenBank Accession No. NC_003550), RCMV RNA-2 (GenBank Accession No. NC_003738), BPMV RNA-2 (GenBank Accession No. NC_003495), CPSMV RNA-2 (GenBank Accession No. NC_003544), SqMV RNA-2 (GenBank Accession No. NC_003800), TuRSV RNA-2 (GenBank Accession No. NC_013219.1). BBtMV RNA-2 (GenBank Accession No. GU810904), BBSV RNA2 (GenBank Accession No. FJ028650), RaMV (GenBank Accession No. NC_003800)

Segments of the bipartite comoviral RNA genome are referred to as RNA-1 and RNA-2. RNA-1 encodes the proteins involved in replication while RNA-2 encodes the proteins necessary for cell-to-cell movement and the two capsid proteins. Any suitable comovirus-based cassette may be used including CPMV, CPSMV, SqMV, RCMV, or BPMV, for example, the expression cassette may be based on CPMV.

"Expression cassette" refers to a nucleotide sequence comprising a nucleic acid of interest under the control of, and operably (or operatively) linked to, an appropriate promoter or other regulatory elements for transcription of the nucleic acid of interest in a host cell.

It has been shown that transformation of *Nicotiana benthamiana* with full-length, replication-competent cDNA copies of both genomic RNAs of CPMV can result in a productive infection (Liu et al., 2004, *Virology* 323, 37-48, herein incorporated by reference). Examples of CPMV-based expression cassettes are described in WO2007/135480; WO2009/087391; and Sainsbury F. et al., (2008, *Plant Physiology;* 148: 1212-1218; Sainsbury F. et al., (2008, *Plant Biotechnology Journal;* 6: 82-92; Sainsbury F. et al., 2009, *Plant Biotechnology Journal;* 7: 682-693; which documents are herein incorporated by reference). As an example, which is not to be considered limiting, the untranslated regions (UTRs) obtained from the genomic RNA 2 of the cowpea mosaic virus (CPMV) in which the two first translation initiation codons found in the 5'leader sequence have been deleted, may be used as described in WO 2009/087391. When combined to the CaMV 35S promoter and the nopaline synthase (NOS) terminator, the modified CPMV UTRs enhanced translation of the flanking coding region. The CPMV-based expression system was named CPMV-HT (hyperanslatable). Expression cassettes, expression constructs and expression systems of the invention may therefore also comprise an CPMV-based expression system such as for example an CPMV-HT expression system.

As described herein, an expression enhancer sequence, which sequence is derived from (or shares homology with) the RNA-2 genome segment of a bipartite RNA virus, such as a comovirus, in which a target initiation site has been mutated, may be used for expressing a nucleic acid sequence of interest. The present invention further provides processes for increasing the expression, or translational enhancing activity, of a sequence derived from an RNA-2 genome segment of a bipartite virus, which processes comprise mutating a target initiation site therein.

"Enhancer" sequences (or enhancer elements), include sequences derived from (or sharing homology with) the RNA-2 genome segment of a bipartite RNA virus, such as a comovirus, in which a target initiation site has been mutated. Such sequences can enhance downstream expression of a heterologous ORF to which they are attached. Without limitation, it is believed that such sequences when present in transcribed RNA, can enhance translation of a heterologous ORF to which they are attached.

The expression systems may also comprise amplification elements from a geminivirus for example, an amplification element from the bean yellow dwarf virus (BeYDV). BeYDV belongs to the Mastreviruses genus adapted to dicotyledonous plants. BeYDV is monopartite having a single-strand circular DNA genome and can replicate to very high copy numbers by a rolling circle mechanism. BeYDV-derived DNA replicon vector systems have been used for rapid high-yield protein production in plants.

As used herein, the phrase "amplification elements" refers to a nucleic acid segment comprising at least a portion of one ore more long intergenic regions (LIR) of a geminivirus genome. As used herein, "long intergenic region" refers to a region of a long intergenic region that contains a rep binding site capable of mediating excision and replication by a geminivirus Rep protein. In some aspects, the nucleic acid segment comprising one or more LIRs, may further comprises a short intergenic region (SIR) of a geminivirus genome. As used herein, "short intergenic region" refers to the complementary strand (the short IR (SIR) of a Mastreviruses). Any suitable geminivirus-derived amplification element may be used herein. See, for example, W02000/20557; WO2010/025285; Zhang X. et al. (2005, *Biotechnology and Bioengineering*, Vol. 93, 271-279), Huang Z. et al. (2009, *Biotechnology and Bioengineering*, Vol. 103, 706-714), Huang Z. et al. (2009, *Biotechnology and Bioengineering*, Vol. 106, 9-17); which are herein incorporated by reference). If more than one LIR is used in the construct, for example two LIRs, then the promoter, CMPV-HT regions and the nucleic acid sequence of interest and the terminator are bracketed by each of the two LIRs.

As described herein, co-delivery of bean yellow dwarf virus (BeYDV)-derived vector and a Rep/RepA-supplying vector, by agroinfiltration of *Nicotiana benthamiana* leaves results in efficient replicon amplification and robust protein production.

A comovirus-based expression cassette and a geminivirus-derived amplification element may be comprised in respective, first and second vectors, or the component parts may be included in one vector. If two vectors are used, the first and second vectors may be introduced into a plant cell simultaneously or separately.

A viral replicase may also be included in the expression system as described herein to increase expression of the nucleic acid of interest. An non-limiting example of a replicase is a BeYDV replicase (pREP110) encoding BeYDV Rep and RepA (C2/C1; Huang et al., 2009, *Biotechnol. Bioeng.* 103, 706-714; which is incorporated herein by reference).

Post-transcriptional gene silencing (PTGS) may be involved in limiting expression of transgenes in plants, and co-expression of a suppressor of silencing from the p19 of Tomato bushy stunt virus (TBSV p19) or potato virus Y (HcPro) may be used to counteract the specific degradation of transgene mRNAs (Brigneti et al., 1998).

Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristexa virus (CTV-p23), p24 of Grapevine leafroll-associated virus-2, (GLRaV-2 p24), p10 of Grapevine virus A, (GVA-p10), p14 of Grapevine virus B (GVB-p14), p10 of

*Heracleum* latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

By "co-expressed" it is meant that two, or more than two, nucleotide sequences are expressed at about the same time within the plant, and within the same tissue of the plant. However, the nucleotide sequences need not be expressed at exactly the same time. Rather, the two or more nucleotide sequences are expressed in a manner such that the encoded products have a chance to interact. For example, the protein that modifies glycosylation of the protein of interest may be expressed either before or during the period when the protein of interest is expressed so that modification of the glycosylation of the protein of interest takes place. The two or more than two nucleotide sequences can be co-expressed using a transient expression system, where the two or more sequences are introduced within the plant at about the same time under conditions that both sequences are expressed. Alternatively, a platform plant comprising one of the nucleotide sequences, for example the sequence encoding the protein that modifies the glycosylation profile of the protein of interest, may be transformed, either transiently or in a stable manner, with an additional sequence encoding the protein of interest. In this case, the sequence encoding the protein that modifies the glycosylation profile of the protein of interest may be expressed within a desired tissue, during a desired stage of development, or its expression may be induced using an inducible promoter, and the additional sequence encoding the protein of interest may be expressed under similar conditions and in the same tissue, to ensure that the nucleotide sequences are co-expressed.

The one or more virus protein may be produced as a transcript from a nucleotide sequence, and the protein cleaved following synthesis, and as required, associated to form a multimeric protein. Therefore, the one or more virus protein also includes a protein or polypeptide comprising subunits that are associated via disulphide bridges (i.e. a multimeric protein). For example, a protein comprising amino acid sequences from two or more than two sources may be processed into subunits, and the subunits associated via disulphide bridges to produce a protein.

The one or more nucleic acid sequences or genetic constructs of the present invention may be expressed in any suitable plant host that is transformed by the nucleotide sequence, or constructs, or vectors of the present invention. Examples of suitable hosts include, but are not limited to, agricultural crops including alfalfa, canola, *Brassica* spp., maize, *Nicotiana* spp., potato, *ginseng*, pea, oat, rice, soybean, wheat, barley, sunflower, cotton and the like.

The one or more genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon Non-limiting examples of suitable 3' regions are the 3' transcribed non-translated regions containing a polyadenylation signal of *Agrobacterium* tumor inducing (Ti) plasmid genes, such as the nopaline synthase (NOS) gene, plant genes such as the soybean storage protein genes, the small subunit of the ribulose-I, 5-bisphosphate carboxylase gene (ssRUBISCO; U.S. Pat. No. 4,962,028; which is incorporated herein by reference), the promoter used in regulating plastocyanin expression, described in U.S. Pat. No. 7,125,978 (which is incorporated herein by reference).

One or more of the genetic constructs of the present invention may also include further enhancers, either translation or transcription enhancers, as may be required. Enhancers may be located 5' or 3' to the sequence being transcribed. Enhancer regions are well known to persons skilled in the art, and may include an ATG initiation codon, adjacent sequences or the like. The initiation codon, if present, may be in phase with the reading frame ("in frame") of the coding sequence to provide for correct translation of the transcribed sequence.

By "transformation" it is meant the interspecific transfer of genetic information (nucleotide sequence) that is manifested genotypically, phenotypically or both. The interspecific transfer of genetic information from a construct to a host may be transient and the transfer of genetic information is not inheritable or the transfer may be heritable and the transfer of genetic information considered stable.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Borsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J Virol Meth, 105:343-348, 2002), U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

As described below, transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al., 1997, which is incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage oft-DNA inside the nucleus is transient.

To aid in identification of transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. However, it is also contemplated that the plant material may be subjected to minimal processing steps as defined below, or more rigorous processing, including partial or substantial protein purification using techniques commonly known within the art including, but not limited to chromatography, electrophoresis and the like.

By the term "minimal processing" it is meant plant matter, for example, a plant or portion thereof comprising a protein of interest which is partially purified to yield a plant extract, homogenate, fraction of plant homogenate or the like (i.e. minimally processed). Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

The plant matter, in the form of plant material or tissue may be orally delivered to a subject. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

It is contemplated that a plant comprising the protein of interest, or expressing the VLP comprising the protein of interest may be administered to a subject or target organism, in a variety of ways depending upon the need and the situation. For example, the protein of interest obtained from the plant may be extracted prior to its use in either a crude, partially purified, or purified form. If the protein is to be purified, then it may be produced in either edible or non-edible plants. Furthermore, if the protein is orally administered, the plant tissue may be harvested and directly feed to the subject, or the harvested tissue may be dried prior to feeding, or an animal may be permitted to graze on the plant with no prior harvest taking place. It is also considered within the scope of this invention for the harvested plant tissues to be provided as a food supplement within animal feed. If the plant tissue is being feed to a subject or an animal with little or not further processing it is preferred that the plant tissue being administered is edible.

The VLP's produced according to the present invention may be purified, partially purified from a plant, portion of a plant or plant matter, or may be administered as an oral vaccine, using methods as know to one of skill in the art. Purification may include production of an apoplast fraction as described in WO 2011/035422 (which is incorporated herein by reference). For preparative size exclusion chromatography, a preparation comprising VLPs may be obtained and insoluble material removed by centrifugation. Precipitation with PEG may also be used. The recovered protein may be quantified using conventional methods (for example, Bradford Assay, BCA), and the extract passed through a size exclusion column, using for example SEPHACRYL™, SEPHADEX™, or similar medium, and the fractions collected. Blue Dextran 2000 or a suitable protein, may be used as a calibration standard. The extract may also be passed through a cation exchange column and active fractions collected. Following chromatography, fractions may be further analyzed by protein electrophoresis, immunoblot, or both, to confirm the presence of VLPs and the protein complement of the fraction.

Also considered part of this invention are transgenic plants, plant cells, seeds or any fraction thereof containing the nucleotide sequences of the present invention. Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

As shown in FIG. 18, HA from B/Brisbane/60/2008 is poorly expressed in agroinfiltrated *Nicotiana benthamiana* leaves (see lanes "1008" or "1029"). However, co-expression of HA-type B with M2 from A/New Caledonia/20/99, results in a significant increase in HA expression (see lanes "1008+1261"; "1009+1261" and 1029+1261"). The increase in HA expression was observed in with both native type B HA or a chimeric HA type B. HA expression was observed in the presence or absence of amplication elements (BeYDV), and across various dilutions of *Agrobacterium*. A similar increase in H3 expression was observed when H3 from A/Perth/16/2009 was co-expressed with M2 from A/New Caledonia/20/99 (FIG. 19; compare lane "1019" H3 alone, with "1019+1261" H3 co-expressed with M2).

The present invention includes nucleotide sequences as set forth in Table 3:

TABLE 3

List of Sequence Identification numbers.

Figures 1A, 1B, 1C:
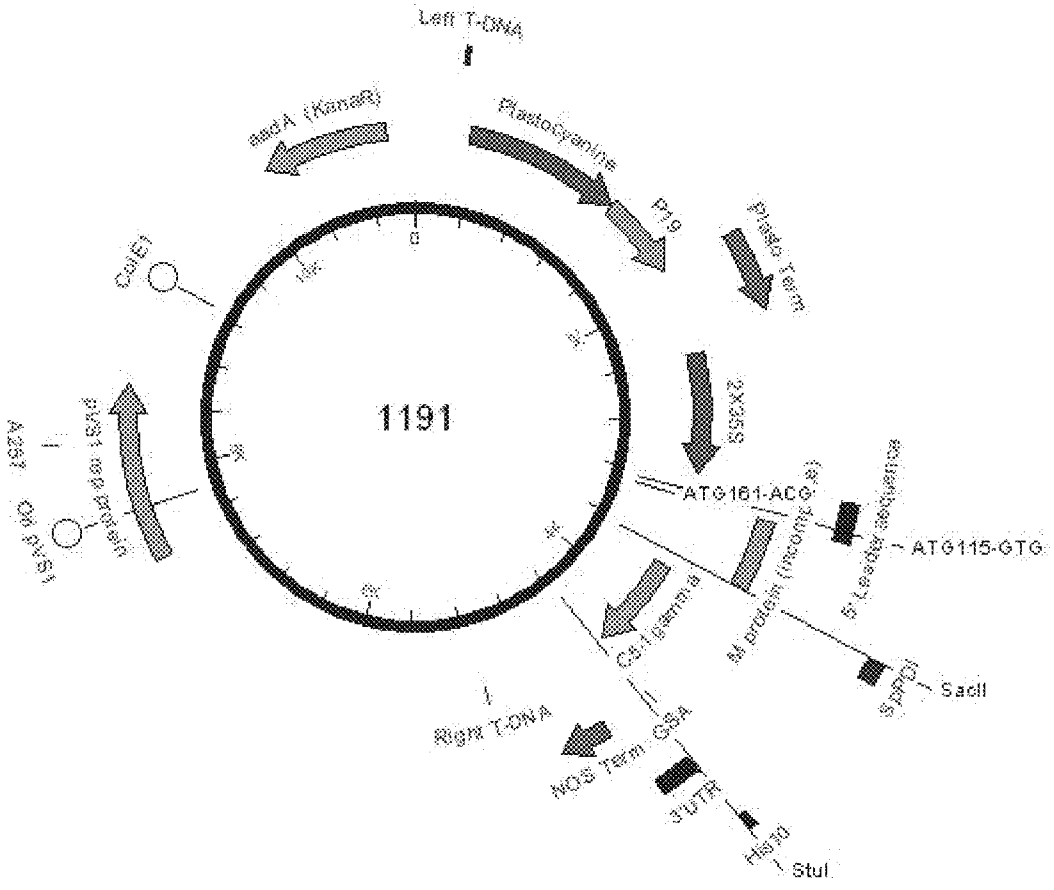
FIG. 1A shows primer IF-H5A-I-05.s1+3c (SEQ ID NO: 2).
FIG. 1B shows primer IF-H5dTm.r (SEQ ID NO: 3).
FIG. 1C shows a schematic representation of construct 1191.

| SEQ ID NO: | Description | FIG. |
|---|---|---|
| 1 | proton channel signature sequence HXXXW | |
| 2 | primer IF-H5A-I-05.s1+3c | FIG. 1A |
| 3 | primer IF-H5dTm.r | FIG. 1B |
| 4 | Construct 1191 | FIG. 1D |
| 5 | Expression cassette number 489 | FIG. 1E |
| 6 | Amino acid sequence of H5 from influenza A/Indonesia/5/2005 (H5N1) | FIG. 1F |
| 7 | primer IF-S1-M1+M2ANC.c | FIG. 2A |
| 8 | primer IF-S1-4-M2ANC.r | FIG. 2B |
| 9 | nucleotide sequence of synthesized M2 gene (DQ508860) | FIG. 2C |
| 10 | Expression cassette number 1261 | FIG. 2D |
| 11 | Amino acid sequence of M2 from influenza A/New Caledonia/20/1999 (H1N1) | FIG. 2E |
| 12 | nucleotide sequence of synthesized M2 gene | FIG. 3A |
| 13 | Expression cassette number 859 | FIG. 3B |
| 14 | Amino acid sequence of M2 from influenza A/Puerto Rico/8/1934 (H1N1) | FIG. 3C |
| 15 | primer IF-H1A-C-09.s2+4c | FIG. 4A |
| 16 | primer IF-H1A-C-09.s1−4r | FIG. 4B |
| 17 | nucleotide sequence of synthesized HI gene | FIG. 4C |
| 18 | Construct 1192 | FIG. 4E |
| 19 | Expression cassette number 484 | FIG. 4F |
| 20 | Amino acid sequence of PDISP-H1 from influenza A/Califomia/7/2009 (H1N1) | FIG. 4G |
| 21 | primer IF-S2+S4-H3 Per.c | FIG. 5A |
| 22 | primer IF-SIa4-H3 Per.r | FIG. 5B |
| 23 | nucleotide sequence of synthesized H3 gene | FIG. 5C |
| 24 | Expression cassette number 1019 | FIG. 5D |
| 25 | Amino acid sequence of PDISP/H3 from influenza A/Perth/16/2009 (H3N2) | FIG. 5E |
| 26 | primer IF-S2+S4-B Bris.c | FIG. 6A |
| 27 | primer IF-S1a4-B Bris.r | FIG. 6B |
| 28 | nucleotide sequence of synthesized HA B Brisbane gene | FIG. 6C |
| 29 | Expression cassette number 1029 | FIG. 6D |
| 30 | Amino acid sequence of PDISP/HA from influenza B/Brisbane/60/2008 | FIG. 6E |
| 31 | Construct 1194 | FIG. 6G |
| 32 | Expression cassette number 1008 | FIG. 6H |
| 33 | primer dTmH5I-B Bris.r | FIG. 7A |
| 34 | primer B Bris-dTmH5I.c | FIG. 7B |
| 35 | primer IF-S1aS4-dTmH5I.r | FIG. 7C |
| 36 | Expression cassette number 1009 | FIG. 7D |
| 37 | Amino acid sequence of PDISP/HA B Brisbane/H5Indo TMCT | FIG. 7E |
| 38 | primer 1039+1059.r | FIG. 8A |
| 39 | primer 1039+1059.c | FIG. 8B |
| 40 | Expression cassette number 1059 from BeYDV left LIR to BeYDV right LIR. PDISP/HA from influenza B/Brisbane/60/2008 with deleted proteolytic loop | FIG. 8C |
| 41 | Amino acid sequence of PDISP/HA from influenza B/Brisbane/60/2008 with deleted proteolytic loop | FIG. 8D |
| 42 | nucleotide sequence encoding H5 from influenza A/Indonesia/5/2005 (H5N1) | FIG. 1G |
| 43 | nucleotide sequence of PDISP/HA from influenza B/Brisbane/60/2008 with deleted proteolytic loop | FIG. 8E |
| 44 | primer IF-H3V36111.S2+4c | FIG. 25A |
| 45 | primer IF-H3V36111.s1−4r | FIG. 25B |
| 46 | nucleotide sequence of synthesized H3 gene | FIG. 25C |
| 47 | expression cassette number 1391 | FIG. 25D |
| 48 | Amino acid sequence of PDISP-H3 from influenza A/Victoria/361/2011 | FIG. 25E |
| 49 | primer IF-HAB110.S1+3c | FIG. 26A |
| 50 | primer IF-HAB110.s1−4r | FIG. 26B |
| 51 | nucleotide sequence of synthesized HA B/Wisconin (JN993010) | FIG. 26C |
| 52 | Construct 193 | FIG. 26E |
| 53 | Expression cassette number 1462 | FIG. 26F |
| 54 | Amino acid sequence of HA from influenza B/Wisconsin/1/2010 | FIG. 26G |
| 55 | primer HAB110(PrL-).r | FIG. 27A |
| 56 | primer HAB110(PrL-).c | FIG. 27B |
| 57 | Expression cassette number 1467 | FIG. 27C |
| 58 | Amino acid sequence of HA from influenza B/Wisconsin/1/2010 with deleted proteolytic loop | FIG. 27D |
| 59 | primer IF-HB-M-04.s2+4c | FIG. 28A |
| 60 | primer IF-HB-M-04.s1−4r | FIG. 28B |
| 61 | nucleotide sequence of synthesized HA B Malaysia | FIG. 28C |
| 62 | Construct 194 | FIG. 28E |
| 63 | Expression cassette number 1631 | FIG. 28F |
| 64 | Amino acid sequence of PDISP-HA from influenza B/Malaysia/2506/2004 | FIG. 28G |

The present invention will be further illustrated in the following examples.

EXAMPLES

Material and Methods: Assembly of Expression Cassettes with Influenza Protein A—2X35S/CPMV-HT/H5 Indonesia/NOS (Construct Number 489)

Figure 15:
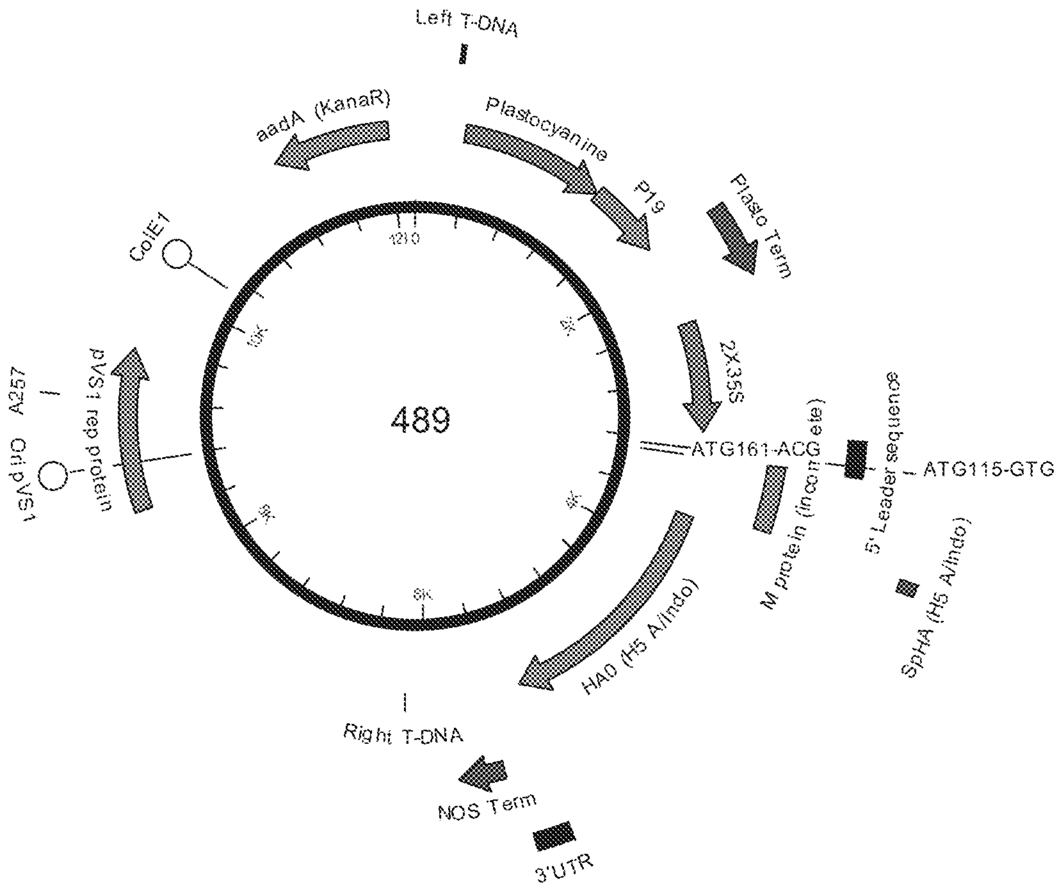
FIG. 15 shows the plasmid map of construct number 489. Construct number 489 directs the expression of wild-type H5 from influenza strain A/Indonesia/05/2005 (H5N1).

A sequence encoding H5 from influenza A/Indonesia/5/2005 (H5N1) was cloned into 2X35S/CPMV-HT/NOS expression system in a plasmid containing Plasto_pro/P19/Plasto_ter expression cassette using the following PCR-based method. A fragment containing the complete H5 coding sequence was amplified using primers IF-H5A-I-05.s1+3c (FIG. 1A, SEQ ID NO: 2) and IF-H5dTm.r (FIG. 1B, SEQ ID NO: 3) using construct number 972 (see FIG. 94, SEQ ID NO: 134 of WO 2010/003225, which is incorporated herein by reference, for the sequence of construct number 972) as template. The PCR product was cloned in 2X355/CPMV-HT/NOS expression system using In-Fusion cloning system (Clontech, Mountain View, Calif.). Construct 1191 (FIG. 1D, SEQ ID NO: 4) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 489 (FIG. 1E, SEQ ID NO: 5). The amino acid sequence of H5 from influenza A/Indonesia/5/2005 (H5N1) is presented in FIG. 1F (SEQ ID NO: 6). A representation of plasmid 489 is presented in FIG. 15.

B—2X355/CPMV-HT/M2 New Caledonia/NOS (Construct Number 1261)

Figure 16:
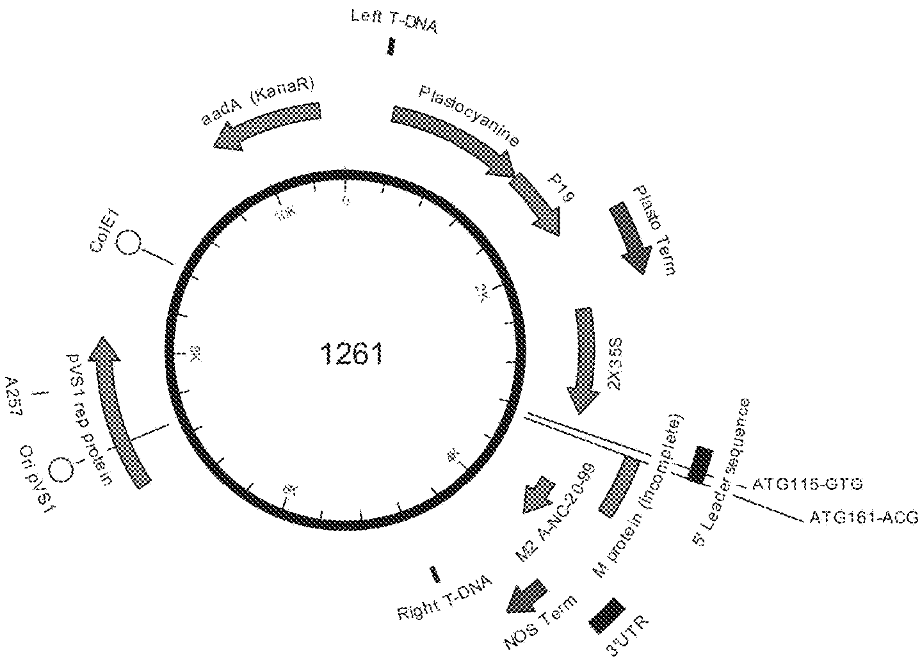
FIG. 16 shows the plasmid map of construct number 1261. Construct number 1261 directs the expression of wild-type M2 from influenza strain A/New Caledonia/20/99 (H1N1).

A sequence encoding M2 from influenza A/New Caledonia/20/1999 (H1N1) was cloned into 2X355/CPMV-HT/NOS expression system in a plasmid containing Plasto_pro/P19/Plasto_ter expression cassette using the following PCR-based method. A fragment containing the complete M2 coding sequence was amplified using primers IF-S1-M1+M2ANC.c (FIG. 2A, SEQ ID NO: 7) and IF-S1-4-M2ANC.r (FIG. 2B, SEQ ID NO: 8) using synthesized M2 gene (corresponding to nt 1-26 joined to nt 715-982 from GenBank accession number DQ508860) (FIG. 2C, SEQ ID NO: 9) as template. The PCR product was cloned in 2X355/CPMV-HT/NOS expression system using In-Fusion cloning system (Clontech, Mountain View, Calif.). Construct 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 1261 (FIG. 2D, SEQ ID NO: 10). The amino acid sequence of M2 from influenza A/New Caledonia/20/1999 (H1N1) is presented in FIG. 2E (SEQ ID NO: 11). A representation of plasmid 1261 is presented in FIG. 16.

C—2X35S/CPMV-HT/M2 Puerto Rico/NOS (Construct Number 859)

Figure 17:
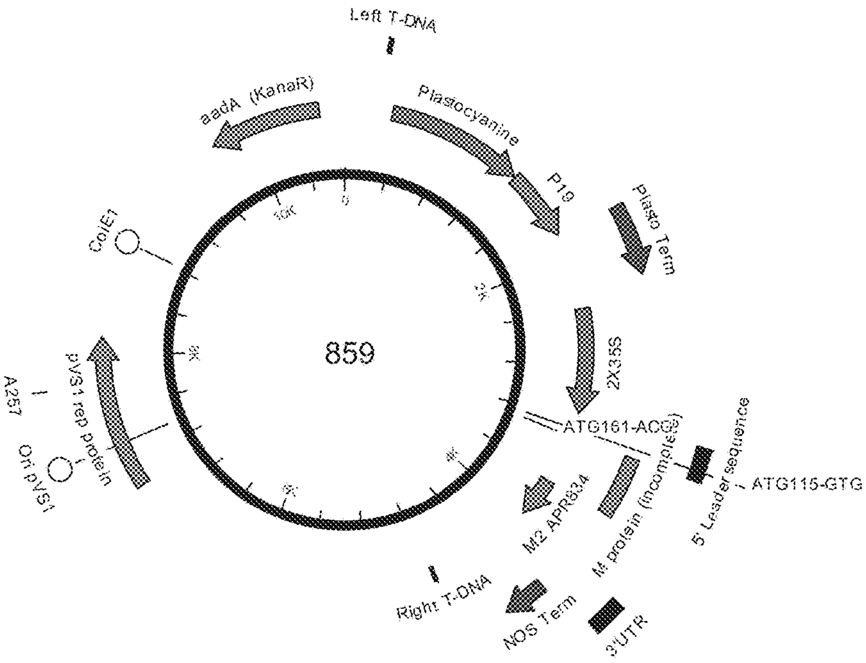
FIG. 17 shows the plasmid map of construct number 859. Construct number 859 directs the expression of wild-type M2 from influenza strain A/Puerto Rico/8/34 (H1N1).

A sequence encoding M2 from influenza A/Puerto Rico/8/1934 (H1N1) was cloned into 2X35S/CPMV-HT/NOS expression system in a plasmid containing Plasto_pro/P19/Plasto_ter expression cassette using the following PCR-based method. A fragment containing the complete M2 coding sequence was amplified using primers IF-S1-M1+M2ANC.c (FIG. 2A, SEQ ID NO: 7) and IF-S1-4-M2ANC.r (FIG. 2B, SEQ ID NO: 8), using synthesized M2 gene (corresponding to nt 26-51 joined to nt 740-1007 from Genbank accession number EF467824) (FIG. 3A, SEQ ID NO: 12) as template. The PCR product was cloned in 2X35S/CPMV-HT/NOS expression system using In-Fusion cloning system (Clontech, Mountain View, Calif.). Construct 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The vector is a pCAMBIA binary plasmid and the sequence from left to right t-DNA borders is presented in FIG. 1D (SEQ ID NO: 4). The resulting construct was given number 859 (FIG. 3B, SEQ ID NO: 13). The amino acid sequence of M2 from influenza A/Puerto Rico/8/1934 (H1N1) is presented in FIG. 3C (SEQ ID NO: 14). A representation of plasmid 859 is presented in FIG. 17.

D—2X35S/CPMV-HT/PDISP/H1 California/NOS (Construct Number 484)

Figure 14:
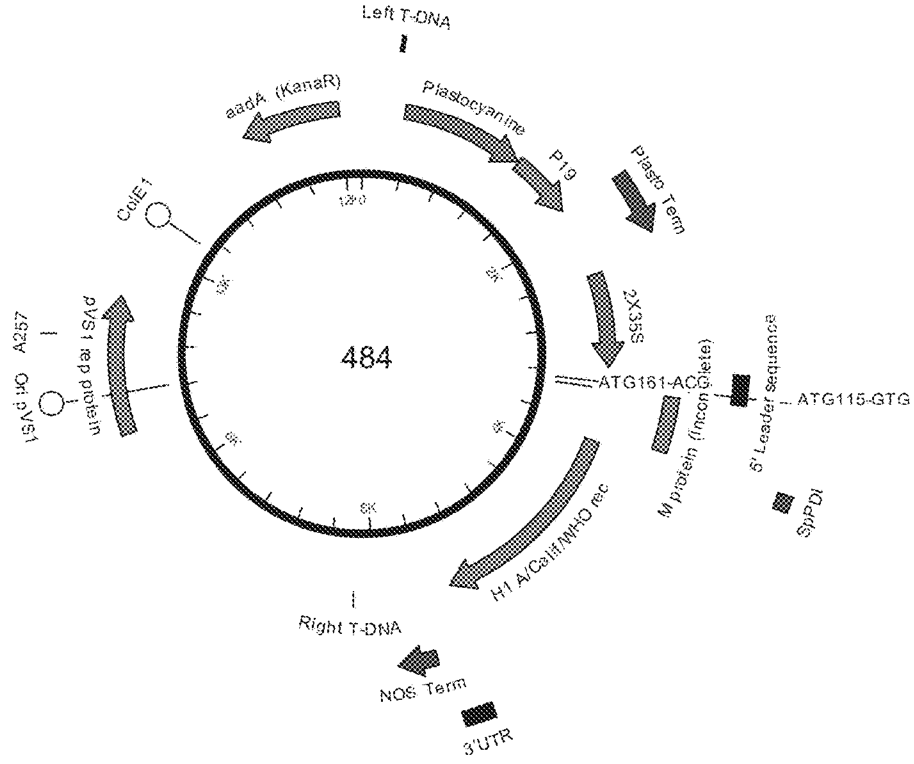
FIG. 14 shows the plasmid map of construct number 484. Construct number 484 directs the expression of wild-type H1 from influenza strain A/California/07/2009 (H1N1).

A sequence encoding H1 from influenza A/California/7/2009 (H1N1) was cloned into 2X355-CPMV-HT-PDISP-NOS expression system in a plasmid containing Plasto_pro/P19/Plasto_ter expression cassette using the following PCR-based method. A fragment containing the H1 coding sequence without his wild type signal peptide was amplified using primers IF-H1A-C-09.s2+4c (FIG. 4A, SEQ ID NO: 15) and IF-H1A-C-09.s1-4r (FIG. 4B, SEQ ID NO: 16), using synthesized H1 gene (Genbank accession number FJ966974) (FIG. 4C, SEQ ID NO: 17) as template. The PCR product was cloned in-frame with alfalfa PDI signal peptide in 2X355/CPMV-HT/NOS expression system using In-Fusion cloning system (Clontech, Mountain View, Calif.). Construct 1192 (FIG. 4D) was digested with SacII and StuI restriction enzyme and the linearized plasmid was used for the In-Fusion assembly reaction. Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 4E (SEQ ID NO: 18). The resulting construct was given number 484 (FIG. 4F, SEQ ID NO: 19). The amino acid sequence of PDISP/H1 from influenza A/California/7/2009 (H1N1) is presented in FIG. 4G (SEQ ID NO: 20). A representation of plasmid 484 is presented in FIG. 14.

E—2X355/CPMV-HT/PDISP/H3 Perth/NOS (Construct Number 1019)

Figure 13:
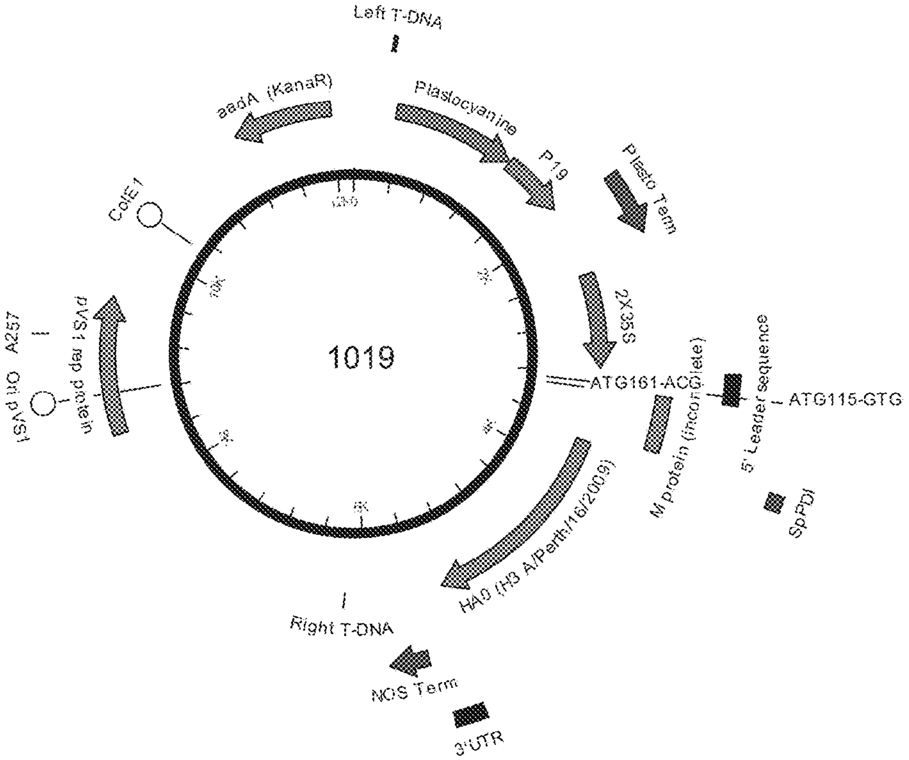
FIG. 13 shows the plasmid map of construct number 1019. Construct number 1019 directs the expression of wild-type H3 from influenza strain A/Perth/16/2009 (H3N2).

A sequence encoding H3 from influenza A/Perth/16/2009 (H3N2) was cloned into 2X35S/CPMV-HT/PDISP/NOS expression system in a plasmid containing Plasto_pro/P19/Plasto_ter expression cassette using the following PCR-based method. A fragment containing the H3 coding sequence without his wild type signal peptide was amplified using primers IF-S2+S4-H3 Per.c (FIG. 5A, SEQ ID NO: 21) and IF-S1 a4-H3 Per.r (FIG. 5B, SEQ ID NO: 22), using synthesized H3 gene (corresponding to nt 26-1726 from Genbank accession number GQ293081) (FIG. 5C, SEQ ID NO: 23) as template. The PCR product was cloned in-frame with alfalfa PDI signal peptide in 2X355/CPMV-HT/NOS expression system using In-Fusion cloning system (Clontech, Mountain View, Calif.). Construct 1192 (FIG. 4D) was digested with SacII and StuI restriction enzyme and the linearized plasmid was used for the In-Fusion assembly reaction. Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 4E (SEQ ID NO: 18). The resulting construct was given number 1019 (FIG. 5D, SEQ ID NO: 24). The amino acid sequence of PDISP/H3 from influenza A/Perth/16/2009 (H3N2) is presented in FIG. 5E (SEQ ID NO: 25). A representation of plasmid 1019 is presented in FIG. 13.

F—2X355/CPMV-HT/PDISP/HA B Brisbane/NOS (Construct Number 1029)

Figure 11:
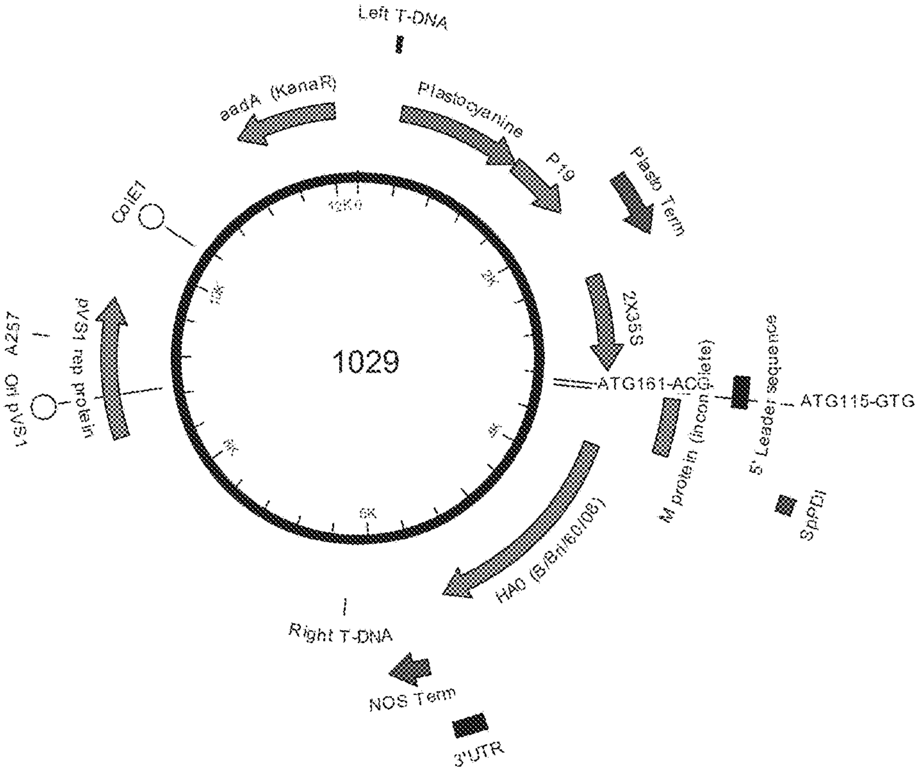
FIG. 11 shows the plasmid map of construct number 1029. Construct number 1029 directs the expression of wild-type HA from influenza strain B/Brisbane/60/2008.

A sequence encoding HA from influenza B/Brisbane/60/2008 was cloned into 2X355/CPMV-HT/PDISP/NOS expression system in a plasmid containing Plasto_pro/P19/Plasto_ter expression cassette using the following PCR-based method. A fragment containing HA B Brisbane coding sequence without his wild type signal peptide was amplified using primers IF-S2+S4-B Bris.c (FIG. 6A, SEQ ID NO: 26) and IF-S1a4-B Bris.r (FIG. 6B, SEQ ID NO: 27), using synthesized HA B Brisbane gene (corresponding to nt 34-1791 from Genbank accession number FJ766840) (FIG. 6C, SEQ ID NO: 28) as template. The PCR product was cloned in-frame with alfalfa PDI signal peptide in 2X355/CPMV-HT/NOS expression system using In-Fusion cloning system (Clontech, Mountain View, Calif.). Construct 1192 (FIG. 4D) was digested with SacII and StuI restriction enzyme and the linearized plasmid was used for the In-Fusion assembly reaction. Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 4E (SEQ ID NO: 18). The resulting construct was given number 1029 (FIG. 6D, SEQ ID NO: 29). The amino acid sequence of PDISP/HA from influenza B/Brisbane/60/2008 is presented in FIG. 6E (SEQ ID NO: 30). A representation of plasmid 1029 is presented in FIG. 11.

G—2X35S/CPMV-HT/PDISP/HA B Brisbane/NOS into BeYDV+Replicase Amplification System (Construct Number 1008)

Figure 9:
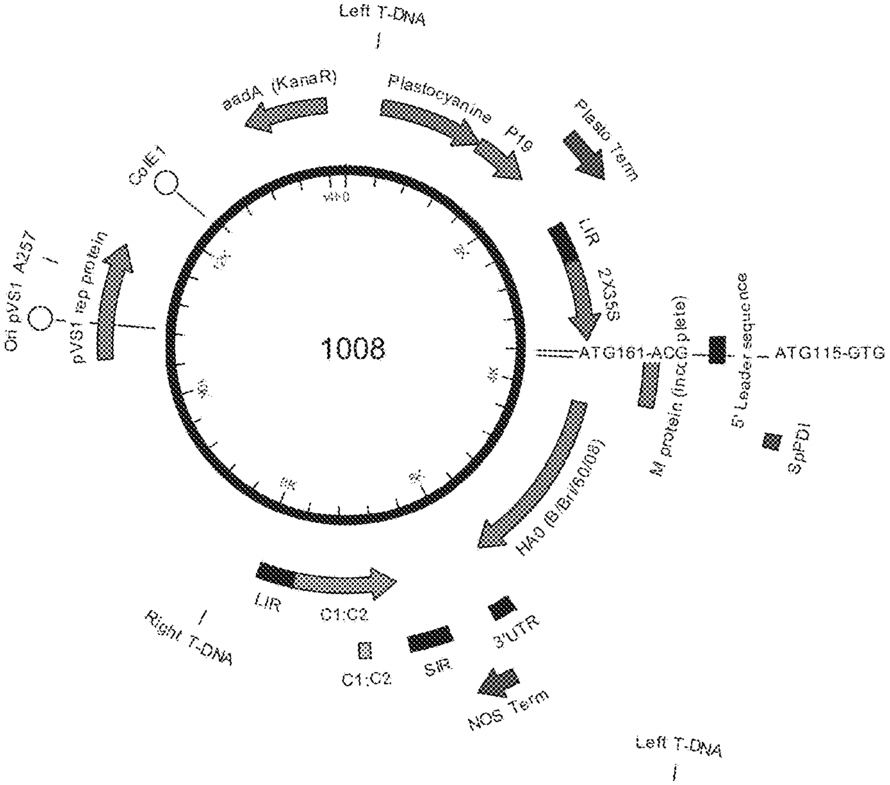
FIG. 9 shows the plasmid map of construct number 1008. Construct number 1008 directs the expression of wild-type HA from influenza strain B/Brisbane/60/2008. This construct comprises BeYDV-derived elements for DNA amplification.

A sequence encoding HA from influenza B/Brisbane/60/2008 was cloned into 2X35S/CPMV-HT/PDISP/NOS comprising the BeYDV+replicase amplification system in a plasmid containing Plasto_pro/P19/Plasto_ter expression cassette using the following PCR-based method. A fragment containing HA B Brisbane coding sequence without his wild type signal peptide was amplified using primers IF-S2+S4-B Bris.c (FIG. 6A, SEQ ID NO: 26) and IF-S1a4-B Bris.r (FIG. 6B, SEQ ID NO: 27), using synthesized HA B Brisbane gene (corresponding to nt 34-1791 from Genbank accession number FJ766840) (FIG. 6C, SEQ ID NO: 28) as template. The PCR product was cloned in-frame with alfalfa PDI signal peptide in 2X355/CPMV-HT/NOS expression cassette into the BeYDV amplification system using In-Fusion cloning system (Clontech, Mountain View, Calif.). Construct 1194 (see FIGS. 6F and 6G) was digested with SacII and StuI restriction enzyme and the linearized plasmid was used for the In-Fusion assembly reaction. Construct number 1194 is an acceptor plasmid intended for "In Fusion" cloning of genes of interest in frame with an alfalfa PDI signal peptide in a CPMV-HT-based expression cassette into the BeYDV amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6G (SEQ ID NO: 31). The resulting construct was given number 1008 (FIG. 6H SEQ ID NO: 32). The amino acid sequence of Influenza PDISP/HA from B/Brisbane/60/08 is presented in FIG. 6E (SEQ ID NO: 30). A representation of plasmid 1008 is presented in FIG. 9.

H—2X35S/CPMV-HT/PDISP/HA B Brisbane/H5 Indonesia Transmembrane Domain and Cytoplasmic Tail (H5Indo TMCT)/NOS into BeYDV+Replicase Amplification System (Construct Number 1009)

Figure 10:
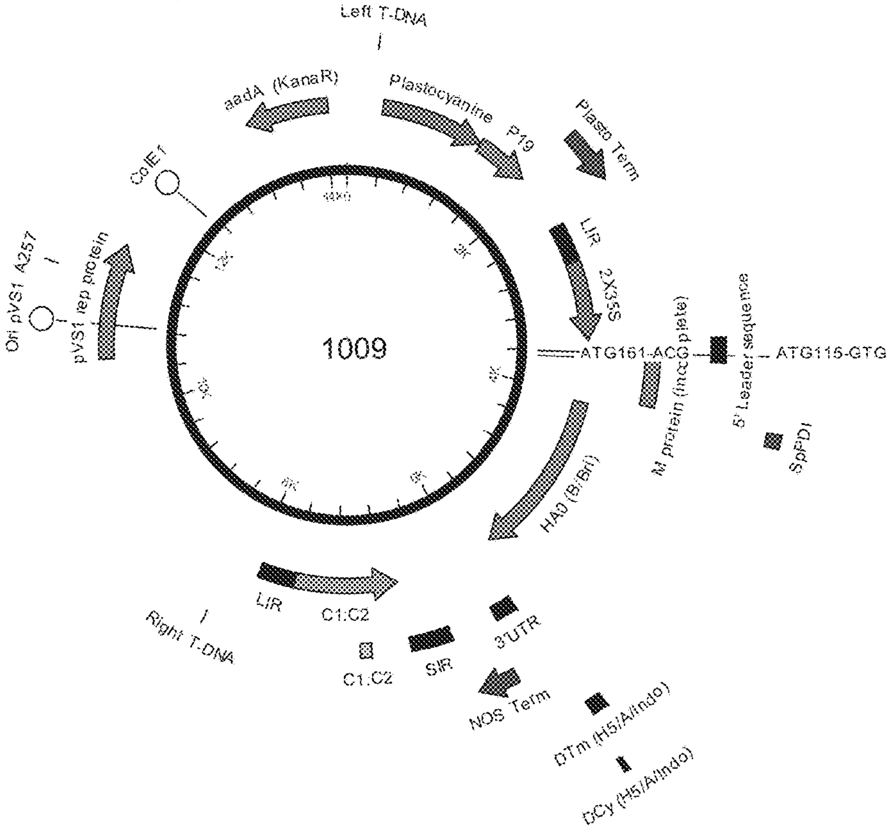
FIG. 10 shows the plasmid map of construct number 1009. Construct number 1009 directs the expression of a chimeric HA from influenza strain B/Brisbane/60/2008 in which the transmembrane domain and cytosolic tail are replaced with those of H5 from influenza A/Indonesia/05/2005. This construct comprises BeYDV-derived elements for DNA amplification.

A sequence encoding HA from influenza B/Brisbane/60/2008 ectodomain fused to the transmembrane and cytosolic domains of H5 from A/Indonesia/5/2005 (H5N1) was cloned into 2X355/CPMV-HT/PDISP/NOS comprising the BeYDV+replicase amplification system in a plasmid containing Plasto_pro/P19/Plasto_ter expression cassette as follows using the PCR-based ligation method presented by Darveau et al. (Methods in Neuroscience 26: 77-85 (1995)). In a first round of PCR, a fragment containing HA B Brisbane ectodomain coding sequence without the native signal peptide, transmembrane and cytoplasmic domains was amplified using primers IF-S2+S4-B Bris.c (FIG. 6A, SEQ ID NO: 26) and dTmH5I-B Bris.r (FIG. 7A, SEQ ID NO: 33), using synthesized HA B Brisbane gene (corresponding to nt 34-1791 from Genbank accession number FJ766840) (FIG. 6C, SEQ ID NO: 28) as template. A second fragment containing the transmembrane and cytoplasmic domains of H5 Indonesia was amplified using primers B Bris-dTmH5I.c (FIG. 7B, SEQ ID NO: 34) and IF-S1a54-dTmH5I.r (FIG. 7C, SEQ ID NO: 35), using construct number 489 (see FIG. 1E, SEQ ID NO: 5) as template. The PCR products from both amplifications were then mixed and used as template for a second round of amplification using IF-S2+S4-B Bris.c (FIG. 6A, SEQ ID NO: 26) and IF-H5dTm.r (FIG. 7C, SEQ ID NO: 34) as primers. The resulting fragment was cloned in-frame with alfalfa PDI signal peptide in 2X355/CPMV-HT/NOS expression cassette into the BeYDV amplification system using In-Fusion cloning system (Clontech, Mountain View, Calif.). Construct 1194 (FIGS. 6F and 6G) was digested with SacII and StuI restriction enzyme and the linearized plasmid was used for the In-Fusion assembly reaction. Construct number 1194 is an acceptor plasmid intended for "In Fusion" cloning of genes of interest in frame with an alfalfa PDI signal peptide in a CPMV HT-based expression cassette into the BeYDV amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6G (SEQ ID NO: 31). The resulting construct was given number 1009 (FIG. 7D, SEQ ID NO: 36). The amino acid sequence of PDISP/HA B Brisbane/H5indo TMCT is presented in FIG. 7E (SEQ ID NO: 37). A representation of plasmid 1009 is presented in FIG. 10.

I—2X355/CPMV-HT/PDISP-HA B Brisbane with Deleted Proteolytic Loop into BeYDV+Replicase Amplification System (Construct Number 1059)

Figure 12:
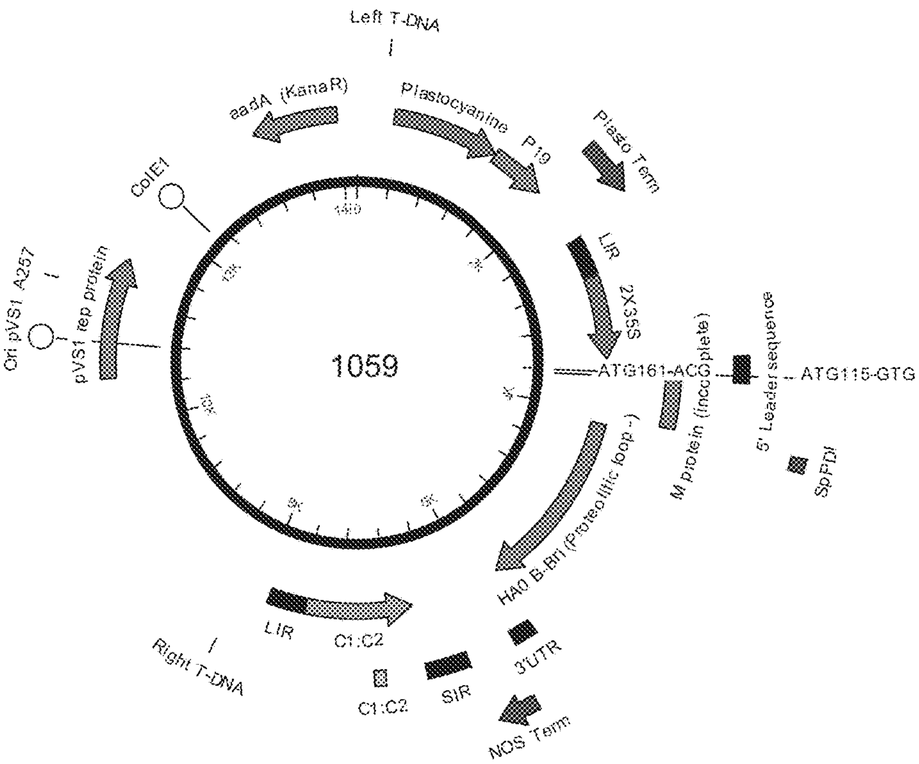
FIG. 12 shows the plasmid map of construct number 1059. Construct number 1059 directs the expression of a mutant HA from influenza strain B/Brisbane/60/2008 with deleted proteolytic loop. This construct comprises BeYDV-derived elements for DNA amplification.

A sequence encoding HA from influenza B/Brisbane/60/2008 with deleted proteolytic loop was cloned into 2X355/CPMV-HT/PDISP/NOS comprising the BeYDV+replicase amplification system in a plasmid containing Plasto_pro/P19/Plasto_ter expression cassette using the following PCR-based ligation method presented by Darveau et al. (Methods in Neuroscience 26: 77-85 (1995)). In a first round of PCR, a fragment containing HA B Brisbane coding sequence from nt 46 to nt 1065 was amplified using primers IF-S2+S4-B Bris.c (FIG. 6A, SEQ ID NO: 26) and 1039+1059.r (FIG. 8A, SEQ ID NO: 38), using synthesized HA B Brisbane gene (corresponding to nt 34-1791 from Genebank accession number FJ766840) (FIG. 6C, SEQ ID NO: 28) as template. A second fragment, containing HA B Brisbane coding sequence from nt 1123 to nt 1758, was amplified using primers 1039+1059.c (FIG. 8B, SEQ ID NO: 39) and IF-S1a4-B Bris.r (FIG. 6B, SEQ ID NO: 27), using synthesized HA B Brisbane gene (corresponding to nt 34-1791 from Genbank accession number FJ766840) (FIG. 6C, SEQ ID NO: 28) as template. The PCR products from both amplifications were then mixed and used as template for a second round of amplification using IF-S2+S4-B Bris.c (FIG. 6A, SEQ ID NO: 26) and IF-H5dTm.r IF-S1a4-B Bris.r (FIG. 6B, SEQ ID NO: 27) as primers. The resulting fragment (encoding HA B/Brisbane/60/2008 Aa.a. 356-374 with a GG linker between fragments) was cloned in-frame with alfalfa PDI signal peptide in 2X355/CPMV-HT/NOS expression cassette comprising the BeYDV amplification system using In-Fusion cloning system (Clontech, Mountain View, Calif.). Construct 1194 (FIGS. 6F and 6G) was digested with SacII and StuI restriction enzyme and the linearized plasmid was used for the In-Fusion assembly reaction. Construct number 1194 is an acceptor plasmid intended for "In Fusion" cloning of genes of interest in frame with an alfalfa PDI signal peptide in a CPMV-HTbased expression cassette into the BeYDV amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6G (SEQ ID NO: 31). The resulting construct was given number 1059 (FIG. 8C, SEQ ID NO: 40). The amino acid sequence of PDISP-HA B/Brisbane/60/2008 with deleted proteolytic loop is presented in FIG. 8D (SEQ ID NO: 41). A representation of plasmid 1059 is presented in FIG. 12.

A—2X355/CPMV-HT/PDISP/H3 Victoria/NOS (Construct Number 1391)

A sequence encoding H3 from influenza A/Victoria/361/2011 (H3N2) was cloned into 2X355-CPMV-HT-PDISP-NOS expression system in a plasmid containing Plasto_pro/P19/Plasto_ter expression cassette using the following PCR-based method. A fragment containing the H3 coding sequence without his wild type signal peptide was amplified using primers IF-H3V36111.52+4c (FIG. 25A, SEQ ID NO: 44) and IF-H3V36111.s1-4r (FIG. 25B, SEQ ID NO: 45), using synthesized H3 gene (corresponding to nt 25 to 1725 from GISAID EPI ISL 101506 isolate HA sequence) (FIG. 25C, SEQ ID NO: 46) as template. The PCR product was cloned in-frame with alfalfa PDI signal peptide in 2X355/CPMV-HT/NOS expression system using In-Fusion cloning system (Clontech, Mountain View, Calif.). Construct 1192 (FIG. 4D) was digested with SacII and StuI restriction enzyme and the linearized plasmid was used for the In-Fusion assembly reaction. Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 4E (SEQ ID NO: 18). The resulting construct was given number 1391 (FIG. 25D, SEQ ID NO: 47). The amino acid sequence of PDISP/H3 from Influenza A/Victoria/361/2011 (H3N2) is presented in FIG. 25E (SEQ ID NO: 48). A representation of plasmid 1391 is presented in FIG. 25F.

B—2X355/CPMV-HT/HA B Wisconsin/NOS into BeYDV(m)+Replicase Amplification System (Construct Number 1462)

A sequence encoding HA from influenza B/Wisconsin/1/2010 was cloned into 2X35S/CPMV-HT/NOS comprising the BeYDV(m)+replicase amplification system in a plasmid containing Plasto_pro/P19/Plasto_ter expression cassette using the following PCR-based method. A fragment containing the complete HA B Wisconsin coding sequence was amplified using primers IF-HAB110.S1+3c (FIG. 26A, SEQ ID NO: 49) and IF-HAB110.s1-4r (FIG. 26B, SEQ ID NO: 50), using synthesized HA B Wisconsin gene (Genbank accession number JN993010) (FIG. 26C, SEQ ID NO: 51) as template. The PCR product was cloned in 2X35S/CPMV-HT/NOS expression cassette into the BeYDV(m) amplification system using In-Fusion cloning system (Clontech, Mountain View, Calif.). Construct 193 (FIG. 26D) was digested with SacII and StuI restriction enzyme and the linearized plasmid was used for the In-Fusion assembly reaction. Construct number 193 is an acceptor plasmid intended for "In Fusion" cloning of genes of interest in a CPMV-HT-based expression cassette into the BeYDV(m) amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 26E (SEQ ID NO: 52). The resulting construct was given number 1462 (FIG. 26F, SEQ ID NO: 53). The amino acid sequence of PDISP/HA from Influenza B/Wisconsin/1/2010 is presented in FIG. 26G (SEQ ID NO: 54). A representation of plasmid 1462 is presented in FIG. 26H.

C—2X355/CPMV-HT/HA B Wisconsin with Deleted Proteolytic Loop into BeYDV(m)+Replicase Amplification System (Construct Number 1467)

A sequence encoding HA from influenza B/Wisconsin/1/2010 with deleted proteolytic loop was cloned into 2X35S/CPMV-HT/NOS comprising the BeYDV(m)+replicase amplification system in a plasmid containing Plasto_pro/P19/Plasto_ter expression cassette using the following PCR-based ligation method presented by Darveau et al. (Methods in Neuroscience 26: 77-85 (1995)). In a first round of PCR, a fragment containing HA B Wisconsin coding sequence from nt 1 to nt 1062 was amplified using primers IF-HAB110.S1+3c (FIG. 26A, SEQ ID NO: 49) and HAB110(PrL-).r (FIG. 27A, SEQ ID NO: 55), using synthesized HA B Wisconsin gene (Genbank accession number JN993010) (FIG. 26C, SEQ ID NO: 51) as template. A second fragment, containing HA B Wisconsin coding sequence from nt 1120 to nt 1755, was amplified using primers HAB110(PrL-).c (FIG. 27B, SEQ ID NO: 56) and IF-HAB110.s1-4r (FIG. 26B, SEQ ID NO: 50), using synthesized HA B Wisconsin gene (Genbank accession number JN993010) (FIG. 26C, SEQ ID NO: 51) as template. The PCR products from both amplifications were then mixed and used as template for a second round of amplification using IF-HAB110.S1+3c (FIG. 26A, SEQ ID NO: 49) and IF-HAB110.s1-4r (FIG. 26B, SEQ ID NO: 50) as primers. The resulting fragment (encoding HA B/Wisconsin/1/2010 Δa.a. 340-358 with a GG linker between fragments) was cloned in 2X355/CPMV-HT/NOS expression cassette comprising the BeYDV(m) amplification system using In-Fusion cloning system (Clontech, Mountain View, Calif.). Construct 193 (FIG. 26D) was digested with SacII and StuI restriction enzyme and the linearized plasmid was used for the In-Fusion assembly reaction. Construct number 193 is an acceptor plasmid intended for "In Fusion" cloning of genes of interest in a CPMV-HT-based expression cassette into the BeYDV(m) amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 26E (SEQ ID NO: 52). The resulting construct was given number 1467 (FIG. 27C, SEQ ID NO: 57). The amino acid sequence of HA from Influenza B/Wisconsin/1/2010 with deleted proteolytic loop is presented in FIG. 27D (SEQ ID NO: 58). A representation of plasmid 1467 is presented in FIG. 27E.

D—2X355/CPMV-HT/PDISP/HA B Malaysia/NOS into BeYDV(m)+Replicase Amplification System (Construct Number 1631)

A sequence encoding HA from influenza B/Malaysia/2506/2004 was cloned into 2X35S/CPMV-HT/PDISP/NOS comprising the BeYDV(m)+replicase amplification system in a plasmid containing Plasto_pro/P19/Plasto_ter expression cassette using the following PCR-based method. A fragment containing HA B Malaysia coding sequence without his wild type signal peptide was amplified using primers IF-HB-M-04.s2+4c (FIG. 28A, SEQ ID NO: 59) and IF-HB-M-04.s1-4r (FIG. 28B, SEQ ID NO: 60), using synthesized HA B Malaysia gene (corresponding to nt 31-1743 from Genbank accession number EU124275. Silent mutations T759C and C888G were inserted in synthesized sequence in order to modify DraIII and BamHI restriction enzyme recognition sites) (FIG. 28C, SEQ ID NO: 61) as template. The PCR product was cloned in-frame with alfalfa PDI signal peptide in 2X355/CPMV-HT/NOS expression cassette into the BeYDV(m) amplification system using In-Fusion cloning system (Clontech, Mountain View, Calif.). Construct 194 (FIG. 28D) was digested with SacII and StuI restriction enzyme and the linearized plasmid was used for the In-Fusion assembly reaction. Construct number 194 is an acceptor plasmid intended for "In Fusion" cloning of genes of interest in frame with an alfalfa PDI signal peptide in a CPMV-HT-based expression cassette into the BeYDV(m) amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 28E (SEQ ID NO: 62). The resulting construct was given number 1631 (FIG. 28F, SEQ ID NO: 63). The amino acid sequence of PDISP/HA from Influenza B/Malaysia/2506/2004 is presented in FIG. 28G (SEQ ID NO: 64). A representation of plasmid 1631 is presented in FIG. 28H.

*Agrobacterium* Transfection

*Agrobacterium* strain AGL1 was transfected by electroporation with the DNA constructs using the methods described by D'Aoust et al 2008 (Plant Biotechnology Journal 6:930-940). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

The terms "biomass" and "plant matter" as used herein are meant to reflect any material derived from a plant. Biomass or plant matter may comprise an entire plant, tissue, cells, or any fraction thereof. Further, biomass or plant matter may comprise intracellular plant components, extracellular plant components, liquid or solid extracts of plants, or a combination thereof. Further, biomass or plant matter may comprise plants, plant cells, tissue, a liquid extract, or a combination thereof, from plant leaves, stems, fruit, roots or a combination thereof. A portion of a plant may comprise plant matter or biomass.

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

Agrobacteria transfected with each construct were grown in a YEB medium supplemented with 10 mM 2-(N-morpholino)ethanesulfonic acid (MES), 20 acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 2-6 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 3 volumes of cold 50 mM Tris pH 8.0, 0.15 M NaCl, 0.1% Triton X-100 and 1 mM phenylmethanesulfonyl fluoride. After homogenization, the slurries were centrifuged at 10,000 g for 10 min at 4° C. and these clarified crude extracts (supernatant) kept for analyses.

Protein Analysis and Immunoblotting

The total protein content of clarified crude extracts was determined by the Bradford assay (Bio-Rad, Hercules, Calif.) using bovine serum albumin as the reference standard. Proteins were separated by SDS-PAGE and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% Tween-20 in Tris-buffered saline (TBS-T) for 16-18 h at 4° C.

Immunoblotting was performed with a first incubation with a primary antibody (Table 4 presents the antibodies and conditions used for the detection of each HA), in 2 μg/ml in 2% skim milk in TBS-Tween 20 0.1%. Secondary antibodies used for chemiluminescence detection were as indicated in Table 4, diluted as indicated in 2% skim milk in TBS-Tween 20 0.1% Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

TABLE 4

Electrophoresis conditions, antibodies, and dilutions for immunoblotting of expressed proteins.

| HA subtype | Influenza strain | Electrophoresis condition | Primary antibody | Dilution | Secondary antibody | Dilution |
|---|---|---|---|---|---|---|
| B | B/Brisbane/60/2008 | Non-reducing | TGA, AS397 | 1:20000 | Rabbit anti-sheep (JIR 313-035-045) | 1:10000 |
| B | B/Wisconsin/1/2010 | Non-reducing | NIBSC 07/356 | 1:2000 | Rabbit anti-sheep (JIR 313-035-045) | 1:10000 |
| B | B/Malaysia/2506/2004 | Non-reducing | NIBSC 07/184 | 1:2000 | Rabbit anti-sheep (JIR | 1:10000 |

TABLE 4-continued

Electrophoresis conditions, antibodies, and dilutions for immunoblotting of expressed proteins.

| HA subtype | Influenza strain | Electro-phoresis condition | Primary antibody | Dilution | Secondary antibody | Dilution |
|---|---|---|---|---|---|---|
| | | | | | 313-035-045) | |
| H3 | A/Perth/16/2009 (H3N2) | Non-reducing | TGA, AS400 | 1:20000 | Rabbit anti-sheep (JIR 313-035-045) | 1:10000 |
| H3 | A/Victoria/361/2011 | Non-reducing | TGA, AS400 | 1:20000 | Rabbit anti-sheep (JIR 313-035-045) | 1:10000 |
| H1 | A/California/07/2009 (H1N1) | Reducing | Sino, 11055-MMO1 | 1 μg/ml | Goat anti-mouse (JIR 115-035-146) | 1:7 500 |
| H5 | A/Indonesia/05/2005 (H5N1) | Reducing | CBER, S-7858 | 1:4000 | Rabbit anti-sheep (JIR 313-035-045) | 1:10000 |

JIR: Jackson ImmunoResearch, West Grove, PA, USA;
CBER: Center for Biologics Evaluation and Research, Rockville, MD, USA.
Sino: Sino Biological inc., Beijing, China.
TGA: Therapeutic Goods Administration, Australia.
NIBSC: National Institute for Biological Standards and Control, United Kingdom Hemagglutination Assay Hemagglutination assay was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, N.Y.) were added to each well, and plates were incubated for 2 h at room temperature. The reciprocal of the highest dilution showing complete hemagglutination was recorded as HA activity. In parallel, a recombinant HA standard (A/Vietnam/1203/2004 H5N1) (Protein Science Corporation, Meriden, Conn.) was diluted in PBS and run as a control on each plate.

Example 1

Effect of Influenza M2 Co-Expression on the Accumulation Level of B HA and H3

The effect of influenza M2 co-expression on the accumulation level of HA from different influenza strains was analyzed by co-transferring constructs driving expression of HA with a construct for the expression of M2 from influenza A/New Caledonia/20/1999 (H1N1) in the agroinfiltration-based transient transformation system.

Western blot analysis of protein extracts from plants transformed with gene constructs driving the expression of influenza B HA (from B/Brisbane/60/2008) (constructs no. 1008, 1009 and 1029) in the presence or absence of M2-expression construct (construct no. 1261) showed that M2 co-expression results in increased accumulation of influenza B HA (FIG. 18). Similarly, the co-expression of M2 with H3 from influenza A/Perth/16/2009 (construct no. 1019+1261) resulted in increased accumulation of H3 in transformed plants when compared to plants transformed with H3-expression construct only (construct no. 1019) as shown in FIG. 19.

Western blot analysis of protein extracts from plants co-expressing M2 with H1 from influenza A/California/07/2009 showed that the co-expression of M2 with H1 resulted in a slight decrease in H1 accumulation level (FIG. 20, 484 vs 484+1261). The co-expression of M2 with H5 from influenza A/Indonesia/05/2005 also resulted in a reduced H5 accumulation when compared to H5 expressed alone (FIG. 21, 489 vs 489+1261).

The co-expression of M2 was further evaluated for its impact on the accumulation level of a modified influenza B HA. Construct no. 1059 encodes an influenza B HA in which the proteolytic loop is replaced by a 2 amino acid linker (GG in place of aa 341-359). The results from western blot analysis presented in FIG. 22A show that the removal of the proteolytic loop resulted in increased influenza B HA accumulation level (compare 1008 with 1059) and that the co-expression of M2 with the modified influenza B HA further increased HA accumulation level (FIG. 22A, 1059 vs 1059+1261). An analysis of hemagglutination activity on crude protein extracts from plants transformed with influenza B HA with or without modification and with or without co-expression of M2 confirmed the positive effect of M2 co-expression on the accumulation level of the native influenza B HA (FIG. 22B, 1008 vs 1008+1261) and the modified influenza B HA (FIG. 22B, 1059 vs 1059+1261).

The efficacy of M2 from influenza A/Puerto Rico/8/1934 to increase accumulation of the modified influenza B HA and H3 was compared to that of M2 from influenza A/New Caledonia/20/1999. For the modified influenza B HA, the comparison was undertaken by western blot analysis of protein extracts from plants transformed with constructs 1059, 1059+1261 and 1059+859. For H3, a similar comparison was performed on protein extracts from plants transformed with 1019, 1019+1261 and 1019+859. The results obtained demonstrated that the co-expression of M2 from influenza A/Puerto Rico/8/1934 (encoded by construct no. 859) was as efficient as the co-expression of M2 from influenza A/New Caledonia/20/1999 (encoded by construct no. 1261) for increasing accumulation of both the modified influenza B HA (FIG. 23A) and H3 (FIG. 23B).

Example 2

Effect of Influenza M2 Co-Expression on the Accumulation Level of Different Strains of B HA and H3

Western blot analysis of protein extracts from plants transformed with gene constructs driving the expression of influenza B HA (from B/Malaysia/2506/2004) (constructs no. 1631) in the presence or absence of M2-expression construct (construct no. 1261) showed that M2 co-expression results in increased accumulation of influenza B HA (FIG. 29).

Western blot analysis of protein extracts from plants transformed with gene constructs driving the expression of influenza B HA (from B/Wisconsin/1/2010) (constructs no. 1462) in the presence or absence of M2-expression construct (construct no. 1261) showed that M2 co-expression results in increased accumulation of influenza B HA (FIG. 30).

The co-expression of M2 was further evaluated for its impact on the accumulation level of a modified influenza B HA. Construct no. 1467 encodes an influenza B HA in which the proteolytic loop is replaced by a 2 amino acid linker (GG in place of aa 341-359). The results from western blot analysis presented in FIG. 30A show that the removal of the proteolytic loop resulted in increased influenza B HA accumulation level (compare 1462 with 1467) and that the co-expression of M2 with the modified influenza B HA further increased HA accumulation level (FIG. 30A, 1467 vs 1467+1261). An analysis of hemagglutination activity on crude protein extracts from plants transformed with influenza B HA with or without modification and with or without co-expression of M2 confirmed the positive effect of M2 co-expression on the accumulation level of the native influenza B HA (FIG. 30B, 1462 vs 1462+1261) and the modified influenza B HA (FIG. 26B, 1467 vs 1467+1261).

Western blot analysis of protein extracts from plants transformed with gene constructs driving the expression of influenza H3 (from H3/Victoria/361/2011) (constructs no. 1391) in the presence or absence of M2-expression construct (construct no. 1261) showed that M2 co-expression results in increased accumulation of influenza H3 (FIG. 31).

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of producing a virus like particle (VLP) in a plant comprising, a) introducing a first nucleic acid comprising a first regulatory region comprising a promoter and operatively linked to a nucleotide sequence encoding an influenza hemagglutinin (HA) protein, selected from the group consisting of influenza type B and H3, the first regulatory region further comprising a 5'UTR and a 3'UTR, into the plant, or portion of the plant, b) introducing a second nucleic acid comprising a second regulatory region comprising a promoter and operatively linked to a nucleotide sequence encoding a proton channel protein, the second regulatory region further comprising a 5'UTR and a 3'UTR, and the proton channel protein is an influenza proton channel protein selected from M2 and BM2, wherein the first and second nucleic acids in steps a) and b) are introduced by agroinfiltration, and c) incubating the plant or portion of the plant under conditions that permit the transient expression of the nucleic acids, thereby producing the VLP, wherein the yield of the type B or the type H3 HA is maintained or increased when compared to the yield of the type B or the type H3 HA expressed in the plant or portion of the plant without co-expression of M2 or BM2.

2. The method of claim 1, wherein the proton channel protein comprises the proton channel signature amino acid sequence of SEQ ID NO. 1.

3. The method of claim 1, wherein one or more than one proteolytic loop of the influenza HA protein has been deleted.

4. The method of claim 1, wherein the influenza type B HA protein is from the influenza strain influenza B/Brisbane/60/2008, B/Malaysia/2506/2004 or B/Wisconsin/1/2010.

5. The method of claim 4, wherein one or more than one proteolytic loop of the influenza type B HA protein has been deleted.

6. The method of claim 1, wherein the influenza H3 HA protein is from the influenza strain influenza A/Perth/16/2009 or from influenza A/Victoria/361/2011.

7. The method of claim 1, wherein the nucleotide sequence encoding the influenza type B hemagglutinin (HA) protein has at least 80% sequence identity to SEQ ID NO: 28.

8. The method of claim 1, wherein the sequence of the influenza hemagglutinin (HA) protein is SEQ ID NO:30.

9. The method of claim 1, wherein the nucleotide sequence encoding the influenza hemagglutinin (HA) protein has at least 70% sequence identity to a sequence selected from the group consisting of SEQ ID NO: 43 and nucleotides 1265-2968 of SEQ ID NO:57.

10. The method of claim 1, wherein the sequence of the influenza hemagglutinin (HA) protein is as shown as in at least one of SEQ ID NO:41 and SEQ ID NO:58.

11. The method of claim 1, wherein the nucleotide sequence encoding the influenza hemagglutinin (HA) protein has at least 70% sequence identity to a sequence selected from the group consisting of SEQ ID NO: 23 and SEQ ID NO:46.

12. The method of claim 1, wherein the sequence of the influenza hemagglutinin (HA) protein is as shown as in at least one of SEQ ID NO:25 and SEQ ID NO:48.

13. The method of claim 1, wherein the first nucleic acid sequence comprises the first regulatory region operatively linked with one or more than one comovirus enhancer, the nucleotide sequence encoding the influenza hemagglutinin (HA) protein, and one or more than one geminivirus amplification element, and a third nucleic acid encoding a geminivirus replicase is introduced into the plant or portion of the plant.

14. The method of claim 13, wherein the one or more than one comovirus enhancer is a comovirus UTR.

15. The method of claim 14, wherein the comovirus UTR is a Cowpea Mosaic Virus (CPMV) UTR.

16. The method of claim 13, wherein the one or more than one geminivirus amplification element is selected from a Bean Yellow Dwarf Virus long intergenic region (BeYDV LIR), and a BeYDV short intergenic region (BeYDV SIR).

17. The method of claim 13, wherein the nucleotide sequence encoding the influenza type B hemagglutinin (HA) protein has at least 80% sequence identity to SEQ ID NO: 28.

18. The method of claim 13, wherein the sequence of the influenza hemagglutinin (HA) protein is SEQ ID NO: 30.

19. The method of claim 13, wherein the nucleotide sequence encoding the influenza hemagglutinin (HA) protein has at least 70% sequence identity to a sequence selected from the group consisting of SEQ ID NO: 43 and nucleotides 1265-2968 of SEQ ID NO: 57.

20. The method of claim 13, wherein the sequence of the influenza hemagglutinin (HA) protein is as shown as in at least one of SEQ ID NO: 41 and SEQ ID NO: 58.

21. The method of claim 13, wherein the nucleotide sequence encoding the influenza hemagglutinin (HA) protein has at least 70% sequence identity to a sequence selected from the group consisting of SEQ ID NO: 23 and SEQ ID NO: 46.

22. The method of claim 13, wherein the sequence of the influenza hemagglutinin (HA) protein is as shown as in at least one of SEQ ID NO: 25 and SEQ ID NO: 48.

23. The method of claim 1 further comprising a step of d) harvesting the plant and purifying the VLPs.

24. The method of claim 1, wherein the VLP does not contain a viral matrix, a core protein or a channel protein.

25. The method of claim 1, further comprising introducing a third nucleic acid sequence, the third nucleic acid sequence encoding a suppressor of silencing.

26. The method of claim 13, further comprising introducing a fourth nucleic acid sequence, the fourth nucleic acid sequence encoding a suppressor of silencing.

27. The method of claim 25 wherein the suppressor of silencing is selected from the group HcPro and p19.

28. The method of claim 1, wherein the VLP does not contain the proton channel protein.

29. The method of claim 1, wherein the influenza hemagglutinin (HA) protein is an HA0 protein.

30. The method of claim 1, wherein the M2 protein is from an influenza strain selected from the group comprising influenza A/Puerto Rico/8/1934 and influenza A/New Caledonia/20/1999.

31. A method of increasing production of an influenza hemagglutinin (HA) protein in a plant comprising, a) introducing a first nucleic acid comprising a first regulatory region comprising a promoter and operatively linked to a nucleotide sequence encoding an influenza hemagglutinin (HA) protein, selected from the group consisting of influenza type B and H3, the first regulatory region further comprising a 5'UTR and a 3'UTR, into the plant, or portion of the plant, b) introducing a second nucleic acid comprising a second regulatory region comprising a promoter and operatively linked to a nucleotide sequence encoding a proton channel protein, the second regulatory region further comprising a 5'UTR and a 3'UTR, and the proton channel protein is an influenza proton channel protein selected from M2 and BM2, wherein the first and second nucleic acids in steps a) and b) are introduced by agroinfiltration; and c) incubating the plant or portion of the plant under conditions that permit the transient expression of the nucleic acids, thereby producing the VLP, wherein the yield of the type B or the type H3 HA is increased when compared to the yield of the type B or the type H3 HA expressed in the plant or portion of the plant without co-expression of M2 or BM2.

* * * * *

SEQUENCE LISTING

```
<160> NUMBER OF SEQ ID NOS: 88

<210> SEQ ID NO 1
<211> LENGTH: 5
<212> TYPE: PRT
<213> ORGANISM: Artificial Sequence
<220> FEATURE:
<223> OTHER INFORMATION: proton channel signature sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 1

His Xaa Xaa Xaa Trp
1               5


<210> SEQ ID NO 2
<211> LENGTH: 41
<212> TYPE: DNA
<213> ORGANISM: Artificial Sequence
<220> FEATURE:
<223> OTHER INFORMATION: primer IF-H5A-I-05.s1+3c

<400> SEQUENCE: 2

aaatttgtcg ggcccatgga gaaaatagtg cttcttcttg c                         41


<210> SEQ ID NO 3
<211> LENGTH: 50
<212> TYPE: DNA
<213> ORGANISM: Artificial Sequence
<220> FEATURE:
<223> OTHER INFORMATION: primer IF-H5dTm.r

<400> SEQUENCE: 3

actaaagaaa ataggccttt aaatgcaaat tctgcattgt aacgatccat               50


<210> SEQ ID NO 4
<211> LENGTH: 4903
<212> TYPE: DNA
<213> ORGANISM: Artificial Sequence
```

<220> FEATURE:
<223> OTHER INFORMATION: Construct 1191

<400> SEQUENCE: 4

```
tggcaggata tattgtggtg taaacaaatt gacgcttaga caacttaata acacattgcg     60
gacgttttta atgtactgaa ttaacgccga atcccgggct ggtatattta tatgttgtca    120
aataactcaa aaaccataaa agtttaagtt agcaagtgtg tacattttta cttgaacaaa    180
aatattcacc tactactgtt ataaatcatt attaaacatt agagtaaaga aatatggatg    240
ataagaacaa gagtagtgat attttgacaa caattttgtt gcaacatttg agaaaatttt    300
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
```

```
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccagtaca acgttttctt   3060
tcactgaagc gaaatcaaag atctctttgt ggacacgtag tgcggcgcca ttaaataacg   3120
tgtacttgtc ctattcttgt cggtgtggtc ttgggaaaag aaagcttgct ggaggctgct   3180
gttcagcccc atacattact tgttacgatt ctgctgactt tcggcgggtg caatatctct   3240
acttctgctt gacgaggtat tgttgcctgt acttctttct tcttcttctt gctgattggt   3300
tctataagaa atctagtatt ttctttgaaa cagagttttc ccgtggtttt cgaacttgga   3360
gaaagattgt taagcttctg tatattctgc ccaaatttgt cgggcccgcg gatggcgaaa   3420
aacgttgcga ttttcggctt attgttttct cttcttgtgt tggttccttc tcagatcttc   3480
gcctgcaggc tcctcagcca aaacgacacc cccatctgtc tatccactgg cccctggatc   3540
tgctgcccaa actaactcca tggtgaccct gggatgcctg gtcaagggct atttccctga   3600
gccagtgaca gtgacctgga actctggatc cctgtccagc ggtgtgcaca ccttcccagc   3660
tgtcctgcag tctgacctct acactctgag cagctcagtg actgtcccct ccagcacctg   3720
gcccagcgag accgtcacct gcaacgttgc ccacccggcc agcagcacca aggtggacaa   3780
gaaaattgtg cccagggatt gtggttgtaa gccttgcata tgtacagtcc cagaagtatc   3840
atctgtcttc atcttccccc caaagcccaa ggatgtgctc accattactc tgactcctaa   3900
ggtcacgtgt gttgtggtag acatcagcaa ggatgatccc gaggtccagt tcagctggtt   3960
tgtagatgat gtggaggtgc acacagctca gacgcaaccc cgggaggagc agttcaacag   4020
cactttccgc tcagtcagtg aacttcccat catgcaccag gactggctca atggcaagga   4080
gcgatcgctc accatcacca tcaccatcac catcaccatt aaaggcctat tttctttagt   4140
ttgaatttac tgttattcgg tgtgcatttc tatgtttggt gagcggtttt ctgtgctcag   4200
agtgtgttta ttttatgtaa tttaatttct ttgtgagctc ctgtttagca ggtcgtccct   4260
tcagcaagga cacaaaaaga ttttaatttt attaaaaaaa aaaaaaaaaa agaccgggaa   4320
ttcgatatca agcttatcga cctgcagatc gttcaaacat ttggcaataa agtttcttaa   4380
gattgaatcc tgttgccggt cttgcgatga ttatcatata atttctgttg aattacgtta   4440
agcatgtaat aattaacatg taatgcatga cgttatttat gagatgggtt tttatgatta   4500
gagtcccgca attatacatt taatacgcga tagaaaacaa aatatagcgc gcaaactagg   4560
ataaattatc gcgcgcggtg tcatctatgt tactagatct ctagagtctc aagcttggcg   4620
```

cgcccacgtg actagtggca ctggccgtcg ttttacaacg tcgtgactgg gaaaaccctg 4680
gcgttaccca acttaatcgc cttgcagcac atcccccttt cgccagctgg cgtaatagcg 4740
aagaggcccg caccgatcgc ccttcccaac agttgcgcag cctgaatggc gaatgctaga 4800
gcagcttgag cttggatcag attgtcgttt cccgccttca gtttaaacta tcagtgtttg 4860
acaggatata ttggcgggta aacctaagag aaaagagcgt tta 4903

<210> SEQ ID NO 5
<211> LENGTH: 3447
<212> TYPE: DNA
<213> ORGANISM: Artificial Sequence
<220> FEATURE:
<223> OTHER INFORMATION: Expression cassette number 489

<400> SEQUENCE: 5
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140
tcttcttgct gattggttct ataagaaatc tagtattttc tttgaaacag agttttcccg 1200
tggttttcga acttggagaa agattgttaa gcttctgtat attctgccca aatttgtcgg 1260
gcccatggag aaaatagtgc ttcttcttgc aatagtcagt cttgttaaaa gtgatcagat 1320
ttgcattggt taccatgcaa acaattcaac agagcaggtt gacacaatca tggaaaagaa 1380
cgttactgtt acacatgccc aagacatact ggaaaagaca cacaacggga agctctgcga 1440
tctagatgga gtgaagcctc taattttaag agattgtagt gtagctggat ggctcctcgg 1500
gaacccaatg tgtgacgaat tcatcaatgt accggaatgg tcttacatag tggagaaggc 1560
caatccaacc aatgacctct gttacccagg gagtttcaac gactatgaag aactgaaaca 1620
cctattgagc agaataaacc attttgagaa aattcaaatc atccccaaaa gttcttggtc 1680
cgatcatgaa gcctcatcag gagttagctc agcatgtcca tacctgggaa gtccctcctt 1740

-continued

```
ttttagaaat gtggtatggc ttatcaaaaa gaacagtaca tacccaacaa taaagaaaag   1800
ctacaataat accaaccaag aggatctttt ggtactgtgg ggaattcacc atcctaatga   1860
tgcggcagag cagacaaggc tatatcaaaa cccaaccacc tatatttcca ttgggacatc   1920
aacactaaac cagagattgg taccaaaaat agctactaga tccaaagtaa acgggcaaag   1980
tggaaggatg gagttcttct ggacaatttt aaaacctaat gatgcaatca acttcgagag   2040
taatggaaat ttcattgctc cagaatatgc atacaaaatt gtcaagaaag ggactcagc    2100
aattatgaaa agtgaattgg aatatggtaa ctgcaacacc aagtgtcaaa ctccaatggg   2160
ggcgataaac tctagtatgc cattccacaa catacaccct ctcaccatcg ggaatgccc    2220
caaatatgtg aaatcaaaca gattagtcct tgcaacaggg ctcagaaata gccctcaaag   2280
agagagcaga agaaaaaaga gaggactatt tggagctata gcaggtttta tagagggagg   2340
atggcaggga atggtagatg gttggtatgg gtaccaccat agcaatgagc aggggagtgg   2400
gtacgctgca gacaaagaat ccactcaaaa ggcaatagat ggagtcacca ataaggtcaa   2460
ctcaatcatt gacaaaatga acactcagtt tgaggccgtt ggaagggaat ttaataactt   2520
agaaaggaga atagagaatt taaacaagaa gatggaagac gggtttctag atgtctggac   2580
ttataatgcc gaacttctgg ttctcatgga aaatgagaga actctagact ttcatgactc   2640
aaatgttaag aacctctacg acaaggtccg actacagctt agggataatg caaaggagct   2700
gggtaacggt tgtttcgagt tctatcacaa atgtgataat gaatgtatgg aaagtataag   2760
aaacggaacg tacaactatc cgcagtattc agaagaagca agattaaaaa gagaggaaat   2820
aagtggggta aaattggaat caataggaac ttaccaaata ctgtcaattt attcaacagt   2880
ggcgagttcc ctagcactgg caatcatgat ggctggtcta tctttatgga tgtgctccaa   2940
tggatcgtta caatgcagaa tttgcattta aaggcctatt ttctttagtt tgaatttact   3000
gttattcggt gtgcatttct atgtttggtg agcggttttc tgtgctcaga gtgtgtttat   3060
tttatgtaat ttaatttctt tgtgagctcc tgtttagcag gtcgtccctt cagcaaggac   3120
acaaaaagat tttaatttta ttaaaaaaaa aaaaaaaaaa gaccgggaat tcgatatcaa   3180
gcttatcgac ctgcagatcg ttcaaacatt tggcaataaa gtttcttaag attgaatcct   3240
gttgccggtc ttgcgatgat tatcatataa tttctgttga attacgttaa gcatgtaata   3300
attaacatgt aatgcatgac gttatttatg agatgggttt ttatgattag agtcccgcaa   3360
ttatacattt aatacgcgat agaaaacaaa atatagcgcg caaactagga taaattatcg   3420
cgcgcggtgt catctatgtt actagat                                       3447
```

<210> SEQ ID NO 6
<211> LENGTH: 568
<212> TYPE: PRT
<213> ORGANISM: Influenza virus

<400> SEQUENCE: 6

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
```

-continued

```
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495
```

```
Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565


<210> SEQ ID NO 7
<211> LENGTH: 42
<212> TYPE: DNA
<213> ORGANISM: Artificial Sequence
<220> FEATURE:
<223> OTHER INFORMATION: primer IF-S1-M1+M2ANC.c

<400> SEQUENCE: 7

aaatttgtcg ggcccatgag tcttctaacc gaggtcgaaa cg                        42


<210> SEQ ID NO 8
<211> LENGTH: 43
<212> TYPE: DNA
<213> ORGANISM: Artificial Sequence
<220> FEATURE:
<223> OTHER INFORMATION: primer IF-S1-4-M2ANC.r

<400> SEQUENCE: 8

actaaagaaa ataggccttt actccagctc tatgctgaca aaa                       43


<210> SEQ ID NO 9
<211> LENGTH: 294
<212> TYPE: DNA
<213> ORGANISM: Artificial Sequence
<220> FEATURE:
<223> OTHER INFORMATION: nucleotide sequence of synthesized M2 gene
      (DQ508860)

<400> SEQUENCE: 9

atgagtcttc taaccgaggt cgaaacgcct atcagaaacg aatgggggtg cagatgcaac     60

gattcaagtg atcctcttgt tgttgccgca agtataattg ggattgtgca cctgatattg    120

tggattattg atcgcctttt ttccaaaagc atttatcgta tctttaaaca cggtttaaaa    180

agagggcctt ctacggaagg agtaccagag tctatgaggg aagaatatcg agaggaacag    240

cagaatgctg tggatgctga cgatggtcat tttgtcagca tagagctgga gtaa          294


<210> SEQ ID NO 10
<211> LENGTH: 2034
<212> TYPE: DNA
<213> ORGANISM: Artificial Sequence
<220> FEATURE:
<223> OTHER INFORMATION: Expression cassette number 1261

<400> SEQUENCE: 10

gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240
```

-continued

```
ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900

cagtacaacg ttttctttca ctgaagcgaa atcaaagatc tctttgtgga cacgtagtgc    960

ggcgccatta aataacgtgt acttgtccta ttcttgtcgg tgtggtcttg ggaaaagaaa   1020

gcttgctgga ggctgctgtt cagccccata cattacttgt tacgattctg ctgactttcg   1080

gcgggtgcaa tatctctact tctgcttgac gaggtattgt tgcctgtact tctttcttct   1140

tcttcttgct gattggttct ataagaaatc tagtattttc tttgaaacag agttttcccg   1200

tggttttcga acttggagaa agattgttaa gcttctgtat attctgccca aatttgtcgg   1260

gcccatgagt cttctaaccg aggtcgaaac gcctatcaga aacgaatggg ggtgcagatg   1320

caacgattca agtgatcctc ttgttgttgc cgcaagtata attgggattg tgcacctgat   1380

attgtggatt attgatcgcc ttttttccaa aagcatttat cgtatcttta aacacggttt   1440

aaaaagaggg ccttctacgg aaggagtacc agagtctatg agggaagaat atcgagagga   1500

acagcagaat gctgtggatg ctgacgatgg tcattttgtc agcatagagc tggagtaaag   1560

gcctattttc tttagtttga atttactgtt attcggtgtg catttctatg tttggtgagc   1620

ggttttctgt gctcagagtg tgtttatttt atgtaattta atttctttgt gagctcctgt   1680

ttagcaggtc gtcccttcag caaggacaca aaaagatttt aattttatta aaaaaaaaaa   1740

aaaaaaagac cgggaattcg atatcaagct tatcgacctg cagatcgttc aaacatttgg   1800

caataaagtt tcttaagatt gaatcctgtt gccggtcttg cgatgattat catataattt   1860

ctgttgaatt acgttaagca tgtaataatt aacatgtaat gcatgacgtt atttatgaga   1920

tgggttttta tgattagagt cccgcaatta tacatttaat acgcgataga aaacaaaata   1980

tagcgcgcaa actaggataa attatcgcgc gcggtgtcat ctatgttact agat         2034
```

```
<210> SEQ ID NO 11
<211> LENGTH: 97
<212> TYPE: PRT
<213> ORGANISM: Influenza virus

<400> SEQUENCE: 11

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Val His Leu Ile Leu Trp Ile Ile Asp Arg Leu Phe Ser
        35                  40                  45

Lys Ser Ile Tyr Arg Ile Phe Lys His Gly Leu Lys Arg Gly Pro Ser
    50                  55                  60
```

-continued

```
Thr Glu Gly Val Pro Glu Ser Met Arg Glu Glu Tyr Arg Glu Glu Gln
65                  70                  75                  80

Gln Asn Ala Val Asp Ala Asp Asp Gly His Phe Val Ser Ile Glu Leu
                85                  90                  95

Glu


<210> SEQ ID NO 12
<211> LENGTH: 294
<212> TYPE: DNA
<213> ORGANISM: Artificial Sequence
<220> FEATURE:
<223> OTHER INFORMATION: nucleotide sequence of synthesized M2 gene

<400> SEQUENCE: 12

atgagtcttc taaccgaggt cgaaacgcct atcagaaacg aatgggggtg cagatgcaac     60

ggttcaagtg atcctctcac tattgccgca aatatcattg ggatcttgca cttgacattg    120

tggattcttg atcgtctttt tttcaaatgc atttaccgtc gctttaaata cggactgaaa    180

ggagggcctt ctacggaagg agtgccaaag tctatgaggg aagaatatcg aaaggaacag    240

cagagtgctg tggatgctga cgatggtcat tttgtcagca tagagctgga gtaa          294


<210> SEQ ID NO 13
<211> LENGTH: 2034
<212> TYPE: DNA
<213> ORGANISM: Artificial Sequence
<220> FEATURE:
<223> OTHER INFORMATION: Expression cassette number 859

<400> SEQUENCE: 13

gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900

cagtacaacg ttttctttca ctgaagcgaa atcaaagatc tctttgtgga cacgtagtgc    960

ggcgccatta aataacgtgt acttgtccta ttcttgtcgg tgtggtcttg ggaaaagaaa   1020

gcttgctgga ggctgctgtt cagccccata cattacttgt tacgattctg ctgactttcg   1080

gcgggtgcaa tatctctact tctgcttgac gaggtattgt tgcctgtact tctttcttct   1140

tcttcttgct gattggttct ataagaaatc tagtattttc tttgaaacag agttttcccg   1200
```

-continued

```
tggttttcga acttggagaa agattgttaa gcttctgtat attctgccca aatttgtcgg   1260

gcccatgagt cttctaaccg aggtcgaaac gcctatcaga aacgaatggg ggtgcagatg   1320

caacggttca agtgatcctc tcactattgc cgcaaatatc attgggatct tgcacttgac   1380

attgtggatt cttgatcgtc tttttttcaa atgcatttac cgtcgcttta aatacggact   1440

gaaaggaggg ccttctacgg aaggagtgcc aaagtctatg agggaagaat atcgaaagga   1500

acagcagagt gctgtggatg ctgacgatgg tcattttgtc agcatagagc tggagtaaag   1560

gcctattttc tttagtttga atttactgtt attcggtgtg catttctatg tttggtgagc   1620

ggttttctgt gctcagagtg tgtttatttt atgtaattta atttctttgt gagctcctgt   1680

ttagcaggtc gtcccttcag caaggacaca aaaagatttt aattttatta aaaaaaaaaa   1740

aaaaaaagac cgggaattcg atatcaagct tatcgacctg cagatcgttc aaacatttgg   1800

caataaagtt tcttaagatt gaatcctgtt gccggtcttg cgatgattat catataattt   1860

ctgttgaatt acgttaagca tgtaataatt aacatgtaat gcatgacgtt atttatgaga   1920

tgggttttta tgattagagt cccgcaatta tacatttaat acgcgataga aaacaaaata   1980

tagcgcgcaa actaggataa attatcgcgc gcggtgtcat ctatgttact agat         2034
```

```
<210> SEQ ID NO 14
<211> LENGTH: 97
<212> TYPE: PRT
<213> ORGANISM: Influenza virus

<400> SEQUENCE: 14

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu


<210> SEQ ID NO 15
<211> LENGTH: 46
<212> TYPE: DNA
<213> ORGANISM: Artificial Sequence
<220> FEATURE:
<223> OTHER INFORMATION: primer IF-H1A-C-09.s2+4c

<400> SEQUENCE: 15

tctcagatct tcgccgacac attatgtata ggttatcatg cgaaca                    46


<210> SEQ ID NO 16
<211> LENGTH: 49
<212> TYPE: DNA
<213> ORGANISM: Artificial Sequence
<220> FEATURE:
<223> OTHER INFORMATION: primer IF-H1A-C-09.s1-4r

<400> SEQUENCE: 16

actaaagaaa ataggccttt aaatacatat tctacactgt agagaccca                 49
```

<210> SEQ ID NO 17
<211> LENGTH: 1701
<212> TYPE: DNA
<213> ORGANISM: Artificial Sequence
<220> FEATURE:
<223> OTHER INFORMATION: nucleotide sequence of synthesized H1 gene

<400> SEQUENCE: 17
atgaaggcaa tactagtagt tctgctatat acatttgcaa ccgcaaatgc agacacatta 60
tgtataggtt atcatgcgaa caattcaaca gacactgtag acacagtact agaaaagaat 120
gtaacagtaa cacactctgt taaccttcta gaagacaagc ataacgggaa actatgcaaa 180
ctaagagggg tagccccatt gcatttgggt aaatgtaaca ttgctggctg gatcctggga 240
aatccagagt gtgaatcact ctccacagca agctcatggt cctacattgt ggaaacacct 300
agttcagaca atggaacgtg ttacccagga gatttcatcg attatgagga gctaagagag 360
caattgagct cagtgtcatc atttgaaagg tttgagatat tccccaagac aagttcatgg 420
cccaatcatg actcgaacaa aggtgtaacg gcagcatgtc ctcatgctgg agcaaaaagc 480
ttctacaaaa atttaatatg gctagttaaa aaaggaaatt catacccaaa gctcagcaaa 540
tcctacatta atgataaagg gaaagaagtc ctcgtgctat ggggcattca ccatccatct 600
actagtgctg accaacaaag tctctatcag aatgcagatg catatgtttt tgtggggtca 660
tcaagataca gcaagaagtt caagccggaa atagcaataa gacccaaagt gagggatcaa 720
gaagggagaa tgaactatta ctggacacta gtagagccgg gagacaaaat aacattcgaa 780
gcaactggaa atctagtggt accgagatat gcattcgcaa tggaaagaaa tgctggatct 840
ggtattatca tttcagatac accagtccac gattgcaata caacttgtca aacacccaag 900
ggtgctataa acaccagcct cccatttcag aatatacatc cgatcacaat tggaaaatgt 960
ccaaaatatg taaaaagcac aaaattgaga ctggccacag gattgaggaa tatcccgtct 1020
attcaatcta gaggcctatt tggggccatt gccggtttca ttgaaggggg gtggacaggg 1080
atggtagatg gatggtacgg ttatcaccat caaaatgagc aggggtcagg atatgcagcc 1140
gacctgaaga gcacacagaa tgccattgac gagattacta acaaagtaaa ttctgttatt 1200
gaaaagatga atacacagtt cacagcagta ggtaaagagt tcaaccacct ggaaaaaaga 1260
atagagaatt taaataaaaa agttgatgat ggtttcctgg acatttggac ttacaatgcc 1320
gaactgttgg ttctattgga aaatgaaaga actttggact accacgattc aaatgtgaag 1380
aacttatatg aaaaggtaag aagccagcta aaaaacaatg ccaaggaaat tggaaacggc 1440
tgctttgaat tttaccacaa atgcgataac acgtgcatgg aaagtgtcaa aaatgggact 1500
tatgactacc caaaatactc agaggaagca aaattaaaca gagaagaaat agatggggta 1560
aagctggaat caacaaggat ttaccagatt ttggcgatct attcaactgt cgccagttca 1620
ttggtactgg tagtctccct gggggcaatc agtttctgga tgtgctctaa tgggtctcta 1680
cagtgtagaa tatgtattta a 1701

<210> SEQ ID NO 18
<211> LENGTH: 4897
<212> TYPE: DNA
<213> ORGANISM: Artificial Sequence
<220> FEATURE:
<223> OTHER INFORMATION: Construct 1192

<400> SEQUENCE: 18

-continued

```
tggcaggata tattgtggtg taaacaaatt gacgcttaga caacttaata acacattgcg     60
gacgttttta atgtactgaa ttaacgccga atcccgggct ggtatattta tatgttgtca    120
aataactcaa aaaccataaa agtttaagtt agcaagtgtg tacattttta cttgaacaaa    180
aatattcacc tactactgtt ataaatcatt attaaacatt agagtaaaga aatatggatg    240
ataagaacaa gagtagtgat attttgacaa caattttgtt gcaacatttg agaaaatttt    300
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
```

-continued cccacccacg aggagcatcg tggaaaaaga agacgttcca accacgtctt caaagcaagt 2460
ggattgatgt gataacatgg tggagcacga cacacttgtc tactccaaaa atatcaaaga 2520
tacagtctca gaagaccaaa gggcaattga gacttttcaa caaagggtaa tatccggaaa 2580
cctcctcgga ttccattgcc cagctatctg tcactttatt gtgaagatag tggaaaagga 2640
aggtggctcc tacaaatgcc atcattgcga taaaggaaag gccatcgttg aagatgcctc 2700
tgccgacagt ggtcccaaag atggaccccc acccacgagg agcatcgtgg aaaaagaaga 2760
cgttccaacc acgtcttcaa agcaagtgga ttgatgtgat atctccactg acgtaaggga 2820
tgacgcacaa tcccactatc cttcgcaaga cccttcctct atataaggaa gttcatttca 2880
tttggagagg tattaaaatc ttaataggtt ttgataaaag cgaacgtggg gaaacccgaa 2940
ccaaaccttc ttctaaactc tctctcatct ctcttaaagc aaacttctct cttgtctttc 3000
ttgcgtgagc gatcttcaac gttgtcagat cgtgcttcgg caccagtaca acgttttctt 3060
tcactgaagc gaaatcaaag atctctttgt ggacacgtag tgcggcgcca ttaaataacg 3120
tgtacttgtc ctattcttgt cggtgtggtc ttgggaaaag aaagcttgct ggaggctgct 3180
gttcagcccc atacattact tgttacgatt ctgctgactt tcggcgggtg caatatctct 3240
acttctgctt gacgaggtat tgttgcctgt acttctttct tcttcttctt gctgattggt 3300
tctataagaa atctagtatt ttctttgaaa cagagttttc ccgtggtttt cgaacttgga 3360
gaaagattgt taagcttctg tatattctgc ccaaatttgt cgggcccatg gcgaaaaacg 3420
ttgcgatttt cggcttattg ttttctcttc ttgtgttggt tccttctcag atcttcgccg 3480
cggctcctca gccaaaacga cacccccatc tgtctatcca ctggcccctg gatctgctgc 3540
ccaaactaac tccatggtga ccctgggatg cctggtcaag ggctatttcc ctgagccagt 3600
gacagtgacc tggaactctg gatccctgtc cagcggtgtg cacaccttcc cagctgtcct 3660
gcagtctgac ctctacactc tgagcagctc agtgactgtc ccctccagca cctggcccag 3720
cgagaccgtc acctgcaacg ttgcccaccc ggccagcagc accaaggtgg acaagaaaat 3780
tgtgcccagg gattgtggtt gtaagccttg catatgtaca gtcccagaag tatcatctgt 3840
cttcatcttc cccccaaagc ccaaggatgt gctcaccatt actctgactc ctaaggtcac 3900
gtgtgttgtg gtagacatca gcaaggatga tcccgaggtc cagttcagct ggtttgtaga 3960
tgatgtggag gtgcacacag ctcagacgca accccgggag gagcagttca acagcacttt 4020
ccgctcagtc agtgaacttc ccatcatgca ccaggactgg ctcaatggca aggagcgatc 4080
gctcaccatc accatcacca tcaccatcac cattaaaggc ctattttctt tagtttgaat 4140
ttactgttat tcggtgtgca tttctatgtt tggtgagcgg ttttctgtgc tcagagtgtg 4200
tttattttat gtaatttaat ttctttgtga gctcctgttt agcaggtcgt cccttcagca 4260
aggacacaaa aagattttaa ttttattaaa aaaaaaaaaa aaaaagaccg ggaattcgat 4320
atcaagctta tcgacctgca gatcgttcaa acatttggca ataaagtttc ttaagattga 4380
atcctgttgc cggtcttgcg atgattatca tataatttct gttgaattac gttaagcatg 4440
taataattaa catgtaatgc atgacgttat ttatgagatg ggtttttatg attagagtcc 4500
cgcaattata catttaatac gcgatagaaa acaaaatata gcgcgcaaac taggataaat 4560
tatcgcgcgc ggtgtcatct atgttactag atctctagag tctcaagctt ggcgcgccca 4620
cgtgactagt ggcactggcc gtcgttttac aacgtcgtga ctgggaaaac cctggcgtta 4680
cccaacttaa tcgccttgca gcacatcccc ctttcgccag ctggcgtaat agcgaagagg 4740

-continued

```
cccgcaccga tcgcccttcc caacagttgc gcagcctgaa tggcgaatgc tagagcagct   4800

tgagcttgga tcagattgtc gtttcccgcc ttcagtttaa actatcagtg tttgacagga   4860

tatattggcg ggtaaaccta agagaaaaga gcgttta                            4897
```

<210> SEQ ID NO 19
<211> LENGTH: 3462
<212> TYPE: DNA
<213> ORGANISM: Artificial Sequence
<220> FEATURE:
<223> OTHER INFORMATION: Expression cassette number 484

<400> SEQUENCE: 19

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900

cagtacaacg ttttctttca ctgaagcgaa atcaaagatc tctttgtgga cacgtagtgc    960

ggcgccatta aataacgtgt acttgtccta ttcttgtcgg tgtggtcttg ggaaaagaaa   1020

gcttgctgga ggctgctgtt cagccccata cattacttgt tacgattctg ctgactttcg   1080

gcgggtgcaa tatctctact tctgcttgac gaggtattgt tgcctgtact tctttcttct   1140

tcttcttgct gattggttct ataagaaatc tagtattttc tttgaaacag agttttcccg   1200

tggttttcga acttggagaa agattgttaa gcttctgtat attctgccca aatttgtcgg   1260

gcccatggcg aaaaacgttg cgattttcgg cttattgttt tctcttcttg tgttggttcc   1320

ttctcagatc ttcgccgaca cattatgtat aggttatcat gcgaacaatt caacagacac   1380

tgtagacaca gtactagaaa agaatgtaac agtaacacac tctgttaacc ttctagaaga   1440

caagcataac gggaaactat gcaaactaag aggggtagcc ccattgcatt tgggtaaatg   1500

taacattgct ggctggatcc tgggaaatcc agagtgtgaa tcactctcca cagcaagctc   1560

atggtcctac attgtggaaa cacctagttc agacaatgga acgtgttacc caggagattt   1620

catcgattat gaggagctaa gagagcaatt gagctcagtg tcatcatttg aaaggtttga   1680

gatattcccc aagacaagtt catggcccaa tcatgactcg aacaaaggtg taacggcagc   1740

atgtcctcat gctggagcaa aaagcttcta caaaaattta atatggctag ttaaaaaagg   1800

aaattcatac ccaaagctca gcaaatccta cattaatgat aaagggaaag aagtcctcgt   1860

gctatggggc attcaccatc catctactag tgctgaccaa caaagtctct atcagaatgc   1920
```

```
agatgcatat gtttttgtgg ggtcatcaag atacagcaag aagttcaagc cggaaatagc   1980
aataagaccc aaagtgaggg atcaagaagg gagaatgaac tattactgga cactagtaga   2040
gccgggagac aaaataacat tcgaagcaac tggaaatcta gtggtaccga gatatgcatt   2100
cgcaatggaa agaaatgctg gatctggtat tatcatttca gatacaccag tccacgattg   2160
caatacaact tgtcaaacac ccaagggtgc tataaacacc agcctcccat ttcagaatat   2220
acatccgatc acaattggaa aatgtccaaa atatgtaaaa agcacaaaat tgagactggc   2280
cacaggattg aggaatatcc cgtctattca atctagaggc ctatttgggg ccattgccgg   2340
tttcattgaa ggggggtgga cagggatggt agatggatgg tacggttatc accatcaaaa   2400
tgagcagggg tcaggatatg cagccgacct gaagagcaca cagaatgcca ttgacgagat   2460
tactaacaaa gtaaattctg ttattgaaaa gatgaataca cagttcacag cagtaggtaa   2520
agagttcaac cacctggaaa aaagaataga gaatttaaat aaaaaagttg atgatggttt   2580
cctggacatt tggacttaca atgccgaact gttggttcta ttggaaaatg aaagaacttt   2640
ggactaccac gattcaaatg tgaagaactt atatgaaaag gtaagaagcc agctaaaaaa   2700
caatgccaag gaaattggaa acggctgctt tgaattttac cacaaatgcg ataacacgtg   2760
catggaaagt gtcaaaaatg ggacttatga ctacccaaaa tactcagagg aagcaaaatt   2820
aaacagagaa gaaatagatg ggtaaagct ggaatcaaca aggatttacc agattttggc   2880
gatctattca actgtcgcca gttcattggt actggtagtc tccctggggg caatcagttt   2940
ctggatgtgc tctaatgggt ctctacagtg tagaatatgt atttaaaggc ctattttctt   3000
tagtttgaat ttactgttat tcggtgtgca tttctatgtt tggtgagcgg ttttctgtgc   3060
tcagagtgtg tttattttat gtaatttaat ttctttgtga gctcctgttt agcaggtcgt   3120
cccttcagca aggacacaaa aagattttaa ttttattaaa aaaaaaaaaa aaaaagaccg   3180
ggaattcgat atcaagctta tcgacctgca gatcgttcaa acatttggca ataaagtttc   3240
ttaagattga atcctgttgc cggtcttgcg atgattatca tataatttct gttgaattac   3300
gttaagcatg taataattaa catgtaatgc atgacgttat ttatgagatg ggtttttatg   3360
attagagtcc cgcaattata catttaatac gcgatagaaa acaaaatata gcgcgcaaac   3420
taggataaat tatcgcgcgc ggtgtcatct atgttactag at                      3462
```

<210> SEQ ID NO 20
<211> LENGTH: 573
<212> TYPE: PRT
<213> ORGANISM: Influenza virus

<400> SEQUENCE: 20

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95
```

-continued

```
Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
```

```
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570


<210> SEQ ID NO 21
<211> LENGTH: 40
<212> TYPE: DNA
<213> ORGANISM: Artificial Sequence
<220> FEATURE:
<223> OTHER INFORMATION: primer IF-S2+S4-H3 Per.c

<400> SEQUENCE: 21

tctcagatct tcgcccaaaa acttcctgga aatgacaaca                          40


<210> SEQ ID NO 22
<211> LENGTH: 45
<212> TYPE: DNA
<213> ORGANISM: Artificial Sequence
<220> FEATURE:
<223> OTHER INFORMATION: primer IF-S1a4-H3 Per.r

<400> SEQUENCE: 22

actaaagaaa ataggccttc aaatgcaaat gttgcaccta atgtt                     45


<210> SEQ ID NO 23
<211> LENGTH: 1701
<212> TYPE: DNA
<213> ORGANISM: Artificial Sequence
<220> FEATURE:
<223> OTHER INFORMATION: nucleotide sequence of synthesized H3 gene

<400> SEQUENCE: 23

atgaagacta tcattgcttt gagctacatt ctatgtctgg ttttcgctca aaaacttcct     60

ggaaatgaca acagcacggc aacgctgtgc cttgggcacc atgcagtacc aaacggaacg    120

atagtgaaaa caatcacgaa tgaccaaatt gaagttacta atgctactga gctggttcag    180

agttcctcaa caggtgaaat atgcgacagt cctcatcaga tccttgatgg aaaaaactgc    240

acactaatag atgctctatt gggagaccct cagtgtgatg gcttccaaaa taagaaatgg    300

gacctttttg ttgaacgcag caaagcctac agcaactgtt acccttatga tgtgccggat    360

tatgcctccc ttaggtcact agttgcctca tccggcacac tggagtttaa caatgaaagc    420

ttcaattgga ctggagtcac tcaaaacgga acaagctctg cttgcataag gagatctaaa    480

aacagtttct ttagtagatt gaattggttg acccacttaa acttcaaata cccagcattg    540

aacgtgacta tgccaaacaa tgaacaattt gacaaattgt acatttgggg ggttcaccac    600

ccgggtacgg acaaagacca aatcttcctg tatgctcaag catcaggaag aatcacagtc    660

tctaccaaaa gaagccaaca aaccgtaagc ccgaatatcg gatctagacc cagagtaagg    720

aatatcccta gcagaataag catctattgg acaatagtaa aaccgggaga catacttttg    780

attaacagca cagggaatct aattgctcct aggggttact tcaaaatacg aagtgggaaa    840

agctcaataa tgagatcaga tgcacccatt ggcaaatgca attctgaatg catcactcca    900

aatggaagca ttcccaatga caaaccattc caaaatgtaa acaggatcac atacggggcc    960

tgtcccagat atgttaagca aaacactctg aaattggcaa cagggatgcg aaatgtacca   1020
```

-continued gagaaacaaa ctagaggcat atttggcgca atcgcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaatagattg 1200
atcgggaaaa ccaacgagaa attccatcag attgaaaaag aattctcaga agtcgaaggg 1260
agaattcagg accttgagaa atatgttgag gacactaaaa tagatctctg gtcatacaac 1320
gcggagcttc ttgttgccct ggagaaccaa catacaattg atctaactga ctcagaaatg 1380
aacaaactgt ttgaaaaaac aaagaagcaa ctgagggaaa atgctgagga tatgggcaat 1440
ggttgtttca aaatatacca caaatgtgac aatgcctgca taggatcaat cagaaatgga 1500
acttatgacc acgatgtata cagagatgaa gcattaaaca accggtttca gatcaaggga 1560
gttgagctga agtcagggta caaagattgg atcctatgga tttcctttgc catatcatgt 1620
tttttgcttt gtgttgcttt gttggggttc atcatgtggg cctgccaaaa aggcaacatt 1680
aggtgcaaca tttgcatttg a 1701

<210> SEQ ID NO 24
<211> LENGTH: 3465
<212> TYPE: DNA
<213> ORGANISM: Artificial Sequence
<220> FEATURE:
<223> OTHER INFORMATION: Expression cassette number 1019

<400> SEQUENCE: 24
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140
tcttcttgct gattggttct ataagaaatc tagtattttc tttgaaacag agttttcccg 1200
tggttttcga acttggagaa agattgttaa gcttctgtat attctgccca aatttgtcgg 1260
gcccatggcg aaaaacgttg cgattttcgg cttattgttt tctcttcttg tgttggttcc 1320
ttctcagatc ttcgcccaaa aacttcctgg aaatgacaac agcacggcaa cgctgtgcct 1380

-continued tgggcaccat gcagtaccaa acggaacgat agtgaaaaca atcacgaatg accaaattga 1440
agttactaat gctactgagc tggttcagag ttcctcaaca ggtgaaatat gcgacagtcc 1500
tcatcagatc cttgatggaa aaaactgcac actaatagat gctctattgg gagaccctca 1560
gtgtgatggc ttccaaaata agaaatggga cctttttgtt gaacgcagca aagcctacag 1620
caactgttac ccttatgatg tgccggatta tgcctccctt aggtcactag ttgcctcatc 1680
cggcacactg gagtttaaca atgaaagctt caattggact ggagtcactc aaaacggaac 1740
aagctctgct tgcataagga gatctaaaaa cagtttcttt agtagattga attggttgac 1800
ccacttaaac ttcaaatacc cagcattgaa cgtgactatg ccaaacaatg aacaatttga 1860
caaattgtac atttgggggg ttcaccaccc gggtacggac aaagaccaaa tcttcctgta 1920
tgctcaagca tcaggaagaa tcacagtctc taccaaaaga agccaacaaa ccgtaagccc 1980
gaatatcgga tctagaccca gagtaaggaa tatccctagc agaataagca tctattggac 2040
aatagtaaaa ccgggagaca tacttttgat taacagcaca gggaatctaa ttgctcctag 2100
gggttacttc aaaatacgaa gtgggaaaag ctcaataatg agatcagatg cacccattgg 2160
caaatgcaat tctgaatgca tcactccaaa tggaagcatt cccaatgaca aaccattcca 2220
aaatgtaaac aggatcacat acggggcctg tcccagatat gttaagcaaa acactctgaa 2280
attggcaaca gggatgcgaa atgtaccaga gaaacaaact agaggcatat ttggcgcaat 2340
cgcgggtttc atagaaaatg gttgggaggg aatggtggat ggttggtacg gtttcaggca 2400
tcaaaattct gagggaagag gacaagcagc agatctcaaa agcactcaag cagcaatcga 2460
tcaaatcaat gggaagctga atagattgat cgggaaaacc aacgagaaat tccatcagat 2520
tgaaaaagaa ttctcagaag tcgaagggag aattcaggac cttgagaaat atgttgagga 2580
cactaaaata gatctctggt catacaacgc ggagcttctt gttgccctgg agaaccaaca 2640
tacaattgat ctaactgact cagaaatgaa caaactgttt gaaaaaacaa agaagcaact 2700
gagggaaaat gctgaggata tgggcaatgg ttgtttcaaa atataccaca aatgtgacaa 2760
tgcctgcata ggatcaatca gaaatggaac ttatgaccac gatgtataca gagatgaagc 2820
attaaacaac cggtttcaga tcaagggagt tgagctgaag tcagggtaca aagattggat 2880
cctatggatt tcctttgcca tatcatgttt tttgctttgt gttgctttgt tggggttcat 2940
catgtgggcc tgccaaaaag gcaacattag gtgcaacatt tgcatttgaa ggcctatttt 3000
ctttagtttg aatttactgt tattcggtgt gcatttctat gtttggtgag cggttttctg 3060
tgctcagagt gtgtttattt tatgtaattt aatttctttg tgagctcctg tttagcaggt 3120
cgtcccttca gcaaggacac aaaaagattt taattttatt aaaaaaaaaa aaaaaaaaga 3180
ccgggaattc gatatcaagc ttatcgacct gcagatcgtt caaacatttg gcaataaagt 3240
ttcttaagat tgaatcctgt tgccggtctt gcgatgatta tcatataatt tctgttgaat 3300
tacgttaagc atgtaataat taacatgtaa tgcatgacgt tatttatgag atgggttttt 3360
atgattagag tcccgcaatt atacatttaa tacgcgatag aaaacaaaat atagcgcgca 3420
aactaggata aattatcgcg cgcggtgtca tctatgttac tagat 3465

<210> SEQ ID NO 25
<211> LENGTH: 574
<212> TYPE: PRT
<213> ORGANISM: Influenza virus

<400> SEQUENCE: 25

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
    50                  55                  60

Glu Leu Val Gln Ser Ser Ser Thr Gly Glu Ile Cys Asp Ser Pro His
65                  70                  75                  80

Gln Ile Leu Asp Gly Lys Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Lys Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ala Ser Gly
    210                 215                 220

Arg Ile Thr Val Ser Thr Lys Arg Ser Gln Gln Thr Val Ser Pro Asn
225                 230                 235                 240

Ile Gly Ser Arg Pro Arg Val Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Asn Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Asn
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
```

```
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570


<210> SEQ ID NO 26
<211> LENGTH: 40
<212> TYPE: DNA
<213> ORGANISM: Artificial Sequence
<220> FEATURE:
<223> OTHER INFORMATION: primer IF-S2+S4-B Bris.c

<400> SEQUENCE: 26

tctcagatct tcgccgatcg aatctgcact ggaataacat                          40


<210> SEQ ID NO 27
<211> LENGTH: 43
<212> TYPE: DNA
<213> ORGANISM: Artificial Sequence
<220> FEATURE:
<223> OTHER INFORMATION: primer IF-S1a4-B Bris.r

<400> SEQUENCE: 27

actaaagaaa ataggccttt atagacagat ggagcaagaa aca                      43


<210> SEQ ID NO 28
<211> LENGTH: 1758
<212> TYPE: DNA
<213> ORGANISM: Artificial Sequence
<220> FEATURE:
<223> OTHER INFORMATION: nucleotide sequence of synthesized HA B
      Brisbane gene

<400> SEQUENCE: 28

atgaaggcaa taattgtact actcatggta gtaacatcca atgcagatcg aatctgcact     60

ggaataacat cgtcaaactc accacatgtc gtcaaaactg ctactcaagg ggaggtcaat    120

gtgactggtg taataccact gacaacaaca cccaccaaat ctcattttgc aaatctcaaa    180

ggaacagaaa ccagggggaa actatgccca aaatgcctca actgcacaga tctggacgta    240

gccttgggca gaccaaaatg cacggggaaa ataccctcgg caagagtttc aatactccat    300

gaagtcagac ctgttacatc tgggtgcttt cctataatgc acgacagaac aaaaattaga    360

cagctgccta accttctccg aggatacgaa catatcaggt tatcaaccca taacgttatc    420

aatgcagaaa atgcaccagg aggaccctac aaaattggaa cctcagggtc ttgccctaac    480
```

-continued attaccaatg gaaacggatt tttcgcaaca atggcttggg ccgtcccaaa aaacgacaaa 540
aacaaaacag caacaaatcc attaacaata gaagtaccat acatttgtac agaaggagaa 600
gaccaaatta ccgtttgggg gttccactct gacaacgaga cccaaatggc aaagctctat 660
ggggactcaa agccccagaa gttcacctca tctgccaacg gagtgaccac acattacgtt 720
tcacagattg gtggcttccc aaatcaaaca gaagacggag gactaccaca aagtggtaga 780
attgttgttg attacatggt gcaaaaatct gggaaaacag gaacaattac ctatcaaagg 840
ggtattttat tgcctcaaaa ggtgtggtgc gcaagtggca ggagcaaggt aataaaagga 900
tccttgcctt taattggaga agcagattgc ctccacgaaa aatacggtgg attaaacaaa 960
agcaagcctt actacacagg ggaacatgca aaggccatag gaaattgccc aatatgggtg 1020
aaaacaccct tgaagctggc caatggaacc aaatatagac ctcctgcaaa actattaaag 1080
gaaaggggtt tcttcggagc tattgctggt ttcttagaag gaggatggga aggaatgatt 1140
gcaggttggc acggatacac atcccatggg gcacatggag tagcggtggc agcagacctt 1200
aagagcactc aagaggccat aaacaagata acaaaaaatc tcaactcttt gagtgagctg 1260
gaagtaaaga atcttcaaag actaagcggt gccatggatg aactccacaa cgaaatacta 1320
gaactagatg agaaagtgga tgatctcaga gctgatacaa taagctcaca aatagaactc 1380
gcagtcctgc tttccaatga aggaataata aacagtgaag atgaacatct cttggcgctt 1440
gaaagaaagc tgaagaaaat gctgggcccc tctgctgtag agatagggaa tggatgcttt 1500
gaaaccaaac acaagtgcaa ccagacctgt ctcgacagaa tagctgctgg tacctttgat 1560
gcaggagaat ttctctcccc cacctttgat tcactgaata ttactgctgc atctttaaat 1620
gacgatggat tggataatca tactatactg ctttactact caactgctgc ctccagtttg 1680
gctgtaacac tgatgatagc tatctttgtt gtttatatgg tctccagaga caatgtttct 1740
tgctccatct gtctataa 1758

<210> SEQ ID NO 29
<211> LENGTH: 3525
<212> TYPE: DNA
<213> ORGANISM: Artificial Sequence
<220> FEATURE:
<223> OTHER INFORMATION: Expression cassette number 1029

<400> SEQUENCE: 29
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720

-continued

```
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggcg aaaaacgttg cgattttcgg cttattgttt tctcttcttg tgttggttcc   1320
ttctcagatc ttcgccgatc gaatctgcac tggaataaca tcgtcaaact caccacatgt   1380
cgtcaaaact gctactcaag gggaggtcaa tgtgactggt gtaataccac tgacaacaac   1440
acccaccaaa tctcatttg caaatctcaa aggaacagaa accaggggga aactatgccc   1500
aaaatgcctc aactgcacag atctggacgt agccttgggc agaccaaaat gcacggggaa   1560
aataccctcg gcaagagttt caatactcca tgaagtcaga cctgttacat ctgggtgctt   1620
tcctataatg cacgacagaa caaaaattag acagctgcct aaccttctcc gaggatacga   1680
acatatcagg ttatcaaccc ataacgttat caatgcagaa aatgcaccag gaggacccta   1740
caaaattgga acctcagggt cttgccctaa cattaccaat ggaaacggat ttttcgcaac   1800
aatggcttgg gccgtcccaa aaaacgacaa aaacaaaaca gcaacaaatc cattaacaat   1860
agaagtacca tacatttgta cagaaggaga agaccaaatt accgtttggg ggttccactc   1920
tgacaacgag acccaaatgg caaagctcta tggggactca aagccccaga agttcacctc   1980
atctgccaac ggagtgacca cacattacgt ttcacagatt ggtggcttcc caaatcaaac   2040
agaagacgga ggactaccac aaagtggtag aattgttgtt gattacatgg tgcaaaaatc   2100
tgggaaaaca ggaacaatta cctatcaaag ggtattttta ttgcctcaaa aggtgtggtg   2160
cgcaagtggc aggagcaagg taataaaagg atccttgcct ttaattggag aagcagattg   2220
cctccacgaa aaatacggtg gattaaacaa aagcaagcct tactacacag gggaacatgc   2280
aaaggccata ggaaattgcc caatatgggt gaaaacaccc ttgaagctgg ccaatggaac   2340
caaatataga cctcctgcaa aactattaaa ggaaaggggt ttcttcggag ctattgctgg   2400
tttcttagaa ggaggatggg aaggaatgat tgcaggttgg cacggataca catcccatgg   2460
ggcacatgga gtagcggtgg cagcagacct taagagcact caagaggcca taaacaagat   2520
aacaaaaaat ctcaactctt tgagtgagct ggaagtaaag aatcttcaaa gactaagcgg   2580
tgccatggat gaactccaca acgaaatact agaactagat gagaaagtgg atgatctcag   2640
agctgataca ataagctcac aaatagaact cgcagtcctg ctttccaatg aaggaataat   2700
aaacagtgaa gatgaacatc tcttggcgct tgaaagaaag ctgaagaaaa tgctgggccc   2760
ctctgctgta gagataggga atggatgctt tgaaaccaaa cacaagtgca accagacctg   2820
tctcgacaga atagctgctg gtacctttga tgcaggagaa ttttctctcc ccacctttga   2880
ttcactgaat attactgctg catctttaaa tgacgatgga ttggataatc atactatact   2940
gctttactac tcaactgctg cctccagttt ggctgtaaca ctgatgatag ctatctttgt   3000
tgtttatatg gtctccagag acaatgtttc ttgctccatc tgtctataaa ggcctatttt   3060
ctttagtttg aatttactgt tattcggtgt gcatttctat gtttggtgag cggttttctg   3120
```

tgctcagagt gtgtttattt tatgtaattt aatttctttg tgagctcctg tttagcaggt 3180
cgtcccttca gcaaggacac aaaaagattt taattttatt aaaaaaaaaa aaaaaaaaga 3240
ccgggaattc gatatcaagc ttatcgacct gcagatcgtt caaacatttg gcaataaagt 3300
ttcttaagat tgaatcctgt tgccggtctt gcgatgatta tcatataatt tctgttgaat 3360
tacgttaagc atgtaataat taacatgtaa tgcatgacgt tatttatgag atgggttttt 3420
atgattagag tcccgcaatt atacatttaa tacgcgatag aaaacaaaat atagcgcgca 3480
aactaggata aattatcgcg cgcggtgtca tctatgttac tagat 3525

<210> SEQ ID NO 30
<211> LENGTH: 594
<212> TYPE: PRT
<213> ORGANISM: Influenza virus

<400> SEQUENCE: 30

Met Ala Lys Asn Val Ala Ile Phe Gly Leu Leu Phe Ser Leu Leu Val
1 5 10 15

Leu Val Pro Ser Gln Ile Phe Ala Asp Arg Ile Cys Thr Gly Ile Thr
20 25 30

Ser Ser Asn Ser Pro His Val Val Lys Thr Ala Thr Gln Gly Glu Val
35 40 45

Asn Val Thr Gly Val Ile Pro Leu Thr Thr Thr Pro Thr Lys Ser His
50 55 60

Phe Ala Asn Leu Lys Gly Thr Glu Thr Arg Gly Lys Leu Cys Pro Lys
65 70 75 80

Cys Leu Asn Cys Thr Asp Leu Asp Val Ala Leu Gly Arg Pro Lys Cys
85 90 95

Thr Gly Lys Ile Pro Ser Ala Arg Val Ser Ile Leu His Glu Val Arg
100 105 110

Pro Val Thr Ser Gly Cys Phe Pro Ile Met His Asp Arg Thr Lys Ile
115 120 125

Arg Gln Leu Pro Asn Leu Leu Arg Gly Tyr Glu His Ile Arg Leu Ser
130 135 140

Thr His Asn Val Ile Asn Ala Glu Asn Ala Pro Gly Gly Pro Tyr Lys
145 150 155 160

Ile Gly Thr Ser Gly Ser Cys Pro Asn Ile Thr Asn Gly Asn Gly Phe
165 170 175

Phe Ala Thr Met Ala Trp Ala Val Pro Lys Asn Asp Lys Asn Lys Thr
180 185 190

Ala Thr Asn Pro Leu Thr Ile Glu Val Pro Tyr Ile Cys Thr Glu Gly
195 200 205

Glu Asp Gln Ile Thr Val Trp Gly Phe His Ser Asp Asn Glu Thr Gln
210 215 220

Met Ala Lys Leu Tyr Gly Asp Ser Lys Pro Gln Lys Phe Thr Ser Ser
225 230 235 240

Ala Asn Gly Val Thr Thr His Tyr Val Ser Gln Ile Gly Gly Phe Pro
245 250 255

Asn Gln Thr Glu Asp Gly Gly Leu Pro Gln Ser Gly Arg Ile Val Val
260 265 270

Asp Tyr Met Val Gln Lys Ser Gly Lys Thr Gly Thr Ile Thr Tyr Gln
275 280 285

Arg Gly Ile Leu Leu Pro Gln Lys Val Trp Cys Ala Ser Gly Arg Ser
290 295 300

```
Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Ala Lys Leu Leu
        355                 360                 365

Lys Glu Arg Gly Phe Phe Gly Ala Ile Ala Gly Phe Leu Glu Gly Gly
    370                 375                 380

Trp Glu Gly Met Ile Ala Gly Trp His Gly Tyr Thr Ser His Gly Ala
385                 390                 395                 400

His Gly Val Ala Val Ala Ala Asp Leu Lys Ser Thr Gln Glu Ala Ile
                405                 410                 415

Asn Lys Ile Thr Lys Asn Leu Asn Ser Leu Ser Glu Leu Glu Val Lys
            420                 425                 430

Asn Leu Gln Arg Leu Ser Gly Ala Met Asp Glu Leu His Asn Glu Ile
        435                 440                 445

Leu Glu Leu Asp Glu Lys Val Asp Asp Leu Arg Ala Asp Thr Ile Ser
    450                 455                 460

Ser Gln Ile Glu Leu Ala Val Leu Leu Ser Asn Glu Gly Ile Ile Asn
465                 470                 475                 480

Ser Glu Asp Glu His Leu Leu Ala Leu Glu Arg Lys Leu Lys Lys Met
                485                 490                 495

Leu Gly Pro Ser Ala Val Glu Ile Gly Asn Gly Cys Phe Glu Thr Lys
            500                 505                 510

His Lys Cys Asn Gln Thr Cys Leu Asp Arg Ile Ala Ala Gly Thr Phe
        515                 520                 525

Asp Ala Gly Glu Phe Ser Leu Pro Thr Phe Asp Ser Leu Asn Ile Thr
    530                 535                 540

Ala Ala Ser Leu Asn Asp Asp Gly Leu Asp Asn His Thr Ile Leu Leu
545                 550                 555                 560

Tyr Tyr Ser Thr Ala Ala Ser Ser Leu Ala Val Thr Leu Met Ile Ala
                565                 570                 575

Ile Phe Val Val Tyr Met Val Ser Arg Asp Asn Val Ser Cys Ser Ile
            580                 585                 590

Cys Leu


<210> SEQ ID NO 31
<211> LENGTH: 6861
<212> TYPE: DNA
<213> ORGANISM: Artificial Sequence
<220> FEATURE:
<223> OTHER INFORMATION: Construct 1194

<400> SEQUENCE: 31

tggcaggata tattgtggtg taaacaaatt gacgcttaga caacttaata acacattgcg      60

gacgttttta atgtactgaa ttaacgccga atcccgggct ggtatattta tatgttgtca     120

aataactcaa aaaccataaa agtttaagtt agcaagtgtg tacattttta cttgaacaaa     180

aatattcacc tactactgtt ataaatcatt attaaacatt agagtaaaga aatatggatg     240

ataagaacaa gagtagtgat attttgacaa caattttgtt gcaacatttg agaaaatttt     300

gttgttctct cttttcattg gtcaaaaaca atagagagag aaaaaggaag agggagaata     360
```

-continued

```
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca cgcgtggcgc gccctagcag aaggcatgtt   2160
gttgtgactc cgaggggttg cctcaaactc tatcttataa ccggcgtgga ggcatggagg   2220
caagggcatt ttggtaattt aagtagttag tggaaaatga cgtcatttac ttaaagacga   2280
agtcttgcga caagggggc ccacgccgaa ttttaatatt accggcgtgg ccccacctta   2340
tcgcgagtgc tttagcacga gcggtccaga tttaaagtag aaaagttccc gcccactagg   2400
gttaaaggtg ttcacactat aaaagcatat acgatgtgat ggtatttgat aaagcgtata   2460
ttgtatcagg tatttccgtc ggatacgaat tattcgtaca agcttcttaa gccggtcaac   2520
atggtggagc acgacacact tgtctactcc aaaaatatca aagatacagt ctcagaagac   2580
caaagggcaa ttgagacttt tcaacaaagg gtaatatccg gaaacctcct cggattccat   2640
tgcccagcta tctgtcactt tattgtgaag atagtggaaa aggaaggtgg ctcctacaaa   2700
tgccatcatt gcgataaagg aaaggccatc gttgaagatg cctctgccga cagtggtccc   2760
```

-continued

```
aaagatggac ccccacccac gaggagcatc gtggaaaaag aagacgttcc aaccacgtct   2820
tcaaagcaag tggattgatg tgataacatg gtggagcacg acacacttgt ctactccaaa   2880
aatatcaaag atacagtctc agaagaccaa agggcaattg agacttttca acaaagggta   2940
atatccggaa acctcctcgg attccattgc ccagctatct gtcactttat tgtgaagata   3000
gtggaaaagg aaggtggctc ctacaaatgc catcattgcg ataaaggaaa ggccatcgtt   3060
gaagatgcct ctgccgacag tggtcccaaa gatggacccc cacccacgag gagcatcgtg   3120
gaaaaagaag acgttccaac cacgtcttca aagcaagtgg attgatgtga tatctccact   3180
gacgtaaggg atgacgcaca atcccactat ccttcgcaag acccttcctc tatataagga   3240
agttcatttc atttggagag gtattaaaat cttaataggt tttgataaaa gcgaacgtgg   3300
ggaaacccga accaaacctt cttctaaact ctctctcatc tctcttaaag caaacttctc   3360
tcttgtcttt cttgcgtgag cgatcttcaa cgttgtcaga tcgtgcttcg gcaccagtac   3420
aacgttttct ttcactgaag cgaaatcaaa gatctctttg tggacacgta gtgcggcgcc   3480
attaaataac gtgtacttgt cctattcttg tcggtgtggt cttgggaaaa gaaagcttgc   3540
tggaggctgc tgttcagccc catacattac ttgttacgat tctgctgact ttcggcgggt   3600
gcaatatctc tacttctgct tgacgaggta ttgttgcctg tacttctttc ttcttcttct   3660
tgctgattgg ttctataaga aatctagtat ttctttgaa acagagtttt cccgtggttt   3720
tcgaacttgg agaaagattg ttaagcttct gtatattctg cccaaatttg tcgggcccat   3780
ggcgaaaaac gttgcgattt tcggcttatt gttttctctt cttgtgttgg ttccttctca   3840
gatcttcgcc gcggctcctc agccaaaacg acaccccat ctgtctatcc actggcccct   3900
ggatctgctg cccaaactaa ctccatggtg accctgggat gcctggtcaa gggctatttc   3960
cctgagccag tgacagtgac ctggaactct ggatccctgt ccagcggtgt gcacaccttc   4020
ccagctgtcc tgcagtctga cctctacact ctgagcagct cagtgactgt cccctccagc   4080
acctggccca gcgagaccgt cacctgcaac gttgcccacc cggccagcag caccaaggtg   4140
gacaagaaaa ttgtgcccag ggattgtggt tgtaagcctt gcatatgtac agtcccagaa   4200
gtatcatctg tcttcatctt ccccccaaag cccaaggatg tgctcaccat tactctgact   4260
cctaaggtca cgtgtgttgt ggtagacatc agcaaggatg atcccgaggt ccagttcagc   4320
tggtttgtag atgatgtgga ggtgcacaca gctcagacgc aaccccggga ggagcagttc   4380
aacagcactt tccgctcagt cagtgaactt cccatcatgc accaggactg gctcaatggc   4440
aaggaaggcc tattttcttt agtttgaatt tactgttatt cggtgtgcat ttctatgttt   4500
ggtgagcggt tttctgtgct cagagtgtgt ttattttatg taatttaatt tctttgtgag   4560
ctcctgttta gcaggtcgtc ccttcagcaa ggacacaaaa agattttaat tttattaaaa   4620
aaaaaaaaaa aaaagaccgg gaattcgata tcaagcttat cgacctgcag atcgttcaaa   4680
catttggcaa taaagtttct taagattgaa tcctgttgcc ggtcttgcga tgattatcat   4740
ataatttctg ttgaattacg ttaagcatgt aataattaac atgtaatgca tgacgttatt   4800
tatgagatgg gtttttatga ttagagtccc gcaattatac atttaatacg cgatagaaaa   4860
caaaatatag cgcgcaaact aggataaatt atcgcgcgcg gtgtcatcta tgttactaga   4920
tctctagagt ctcaagcttg gcgcggggta ccgagctcga attccgagtg tacttcaagt   4980
cagttggaaa tcaataaaat gattatttta tgaatatatt tcattgtgca agtagataga   5040
aattacatat gttacataac acacgaaata aacaaaaaaa cacaatccaa aacaaacacc   5100
```

ccaaacaaaa taacactata tatatcctcg tatgaggaga ggcacgttca gtgactcgac 5160
gattcccgag caaaaaaagt ctccccgtca cacatatagt gggtgacgca attatcttca 5220
aagtaatcct tctgttgact tgtcattgat aacatccagt cttcgtcagg attgcaaaga 5280
attatagaag ggatcccacc ttttattttc ttcttttttc catatttagg gttgacagtg 5340
aaatcagact ggcaacctat taattgcttc cacaatggga cgaacttgaa ggggatgtcg 5400
tcgatgatat tataggtggc gtgttcatcg tagttggtga agtcgatggt cccgttccag 5460
tagttgtgtc gcccgagact tctagcccag gtggtctttc cggtacgagt tggtccgcag 5520
atgtagaggc tggggtgtct gaccccagtc cttccctcat cctggttaga tcggccatcc 5580
actcaaggtc agattgtgct tgatcgtagg agacaggatg tatgaaagtg taggcatcga 5640
tgcttacatg atataggtgc gtctctctcc agttgtgcag atcttcgtgg cagcggagat 5700
ctgattctgt gaagggcgac acgtactgct caggttgtgg aggaaataat ttgttggctg 5760
aatattccag ccattgaagc tttgttgccc attcatgagg gaattcttct ttgatcatgt 5820
caagatactc ctccttagac gttgcagtct ggataatagt tcgccatcgt gcgtcagatt 5880
tgcgaggaga gaccttatga tctcggaaat ctcctctggt tttaatatct ccgtcctttg 5940
atatgtaatc aaggacttgt ttagagtttc tagctggctg gatattaggg tgatttcctt 6000
caaaatcgaa aaaagaagga tccctaatac aaggtttttt atcaagctgg ataagagcat 6060
gatagtgggt agtgccatct tgatgaagct cagaagcaac accaaggaag aaaataagaa 6120
aaggtgtgag tttctcccag agaaactgga ataaatcatc tctttgagat gagcacttgg 6180
ggtaggtaag gaaaacatat ttagattgga gtctgaagtt cttgctagca gaaggcatgt 6240
tgttgtgact ccgaggggtt gcctcaaact ctatcttata accggcgtgg aggcatggag 6300
gcaagggcat tttggtaatt taagtagtta gtggaaaatg acgtcattta cttaaagacg 6360
aagtcttgcg acaagggggg cccacgccga attttaatat taccggcgtg gccccacctt 6420
atcgcgagtg ctttagcacg agcggtccag atttaaagta gaaaagttcc cgcccactag 6480
ggttaaaggt gttcacacta taaaagcata tacgatgtga tggtatttga tggagcgtat 6540
attgtatcag gtatttccgt cggatacgaa ttattcgtac ggccggccac tagtggcact 6600
ggccgtcgtt ttacaacgtc gtgactggga aaaccctggc gttacccaac ttaatcgcct 6660
tgcagcacat ccccctttcg ccagctggcg taatagcgaa gaggcccgca ccgatcgccc 6720
ttcccaacag ttgcgcagcc tgaatggcga atgctagagc agcttgagct tggatcagat 6780
tgtcgtttcc cgccttcagt ttaaactatc agtgtttgac aggatatatt ggcgggtaaa 6840
cctaagagaa aagagcgttt a 6861

<210> SEQ ID NO 32
<211> LENGTH: 5555
<212> TYPE: DNA
<213> ORGANISM: Artificial Sequence
<220> FEATURE:
<223> OTHER INFORMATION: Expression cassette number 1008

<400> SEQUENCE: 32
ctagcagaag gcatgttgtt gtgactccga ggggttgcct caaactctat cttataaccg 60
gcgtggaggc atggaggcaa gggcattttg gtaatttaag tagttagtgg aaaatgacgt 120
catttactta aagacgaagt cttgcgacaa ggggggccca cgccgaattt taatattacc 180
ggcgtggccc caccttatcg cgagtgcttt agcacgagcg gtccagattt aaagtagaaa 240
agttcccgcc cactagggtt aaaggtgttc acactataaa agcatatacg atgtgatggt 300

```
atttgataaa gcgtatattg tatcaggtat ttccgtcgga tacgaattat tcgtacaagc    360
ttcttaagcc ggtcaacatg gtggagcacg acacacttgt ctactccaaa aatatcaaag    420
atacagtctc agaagaccaa agggcaattg agacttttca acaaagggta atatccggaa    480
acctcctcgg attccattgc ccagctatct gtcactttat tgtgaagata gtggaaaagg    540
aaggtggctc ctacaaatgc catcattgcg ataaaggaaa ggccatcgtt gaagatgcct    600
ctgccgacag tggtcccaaa gatggacccc cacccacgag gagcatcgtg gaaaaagaag    660
acgttccaac cacgtcttca aagcaagtgg attgatgtga taacatggtg gagcacgaca    720
cacttgtcta ctccaaaaat atcaaagata cagtctcaga agaccaaagg gcaattgaga    780
cttttcaaca aagggtaata tccggaaacc tcctcggatt ccattgccca gctatctgtc    840
actttattgt gaagatagtg gaaaaggaag gtggctccta caaatgccat cattgcgata    900
aaggaaaggc catcgttgaa gatgcctctg ccgacagtgg tcccaaagat ggacccccac    960
ccacgaggag catcgtggaa aaagaagacg ttccaaccac gtcttcaaag caagtggatt   1020
gatgtgatat ctccactgac gtaagggatg acgcacaatc ccactatcct tcgcaagacc   1080
cttcctctat ataaggaagt tcatttcatt tggagaggta ttaaaatctt aataggtttt   1140
gataaaagcg aacgtgggga aacccgaacc aaaccttctt ctaaactctc tctcatctct   1200
cttaaagcaa acttctctct tgtctttctt gcgtgagcga tcttcaacgt tgtcagatcg   1260
tgcttcggca ccagtacaac gttttctttc actgaagcga aatcaaagat ctctttgtgg   1320
acacgtagtg cggcgccatt aaataacgtg tacttgtcct attcttgtcg gtgtggtctt   1380
gggaaaagaa agcttgctgg aggctgctgt tcagccccat acattacttg ttacgattct   1440
gctgactttc ggcgggtgca atatctctac ttctgcttga cgaggtattg ttgcctgtac   1500
ttctttcttc ttcttcttgc tgattggttc tataagaaat ctagtatttt ctttgaaaca   1560
gagttttccc gtggttttcg aacttggaga aagattgtta agcttctgta tattctgccc   1620
aaatttgtcg ggcccatggc gaaaaacgtt gcgattttcg gcttattgtt ttctcttctt   1680
gtgttggttc cttctcagat cttcgccgat cgaatctgca ctggaataac atcgtcaaac   1740
tcaccacatg tcgtcaaaac tgctactcaa ggggaggtca atgtgactgg tgtaatacca   1800
ctgacaacaa cacccaccaa atctcatttt gcaaatctca aggaacaga aaccaggggg   1860
aaactatgcc caaaatgcct caactgcaca gatctggacg tagccttggg cagaccaaaa   1920
tgcacgggga aaataccctc ggcaagagtt tcaatactcc atgaagtcag acctgttaca   1980
tctgggtgct ttcctataat gcacgacaga acaaaaatta gacagctgcc taaccttctc   2040
cgaggatacg aacatatcag gttatcaacc cataacgtta tcaatgcaga aaatgcacca   2100
ggaggaccct acaaaattgg aacctcaggg tcttgcccta acattaccaa tggaaacgga   2160
tttttcgcaa caatggcttg ggccgtccca aaaaacgaca aaaacaaaac agcaacaaat   2220
ccattaacaa tagaagtacc atacatttgt acagaaggag aagaccaaat taccgtttgg   2280
gggttccact ctgacaacga gacccaaatg gcaaagctct atggggactc aaagccccag   2340
aagttcacct catctgccaa cggagtgacc acacattacg tttcacagat tggtggcttc   2400
ccaaatcaaa cagaagacgg aggactacca caaagtggta gaattgttgt tgattacatg   2460
gtgcaaaaat ctgggaaaac aggaacaatt acctatcaaa ggggtatttt attgcctcaa   2520
aaggtgtggt gcgcaagtgg caggagcaag gtaataaaag gatccttgcc tttaattgga   2580
gaagcagatt gcctccacga aaaatacggt ggattaaaca aaagcaagcc ttactacaca   2640
```

-continued

```
ggggaacatg caaaggccat aggaaattgc ccaatatggg tgaaaacacc cttgaagctg   2700
gccaatggaa ccaaatatag acctcctgca aaactattaa aggaaagggg tttcttcgga   2760
gctattgctg gtttcttaga aggaggatgg gaaggaatga ttgcaggttg gcacggatac   2820
acatcccatg ggcacatgg agtagcggtg gcagcagacc ttaagagcac tcaagaggcc    2880
ataaacaaga taacaaaaaa tctcaactct ttgagtgagc tggaagtaaa gaatcttcaa   2940
agactaagcg gtgccatgga tgaactccac aacgaaatac tagaactaga tgagaaagtg   3000
gatgatctca gagctgatac aataagctca caaatagaac tcgcagtcct gctttccaat   3060
gaaggaataa taaacagtga agatgaacat ctcttggcgc ttgaaagaaa gctgaagaaa   3120
atgctgggcc cctctgctgt agagataggg aatggatgct ttgaaaccaa acacaagtgc   3180
aaccagacct gtctcgacag aatagctgct ggtacctttg atgcaggaga attttctctc   3240
cccacctttg attcactgaa tattactgct gcatctttaa atgacgatgg attggataat   3300
catactatac tgctttacta ctcaactgct gcctccagtt tggctgtaac actgatgata   3360
gctatctttg ttgtttatat ggtctccaga gacaatgttt cttgctccat ctgtctataa   3420
aggcctattt tctttagttt gaatttactg ttattcggtg tgcatttcta tgtttggtga   3480
gcggttttct gtgctcagag tgtgtttatt ttatgtaatt taatttcttt gtgagctcct   3540
gtttagcagg tcgtcccttc agcaaggaca caaaaagatt ttaattttat taaaaaaaaa   3600
aaaaaaaaag accgggaatt cgatatcaag cttatcgacc tgcagatcgt tcaaacattt   3660
ggcaataaag tttcttaaga ttgaatcctg ttgccggtct tgcgatgatt atcatataat   3720
ttctgttgaa ttacgttaag catgtaataa ttaacatgta atgcatgacg ttatttatga   3780
gatgggtttt tatgattaga gtcccgcaat tatacattta atacgcgata gaaaacaaaa   3840
tatagcgcgc aaactaggat aaattatcgc gcgcggtgtc atctatgtta ctagatctct   3900
agagtctcaa gcttggcgcg gggtaccgag ctcgaattcc gagtgtactt caagtcagtt   3960
ggaaatcaat aaaatgatta ttttatgaat atatttcatt gtgcaagtag atagaaatta   4020
catatgttac ataacacacg aaataaacaa aaaaacacaa tccaaaacaa acaccccaaa   4080
caaaataaca ctatatatat cctcgtatga ggagaggcac gttcagtgac tcgacgattc   4140
ccgagcaaaa aaagtctccc cgtcacacat atagtgggtg acgcaattat cttcaaagta   4200
atccttctgt tgacttgtca ttgataacat ccagtcttcg tcaggattgc aaagaattat   4260
agaagggatc ccacctttta ttttcttctt ttttccatat ttagggttga cagtgaaatc   4320
agactggcaa cctattaatt gcttccacaa tgggacgaac ttgaagggga tgtcgtcgat   4380
gatattatag gtggcgtgtt catcgtagtt ggtgaagtcg atggtcccgt tccagtagtt   4440
gtgtcgcccg agacttctag cccaggtggt ctttccggta cgagttggtc cgcagatgta   4500
gaggctgggg tgtctgaccc cagtccttcc ctcatcctgg ttagatcggc catccactca   4560
aggtcagatt gtgcttgatc gtaggagaca ggatgtatga aagtgtaggc atcgatgctt   4620
acatgatata ggtgcgtctc tctccagttg tgcagatctt cgtggcagcg gagatctgat   4680
tctgtgaagg gcgacacgta ctgctcaggt tgtggaggaa ataatttgtt ggctgaatat   4740
tccagccatt gaagctttgt tgcccattca tgagggaatt cttctttgat catgtcaaga   4800
tactcctcct tagacgttgc agtctggata atagttcgcc atcgtgcgtc agatttgcga   4860
ggagagacct tatgatctcg gaaatctcct ctggttttaa tatctccgtc ctttgatatg   4920
taatcaagga cttgtttaga gtttctagct ggctggatat tagggtgatt tccttcaaaa   4980
tcgaaaaaag aaggatccct aatacaaggt tttttatcaa gctggataag agcatgatag   5040
```

tgggtagtgc catcttgatg aagctcagaa gcaacaccaa ggaagaaaat aagaaaaggt 5100
gtgagtttct cccagagaaa ctggaataaa tcatctcttt gagatgagca cttggggtag 5160
gtaaggaaaa catatttaga ttggagtctg aagttcttgc tagcagaagg catgttgttg 5220
tgactccgag ggttgcctc aaactctatc ttataaccgg cgtggaggca tggaggcaag 5280
ggcattttgg taatttaagt agttagtgga aaatgacgtc atttacttaa agacgaagtc 5340
ttgcgacaag gggggcccac gccgaatttt aatattaccg gcgtggcccc accttatcgc 5400
gagtgcttta gcacgagcgg tccagattta aagtagaaaa gttcccgccc actagggtta 5460
aaggtgttca cactataaaa gcatatacga tgtgatggta tttgatggag cgtatattgt 5520
atcaggtatt tccgtcggat acgaattatt cgtac 5555

<210> SEQ ID NO 33
<211> LENGTH: 50
<212> TYPE: DNA
<213> ORGANISM: Artificial Sequence
<220> FEATURE:
<223> OTHER INFORMATION: primer dTmH5I-B Bris.r

<400> SEQUENCE: 33
ttgacagtat ttggtaatta tccaatccat cgtcatttaa agatgcagca 50

<210> SEQ ID NO 34
<211> LENGTH: 50
<212> TYPE: DNA
<213> ORGANISM: Artificial Sequence
<220> FEATURE:
<223> OTHER INFORMATION: primer B Bris-dTmH5I.c

<400> SEQUENCE: 34
catctttaaa tgacgatgga ttggataatt accaaatact gtcaatttat 50

<210> SEQ ID NO 35
<211> LENGTH: 50
<212> TYPE: DNA
<213> ORGANISM: Artificial Sequence
<220> FEATURE:
<223> OTHER INFORMATION: primer IF-S1aS4-dTmH5I.r

<400> SEQUENCE: 35
actaaagaaa ataggccttt aaatgcaaat tctgcattgt aacgatccat 50

<210> SEQ ID NO 36
<211> LENGTH: 5555
<212> TYPE: DNA
<213> ORGANISM: Artificial Sequence
<220> FEATURE:
<223> OTHER INFORMATION: Expression cassette number 1009

<400> SEQUENCE: 36
ctagcagaag gcatgttgtt gtgactccga ggggttgcct caaactctat cttataaccg 60
gcgtggaggc atggaggcaa gggcattttg gtaatttaag tagttagtgg aaaatgacgt 120
catttactta aagacgaagt cttgcgacaa ggggggccca cgccgaattt taatattacc 180
ggcgtggccc caccttatcg cgagtgcttt agcacgagcg gtccagattt aaagtagaaa 240
agttcccgcc cactagggtt aaaggtgttc acactataaa agcatatacg atgtgatggt 300
atttgataaa gcgtatattg tatcaggtat ttccgtcgga tacgaattat tcgtacaagc 360
ttcttaagcc ggtcaacatg gtggagcacg acacacttgt ctactccaaa aatatcaaag 420

-continued

```
atacagtctc agaagaccaa agggcaattg agacttttca acaaagggta atatccggaa     480
acctcctcgg attccattgc ccagctatct gtcactttat tgtgaagata gtggaaaagg     540
aaggtggctc ctacaaatgc catcattgcg ataaaggaaa ggccatcgtt gaagatgcct     600
ctgccgacag tggtcccaaa gatggacccc cacccacgag gagcatcgtg gaaaaagaag     660
acgttccaac cacgtcttca aagcaagtgg attgatgtga taacatggtg gagcacgaca     720
cacttgtcta ctccaaaaat atcaaagata cagtctcaga agaccaaagg gcaattgaga     780
cttttcaaca aagggtaata tccggaaacc tcctcggatt ccattgccca gctatctgtc     840
actttattgt gaagatagtg gaaaaggaag gtggctccta caaatgccat cattgcgata     900
aaggaaaggc catcgttgaa gatgcctctg ccgacagtgg tcccaaagat ggacccccac     960
ccacgaggag catcgtggaa aaagaagacg ttccaaccac gtcttcaaag caagtggatt    1020
gatgtgatat ctccactgac gtaagggatg acgcacaatc ccactatcct tcgcaagacc    1080
cttcctctat ataaggaagt tcatttcatt tggagaggta ttaaaatctt aataggtttt    1140
gataaaagcg aacgtgggga aacccgaacc aaaccttctt ctaaactctc tctcatctct    1200
cttaaagcaa acttctctct tgtctttctt gcgtgagcga tcttcaacgt tgtcagatcg    1260
tgcttcggca ccagtacaac gttttctttc actgaagcga aatcaaagat ctctttgtgg    1320
acacgtagtg cggcgccatt aaataacgtg tacttgtcct attcttgtcg gtgtggtctt    1380
gggaaaagaa agcttgctgg aggctgctgt tcagccccat acattacttg ttacgattct    1440
gctgactttc ggcgggtgca atatctctac ttctgcttga cgaggtattg ttgcctgtac    1500
ttctttcttc ttcttcttgc tgattggttc tataagaaat ctagtatttt ctttgaaaca    1560
gagttttccc gtggttttcg aacttggaga aagattgtta agcttctgta tattctgccc    1620
aaatttgtcg ggcccatggc gaaaaacgtt gcgattttcg gcttattgtt ttctcttctt    1680
gtgttggttc cttctcagat cttcgccgat cgaatctgca ctggaataac atcgtcaaac    1740
tcaccacatg tcgtcaaaac tgctactcaa ggggaggtca atgtgactgg tgtaatacca    1800
ctgacaacaa cacccaccaa atctcatttt gcaaatctca aaggaacaga aaccaggggg    1860
aaactatgcc caaaatgcct caactgcaca gatctggacg tagccttggg cagaccaaaa    1920
tgcacgggga aaataccctc ggcaagagtt tcaatactcc atgaagtcag acctgttaca    1980
tctgggtgct ttcctataat gcacgacaga acaaaaatta gacagctgcc taaccttctc    2040
cgaggatacg aacatatcag gttatcaacc cataacgtta tcaatgcaga aaatgcacca    2100
ggaggaccct acaaaattgg aacctcaggg tcttgcccta acattaccaa tggaaacgga    2160
tttttcgcaa caatggcttg ggccgtccca aaaaacgaca aaaacaaaac agcaacaaat    2220
ccattaacaa tagaagtacc atacatttgt acagaaggag aagaccaaat taccgtttgg    2280
gggttccact ctgacaacga gacccaaatg gcaaagctct atggggactc aaagccccag    2340
aagttcacct catctgccaa cggagtgacc acacattacg tttcacagat tggtggcttc    2400
ccaaatcaaa cagaagacgg aggactacca caaagtggta gaattgttgt tgattacatg    2460
gtgcaaaaat ctgggaaaac aggaacaatt acctatcaaa ggggtatttt attgcctcaa    2520
aaggtgtggt gcgcaagtgg caggagcaag gtaataaaag gatccttgcc tttaattgga    2580
gaagcagatt gcctccacga aaaatacggt ggattaaaca aaagcaagcc ttactacaca    2640
ggggaacatg caaaggccat aggaaattgc ccaatatggg tgaaaacacc cttgaagctg    2700
gccaatggaa ccaaatatag acctcctgca aaactattaa aggaaagggg tttcttcgga    2760
gctattgctg gtttcttaga aggaggatgg gaaggaatga ttgcaggttg gcacggatac    2820
```

acatcccatg gggcacatgg agtagcggtg gcagcagacc ttaagagcac tcaagaggcc 2880
ataaacaaga taacaaaaaa tctcaactct ttgagtgagc tggaagtaaa gaatcttcaa 2940
agactaagcg gtgccatgga tgaactccac aacgaaatac tagaactaga tgagaaagtg 3000
gatgatctca gagctgatac aataagctca caaatagaac tcgcagtcct gctttccaat 3060
gaaggaataa taaacagtga agatgaacat ctcttggcgc ttgaaagaaa gctgaagaaa 3120
atgctgggcc cctctgctgt agagataggg aatggatgct ttgaaaccaa acacaagtgc 3180
aaccagacct gtctcgacag aatagctgct ggtacctttg atgcaggaga attttctctc 3240
cccacctttg attcactgaa tattactgct gcatctttaa atgacgatgg attggataat 3300
taccaaatac tgtcaattta ttcaacagtg gcgagttccc tagcactggc aatcatgatg 3360
gctggtctat ctttatggat gtgctccaat ggatcgttac aatgcagaat ttgcatttaa 3420
aggcctattt tctttagttt gaatttactg ttattcggtg tgcatttcta tgtttggtga 3480
gcggttttct gtgctcagag tgtgtttatt ttatgtaatt taatttcttt gtgagctcct 3540
gtttagcagg tcgtcccttc agcaaggaca caaaaagatt ttaattttat taaaaaaaaa 3600
aaaaaaaaag accgggaatt cgatatcaag cttatcgacc tgcagatcgt tcaaacattt 3660
ggcaataaag tttcttaaga ttgaatcctg ttgccggtct tgcgatgatt atcatataat 3720
ttctgttgaa ttacgttaag catgtaataa ttaacatgta atgcatgacg ttatttatga 3780
gatgggtttt tatgattaga gtcccgcaat tatacattta atacgcgata gaaaacaaaa 3840
tatagcgcgc aaactaggat aaattatcgc gcgcggtgtc atctatgtta ctagatctct 3900
agagtctcaa gcttggcgcg gggtaccgag ctcgaattcc gagtgtactt caagtcagtt 3960
ggaaatcaat aaaatgatta ttttatgaat atatttcatt gtgcaagtag atagaaatta 4020
catatgttac ataacacacg aaataaacaa aaaaacacaa tccaaaacaa acaccccaaa 4080
caaaataaca ctatatatat cctcgtatga ggagaggcac gttcagtgac tcgacgattc 4140
ccgagcaaaa aaagtctccc cgtcacacat atagtgggtg acgcaattat cttcaaagta 4200
atccttctgt tgacttgtca ttgataacat ccagtcttcg tcaggattgc aaagaattat 4260
agaagggatc ccacctttta ttttcttctt ttttccatat ttagggttga cagtgaaatc 4320
agactggcaa cctattaatt gcttccacaa tgggacgaac ttgaagggga tgtcgtcgat 4380
gatattatag gtggcgtgtt catcgtagtt ggtgaagtcg atggtcccgt tccagtagtt 4440
gtgtcgcccg agacttctag cccaggtggt ctttccggta cgagttggtc cgcagatgta 4500
gaggctgggg tgtctgaccc cagtccttcc ctcatcctgg ttagatcggc catccactca 4560
aggtcagatt gtgcttgatc gtaggagaca ggatgtatga aagtgtaggc atcgatgctt 4620
acatgatata ggtgcgtctc tctccagttg tgcagatctt cgtggcagcg gagatctgat 4680
tctgtgaagg gcgacacgta ctgctcaggt tgtggaggaa ataatttgtt ggctgaatat 4740
tccagccatt gaagctttgt tgcccattca tgagggaatt cttctttgat catgtcaaga 4800
tactcctcct tagacgttgc agtctggata atagttcgcc atcgtgcgtc agatttgcga 4860
ggagagacct tatgatctcg gaaatctcct ctggttttaa tatctccgtc ctttgatatg 4920
taatcaagga cttgtttaga gtttctagct ggctggatat tagggtgatt tccttcaaaa 4980
tcgaaaaaag aaggatccct aatacaaggt tttttatcaa gctggataag agcatgatag 5040
tgggtagtgc catcttgatg aagctcagaa gcaacaccaa ggaagaaaat aagaaaaggt 5100
gtgagtttct cccagagaaa ctggaataaa tcatctcttt gagatgagca cttggggtag 5160

-continued

```
gtaaggaaaa catatttaga ttggagtctg aagttcttgc tagcagaagg catgttgttg   5220

tgactccgag gggttgcctc aaactctatc ttataaccgg cgtggaggca tggaggcaag   5280

ggcattttgg taatttaagt agttagtgga aaatgacgtc atttacttaa agacgaagtc   5340

ttgcgacaag gggggcccac gccgaatttt aatattaccg gcgtggcccc accttatcgc   5400

gagtgcttta gcacgagcgg tccagattta aagtagaaaa gttcccgccc actagggtta   5460

aaggtgttca cactataaaa gcatatacga tgtgatggta tttgatggag cgtatattgt   5520

atcaggtatt tccgtcggat acgaattatt cgtac                              5555
```

<210> SEQ ID NO 37
<211> LENGTH: 594
<212> TYPE: PRT
<213> ORGANISM: Influenza virus

<400> SEQUENCE: 37

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300
```

```
Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Ala Lys Leu Leu
        355                 360                 365

Lys Glu Arg Gly Phe Phe Gly Ala Ile Ala Gly Phe Leu Glu Gly Gly
    370                 375                 380

Trp Glu Gly Met Ile Ala Gly Trp His Gly Tyr Thr Ser His Gly Ala
385                 390                 395                 400

His Gly Val Ala Val Ala Ala Asp Leu Lys Ser Thr Gln Glu Ala Ile
                405                 410                 415

Asn Lys Ile Thr Lys Asn Leu Asn Ser Leu Ser Glu Leu Glu Val Lys
            420                 425                 430

Asn Leu Gln Arg Leu Ser Gly Ala Met Asp Glu Leu His Asn Glu Ile
        435                 440                 445

Leu Glu Leu Asp Glu Lys Val Asp Asp Leu Arg Ala Asp Thr Ile Ser
    450                 455                 460

Ser Gln Ile Glu Leu Ala Val Leu Leu Ser Asn Glu Gly Ile Ile Asn
465                 470                 475                 480

Ser Glu Asp Glu His Leu Leu Ala Leu Glu Arg Lys Leu Lys Lys Met
                485                 490                 495

Leu Gly Pro Ser Ala Val Glu Ile Gly Asn Gly Cys Phe Glu Thr Lys
            500                 505                 510

His Lys Cys Asn Gln Thr Cys Leu Asp Arg Ile Ala Ala Gly Thr Phe
        515                 520                 525

Asp Ala Gly Glu Phe Ser Leu Pro Thr Phe Asp Ser Leu Asn Ile Thr
    530                 535                 540

Ala Ala Ser Leu Asn Asp Asp Gly Leu Asp Asn Tyr Gln Ile Leu Ser
545                 550                 555                 560

Ile Tyr Ser Thr Val Ala Ser Ser Leu Ala Leu Ala Ile Met Met Ala
                565                 570                 575

Gly Leu Ser Leu Trp Met Cys Ser Asn Gly Ser Leu Gln Cys Arg Ile
            580                 585                 590

Cys Ile
```

<210> SEQ ID NO 38
<211> LENGTH: 52
<212> TYPE: DNA
<213> ORGANISM: Artificial Sequence
<220> FEATURE:
<223> OTHER INFORMATION: primer 1039+1059.r

<400> SEQUENCE: 38
cttcccatcc tccaccagga ggtctatatt tggttccatt ggccagcttc aa 52

<210> SEQ ID NO 39
<211> LENGTH: 52
<212> TYPE: DNA
<213> ORGANISM: Artificial Sequence
<220> FEATURE:
<223> OTHER INFORMATION: primer 1039+1059.c

<400> SEQUENCE: 39
caaatataga cctcctggtg gaggatggga aggaatgatt gcaggttggc ac 52

<210> SEQ ID NO 40
<211> LENGTH: 5504
<212> TYPE: DNA
<213> ORGANISM: Artificial Sequence
<220> FEATURE:
<223> OTHER INFORMATION: Expression cassette number 1059 from BeYDV left LIR to BeYDV right LIR. PDISP/HA from influenza B/Brisbane/60/2008 with deleted proteolytic loop

<400> SEQUENCE: 40

```
ctagcagaag gcatgttgtt gtgactccga ggggttgcct caaactctat cttataaccg     60

gcgtggaggc atggaggcaa gggcattttg gtaatttaag tagttagtgg aaaatgacgt    120

catttactta aagacgaagt cttgcgacaa ggggggccca cgccgaattt taatattacc    180

ggcgtggccc caccttatcg cgagtgcttt agcacgagcg gtccagattt aaagtagaaa    240

agttcccgcc cactagggtt aaaggtgttc acactataaa agcatatacg atgtgatggt    300

atttgataaa gcgtatattg tatcaggtat ttccgtcgga tacgaattat tcgtacaagc    360

ttcttaagcc ggtcaacatg gtggagcacg acacacttgt ctactccaaa aatatcaaag    420

atacagtctc agaagaccaa agggcaattg agacttttca acaaagggta atatccggaa    480

acctcctcgg attccattgc ccagctatct gtcactttat tgtgaagata gtggaaaagg    540

aaggtggctc ctacaaatgc catcattgcg ataaaggaaa ggccatcgtt gaagatgcct    600

ctgccgacag tggtcccaaa gatggacccc cacccacgag gagcatcgtg gaaaaagaag    660

acgttccaac cacgtcttca aagcaagtgg attgatgtga taacatggtg gagcacgaca    720

cacttgtcta ctccaaaaat atcaaagata cagtctcaga agaccaaagg gcaattgaga    780

cttttcaaca aagggtaata tccggaaacc tcctcggatt ccattgccca gctatctgtc    840

actttattgt gaagatagtg gaaaaggaag gtggctccta caaatgccat cattgcgata    900

aaggaaaggc catcgttgaa gatgcctctg ccgacagtgg tcccaaagat ggacccccac    960

ccacgaggag catcgtggaa aaagaagacg ttccaaccac gtcttcaaag caagtggatt   1020

gatgtgatat ctccactgac gtaagggatg acgcacaatc ccactatcct tcgcaagacc   1080

cttcctctat ataaggaagt tcatttcatt tggagaggta ttaaaatctt aataggtttt   1140

gataaaagcg aacgtgggga aacccgaacc aaaccttctt ctaaactctc tctcatctct   1200

cttaaagcaa acttctctct tgtctttctt gcgtgagcga tcttcaacgt tgtcagatcg   1260

tgcttcggca ccagtacaac gttttctttc actgaagcga aatcaaagat ctctttgtgg   1320

acacgtagtg cggcgccatt aaataacgtg tacttgtcct attcttgtcg gtgtggtctt   1380

gggaaaagaa agcttgctgg aggctgctgt tcagccccat acattacttg ttacgattct   1440

gctgactttc ggcgggtgca atatctctac ttctgcttga cgaggtattg ttgcctgtac   1500

ttctttcttc ttcttcttgc tgattggttc tataagaaat ctagtatttt ctttgaaaca   1560

gagttttccc gtggttttcg aacttggaga aagattgtta agcttctgta tattctgccc   1620

aaatttgtcg ggcccatggc gaaaaacgtt gcgattttcg gcttattgtt ttctcttctt   1680

gtgttggttc cttctcagat cttcgccgat cgaatctgca ctggaataac atcgtcaaac   1740

tcaccacatg tcgtcaaaac tgctactcaa ggggaggtca atgtgactgg tgtaatacca   1800

ctgacaacaa cacccaccaa atctcatttt gcaaatctca aaggaacaga aaccaggggg   1860

aaactatgcc caaaatgcct caactgcaca gatctggacg tagccttggg cagaccaaaa   1920

tgcacgggga aaataccctc ggcaagagtt tcaatactcc atgaagtcag acctgttaca   1980
```

-continued

```
tctgggtgct ttcctataat gcacgacaga acaaaaatta gacagctgcc taaccttctc   2040
cgaggatacg aacatatcag gttatcaacc cataacgtta tcaatgcaga aaatgcacca   2100
ggaggaccct acaaaattgg aacctcaggg tcttgcccta acattaccaa tggaaacgga   2160
tttttcgcaa caatggcttg ggccgtccca aaaaacgaca aaaacaaaac agcaacaaat   2220
ccattaacaa tagaagtacc atacatttgt acagaaggag aagaccaaat taccgtttgg   2280
gggttccact ctgacaacga gacccaaatg gcaaagctct atggggactc aaagccccag   2340
aagttcacct catctgccaa cggagtgacc acacattacg tttcacagat tggtggcttc   2400
ccaaatcaaa cagaagacgg aggactacca caaagtggta gaattgttgt tgattacatg   2460
gtgcaaaaat ctgggaaaac aggaacaatt acctatcaaa ggggtatttt attgcctcaa   2520
aaggtgtggt gcgcaagtgg caggagcaag gtaataaaag gatccttgcc tttaattgga   2580
gaagcagatt gcctccacga aaaatacggt ggattaaaca aaagcaagcc ttactacaca   2640
ggggaacatg caaaggccat aggaaattgc ccaatatggg tgaaaacacc cttgaagctg   2700
gccaatggaa ccaaatatag acctcctggt ggaggatggg aaggaatgat tgcaggttgg   2760
cacggataca catcccatgg ggcacatgga gtagcggtgg cagcagacct taagagcact   2820
caagaggcca taaacaagat aacaaaaaat ctcaactctt tgagtgagct ggaagtaaag   2880
aatcttcaaa gactaagcgg tgccatggat gaactccaca acgaaatact agaactagat   2940
gagaaagtgg atgatctcag agctgataca ataagctcac aaatagaact cgcagtcctg   3000
ctttccaatg aaggaataat aaacagtgaa gatgaacatc tcttggcgct tgaaagaaag   3060
ctgaagaaaa tgctgggccc ctctgctgta gagataggga atggatgctt tgaaaccaaa   3120
cacaagtgca accagacctg tctcgacaga atagctgctg gtacctttga tgcaggagaa   3180
ttttctctcc ccacctttga ttcactgaat attactgctg catctttaaa tgacgatgga   3240
ttggataatc atactatact gctttactac tcaactgctg cctccagttt ggctgtaaca   3300
ctgatgatag ctatctttgt tgtttatatg gtctccagag acaatgtttc ttgctccatc   3360
tgtctataaa ggcctatttt ctttagtttg aatttactgt tattcggtgt gcatttctat   3420
gtttggtgag cggttttctg tgctcagagt gtgtttattt tatgtaattt aatttctttg   3480
tgagctcctg tttagcaggt cgtcccttca gcaaggacac aaaaagattt taattttatt   3540
aaaaaaaaaa aaaaaaaaga ccgggaattc gatatcaagc ttatcgacct gcagatcgtt   3600
caaacatttg gcaataaagt ttcttaagat tgaatcctgt tgccggtctt gcgatgatta   3660
tcatataatt tctgttgaat tacgttaagc atgtaataat taacatgtaa tgcatgacgt   3720
tatttatgag atgggttttt atgattagag tcccgcaatt atacatttaa tacgcgatag   3780
aaaacaaaat atagcgcgca aactaggata aattatcgcg cgcggtgtca tctatgttac   3840
tagatctcta gagtctcaag cttggcgcgg ggtaccgagc tcgaattccg agtgtacttc   3900
aagtcagttg gaaatcaata aaatgattat tttatgaata tatttcattg tgcaagtaga   3960
tagaaattac atatgttaca taacacacga aataaacaaa aaaacacaat ccaaaacaaa   4020
caccccaaac aaaataacac tatatatatc ctcgtatgag gagaggcacg ttcagtgact   4080
cgacgattcc cgagcaaaaa aagtctcccc gtcacacata tagtgggtga cgcaattatc   4140
ttcaaagtaa tccttctgtt gacttgtcat tgataacatc cagtcttcgt caggattgca   4200
aagaattata gaagggatcc caccttttat tttcttcttt tttccatatt tagggttgac   4260
agtgaaatca gactggcaac ctattaattg cttccacaat gggacgaact tgaaggggat   4320
gtcgtcgatg atattatagg tggcgtgttc atcgtagttg gtgaagtcga tggtcccgtt   4380
```

```
ccagtagttg tgtcgcccga gacttctagc ccaggtggtc tttccggtac gagttggtcc   4440

gcagatgtag aggctggggt gtctgacccc agtccttccc tcatcctggt tagatcggcc   4500

atccactcaa ggtcagattg tgcttgatcg taggagacag gatgtatgaa agtgtaggca   4560

tcgatgctta catgatatag gtgcgtctct ctccagttgt gcagatcttc gtggcagcgg   4620

agatctgatt ctgtgaaggg cgacacgtac tgctcaggtt gtggaggaaa taatttgttg   4680

gctgaatatt ccagccattg aagctttgtt gcccattcat gagggaattc ttctttgatc   4740

atgtcaagat actcctcctt agacgttgca gtctggataa tagttcgcca tcgtgcgtca   4800

gatttgcgag gagagacctt atgatctcgg aaatctcctc tggttttaat atctccgtcc   4860

tttgatatgt aatcaaggac ttgtttagag tttctagctg gctggatatt agggtgattt   4920

ccttcaaaat cgaaaaaaga aggatcccta atacaaggtt ttttatcaag ctggataaga   4980

gcatgatagt gggtagtgcc atcttgatga agctcagaag caacaccaag gaagaaaata   5040

agaaaaggtg tgagtttctc ccagagaaac tggaataaat catctctttg agatgagcac   5100

ttggggtagg taaggaaaac atatttagat tggagtctga agttcttgct agcagaaggc   5160

atgttgttgt gactccgagg ggttgcctca aactctatct tataaccggc gtggaggcat   5220

ggaggcaagg gcattttggt aatttaagta gttagtggaa aatgacgtca tttacttaaa   5280

gacgaagtct tgcgacaagg ggggcccacg ccgaatttta atattaccgg cgtggcccca   5340

ccttatcgcg agtgctttag cacgagcggt ccagatttaa agtagaaaag ttcccgccca   5400

ctagggttaa aggtgttcac actataaaag catatacgat gtgatggtat ttgatggagc   5460

gtatattgta tcaggtattt ccgtcggata cgaattattc gtac                    5504
```

```
<210> SEQ ID NO 41
<211> LENGTH: 577
<212> TYPE: PRT
<213> ORGANISM: Influenza virus

<400> SEQUENCE: 41

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175
```

-continued

```
Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
        515                 520                 525

Ala Ser Leu Asn Asp Asp Gly Leu Asp Asn His Thr Ile Leu Leu Tyr
    530                 535                 540

Tyr Ser Thr Ala Ala Ser Ser Leu Ala Val Thr Leu Met Ile Ala Ile
545                 550                 555                 560

Phe Val Val Tyr Met Val Ser Arg Asp Asn Val Ser Cys Ser Ile Cys
                565                 570                 575

Leu
```

<210> SEQ ID NO 42
<211> LENGTH: 1707
<212> TYPE: DNA
<213> ORGANISM: Influenza virus

<400> SEQUENCE: 42

```
atggagaaaa tagtgcttct tcttgcaata gtcagtcttg ttaaaagtga tcagatttgc     60

attggttacc atgcaaacaa ttcaacagag caggttgaca caatcatgga aaagaacgtt    120

actgttacac atgcccaaga catactggaa aagacacaca acgggaagct ctgcgatcta    180

gatggagtga agcctctaat tttaagagat tgtagtgtag ctggatggct cctcgggaac    240

ccaatgtgtg acgaattcat caatgtaccg gaatggtctt acatagtgga gaaggccaat    300

ccaaccaatg acctctgtta cccagggagt ttcaacgact atgaagaact gaaacaccta    360

ttgagcagaa taaaccattt tgagaaaatt caaatcatcc ccaaaagttc ttggtccgat    420

catgaagcct catcaggagt tagctcagca tgtccatacc tgggaagtcc ctccttttt    480

agaaatgtgg tatggcttat caaaaagaac agtacatacc caacaataaa gaaaagctac    540

aataatacca accaagagga tcttttggta ctgtggggaa ttcaccatcc taatgatgcg    600

gcagagcaga caaggctata tcaaaaccca accacctata tttccattgg gacatcaaca    660

ctaaaccaga gattggtacc aaaaatagct actagatcca aagtaaacgg gcaaagtgga    720

aggatggagt tcttctggac aattttaaaa cctaatgatg caatcaactt cgagagtaat    780

ggaaatttca ttgctccaga atatgcatac aaaattgtca agaaagggga ctcagcaatt    840

atgaaaagtg aattggaata tggtaactgc aacaccaagt gtcaaactcc aatgggggcg    900

ataaactcta gtatgccatt ccacaacata caccctctca ccatcgggga atgccccaaa    960

tatgtgaaat caaacagatt agtccttgca acagggctca gaaatagccc tcaaagagag   1020

agcagaagaa aaaagagagg actatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactca   1200

atcattgaca aaatgaacac tcagtttgag gccgttggaa gggaatttaa taacttagaa   1260

aggagaatag agaatttaaa caagaagatg gaagacgggt ttctagatgt ctggacttat   1320

aatgccgaac ttctggttct catggaaaat gagagaactc tagactttca tgactcaaat   1380

gttaagaacc tctacgacaa ggtccgacta cagcttaggg ataatgcaaa ggagctgggt   1440

aacggttgtt tcgagttcta tcacaaatgt gataatgaat gtatggaaag tataagaaac   1500

ggaacgtaca actatccgca gtattcagaa gaagcaagat taaaaagaga ggaaataagt   1560

ggggtaaaat tggaatcaat aggaacttac caaatactgt caatttattc aacagtggcg   1620

agttccctag cactggcaat catgatggct ggtctatctt tatggatgtg ctccaatgga   1680

tcgttacaat gcagaatttg catttaa                                       1707
```

<210> SEQ ID NO 43
<211> LENGTH: 1734
<212> TYPE: DNA
<213> ORGANISM: Influenza virus

<400> SEQUENCE: 43

```
atggcgaaaa acgttgcgat tttcggctta ttgttttctc ttcttgtgtt ggttccttct     60

cagatcttcg ccgatcgaat ctgcactgga ataacatcgt caaactcacc acatgtcgtc    120

aaaactgcta ctcaagggga ggtcaatgtg actggtgtaa taccactgac aacaacaccc    180
```

-continued

```
accaaatctc attttgcaaa tctcaaagga acagaaacca gggggaaact atgcccaaaa    240

tgcctcaact gcacagatct ggacgtagcc ttgggcagac caaaatgcac ggggaaaata    300

ccctcggcaa gagtttcaat actccatgaa gtcagacctg ttacatctgg gtgctttcct    360

ataatgcacg acagaacaaa aattagacag ctgcctaacc ttctccgagg atacgaacat    420

atcaggttat caacccataa cgttatcaat gcagaaaatg caccaggagg accctacaaa    480

attggaacct cagggtcttg ccctaacatt accaatggaa acggattttt cgcaacaatg    540

gcttgggccg tcccaaaaaa cgacaaaaac aaaacagcaa caaatccatt aacaatagaa    600

gtaccataca tttgtacaga aggagaagac caaattaccg tttgggggtt ccactctgac    660

aacgagaccc aaatggcaaa gctctatggg gactcaaagc cccagaagtt cacctcatct    720

gccaacggag tgaccacaca ttacgtttca cagattggtg gcttcccaaa tcaaacagaa    780

gacggaggac taccacaaag tggtagaatt gttgttgatt acatggtgca aaaatctggg    840

aaaacaggaa caattaccta tcaaaggggt attttattgc ctcaaaaggt gtggtgcgca    900

agtggcagga gcaaggtaat aaaaggatcc ttgcctttaa ttggagaagc agattgcctc    960

cacgaaaaat acggtggatt aaacaaaagc aagccttact acacagggga acatgcaaag   1020

gccataggaa attgcccaat atgggtgaaa acacccttga agctggccaa tggaaccaaa   1080

tatagacctc ctggtggagg atgggaagga atgattgcag gttggcacgg atacacatcc   1140

catggggcac atggagtagc ggtggcagca gaccttaaga gcactcaaga ggccataaac   1200

aagataacaa aaaatctcaa ctctttgagt gagctggaag taaagaatct tcaaagacta   1260

agcggtgcca tggatgaact ccacaacgaa atactagaac tagatgagaa agtggatgat   1320

ctcagagctg atacaataag ctcacaaata gaactcgcag tcctgctttc caatgaagga   1380

ataataaaca gtgaagatga acatctcttg gcgcttgaaa gaaagctgaa gaaaatgctg   1440

ggcccctctg ctgtagagat agggaatgga tgctttgaaa ccaaacacaa gtgcaaccag   1500

acctgtctcg acagaatagc tgctggtacc tttgatgcag gagaattttc tctccccacc   1560

tttgattcac tgaatattac tgctgcatct ttaaatgacg atggattgga taatcatact   1620

atactgcttt actactcaac tgctgcctcc agtttggctg taacactgat gatagctatc   1680

tttgttgttt atatggtctc cagagacaat gtttcttgct ccatctgtct ataa         1734
```

<210> SEQ ID NO 44
<211> LENGTH: 48
<212> TYPE: DNA
<213> ORGANISM: Artificial Sequence
<220> FEATURE:
<223> OTHER INFORMATION: primer IF-H3V36111.S2+4c

<400> SEQUENCE: 44

```
tctcagatct tcgcccaaaa acttcctgga aatgacaaca gcacggca                  48
```

<210> SEQ ID NO 45
<211> LENGTH: 51
<212> TYPE: DNA
<213> ORGANISM: Artificial Sequence
<220> FEATURE:
<223> OTHER INFORMATION: primer IF-H3V36111.s1-4r

<400> SEQUENCE: 45

```
actaaagaaa ataggccttc aaatgcaaat gttgcaccta atgttgccct t               51
```

<210> SEQ ID NO 46
<211> LENGTH: 1701

-continued

<212> TYPE: DNA
<213> ORGANISM: Artificial Sequence
<220> FEATURE:
<223> OTHER INFORMATION: nucleotide sequence of synthesized H3 gene

<400> SEQUENCE: 46
atgaagacta tcattgcttt gagccacatt ctatgtctgg ttttcgctca aaaacttcct 60
ggaaatgaca acagcacggc aacgctgtgc cttgggcacc atgcagtacc aaacggaacg 120
atagtgaaaa caatcacgaa tgaccaaatt gaagttacta atgctactga gctggttcag 180
aattcctcaa taggtgaaat atgcgacagt cctcatcaga tccttgatgg agaaaactgc 240
acactaatag atgctctatt gggagaccct cagtgtgatg gcttccaaaa taagaaatgg 300 gaccttttg ttgaacgaag caaagcctac agcaactgtt acccttatga tgtgccggat 360
tatgcctccc ttaggtcact agttgcctca tccggcacac tggagtttaa caatgaaagc 420
ttcaattgga ctggagtcac tcaaaacgga acaagttctg cttgcataag gagatctaat 480
aatagtttct ttagtagatt aaattggttg acccacttaa acttcaaata cccagcattg 540
aacgtgacta tgccaaacaa tgaacaattt gacaaattgt acatttgggg ggttcaccac 600
ccgggtacgg acaaggacca aatcttcctg tatgctcaat catcaggaag aatcacagta 660
tctaccaaaa gaagccaaca agctgtaatc ccgaatatcg gatctagacc cagaataagg 720
aatatcccta gcagaataag catctattgg acaatagtaa aaccgggaga catacttttg 780
attaacagca cagggaatct aattgctcct aggggttact tcaaaatacg aagtgggaaa 840
agctcaataa tgagatcaga tgcacccatt ggcaaatgca attctgaatg catcactcca 900
aatggaagca ttcccaatga caaaccattc caaaatgtaa acaggatcac atacggggcc 960
tgtcccagat atgttaagca aagcactctg aaattggcaa caggaatgcg aaatgtacca 1020
gagaaacaaa ctagaggcat atttggcgca atagcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaatcgattg 1200
atcgggaaaa ccaacgagaa attccatcag attgaaaaag aattctcaga agtcgaaggg 1260
agaattcagg accttgagaa atatgttgag gacactaaaa tagatctctg gtcatacaac 1320
gcggagcttc ttgttgccct ggagaaccaa catacaattg atctaactga ctcagaaatg 1380
aacaaactgt ttgaaaaaac aaagaagcaa ctaagggaaa atgctgagga tatgggcaat 1440
ggttgtttca aaatatacca caaatgtgac aatgcctgca taggatcaat cagaaatgga 1500
acttatgacc acgatgtata cagagatgaa gcattaaaca accggttcca gatcaaggga 1560
gttgagctga agtcagggta caaagattgg atcctatgga tttcctttgc catatcatgt 1620
tttttgcttt gtgttgcttt gttggggttc atcatgtggg cctgccaaaa gggcaacatt 1680
aggtgcaaca tttgcatttg a 1701

<210> SEQ ID NO 47
<211> LENGTH: 3465
<212> TYPE: DNA
<213> ORGANISM: Artificial Sequence
<220> FEATURE:
<223> OTHER INFORMATION: expression cassette number 1391

<400> SEQUENCE: 47
gtcaacatgg tggagcacga cacacttgtc tactccaaaa atatcaaaga tacagtctca 60
gaagaccaaa gggcaattga gacttttcaa caaagggtaa tatccggaaa cctcctcgga 120

-continued

```
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggcg aaaaacgttg cgattttcgg cttattgttt tctcttcttg tgttggttcc   1320
ttctcagatc ttcgcccaaa aacttcctgg aaatgacaac agcacggcaa cgctgtgcct   1380
tgggcaccat gcagtaccaa acggaacgat agtgaaaaca atcacgaatg accaaattga   1440
agttactaat gctactgagc tggttcagaa ttcctcaata ggtgaaatat gcgacagtcc   1500
tcatcagatc cttgatggag aaaactgcac actaatagat gctctattgg gagaccctca   1560
gtgtgatggc ttccaaaata agaaatggga ccttttttgtt gaacgaagca aagcctacag   1620
caactgttac ccttatgatg tgccggatta tgcctccctt aggtcactag ttgcctcatc   1680
cggcacactg gagtttaaca atgaaagctt caattggact ggagtcactc aaaacggaac   1740
aagttctgct tgcataagga gatctaataa tagtttcttt agtagattaa attggttgac   1800
ccacttaaac ttcaaatacc cagcattgaa cgtgactatg ccaaacaatg aacaatttga   1860
caaattgtac atttgggggg ttcaccaccc gggtacggac aaggaccaaa tcttcctgta   1920
tgctcaatca tcaggaagaa tcacagtatc taccaaaaga agccaacaag ctgtaatccc   1980
gaatatcgga tctagaccca gaataaggaa tatccctagc agaataagca tctattggac   2040
aatagtaaaa ccgggagaca tacttttgat taacagcaca gggaatctaa ttgctcctag   2100
gggttacttc aaaatacgaa gtgggaaaag ctcaataatg agatcagatg cacccattgg   2160
caaatgcaat tctgaatgca tcactccaaa tggaagcatt cccaatgaca aaccattcca   2220
aaatgtaaac aggatcacat acggggcctg tcccagatat gttaagcaaa gcactctgaa   2280
attggcaaca ggaatgcgaa atgtaccaga gaaacaaact agaggcatat ttggcgcaat   2340
agcgggtttc atagaaaatg gttgggaggg aatggtggat ggttggtacg gtttcaggca   2400
tcaaaattct gagggaagag gacaagcagc agatctcaaa agcactcaag cagcaatcga   2460
tcaaatcaat gggaagctga atcgattgat cgggaaaacc aacgagaaat tccatcagat   2520
```

```
tgaaaaagaa ttctcagaag tcgaagggag aattcaggac cttgagaaat atgttgagga   2580

cactaaaata gatctctggt catacaacgc ggagcttctt gttgccctgg agaaccaaca   2640

tacaattgat ctaactgact cagaaatgaa caaactgttt gaaaaaacaa agaagcaact   2700

aagggaaaat gctgaggata tgggcaatgg ttgtttcaaa atataccaca aatgtgacaa   2760

tgcctgcata ggatcaatca gaaatggaac ttatgaccac gatgtataca gagatgaagc   2820

attaaacaac cggttccaga tcaagggagt tgagctgaag tcagggtaca aagattggat   2880

cctatggatt tcctttgcca tatcatgttt tttgctttgt gttgctttgt tggggttcat   2940

catgtgggcc tgccaaaagg gcaacattag gtgcaacatt tgcatttgaa ggcctatttt   3000

ctttagtttg aatttactgt tattcggtgt gcatttctat gtttggtgag cggttttctg   3060

tgctcagagt gtgtttattt tatgtaattt aatttctttg tgagctcctg tttagcaggt   3120

cgtcccttca gcaaggacac aaaaagattt taattttatt aaaaaaaaaa aaaaaaaaga   3180

ccgggaattc gatatcaagc ttatcgacct gcagatcgtt caaacatttg gcaataaagt   3240

ttcttaagat tgaatcctgt tgccggtctt gcgatgatta tcatataatt tctgttgaat   3300

tacgttaagc atgtaataat taacatgtaa tgcatgacgt tatttatgag atgggttttt   3360

atgattagag tcccgcaatt atacatttaa tacgcgatag aaaacaaaat atagcgcgca   3420

aactaggata aattatcgcg cgcggtgtca tctatgttac tagat                   3465
```

<210> SEQ ID NO 48
<211> LENGTH: 574
<212> TYPE: PRT
<213> ORGANISM: Influenza virus

<400> SEQUENCE: 48

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Asn Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205
```

```
Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Asn Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 49
<211> LENGTH: 46
<212> TYPE: DNA
<213> ORGANISM: Artificial Sequence
<220> FEATURE:
<223> OTHER INFORMATION: primer IF-HAB110.S1+3c

<400> SEQUENCE: 49
aaatttgtcg ggcccatgaa ggcaataatt gtactactca tggtag 46

<210> SEQ ID NO 50
<211> LENGTH: 52
<212> TYPE: DNA
<213> ORGANISM: Artificial Sequence
<220> FEATURE:
<223> OTHER INFORMATION: primer IF-HAB110.s1-4r

<400> SEQUENCE: 50
actaaagaaa ataggccttt atagacagat ggagcatgaa acgttgtctc tg 52

<210> SEQ ID NO 51
<211> LENGTH: 1755
<212> TYPE: DNA
<213> ORGANISM: Artificial Sequence
<220> FEATURE:
<223> OTHER INFORMATION: nucleotide sequence of synthesized HA
B/Wisconin (JN993010)

<400> SEQUENCE: 51
atgaaggcaa taattgtact actcatggta gtaacatcca atgcagatcg aatctgcact 60
gggataacat cttcaaactc acctcatgtg gtcaaaacag ctactcaagg ggaggtcaat 120
gtgactggcg tgataccact gacaacaaca ccaacaaaat cttattttgc aaatctcaaa 180
ggaacaagga ccagagggaa actatgcccg gactgtctca actgtacaga tctggatgtg 240
gccttgggca ggccaatgtg tgtggggacc acaccttctg ctaaagcttc aatactccac 300
gaggtcagac ctgttacatc cgggtgcttt cctataatgc acgacagaac aaaaatcagg 360
caactaccca atcttctcag aggatatgaa aatatcaggt tatcaaccca aaacgttatc 420
gatgcagaaa aagcaccagg aggaccctac agacttggaa cctcaggatc ttgccctaac 480
gctaccagta aaatcggatt ttttgcaaca atggcttggg ctgtcccaaa ggacaactac 540
aaaaatgcaa cgaacccact aacagtagaa gtaccataca tttgtacaga aggggaagac 600
caaattactg tttgggggtt ccattcagat aacaaaaccc aaatgaagag cctctatgga 660
gactcaaatc ctcaaaagtt cacctcatct gctaatggag taaccacaca ttatgtttct 720
cagattggcg acttcccaga tcaaacagaa gacggaggac taccacaaag cggcagaatt 780
gttgttgatt acatgatgca aaaacctggg aaaacaggaa caattgtcta tcaaagaggt 840
gttttgttgc ctcaaaaggt gtggtgcgcg agtggcagga gcaaagtaat aaaagggtca 900
ttgcctttaa ttggtgaagc agattgcctt catgaaaaat acggtggatt aaacaaaagc 960
aagccttact acacaggaga acatgcaaaa gccataggaa attgcccaat atgggtaaaa 1020
acacctttga agcttgccaa tggaaccaaa tatagacctc ctgcaaaact attgaaggaa 1080
aggggtttct tcggagctat tgctggtttc ctagaaggag gatgggaagg aatgattgca 1140
ggttggcacg gatacacatc tcacggagca catggagtgg cagtggcggc agaccttaag 1200
agtacacaag aagctataaa taagataaca aaaaatctca attctttgag tgagctagaa 1260
gtaaagaacc ttcaaagact aagtggtgcc atggatgaac tccacaacga aatactcgag 1320
ctggatgaga aagtggatga tctcagagct gacactataa gctcacaaat agaacttgca 1380
gtcttgcttt ccaacgaagg aataataaac agtgaagacg agcatctatt ggcacttgag 1440
agaaaactaa agaaaatgct gggtccctct gctgtagaca taggaaacgg atgcttcgaa 1500
accaaacaca aatgcaacca gacctgctta gacaggatag ctgctggcac ctttaatgca 1560
ggagaatttt ctctccccac ttttgattca ttgaacatta ctgctgcatc tttaaatgat 1620
gatggattgg ataaccatac tatactgctc tattactcaa ctgctgcttc tagtttggct 1680
gtaacattaa tgctagctat ttttattgtt tatatggtct ccagagacaa cgtttcatgc 1740
tccatctgtc tataa 1755

<210> SEQ ID NO 52
<211> LENGTH: 6745
<212> TYPE: DNA
<213> ORGANISM: Artificial Sequence
<220> FEATURE:
<223> OTHER INFORMATION: Construct 193

<400> SEQUENCE: 52
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840
acatccaatc caaccaatca caacaatcct gatgagataa cccactttaa gcccacgcat 900
ctgtggcaca tctacattat ctaaatcaca cattcttcca cacatctgag ccacacaaaa 960
accaatccac atctttatca cccattctat aaaaaatcac actttgtgag tctacacttt 1020
gattcccttc aaacacatac aaagagaaga gactaattaa ttaattaatc atcttgagag 1080
aaaatggaac gagctataca aggaaacgac gctagggaac aagctaacag tgaacgttgg 1140
gatggaggat caggaggtac cacttctccc ttcaaacttc ctgacgaaag tccgagttgg 1200
actgagtggc ggctacataa cgatgagacg aattcgaatc aagataatcc ccttggtttc 1260
aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500
tctaagcaag aactgctaca gcttgcccca atcgaagtgg aaagtaatgt atcaagagga 1560
tgccctgaag gtactcaaac cttcgaaaaa gaaagcgagt aagttaaaat gcttcttcgt 1620
ctcctattta taatatggtt tgttattgtt aattttgttc ttgtagaaga gcttaattaa 1680
tcgttgttgt tatgaaatac tatttgtatg agatgaactg gtgtaatgta attcatttac 1740
ataagtggag tcagaatcag aatgtttcct ccataactaa ctagacatga agacctgccg 1800
cgtacaattg tcttatattt gaacaactaa aattgaacat cttttgccac aactttataa 1860

-continued

```
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaga cgcgttgttg ttgtgactcc gaggggttgc   2160
ctcaaactct atcttataac cggcgtggag gcatggaggc aggggtattt tggtcatttt   2220
aatagatagt ggaaaatgac gtggaattta cttaaagacg aagtctttgc gacaaggggg   2280
ggcccacgcc gaatttaata ttaccggcgt ggcccccctt tatcgcgagt gctttagcac   2340
gagcggtcca gatttaaagt agaaaatttc ccgcccacta gggttaaagg tgttcacact   2400
ataaaagcat atacgatgtg atggtatttg gtcgacaagc ttgcatgccg gtcaacatgg   2460
tggagcacga cacacttgtc tactccaaaa atatcaaaga tacagtctca gaagaccaaa   2520
gggcaattga gacttttcaa caaagggtaa tatccggaaa cctcctcgga ttccattgcc   2580
cagctatctg tcactttatt gtgaagatag tggaaaagga aggtggctcc tacaaatgcc   2640
atcattgcga taaaggaaag gccatcgttg aagatgcctc tgccgacagt ggtcccaaag   2700
atggaccccc acccacgagg agcatcgtgg aaaaagaaga cgttccaacc acgtcttcaa   2760
agcaagtgga ttgatgtgat aacatggtgg agcacgacac acttgtctac tccaaaaata   2820
tcaaagatac agtctcagaa gaccaaaggg caattgagac ttttcaacaa agggtaatat   2880
ccggaaacct cctcggattc cattgcccag ctatctgtca ctttattgtg aagatagtgg   2940
aaaaggaagg tggctcctac aaatgccatc attgcgataa aggaaaggcc atcgttgaag   3000
atgcctctgc cgacagtggt cccaaagatg gacccccacc cacgaggagc atcgtggaaa   3060
aagaagacgt tccaaccacg tcttcaaagc aagtggattg atgtgatatc tccactgacg   3120
taagggatga cgcacaatcc cactatcctt cgcaagaccc ttcctctata taaggaagtt   3180
catttcattt ggagaggtat taaaatctta ataggttttg ataaaagcga acgtggggaa   3240
acccgaacca aaccttcttc taaactctct ctcatctctc ttaaagcaaa cttctctctt   3300
gtctttcttg cgtgagcgat cttcaacgtt gtcagatcgt gcttcggcac cagtacaacg   3360
ttttctttca ctgaagcgaa atcaaagatc tctttgtgga cacgtagtgc ggcgccatta   3420
aataacgtgt acttgtccta ttcttgtcgg tgtggtcttg ggaaaagaaa gcttgctgga   3480
ggctgctgtt cagccccata cattacttgt tacgattctg ctgactttcg gcgggtgcaa   3540
tatctctact tctgcttgac gaggtattgt tgcctgtact tctttcttct tcttcttgct   3600
gattggttct ataagaaatc tagtattttc tttgaaacag agttttcccg tggttttcga   3660
acttggagaa agattgttaa gcttctgtat attctgccca aatttgtcgg gcccgcggat   3720
ggcgaaaaac gttgcgattt tcggcttatt gttttctctt cttgtgttgg ttccttctca   3780
gatcttcgcc tgcaggctcc tcagccaaaa cgacaccccc atctgtctat ccactggccc   3840
ctggatctgc tgcccaaact aactccatgg tgaccctggg atgcctggtc aagggctatt   3900
tccctgagcc agtgacagtg acctggaact ctggatccct gtccagcggt gtgcacacct   3960
tcccagctgt cctgcagtct gacctctaca ctctgagcag ctcagtgact gtcccctcca   4020
gcacctggcc cagcgagacc gtcacctgca acgttgccca cccggccagc agcaccaagg   4080
tggacaagaa aattgtgccc agggattgtg gttgtaagcc ttgcatatgt acagtcccag   4140
aagtatcatc tgtcttcatc ttccccccaa agcccaagga tgtgctcacc attactctga   4200
ctcctaaggt cacgtgtgtt gtggtagaca tcagcaagga tgatcccgag gtccagttca   4260
```

-continued gctggtttgt agatgatgtg gaggtgcaca cagctcagac gcaaccccgg gaggagcagt 4320
tcaacagcac tttccgctca gtcagtgaac ttcccatcat gcaccaggac tggctcaatg 4380
gcaaggagcg atcgctcacc atcaccatca ccatcaccat caccattaaa ggcctatttt 4440
ctttagtttg aatttactgt tattcggtgt gcatttctat gtttggtgag cggttttctg 4500
tgctcagagt gtgtttattt tatgtaattt aatttctttg tgagctcctg tttagcaggt 4560
cgtcccttca gcaaggacac aaaaagattt taattttatt aaaaaaaaaa aaaaaaaaga 4620
ccgggaattc gatatcaagc ttatcgacct gcagatcgtt caaacatttg gcaataaagt 4680
ttcttaagat tgaatcctgt tgccggtctt gcgatgatta tcatataatt tctgttgaat 4740
tacgttaagc atgtaataat taacatgtaa tgcatgacgt tatttatgag atgggttttt 4800
atgattagag tcccgcaatt atacatttaa tacgcgatag aaaacaaaat atagcgcgca 4860
aactaggata aattatcgcg cgcggtgtca tctatgttac tagatctcta gagtctcaag 4920
cttggcgcgc cataaaatga ttattttatg aatatatttc attgtgcaag tagatagaaa 4980
ttacatatgt tacataacac acgaaataaa caaaaaaaga caatccaaaa acaaacaccc 5040
caaaaaaaat aatcacttta gataaactcg tatgaggaga ggcacgttca gtgactcgac 5100
gattcccgag caaaaaaagt ctccccgtca cacatatagt gggtgacgca attatcttta 5160
aagtaatcct tctgttgact tgtcattgat aacatccagt cttcgtcagg attgcaaaga 5220
attatagaag ggatcccacc ttttatttc ttcttttttc catatttagg gttgacagtg 5280
aaatcagact ggcaacctat taattgcttc cacaatggga cgaacttgaa ggggatgtcg 5340
tcgatgatat tataggtggc gtgttcatcg tagttggtga aatcgatggt accgttccaa 5400
tagttgtgtc gtccgagact tctagcccag gtggtctttc cggtacgagt tggtccgcag 5460
atgtagaggc tggggtgtcg gattccattc cttccattgt cctggttaaa tcggccatcc 5520
attcaaggtc agattgagct tgttggtatg agacaggatg tatgtaagta taagcgtcta 5580
tgcttacatg gtatagatgg gtttccctcc aggagtgtag atcttcgtgg cagcgaagat 5640
ctgattctgt gaagggcgac acatacggtt caggttgtgg agggaataat ttgttggctg 5700
aatattccag ccattgaagt tttgttgccc attcatgagg gaattcttcc ttgatcatgt 5760
caagatattc ctccttagac gttgcagtct ggataatagt tctccatcgt gcgtcagatt 5820
tgcgaggaga gaccttatga tctcggaaat ctcctctggt tttaatatct ccgtcctttg 5880
atatgtaatc aaggacttgt ttagagtttc tagctggctg gatattaggg tgatttcctt 5940
caaaatcgaa aaaagaagga tccctaatac aaggtttttt atcaagctgg agaagagcat 6000
gatagtgggt agtgccatct tgatgaagct cagaagcaac accaaggaag aaaataagaa 6060
aaggtgtgag tttctcccag agaaactgga ataaatcatc tctttgagat gagcacttgg 6120
gataggtaag gaaaacatat ttagattgga gtctgaagtt cttactagca gaaggcatgt 6180
tgttgtgact ccgaggggtt gcctcaaact ctatcttata accggcgtgg aggcatggag 6240
gcaggggtat tttggtcatt ttaatagata gtggaaaatg acgtggaatt tacttaaaga 6300
cgaagtcttt gcgacaaggg ggggcccacg ccgaatttaa tattaccggc gtggcccccc 6360
cttatcgcga gtgctttagc acgagcggtc cagatttaaa gtagaaaatt tcccgcccac 6420
tagggttaaa ggtgttcaca ctataaaagc atatacgatg tgatggtatt tgactagtgg 6480
cactggccgt cgttttacaa cgtcgtgact gggaaaaccc tggcgttacc caacttaatc 6540
gccttgcagc acatccccct ttcgccagct ggcgtaatag cgaagaggcc cgcaccgatc 6600
gcccttccca acagttgcgc agcctgaatg gcgaatgcta gagcagcttg agcttggatc 6660
agattgtcgt ttcccgcctt cagtttaaac tatcagtgtt tgacaggata tattggcggg 6720
taaacctaag agaaaagagc gttta 6745

<210> SEQ ID NO 53
<211> LENGTH: 3495
<212> TYPE: DNA
<213> ORGANISM: Artificial Sequence
<220> FEATURE:
<223> OTHER INFORMATION: Expression cassette number 1462

<400> SEQUENCE: 53
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140
tcttcttgct gattggttct ataagaaatc tagtattttc tttgaaacag agttttcccg 1200
tggttttcga acttggagaa agattgttaa gcttctgtat attctgccca aatttgtcgg 1260
gcccatgaag gcaataattg tactactcat ggtagtaaca tccaatgcag atcgaatctg 1320
cactgggata acatcttcaa actcacctca tgtggtcaaa acagctactc aaggggaggt 1380
caatgtgact ggcgtgatac cactgacaac aacaccaaca aaatcttatt ttgcaaatct 1440
caaaggaaca aggaccagag ggaaactatg cccggactgt ctcaactgta cagatctgga 1500
tgtggccttg ggcaggccaa tgtgtgtggg gaccacacct tctgctaaag cttcaatact 1560
ccacgaggtc agacctgtta catccgggtg ctttcctata atgcacgaca gaacaaaaat 1620
caggcaacta cccaatcttc tcagaggata tgaaaatatc aggttatcaa cccaaaacgt 1680
tatcgatgca gaaaaagcac caggaggacc ctacagactt ggaacctcag gatcttgccc 1740
taacgctacc agtaaaatcg gattttttgc aacaatggct tgggctgtcc caaaggacaa 1800
ctacaaaaat gcaacgaacc cactaacagt agaagtacca tacatttgta cagaagggga 1860
agaccaaatt actgtttggg ggttccattc agataacaaa acccaaatga agagcctcta 1920

```
tggagactca aatcctcaaa agttcacctc atctgctaat ggagtaacca cacattatgt   1980

ttctcagatt ggcgacttcc cagatcaaac agaagacgga ggactaccac aaagcggcag   2040

aattgttgtt gattacatga tgcaaaaacc tgggaaaaca ggaacaattg tctatcaaag   2100

aggtgttttg ttgcctcaaa aggtgtggtg cgcgagtggc aggagcaaag taataaaagg   2160

gtcattgcct ttaattggtg aagcagattg ccttcatgaa aaatacggtg gattaaacaa   2220

aagcaagcct tactacacag gagaacatgc aaaagccata ggaaattgcc caatatgggt   2280

aaaaacacct ttgaagcttg ccaatggaac caaatataga cctcctgcaa aactattgaa   2340

ggaaaggggt ttcttcggag ctattgctgg tttcctagaa ggaggatggg aaggaatgat   2400

tgcaggttgg cacggataca catctcacgg agcacatgga gtggcagtgg cggcagacct   2460

taagagtaca caagaagcta taaataagat aacaaaaaat ctcaattctt tgagtgagct   2520

agaagtaaag aaccttcaaa gactaagtgg tgccatggat gaactccaca acgaaatact   2580

cgagctggat gagaaagtgg atgatctcag agctgacact ataagctcac aaatagaact   2640

tgcagtcttg ctttccaacg aaggaataat aaacagtgaa gacgagcatc tattggcact   2700

tgagagaaaa ctaaagaaaa tgctgggtcc ctctgctgta gacataggaa acggatgctt   2760

cgaaaccaaa cacaaatgca accagacctg cttagacagg atagctgctg gcacctttaa   2820

tgcaggagaa ttttctctcc ccacttttga ttcattgaac attactgctg catctttaaa   2880

tgatgatgga ttggataacc atactatact gctctattac tcaactgctg cttctagttt   2940

ggctgtaaca ttaatgctag ctatttttat tgtttatatg gtctccagag acaacgtttc   3000

atgctccatc tgtctataaa ggcctatttt ctttagtttg aatttactgt tattcggtgt   3060

gcatttctat gtttggtgag cggttttctg tgctcagagt gtgtttattt tatgtaattt   3120

aatttctttg tgagctcctg tttagcaggt cgtcccttca gcaaggacac aaaaagattt   3180

taattttatt aaaaaaaaaa aaaaaaaaga ccgggaattc gatatcaagc ttatcgacct   3240

gcagatcgtt caaacatttg gcaataaagt ttcttaagat tgaatcctgt tgccggtctt   3300

gcgatgatta tcatataatt tctgttgaat tacgttaagc atgtaataat taacatgtaa   3360

tgcatgacgt tatttatgag atgggttttt atgattagag tcccgcaatt atacatttaa   3420

tacgcgatag aaaacaaaat atagcgcgca aactaggata aattatcgcg cgcggtgtca   3480

tctatgttac tagat                                                    3495
```

<210> SEQ ID NO 54
<211> LENGTH: 584
<212> TYPE: PRT
<213> ORGANISM: Influenza virus

<400> SEQUENCE: 54

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
```

-continued

```
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510
```

```
Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580
```

<210> SEQ ID NO 55
<211> LENGTH: 56
<212> TYPE: DNA
<213> ORGANISM: Artificial Sequence
<220> FEATURE:
<223> OTHER INFORMATION: primer HAB110(PrL-).r

<400> SEQUENCE: 55
tccttcccat cctccaccag gaggtctata tttggttcca ttggcaagct tcaaag 56

<210> SEQ ID NO 56
<211> LENGTH: 52
<212> TYPE: DNA
<213> ORGANISM: Artificial Sequence
<220> FEATURE:
<223> OTHER INFORMATION: primer HAB110(PrL-).c

<400> SEQUENCE: 56
atatagacct cctggtggag gatgggaagg aatgattgca ggttggcacg ga 52

<210> SEQ ID NO 57
<211> LENGTH: 3444
<212> TYPE: DNA
<213> ORGANISM: Artificial Sequence
<220> FEATURE:
<223> OTHER INFORMATION: Expression cassette number 1467

<400> SEQUENCE: 57
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140
tcttcttgct gattggttct ataagaaatc tagtattttc tttgaaacag agttttcccg 1200
tggttttcga acttggagaa agattgttaa gcttctgtat attctgccca aatttgtcgg 1260
gcccatgaag gcaataattg tactactcat ggtagtaaca tccaatgcag atcgaatctg 1320
cactgggata acatcttcaa actcacctca tgtggtcaaa acagctactc aaggggaggt 1380
caatgtgact ggcgtgatac cactgacaac aacaccaaca aaatcttatt ttgcaaatct 1440
caaaggaaca aggaccagag ggaaactatg cccggactgt ctcaactgta cagatctgga 1500
tgtggccttg ggcaggccaa tgtgtgtggg gaccacacct tctgctaaag cttcaatact 1560
ccacgaggtc agacctgtta catccgggtg ctttcctata atgcacgaca gaacaaaaat 1620
caggcaacta cccaatcttc tcagaggata tgaaaatatc aggttatcaa cccaaaacgt 1680
tatcgatgca gaaaaagcac caggaggacc ctacagactt ggaacctcag gatcttgccc 1740
taacgctacc agtaaaatcg gatttttgc aacaatggct tgggctgtcc caaaggacaa 1800
ctacaaaaat gcaacgaacc cactaacagt agaagtacca tacatttgta cagaaggga 1860
agaccaaatt actgtttggg ggttccattc agataacaaa acccaaatga agagcctcta 1920
tggagactca aatcctcaaa agttcacctc atctgctaat ggagtaacca cacattatgt 1980
ttctcagatt ggcgacttcc cagatcaaac agaagacgga ggactaccac aaagcggcag 2040
aattgttgtt gattacatga tgcaaaaacc tgggaaaaca ggaacaattg tctatcaaag 2100
aggtgttttg ttgcctcaaa aggtgtggtg cgcgagtggc aggagcaaag taataaaagg 2160
gtcattgcct ttaattggtg aagcagattg ccttcatgaa aaatacggtg gattaaacaa 2220
aagcaagcct tactacacag gagaacatgc aaaagccata ggaaattgcc caatatgggt 2280
aaaaacacct ttgaagcttg ccaatggaac caaatataga cctcctggtg gaggatggga 2340
aggaatgatt gcaggttggc acggatacac atctcacgga gcacatggag tggcagtggc 2400
ggcagacctt aagagtacac aagaagctat aaataagata acaaaaaatc tcaattcttt 2460
gagtgagcta gaagtaaaga accttcaaag actaagtggt gccatggatg aactccacaa 2520
cgaaatactc gagctggatg agaaagtgga tgatctcaga gctgacacta taagctcaca 2580
aatagaactt gcagtcttgc tttccaacga aggaataata aacagtgaag acgagcatct 2640
attggcactt gagagaaaac taaagaaaat gctgggtccc tctgctgtag acataggaaa 2700
cggatgcttc gaaaccaaac acaaatgcaa ccagacctgc ttagacagga tagctgctgg 2760
cacctttaat gcaggagaat ttctctccc cacttttgat tcattgaaca ttactgctgc 2820
atctttaaat gatgatggat tggataacca tactatactg ctctattact caactgctgc 2880
ttctagtttg gctgtaacat taatgctagc tattttatt gtttatatgg tctccagaga 2940
caacgtttca tgctccatct gtctataaag gcctattttc tttagtttga atttactgtt 3000
attcggtgtg catttctatg tttggtgagc ggttttctgt gctcagagtg tgtttatttt 3060
atgtaattta atttctttgt gagctcctgt ttagcaggtc gtcccttcag caaggacaca 3120
aaaagatttt aattttatta aaaaaaaaaa aaaaaaagac cgggaattcg atatcaagct 3180
tatcgacctg cagatcgttc aaacatttgg caataaagtt tcttaagatt gaatcctgtt 3240

-continued

```
gccggtcttg cgatgattat catataattt ctgttgaatt acgttaagca tgtaataatt   3300

aacatgtaat gcatgacgtt atttatgaga tgggttttta tgattagagt cccgcaatta   3360

tacatttaat acgcgataga aaacaaaata tagcgcgcaa actaggataa attatcgcgc   3420

gcggtgtcat ctatgttact agat                                          3444


<210> SEQ ID NO 58
<211> LENGTH: 567
<212> TYPE: PRT
<213> ORGANISM: Influenza virus

<400> SEQUENCE: 58

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335
```

-continued

```
Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

His Thr Ile Leu Leu Tyr Tyr Ser Thr Ala Ala Ser Ser Leu Ala Val
    530                 535                 540

Thr Leu Met Leu Ala Ile Phe Ile Val Tyr Met Val Ser Arg Asp Asn
545                 550                 555                 560

Val Ser Cys Ser Ile Cys Leu
                565
```

<210> SEQ ID NO 59
<211> LENGTH: 44
<212> TYPE: DNA
<213> ORGANISM: Artificial Sequence
<220> FEATURE:
<223> OTHER INFORMATION: primer IF-HB-M-04.s2+4c

<400> SEQUENCE: 59
tctcagatct tcgccgatcg aatctgcact gggataacat cgtc 44

<210> SEQ ID NO 60
<211> LENGTH: 46
<212> TYPE: DNA
<213> ORGANISM: Artificial Sequence
<220> FEATURE:
<223> OTHER INFORMATION: primer IF-HB-M-04.s1-4r

<400> SEQUENCE: 60
actaaagaaa ataggccttt atagacagat ggagcaagaa acattg 46

<210> SEQ ID NO 61
<211> LENGTH: 1713
<212> TYPE: DNA
<213> ORGANISM: Artificial Sequence
<220> FEATURE:
<223> OTHER INFORMATION: nucleotide sequence of synthesized HA B
      Malaysia

<400> SEQUENCE: 61
gatcgaatct gcactgggat aacatcgtca aactcaccac atgttgtcaa aactgctact 60
caaggggagg tcaatgtgac tggtgtaata ccactgacaa caacacccac caaatctcat 120
tttgcaaatc tcaaaggaac agaaaccaga gggaaactat gcccaaaatg cctcaactgc 180
acagatctgg acgtggcctt gggcagacca aaatgcacgg ggaacatacc ctcggcaaga 240
gtttcaatac tccatgaagt cagacctgtt acatctgggt gctttcctat aatgcacgac 300
agaacaaaaa ttagacagct gcctaaactt ctcagaggat acgaacatat caggttatca 360
actcataacg ttatcaatgc agaaaatgca ccaggaggac cctacaaaat tggaacctca 420
gggtcttgcc ctaacgttac caatggaaac ggatttttcg caacaatggc ttgggccgtc 480
ccaaaaaacg acaacaacaa aacagcaaca aattcattaa caatagaagt accatacatt 540
tgtacagaag gagaagacca aattaccgtt tgggggttcc actctgataa cgaaacccaa 600
atggcaaagc tctatgggga ctcaaagccc cagaagttca cctcatctgc caacggagtg 660
accacacatt acgtttcaca gattggtggc ttcccaaatc aaacagaaga cggaggacta 720
ccacaaagcg gtagaattgt tgttgattac atggtgcaaa aatctgggaa aacaggaaca 780
attacctatc aaagaggtat tttattgcct caaaaagtgt ggtgcgcaag tggcaggagc 840
aaggtaataa aaggatcgtt gcctttaatt ggagaagcag attgcctcca cgaaaaatac 900
ggtggattaa acaaaagcaa gccttactac acaggggaac atgcaaaggc cataggaaat 960
tgcccaatat gggtgaaaac acccttgaag ctggccaatg gaaccaaata tagacctcct 1020
gcaaaactat taaaggaaag ggtttcttc ggagctattg ctggtttctt agaaggagga 1080
tgggaaggaa tgattgcagg ttggcacgga tacacatccc atggggcaca tggagtagcg 1140
gtggcagcag accttaagag cactcaagag gccataaaca agataacaaa aaatctcaac 1200
tctttgagtg agctggaagt aaagaatctt caaagactaa gcggtgccat ggatgaactc 1260
cacaacgaaa tactagaact agacgagaaa gtggatgatc tcagagctga tacaataagc 1320
tcacaaatag aactcgcagt cctgctttcc aatgaaggaa taataaacag tgaagatgag 1380
catctcttgg cgcttgaaag aaagctgaag aaaatgctgg gcccctctgc tgtagagata 1440
gggaatggat gctttgaaac caaacacaag tgcaaccaga cctgtctcga cagaatagct 1500
gctggtacct ttgatgcagg agaattttct ctccccactt ttgattcact gaatattact 1560
gctgcatctt taaatgacga tggattggat aatcatacta tactgcttta ctactcaact 1620
gctgcctcca gtttggctgt aacattgatg atagctatct ttgttgttta tatggtctcc 1680
agagacaatg tttcttgctc catctgtcta taa 1713

<210> SEQ ID NO 62
<211> LENGTH: 6739
<212> TYPE: DNA
<213> ORGANISM: Artificial Sequence
<220> FEATURE:
<223> OTHER INFORMATION: Construct 194

<400> SEQUENCE: 62
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300

-continued

```
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaga cgcgttgttg ttgtgactcc gaggggttgc   2160
ctcaaactct atcttataac cggcgtggag gcatggaggc aggggtattt tggtcatttt   2220
aatagatagt ggaaaatgac gtggaattta cttaaagacg aagtctttgc gacaaggggg   2280
ggcccacgcc gaatttaata ttaccggcgt ggcccccccct tatcgcgagt gctttagcac   2340
gagcggtcca gatttaaagt agaaaatttc ccgcccacta gggttaaagg tgttcacact   2400
ataaaagcat atacgatgtg atggtatttg gtcgacaagc ttgcatgccg gtcaacatgg   2460
tggagcacga cacacttgtc tactccaaaa atatcaaaga tacagtctca gaagaccaaa   2520
gggcaattga gacttttcaa caaagggtaa tatccggaaa cctcctcgga ttccattgcc   2580
cagctatctg tcactttatt gtgaagatag tggaaaagga aggtggctcc tacaaatgcc   2640
atcattgcga taaaggaaag gccatcgttg aagatgcctc tgccgacagt ggtcccaaag   2700
```

-continued

```
atggaccccc acccacgagg agcatcgtgg aaaaagaaga cgttccaacc acgtcttcaa   2760
agcaagtgga ttgatgtgat aacatggtgg agcacgacac acttgtctac tccaaaaata   2820
tcaaagatac agtctcagaa gaccaaaggg caattgagac ttttcaacaa agggtaatat   2880
ccggaaacct cctcggattc cattgcccag ctatctgtca ctttattgtg aagatagtgg   2940
aaaaggaagg tggctcctac aaatgccatc attgcgataa aggaaaggcc atcgttgaag   3000
atgcctctgc cgacagtggt cccaaagatg gacccccacc cacgaggagc atcgtggaaa   3060
aagaagacgt tccaaccacg tcttcaaagc aagtggattg atgtgatatc tccactgacg   3120
taagggatga cgcacaatcc cactatcctt cgcaagaccc ttcctctata taaggaagtt   3180
catttcattt ggagaggtat taaaatctta ataggttttg ataaaagcga acgtggggaa   3240
acccgaacca aaccttcttc taaactctct ctcatctctc ttaaagcaaa cttctctctt   3300
gtctttcttg cgtgagcgat cttcaacgtt gtcagatcgt gcttcggcac cagtacaacg   3360
ttttctttca ctgaagcgaa atcaaagatc tctttgtgga cacgtagtgc ggcgccatta   3420
aataacgtgt acttgtccta ttcttgtcgg tgtggtcttg ggaaaagaaa gcttgctgga   3480
ggctgctgtt cagccccata cattacttgt tacgattctg ctgactttcg gcgggtgcaa   3540
tatctctact tctgcttgac gaggtattgt tgcctgtact tctttcttct tcttcttgct   3600
gattggttct ataagaaatc tagtattttc tttgaaacag agttttcccg tggttttcga   3660
acttggagaa agattgttaa gcttctgtat attctgccca aatttgtcgg gcccatggcg   3720
aaaaacgttg cgattttcgg cttattgttt tctcttcttg tgttggttcc ttctcagatc   3780
ttcgccgcgg ctcctcagcc aaaacgacac ccccatctgt ctatccactg gcccctggat   3840
ctgctgccca aactaactcc atggtgaccc tgggatgcct ggtcaagggc tatttccctg   3900
agccagtgac agtgacctgg aactctggat ccctgtccag cggtgtgcac accttcccag   3960
ctgtcctgca gtctgacctc tacactctga gcagctcagt gactgtcccc tccagcacct   4020
ggcccagcga gaccgtcacc tgcaacgttg cccacccggc cagcagcacc aaggtggaca   4080
agaaaattgt gcccagggat tgtggttgta agccttgcat atgtacagtc ccagaagtat   4140
catctgtctt catcttcccc ccaaagccca aggatgtgct caccattact ctgactccta   4200
aggtcacgtg tgttgtggta gacatcagca aggatgatcc cgaggtccag ttcagctggt   4260
ttgtagatga tgtggaggtg cacacagctc agacgcaacc ccgggaggag cagttcaaca   4320
gcactttccg ctcagtcagt gaacttccca tcatgcacca ggactggctc aatggcaagg   4380
agcgatcgct caccatcacc atcaccatca ccatcaccat taaaggccta ttttctttag   4440
tttgaattta ctgttattcg gtgtgcattt ctatgtttgg tgagcggttt tctgtgctca   4500
gagtgtgttt attttatgta atttaatttc tttgtgagct cctgtttagc aggtcgtccc   4560
ttcagcaagg acacaaaaag attttaattt tattaaaaaa aaaaaaaaaa aagaccggga   4620
attcgatatc aagcttatcg acctgcagat cgttcaaaca tttggcaata aagtttctta   4680
agattgaatc ctgttgccgg tcttgcgatg attatcatat aatttctgtt gaattacgtt   4740
aagcatgtaa taattaacat gtaatgcatg acgttattta tgagatgggt ttttatgatt   4800
agagtcccgc aattatacat ttaatacgcg atagaaaaca aaatatagcg cgcaaactag   4860
gataaattat cgcgcgcggt gtcatctatg ttactagatc tctagagtct caagcttggc   4920
gcgccataaa atgattattt tatgaatata tttcattgtg caagtagata gaaattacat   4980
atgttacata acacacgaaa taaacaaaaa aagacaatcc aaaaacaaac accccaaaaa   5040
```

```
aaataatcac tttagataaa ctcgtatgag gagaggcacg ttcagtgact cgacgattcc   5100

cgagcaaaaa aagtctcccc gtcacacata tagtgggtga cgcaattatc tttaaagtaa   5160

tccttctgtt gacttgtcat tgataacatc cagtcttcgt caggattgca aagaattata   5220

gaagggatcc caccttttat tttcttcttt tttccatatt tagggttgac agtgaaatca   5280

gactggcaac ctattaattg cttccacaat gggacgaact tgaaggggat gtcgtcgatg   5340

atattatagg tggcgtgttc atcgtagttg gtgaaatcga tggtaccgtt ccaatagttg   5400

tgtcgtccga gacttctagc ccaggtggtc tttccggtac gagttggtcc gcagatgtag   5460

aggctggggt gtcggattcc attccttcca ttgtcctggt taaatcggcc atccattcaa   5520

ggtcagattg agcttgttgg tatgagacag gatgtatgta agtataagcg tctatgctta   5580

catggtatag atgggtttcc ctccaggagt gtagatcttc gtggcagcga agatctgatt   5640

ctgtgaaggg cgacacatac ggttcaggtt gtggagggaa taatttgttg gctgaatatt   5700

ccagccattg aagttttgtt gcccattcat gagggaattc ttccttgatc atgtcaagat   5760

attcctcctt agacgttgca gtctggataa tagttctcca tcgtgcgtca gatttgcgag   5820

gagagacctt atgatctcgg aaatctcctc tggttttaat atctccgtcc tttgatatgt   5880

aatcaaggac ttgtttagag tttctagctg gctggatatt agggtgattt ccttcaaaat   5940

cgaaaaaaga aggatcccta atacaaggtt ttttatcaag ctggagaaga gcatgatagt   6000

gggtagtgcc atcttgatga agctcagaag caacaccaag gaagaaaata agaaaaggtg   6060

tgagtttctc ccagagaaac tggaataaat catctctttg agatgagcac ttgggatagg   6120

taaggaaaac atatttagat tggagtctga agttcttact agcagaaggc atgttgttgt   6180

gactccgagg ggttgcctca aactctatct tataaccggc gtggaggcat ggaggcaggg   6240

gtattttggt cattttaata gatagtggaa aatgacgtgg aatttactta aagacgaagt   6300

ctttgcgaca aggggggggcc cacgccgaat ttaatattac cggcgtggcc cccccttatc   6360

gcgagtgctt tagcacgagc ggtccagatt taaagtagaa aatttcccgc ccactagggt   6420

taaaggtgtt cacactataa aagcatatac gatgtgatgg tatttgacta gtggcactgg   6480

ccgtcgtttt acaacgtcgt gactgggaaa accctggcgt tacccaactt aatcgccttg   6540

cagcacatcc ccctttcgcc agctggcgta atagcgaaga ggcccgcacc gatcgccctt   6600

cccaacagtt gcgcagcctg aatggcgaat gctagagcag cttgagcttg gatcagattg   6660

tcgtttcccg ccttcagttt aaactatcag tgtttgacag gatatattgg cgggtaaacc   6720

taagagaaaa gagcgttta                                                6739
```

<210> SEQ ID NO 63
<211> LENGTH: 3525
<212> TYPE: DNA
<213> ORGANISM: Artificial Sequence
<220> FEATURE:
<223> OTHER INFORMATION: Expression cassette number 1631

<400> SEQUENCE: 63

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360
```

-continued

```
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggcg aaaaacgttg cgattttcgg cttattgttt tctcttcttg tgttggttcc   1320
ttctcagatc ttcgccgatc gaatctgcac tgggataaca tcgtcaaact caccacatgt   1380
tgtcaaaact gctactcaag gggaggtcaa tgtgactggt gtaataccac tgacaacaac   1440
acccaccaaa tctcattttg caaatctcaa aggaacagaa accagaggga aactatgccc   1500
aaaatgcctc aactgcacag atctggacgt ggccttgggc agaccaaaat gcacggggaa   1560
cataccctcg gcaagagttt caatactcca tgaagtcaga cctgttacat ctgggtgctt   1620
tcctataatg cacgacagaa caaaaattag acagctgcct aaacttctca gaggatacga   1680
acatatcagg ttatcaactc ataacgttat caatgcagaa aatgcaccag gaggacccta   1740
caaaattgga acctcagggt cttgccctaa cgttaccaat ggaaacggat ttttcgcaac   1800
aatggcttgg gccgtcccaa aaaacgacaa caacaaaaca gcaacaaatt cattaacaat   1860
agaagtacca tacatttgta cagaaggaga agaccaaatt accgtttggg ggttccactc   1920
tgataacgaa acccaaatgg caaagctcta tggggactca aagccccaga agttcacctc   1980
atctgccaac ggagtgacca cacattacgt ttcacagatt ggtggcttcc caaatcaaac   2040
agaagacgga ggactaccac aaagcggtag aattgttgtt gattacatgg tgcaaaaatc   2100
tgggaaaaca ggaacaatta cctatcaaag aggtatttta ttgcctcaaa aagtgtggtg   2160
cgcaagtggc aggagcaagg taataaaagg atcgttgcct ttaattggag aagcagattg   2220
cctccacgaa aaatacggtg gattaaacaa aagcaagcct tactacacag gggaacatgc   2280
aaaggccata ggaaattgcc caatatgggt gaaaacaccc ttgaagctgg ccaatggaac   2340
caaatataga cctcctgcaa aactattaaa ggaaaggggt ttcttcggag ctattgctgg   2400
tttcttagaa ggaggatggg aaggaatgat tgcaggttgg cacggataca catcccatgg   2460
ggcacatgga gtagcggtgg cagcagacct taagagcact caagaggcca taaacaagat   2520
aacaaaaaat ctcaactctt tgagtgagct ggaagtaaag aatcttcaaa gactaagcgg   2580
tgccatggat gaactccaca acgaaatact agaactagac gagaaagtgg atgatctcag   2640
agctgataca ataagctcac aaatagaact cgcagtcctg ctttccaatg aaggaataat   2700
```

```
aaacagtgaa gatgagcatc tcttggcgct tgaaagaaag ctgaagaaaa tgctgggccc   2760

ctctgctgta gagataggga atggatgctt tgaaaccaaa cacaagtgca accagacctg   2820

tctcgacaga atagctgctg gtacctttga tgcaggagaa ttttctctcc ccacttttga   2880

ttcactgaat attactgctg catctttaaa tgacgatgga ttggataatc atactatact   2940

gctttactac tcaactgctg cctccagttt ggctgtaaca ttgatgatag ctatctttgt   3000

tgtttatatg gtctccagag acaatgtttc ttgctccatc tgtctataaa ggcctatttt   3060

ctttagtttg aatttactgt tattcggtgt gcatttctat gtttggtgag cggttttctg   3120

tgctcagagt gtgtttattt tatgtaattt aatttctttg tgagctcctg tttagcaggt   3180

cgtcccttca gcaaggacac aaaaagattt taattttatt aaaaaaaaaa aaaaaaaaga   3240

ccgggaattc gatatcaagc ttatcgacct gcagatcgtt caaacatttg gcaataaagt   3300

ttcttaagat tgaatcctgt tgccggtctt gcgatgatta tcatataatt tctgttgaat   3360

tacgttaagc atgtaataat taacatgtaa tgcatgacgt tatttatgag atgggttttt   3420

atgattagag tcccgcaatt atacatttaa tacgcgatag aaaacaaaat atagcgcgca   3480

aactaggata aattatcgcg cgcggtgtca tctatgttac tagat                  3525
```

<210> SEQ ID NO 64
<211> LENGTH: 594
<212> TYPE: PRT
<213> ORGANISM: Influenza virus

<400> SEQUENCE: 64

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Asn Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Lys Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Val Thr Asn Gly Asn Gly Phe
                165                 170                 175

Phe Ala Thr Met Ala Trp Ala Val Pro Lys Asn Asp Asn Asn Lys Thr
            180                 185                 190

Ala Thr Asn Ser Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
```

```
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Ala Lys Leu Leu
        355                 360                 365

Lys Glu Arg Gly Phe Phe Gly Ala Ile Ala Gly Phe Leu Glu Gly Gly
    370                 375                 380

Trp Glu Gly Met Ile Ala Gly Trp His Gly Tyr Thr Ser His Gly Ala
385                 390                 395                 400

His Gly Val Ala Val Ala Ala Asp Leu Lys Ser Thr Gln Glu Ala Ile
                405                 410                 415

Asn Lys Ile Thr Lys Asn Leu Asn Ser Leu Ser Glu Leu Glu Val Lys
            420                 425                 430

Asn Leu Gln Arg Leu Ser Gly Ala Met Asp Glu Leu His Asn Glu Ile
        435                 440                 445

Leu Glu Leu Asp Glu Lys Val Asp Asp Leu Arg Ala Asp Thr Ile Ser
    450                 455                 460

Ser Gln Ile Glu Leu Ala Val Leu Leu Ser Asn Glu Gly Ile Ile Asn
465                 470                 475                 480

Ser Glu Asp Glu His Leu Leu Ala Leu Glu Arg Lys Leu Lys Lys Met
                485                 490                 495

Leu Gly Pro Ser Ala Val Glu Ile Gly Asn Gly Cys Phe Glu Thr Lys
            500                 505                 510

His Lys Cys Asn Gln Thr Cys Leu Asp Arg Ile Ala Ala Gly Thr Phe
        515                 520                 525

Asp Ala Gly Glu Phe Ser Leu Pro Thr Phe Asp Ser Leu Asn Ile Thr
    530                 535                 540

Ala Ala Ser Leu Asn Asp Asp Gly Leu Asp Asn His Thr Ile Leu Leu
545                 550                 555                 560

Tyr Tyr Ser Thr Ala Ala Ser Ser Leu Ala Val Thr Leu Met Ile Ala
                565                 570                 575

Ile Phe Val Val Tyr Met Val Ser Arg Asp Asn Val Ser Cys Ser Ile
            580                 585                 590

Cys Leu


<210> SEQ ID NO 65
<211> LENGTH: 9
<212> TYPE: PRT
<213> ORGANISM: Artificial Sequence
<220> FEATURE:
<223> OTHER INFORMATION: Polybasic cleavage of H5

<400> SEQUENCE: 65
```

Arg Glu Arg Arg Arg Lys Lys Arg Gly
1 5

<210> SEQ ID NO 66
<211> LENGTH: 4
<212> TYPE: PRT
<213> ORGANISM: Artificial Sequence
<220> FEATURE:
<223> OTHER INFORMATION: First 4 charged amino acids deleted from polybasic cleavage site of H5

<400> SEQUENCE: 66

Arg Glu Arg Arg
1

<210> SEQ ID NO 67
<211> LENGTH: 4
<212> TYPE: PRT
<213> ORGANISM: Artificial Sequence
<220> FEATURE:
<223> OTHER INFORMATION: Polybasic cleavage site of H5

<400> SEQUENCE: 67

Arg Lys Lys Arg
1

<210> SEQ ID NO 68
<211> LENGTH: 4
<212> TYPE: PRT
<213> ORGANISM: Artificial Sequence
<220> FEATURE:
<223> OTHER INFORMATION: Modification of polybasic cleavage site of H5

<400> SEQUENCE: 68

Thr Glu Thr Arg
1

<210> SEQ ID NO 69
<211> LENGTH: 9
<212> TYPE: PRT
<213> ORGANISM: Artificial Sequence
<220> FEATURE:
<223> OTHER INFORMATION: Polybasic site

<400> SEQUENCE: 69

Gly Glu Arg Arg Arg Lys Lys Arg Gly
1 5

<210> SEQ ID NO 70
<211> LENGTH: 4
<212> TYPE: PRT
<213> ORGANISM: Artificial Sequence
<220> FEATURE:
<223> OTHER INFORMATION: Replacement to polybasic site

<400> SEQUENCE: 70

Arg Glu Thr Arg
1

<210> SEQ ID NO 71
<211> LENGTH: 4
<212> TYPE: PRT
<213> ORGANISM: Artificial Sequence
<220> FEATURE:
<223> OTHER INFORMATION: Replacement amino acids to polybasic site

<400> SEQUENCE: 71

Ile Glu Thr Arg
1

<210> SEQ ID NO 72
<211> LENGTH: 5
<212> TYPE: PRT
<213> ORGANISM: Artificial Sequence
<220> FEATURE:
<223> OTHER INFORMATION: Monoasic site of H6

<400> SEQUENCE: 72

Ile Glu Thr Arg Gly
1 5

<210> SEQ ID NO 73
<211> LENGTH: 8
<212> TYPE: PRT
<213> ORGANISM: Artificial Sequence
<220> FEATURE:
<223> OTHER INFORMATION: Deletion sequence at C-terminus of HA1

<400> SEQUENCE: 73

Ala Leu Lys Leu Leu Lys Glu Arg
1 5

<210> SEQ ID NO 74
<211> LENGTH: 12
<212> TYPE: PRT
<213> ORGANISM: Artificial Sequence
<220> FEATURE:
<223> OTHER INFORMATION: Deletion sequence of N-terminus of HA2

<400> SEQUENCE: 74

Gly Phe Phe Gly Ala Ile Ala Gly Phe Leu Glu Gly
1 5 10

<210> SEQ ID NO 75
<211> LENGTH: 34
<212> TYPE: PRT
<213> ORGANISM: H1 New Cal influenza

<400> SEQUENCE: 75

Val Arg Ser Ala Lys Leu Arg Met Val Thr Gly Leu Arg Asn Ile Pro
1 5 10 15

Ser Ile Gln Ser Arg Gly Leu Phe Gly Ala Ile Ala Gly Phe Ile Glu
20 25 30

Gly Gly

<210> SEQ ID NO 76
<211> LENGTH: 34
<212> TYPE: PRT
<213> ORGANISM: H1 Brisbane Influenza

<400> SEQUENCE: 76

Val Arg Ser Ala Lys Leu Arg Met Val Thr Gly Leu Arg Asn Ile Pro
1 5 10 15

Ser Ile Gln Ser Arg Gly Leu Phe Gly Ala Ile Ala Gly Phe Ile Glu
20 25 30

Gly Gly

<210> SEQ ID NO 77
<211> LENGTH: 34
<212> TYPE: PRT

<213> ORGANISM: H1 Sol Islands Infleunza

<400> SEQUENCE: 77

Val Arg Ser Ala Lys Leu Arg Met Val Thr Gly Leu Arg Asn Ile Pro
1               5                   10                  15

Ser Ile Gln Ser Arg Gly Leu Phe Gly Ala Ile Ala Gly Phe Ile Glu
            20                  25                  30

Gly Gly

<210> SEQ ID NO 78
<211> LENGTH: 34
<212> TYPE: PRT
<213> ORGANISM: H2 A Singapore Influenza

<400> SEQUENCE: 78

Val Lys Ser Glu Lys Leu Val Leu Ala Thr Gly Leu Arg Asn Val Pro
1               5                   10                  15

Gln Ile Glu Ser Arg Gly Leu Phe Gly Ala Ile Ala Gly Phe Ile Glu
            20                  25                  30

Gly Gly

<210> SEQ ID NO 79
<211> LENGTH: 34
<212> TYPE: PRT
<213> ORGANISM: H3 A Brisbane Influenza

<400> SEQUENCE: 79

Val Lys Gln Asn Thr Leu Lys Leu Ala Thr Gly Met Arg Asn Val Pro
1               5                   10                  15

Glu Lys Gln Thr Arg Gly Ile Phe Gly Ala Ile Ala Gly Phe Ile Glu
            20                  25                  30

Asn Gly

<210> SEQ ID NO 80
<211> LENGTH: 34
<212> TYPE: PRT
<213> ORGANISM: H3 A WCN Influenza

<400> SEQUENCE: 80

Val Lys Gln Asn Thr Leu Lys Leu Ala Thr Gly Met Arg Asn Val Pro
1               5                   10                  15

Glu Lys Gln Thr Arg Gly Ile Phe Gly Ala Ile Ala Gly Phe Ile Glu
            20                  25                  30

Asn Gly

<210> SEQ ID NO 81
<211> LENGTH: 37
<212> TYPE: PRT
<213> ORGANISM: H5 Anhui Influenza

<400> SEQUENCE: 81

Val Lys Ser Asn Lys Leu Val Leu Ala Thr Gly Leu Arg Asn Ser Pro
1               5                   10                  15

Leu Arg Glu Arg Arg Arg Lys Arg Gly Leu Phe Gly Ala Ile Ala Gly
            20                  25                  30

Phe Ile Glu Gly Gly
        35

<210> SEQ ID NO 82

<211> LENGTH: 38
<212> TYPE: PRT
<213> ORGANISM: H5 Indo Influenza

<400> SEQUENCE: 82

Val Lys Ser Asn Arg Leu Val Leu Ala Thr Gly Leu Arg Asn Ser Pro
1 5 10 15

Gln Arg Glu Ser Arg Arg Lys Lys Arg Gly Leu Phe Gly Ala Ile Ala
20 25 30

Gly Phe Ile Glu Gly Gly
35

<210> SEQ ID NO 83
<211> LENGTH: 38
<212> TYPE: PRT
<213> ORGANISM: H5 Viet Nam Influenza

<400> SEQUENCE: 83

Val Lys Ser Asn Arg Leu Val Leu Ala Thr Gly Leu Arg Asn Ser Pro
1 5 10 15

Gln Arg Glu Arg Arg Arg Lys Lys Arg Gly Leu Phe Gly Ala Ile Ala
20 25 30

Gly Phe Ile Glu Gly Gly
35

<210> SEQ ID NO 84
<211> LENGTH: 34
<212> TYPE: PRT
<213> ORGANISM: H6 Teal HK Influenza

<400> SEQUENCE: 84

Val Lys Ser Glu Ser Leu Arg Leu Ala Thr Gly Leu Arg Asn Val Pro
1 5 10 15

Gln Ile Glu Thr Arg Gly Leu Phe Gly Ala Ile Ala Gly Phe Ile Glu
20 25 30

Gly Gly

<210> SEQ ID NO 85
<211> LENGTH: 45
<212> TYPE: PRT
<213> ORGANISM: H6 Eq Prague Influenza

<400> SEQUENCE: 85

Val Lys Gln Lys Ser Leu Met Leu Ala Thr Gly Met Lys Asn Val Pro
1 5 10 15

Glu Ala Pro Ala His Lys Gln Leu Thr His His Met Arg Lys Lys Arg
20 25 30

Gly Leu Phe Gly Ala Ile Ala Gly Phe Ile Glu Asn Gly
35 40 45

<210> SEQ ID NO 86
<211> LENGTH: 34
<212> TYPE: PRT
<213> ORGANISM: H9A HK Influenza

<400> SEQUENCE: 86

Val Arg Val Asn Ser Leu Lys Leu Ala Val Gly Leu Arg Asn Val Pro
1 5 10 15

Ala Arg Ser Ser Arg Gly Leu Phe Gly Ala Ile Ala Gly Phe Ile Glu
20 25 30

-continued

```
Gly Gly


<210> SEQ ID NO 87
<211> LENGTH: 46
<212> TYPE: PRT
<213> ORGANISM: B Florida Influenza

<400> SEQUENCE: 87

Ala Lys Ala Ile Gly Asn Cys Pro Ile Trp Val Lys Thr Pro Leu Lys
1               5                   10                  15

Leu Ala Asn Gly Thr Lys Tyr Arg Pro Pro Ala Lys Leu Leu Lys Glu
            20                  25                  30

Arg Gly Phe Phe Gly Ala Ile Ala Gly Phe Leu Glu Gly Gly
        35                  40                  45


<210> SEQ ID NO 88
<211> LENGTH: 46
<212> TYPE: PRT
<213> ORGANISM: B Malaysia Influenza

<400> SEQUENCE: 88

Ala Lys Ala Ile Gly Asn Cys Pro Ile Trp Val Lys Thr Pro Leu Lys
1               5                   10                  15

Leu Ala Asn Gly Thr Lys Tyr Arg Pro Pro Ala Lys Leu Leu Lys Glu
            20                  25                  30

Arg Gly Phe Phe Gly Ala Ile Ala Gly Phe Leu Glu Gly Gly
        35                  40                  45
```